(12) United States Patent
Suh et al.

(10) Patent No.: US 12,041,851 B2
(45) Date of Patent: Jul. 16, 2024

(54) COMPOUND AND ORGANIC LIGHT EMITTING DEVICE COMPRISING SAME

(71) Applicant: LG CHEM, LTD., Seoul (KR)

(72) Inventors: Sang Duk Suh, Daejeon (KR); Minjun Kim, Daejeon (KR); Min Woo Jung, Daejeon (KR); Jungha Lee, Daejeon (KR); Donghee Kim, Daejeon (KR); Sunghyun Hwang, Daejeon (KR); Dong Hoon Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 607 days.

(21) Appl. No.: 17/291,539

(22) PCT Filed: Jan. 15, 2020

(86) PCT No.: PCT/KR2020/000737
§ 371 (c)(1),
(2) Date: May 5, 2021

(87) PCT Pub. No.: WO2020/153654
PCT Pub. Date: Jul. 30, 2020

(65) Prior Publication Data
US 2021/0408396 A1    Dec. 30, 2021

(30) Foreign Application Priority Data

Jan. 25, 2019    (KR) .................. 10-2019-0009978

(51) Int. Cl.
*H10K 85/60*   (2023.01)
*C07D 487/16*  (2006.01)
*C09K 11/06*   (2006.01)
*H10K 50/11*   (2023.01)
*H10K 101/10*  (2023.01)

(52) U.S. Cl.
CPC ....... *H10K 85/6572* (2023.02); *C07D 487/16* (2013.01); *C09K 11/06* (2013.01); *H10K 85/615* (2023.02); *H10K 85/654* (2023.02); *H10K 85/6574* (2023.02); *H10K 85/6576* (2023.02); *C09K 2211/1018* (2013.01); *H10K 50/11* (2023.02); *H10K 2101/10* (2023.02)

(58) Field of Classification Search
None
See application file for complete search history.

(56) References Cited

U.S. PATENT DOCUMENTS

| | | | |
|---|---|---|---|
| 2016/0293853 A1 | 10/2016 | Zeng et al. | |
| 2017/0179406 A1 | 6/2017 | Kang et al. | |
| 2019/0010179 A1* | 1/2019 | Li | ............... C09K 11/025 |
| 2019/0189927 A1 | 6/2019 | Lee et al. | |

FOREIGN PATENT DOCUMENTS

| | | | | |
|---|---|---|---|---|
| CN | 106046006 A | 10/2016 | | |
| CN | 109020979 A | * 12/2018 | ........... | C07D 487/06 |
| CN | 113015734 A | 6/2021 | | |
| KR | 10-2014-0034710 A | 3/2014 | | |
| KR | 10-2014-0065130 A | 5/2014 | | |
| KR | 10-2016-0006617 A | 1/2016 | | |
| KR | 10-2016-0028979 A | 3/2016 | | |
| KR | 10-2016-0046077 A | 4/2016 | | |
| KR | 10-2018-0040100 A | 4/2018 | | |
| KR | 10-2018-0096444 A | 8/2018 | | |
| WO | 2018/021737 A1 | 2/2018 | | |

* cited by examiner

*Primary Examiner* — Robert S Loewe
(74) *Attorney, Agent, or Firm* — Bryan Cave Leighton Paisner LLP

(57) ABSTRACT

A compound of Chemical Formula 1, and an organic light emitting device comprising the same, the compound used as a material of an organic material layer of the organic light emitting device and providing enhanced efficiency and low driving voltage of the organic light emitting device.

[Chemical Formula 1]

20 Claims, 4 Drawing Sheets

【FIG. 1】
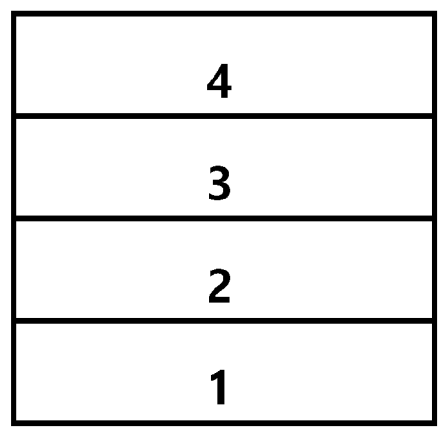

[FIG. 2]
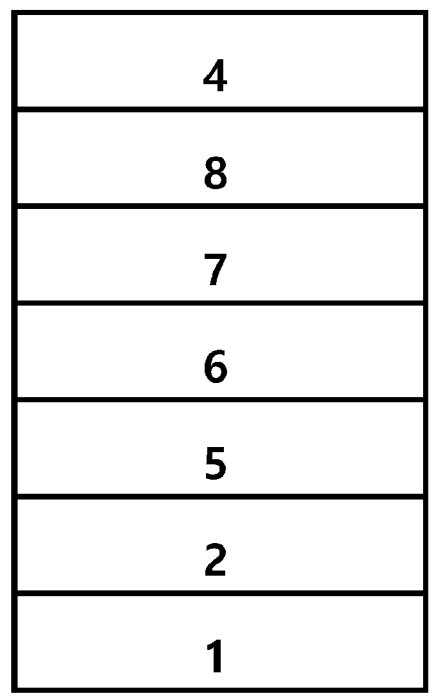

[FIG. 3]
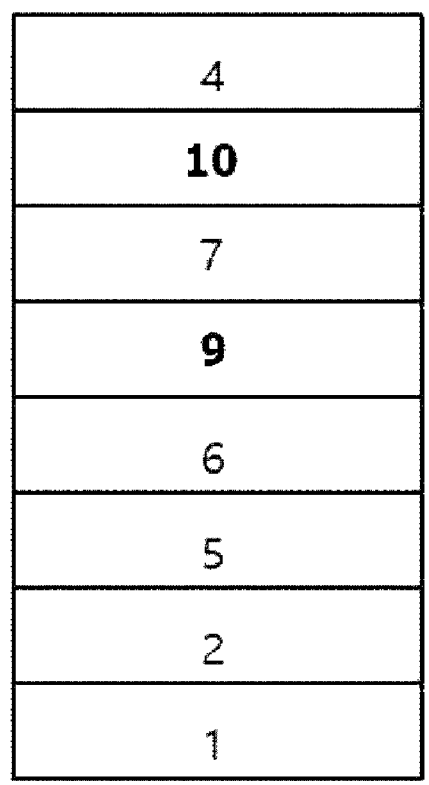

[FIG. 4]
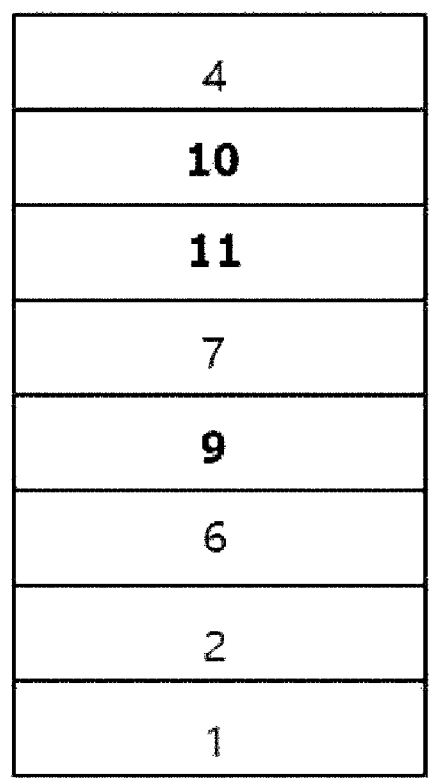

COMPOUND AND ORGANIC LIGHT EMITTING DEVICE COMPRISING SAME

CROSS-REFERENCE TO RELATED APPLICATION(S)

This application is a National Stage Application of International Application No. PCT/KR2020/000737 filed on Jan. 15, 2020, which claims priority to and the benefits of Korean Patent Application No. 10-2019-0009978 filed on Jan. 25, 2019, the disclosures of which are incorporated herein by reference in their entireties.

FIELD OF DISCLOSURE

The present specification relates to a compound and an organic light emitting device comprising the same.

BACKGROUND

An organic light emitting device is a light emitting device using an organic semiconductor material, and requires an exchange of holes and/or electrons between an electrode and the organic semiconductor material. An organic light emitting device may be largely divided into two types as follows depending on the operation principle. The first is a light emitting device type in which excitons are formed in an organic material layer by photons introduced to a device from an external light source, these excitons are separated into electrons and holes, and these electrons and holes are each transferred to different electrodes and used as a current source (voltage source). The second is a light emitting device type in which, by applying a voltage or current to two or more electrodes, holes and/or electrons are injected into an organic semiconductor material layer forming an interface with the electrodes, and the light emitting device is operated by the injected electrons and holes.

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron blocking layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state. Such an organic light emitting device is known to have properties such as self-emission, high luminance, high efficiency, low driving voltage, wide viewing angle and high contrast.

Materials used as an organic material layer in an organic light emitting device may be divided into a light emitting material and a charge transfer material, for example, a hole injection material, a hole transfer material, an electron blocking material, an electron transfer material, an electron injection material and the like depending on the function. The light emitting material includes, depending on light emitting color, blue, green and red light emitting materials, and yellow and orange light emitting materials required for obtaining better natural colors.

In addition, in order to increase color purity and light emission efficiency through energy transition, a host/dopant-based may be used as the light emitting material. The principle is that light with high efficiency is produced when mixing a small amount of dopant having a smaller energy band gap and superior light emission efficiency compared to a host mainly consisting a light emitting layer into the light emitting layer by the transferring of excitons produced in the host to the dopant. Herein, the wavelength of the host is shifted to the wavelength band of the dopant, and therefore, light with a target wavelength may be obtained depending on the types of the dopant used.

In order to sufficiently exhibit excellent properties that the above-described organic light emitting device has, materials forming an organic material layer in the device, for example, a hole injection material, a hole transfer material, a light emitting material, an electron blocking material, an electron transfer material, an electron injection material and the like are supported by stable and efficient materials, and therefore, development of new materials has been continuously required.

SUMMARY

The present specification describes a compound, and an organic light emitting device comprising same.

One embodiment of the present specification provides a compound represented by the following Chemical Formula 1.

[Chemical Formula 1]

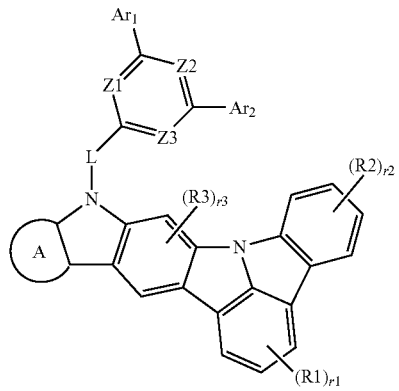

In Chemical Formula 1, $Ar_1$ and $Ar_2$ are the same as or different from each other, and each independently a substituted or unsubstituted aryl group; or a substituted or unsubstituted heterocyclic group, at least two of Z1 to Z3 are N, and the rest is CR, L is a substituted or unsubstituted arylene group; or a substituted or unsubstituted divalent heterocyclic group, A is substituted or unsubstituted benzene; or substituted or unsubstituted naphthalene, R and R1 to R3 are the same as or different from each other, and each independently hydrogen; deuterium; a halogen group; a cyano group; a substituted or unsubstituted alkyl group; a substituted or unsubstituted cycloalkyl group; a substituted or unsubstituted aryl group; or a substituted or unsubstituted heteroaryl group, r1 is an integer of 0 to 3, r2 is an integer of 0 to 4, r3 is an integer of 0 to 2, and when r1 to r3 are 2 or greater, the two or more groups in parentheses are the same as or different from each other.

Another embodiment of the present specification provides an organic light emitting device including a first electrode; a second electrode provided to face the first electrode; and one or more organic material layers provided between the first electrode and the second electrode, wherein one or more layers of the organic material layers include the compound described above.

Advantageous Effects

A compound represented by Chemical Formula 1 of the present disclosure can be used as a material of an organic material layer of an organic light emitting device.

An organic light emitting device including the compound represented by Chemical Formula 1 according to one embodiment of the present specification is capable of enhancing efficiency.

An organic light emitting device including the compound represented by Chemical Formula 1 according to one embodiment of the present specification has an advantage of low driving voltage.

DESCRIPTION OF DRAWINGS

FIG. 1 illustrates an organic light emitting device according to one embodiment of the present specification.

FIG. 2 illustrates an organic light emitting device according to another embodiment of the present specification.

FIG. 3 illustrates an organic light emitting device according to still another embodiment of the present specification.

FIG. 4 illustrates an organic light emitting device according to still another embodiment of the present specification.

DESCRIPTION OF REFERENCE NUMERALS

1: Substrate
2: Anode
3: Light Emitting Layer
4: Cathode
5: Hole Injection Layer
6: Hole Transfer Layer
7: Light Emitting Layer
8: Electron Transfer Layer
9: Electron Blocking Layer
10: Electron Transfer and Injection Layer
11: Hole Blocking Layer

DETAILED DESCRIPTION

Hereinafter, the present specification will be described in detail.

One embodiment of the present specification provides a compound represented by Chemical Formula 1.

An organic light emitting device including the compound represented by Chemical Formula 1 according to one embodiment of the present specification is capable of enhancing efficiency.

An organic light emitting device including the compound represented by Chemical Formula 1 according to one embodiment of the present specification has an advantage of low driving voltage.

The compound represented by Chemical Formula 1 of the present application has a structure in which a monocyclic nitrogen-containing heteroring unit having strong electron acceptor properties and a unit having strong electron donor properties by including two nitrogen atoms acting as an electron donor in the ring are linked through L. When strong two units with very different properties directly bond, internal charge transfer becomes too strong losing an ability to transfer other charges. The compound represented by Chemical Formula 1 of the present application mitigates internal charge transfer by introducing L between the two units and thereby separating the electron donor unit and the electron acceptor unit, which is advantageous for both hole and electron transfer, and suitable properties as a light emitting layer host are obtained.

In addition, the nitrogen atoms of the electron donor unit are fused so as to be located in a meta position to each other, and, whereas the ortho position does not properly push electrons to the nitrogen atom linked to L and the para position pushes too excessively, the meta position allows a proper electron donor role and thereby performs a role of balancing hole and electron transfer. At the same time, it is fused to be structurally separated from other units including L linked to the nitrogen atom, which leads to low structural interference and high stability due to a flat structure, and as a result, properties of long lifetime are obtained when used in an organic electroluminescent device.

In the present specification, a description of a certain part "including" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

In the present specification, -⌇- means a site bonding to other substituents or bonding sites.

Examples of substituents in the present specification are described below, however, the substituents are not limited thereto.

The term "substitution" means a hydrogen atom bonding to a carbon atom of a compound being changed to another substituent, and the position of substitution is not limited as long as it is a position at which a hydrogen atom is substituted, that is, a position at which a substituent may substitute, and when two or more substituents substitute, the two or more substituents may be the same as or different from each other.

In the present specification, the term "substituted or unsubstituted" means being substituted with one, two or more substituents selected from the group consisting of deuterium (-D); a halogen group; a nitrile group; a nitro group; a hydroxyl group; a silyl group; a boron group; an alkoxy group; an alkyl group; a cycloalkyl group; an aryl group; and a heterocyclic group, or being substituted with a substituent linking two or more substituents among the substituents illustrated above, or having no substituents. For example, "a substituent linking two or more substituents" may include a biphenyl group. In other words, a biphenyl group may be an aryl group, or interpreted as a substituent linking two phenyl groups.

In the present specification, examples of the halogen group may include fluorine (F), chlorine (Cl), bromine (Br) or iodine (I).

In the present specification, the silyl group may be represented by a chemical formula of -SiYaYbYc, and Ya, Yb and Yc may each be hydrogen; deuterium; halogen; a nitrile group; a substituted or unsubstituted alkyl group; a substituted or unsubstituted cycloalkyl group; a substituted or unsubstituted aryl group; or a substituted or unsubstituted heterocyclic group. Specific examples of the silyl group may include a trimethylsilyl group, a triethylsilyl group, a tert-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be represented by a chemical formula of -BYdYe, and Yd and Ye may each be hydrogen; deuterium; halogen; a nitrile group; a substituted or unsubstituted alkyl group; a substituted or unsubstituted cycloalkyl group; a substituted or unsubstituted aryl group; or a substituted or unsubstituted heterocyclic group. Specific examples of the boron group may include a trimethylboron group, a triethylboron group, a tert-butyldimethylboron group, a triphenylboron group, a phenylboron group and the like, but are not limited thereto.

In the present specification, the alkyl group may be linear or branched, and although not particularly limited thereto, the number of carbon atoms is preferably from 1 to 60. According to one embodiment, the number of carbon atoms of the alkyl group is from 1 to 30. According to another embodiment, the number of carbon atoms of the alkyl group is from 1 to 20. According to another embodiment, the number of carbon atoms of the alkyl group is from 1 to 10. Specific examples of the alkyl group may include a methyl group, an ethyl group, a propyl group, an n-propyl group, an isopropyl group, a butyl group, an n-butyl group, an isobutyl group, a tert-butyl group, a pentyl group, an n-pentyl group, a hexyl group, an n-hexyl group, a heptyl group, an n-heptyl group, an octyl group, an n-octyl group and the like, but are not limited thereto.

In the present specification, the alkenyl group may be linear or branched, and although not particularly limited thereto, the number of carbon atoms is preferably from 2 to 30. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the alkoxy group may be linear, branched or cyclic. The number of carbon atoms of the alkoxy group is not particularly limited, but is preferably from 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy and the like, but are not limited thereto.

The alkyl group, the alkoxy group and substituents including other alkyl group parts described in the present specification include all of linear or branched forms.

In the present specification, the cycloalkyl group is not particularly limited, but preferably has 3 to 60 carbon atoms, and according to one embodiment, the number of carbon atoms of the cycloalkyl group is from 3 to 30. According to another embodiment, the number of carbon atoms of the cycloalkyl group is from 3 to 20. According to another embodiment, the number of carbon atoms of the cycloalkyl group is from 3 to 6. Specific examples thereof may include a cyclopropyl group, a cyclobutyl group, a cyclopentyl group, a cyclohexyl group, a cycloheptyl group, a cyclooctyl group and the like, but are not limited thereto.

In the present specification, the aryl group is not particularly limited, but preferably has 6 to 60 carbon atoms, and may be a monocyclic aryl group or a polycyclic aryl group. According to one embodiment, the number of carbon atoms of the aryl group is from 6 to 30. According to one embodiment, the number of carbon atoms of the aryl group is from 6 to 20. When the aryl group is a monocyclic aryl group, examples thereof may include a phenyl group, a biphenyl group, a terphenyl group, a quaterphenyl group and the like, but are not limited thereto. Examples of the polycyclic aryl group may include a naphthyl group, an anthracenyl group, a phenanthrenyl group, a pyrenyl group, a perylenyl group, a triphenyl group, a chrysenyl group, a fluorenyl group, a triphenylenyl group and the like, but are not limited thereto.

In the present specification, the fluorene group may be substituted, and two substituents may bond to each other to form a spiro structure.

When the fluorene group is substituted, a spirofluorene group such as

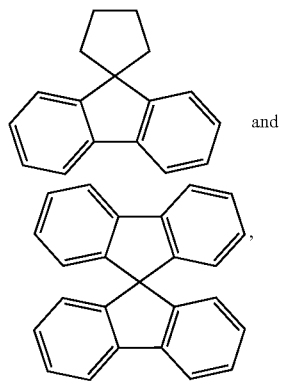

and a substituted fluorene group such as

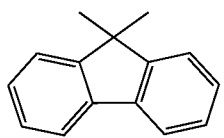

(9,9-dimethylfluorene group) and

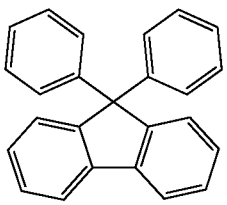 [SMILES: c1ccc(C2(c3ccccc3)c3ccccc3-c3ccccc32)cc1]

(9,9-diphenylfluorene group) may be included, however, the structure is not limited thereto.

In the present specification, the heterocyclic group is a cyclic group including one or more of N, O, P, S, Si and Se as a heteroatom, and although not particularly limited thereto, the number of carbon atoms is preferably from 2 to 60. According to one embodiment, the number of carbon atoms of the heterocyclic group is from 2 to 20. Examples of the heterocyclic group may include a pyridine group, a pyrrole group, a pyrimidine group, a quinoline group, a pyridazine group, a furan group, a thiophene group, an imidazole group, a pyrazole group, a dibenzofuran group, a dibenzothiophene group, a carbazole group, a benzocarbazole group, a benzonaphthofuran group, a benzonaphthothiophene group, an indenocarbazole group, an indolocarbazole group and the like, but are not limited thereto.

In the present specification, the descriptions on the heterocyclic group provided above may be applied to the heteroaryl group except that it is aromatic.

According to one embodiment of the present specification, $Ar_1$ and $Ar_2$ are each independently a substituted or unsubstituted aryl group; or a substituted or unsubstituted heterocyclic group.

According to one embodiment of the present specification, $Ar_1$ and $Ar_2$ are each independently a substituted or unsubstituted aryl group having 6 to 60 carbon atoms; or a substituted or unsubstituted heterocyclic group having 2 to 60 carbon atoms.

According to one embodiment of the present specification, $Ar_1$ and $Ar_2$ are each independently a substituted or unsubstituted aryl group having 6 to 30 carbon atoms; or a substituted or unsubstituted heterocyclic group having 2 to 30 carbon atoms.

According to one embodiment of the present specification, $Ar_1$ and $Ar_2$ are the same as or different from each other, and each independently an aryl group having 6 to 30 carbon atoms unsubstituted or substituted with deuterium; or a heterocyclic group having 2 to 30 carbon atoms unsubstituted or substituted with deuterium.

According to one embodiment of the present specification, $Ar_1$ and $Ar_2$ are each independently a substituted or unsubstituted phenyl group; a substituted or unsubstituted naphthyl group; a substituted or unsubstituted biphenyl group;

a substituted or unsubstituted carbazole group; a substituted or unsubstituted fluorene group; a substituted or unsubstituted dibenzofuran group; a substituted or unsubstituted dibenzothiophene group; or a substituted or unsubstituted dicyclic heterocyclic group including N and S.

According to one embodiment of the present specification, $Ar_1$ and $Ar_2$ are the same as or different from each other, and each independently a substituted or unsubstituted phenyl group; a substituted or unsubstituted naphthyl group; a substituted or unsubstituted biphenyl group; a substituted or unsubstituted dibenzofuran group; or a substituted or unsubstituted dibenzothiophene group.

According to one embodiment of the present specification, $Ar_1$ and $Ar_2$ are the same as or different from each other, and each independently a phenyl group unsubstituted or substituted with deuterium; a naphthyl group unsubstituted or substituted with deuterium; a biphenyl group unsubstituted or substituted with deuterium; a dibenzofuran group unsubstituted or substituted with deuterium; or a dibenzothiophene group unsubstituted or substituted with deuterium.

According to one embodiment of the present specification, $Ar_1$ and $Ar_2$ are the same as or different from each other, and each independently a phenyl group unsubstituted or substituted with deuterium; a naphthyl group; a biphenyl group; a dibenzofuran group; or a dibenzothiophene group.

According to one embodiment of the present specification, $Ar_1$ and $Ar_2$ are the same as or different from each other, and each independently a phenyl group unsubstituted or substituted with deuterium; a naphthyl group; a biphenyl group; or a dibenzofuran group.

According to one embodiment of the present specification, $Ar_1$ and $Ar_2$ are the same as or different from each other, and each independently a phenyl group; a naphthyl group; or a biphenyl group.

According to one embodiment of the present specification, $Ar_1$ and $Ar_2$ are the same as or different from each other, and each independently a phenyl group.

According to one embodiment of the present specification, $Ar_1$ and $Ar_2$ are the same as or different from each other, and each independently any one selected from the group consisting of the following structures.

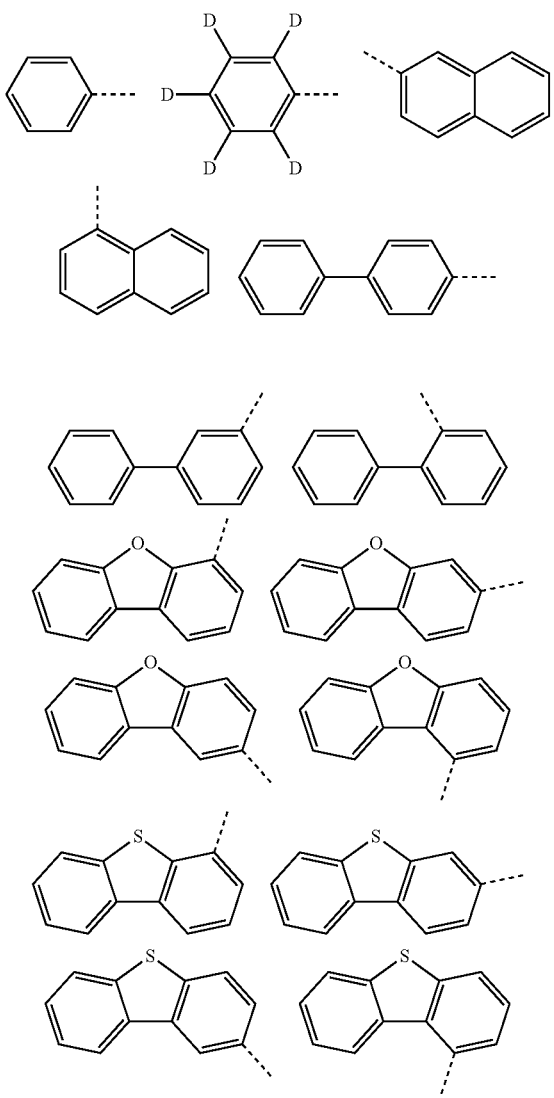

In the above structures, the dotted line is a bonding position.

According to one embodiment of the present specification, $Ar_1$ and $Ar_2$ are the same as or different from each other, and each independently any one selected from the group consisting of the following structures.

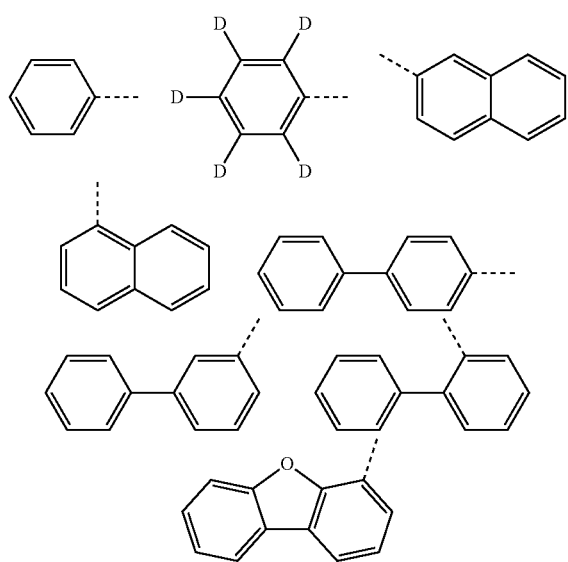

In the above structures, the dotted line is a bonding position.

According to one embodiment of the present specification, $Ar_1$ and $Ar_2$ may be each independently any one selected from the group consisting of the following structures.

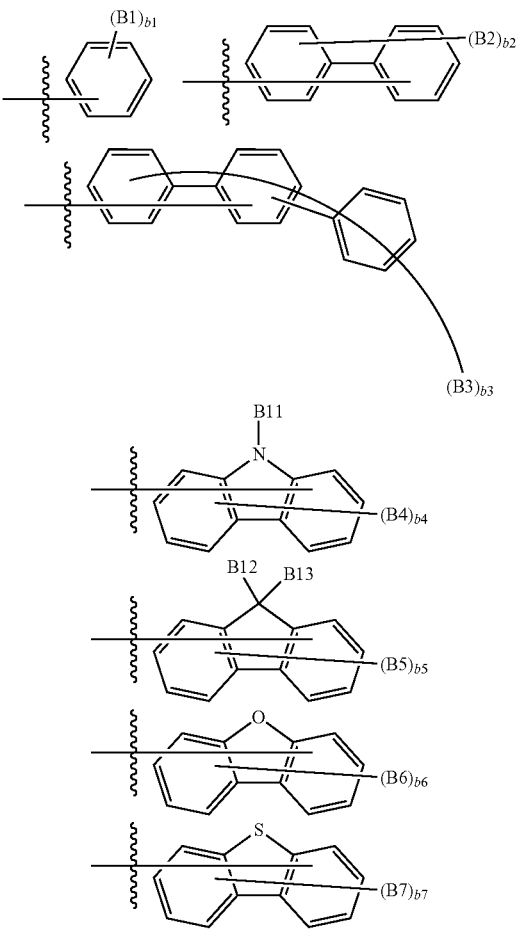

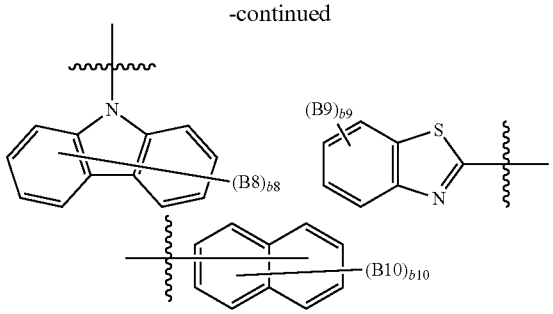

In the above structures,

B1 to B13 are the same as or different from each other, and each independently hydrogen; deuterium; a halogen group; a cyano group; a substituted or unsubstituted alkyl group; or a substituted or unsubstituted aryl group, b1 is an integer of 0 to 5,
b2 is an integer of 0 to 9,
b3 is an integer of 0 to 13,
b4 to b7 are each an integer of 0 to 7,
b8 is an integer of 0 to 8,
b9 is an integer of 0 to 4,
b10 is an integer of 0 to 7, and
when b1 to b10 are 2 or greater, the two or more groups in parentheses are the same as or different from each other.

According to one embodiment of the present specification, B1 to B10 are hydrogen.

According to one embodiment of the present specification, B11 to B13 are the same as or different from each other, and each independently a substituted or unsubstituted alkyl group; or a substituted or unsubstituted aryl group.

According to one embodiment of the present specification, B11 to B13 are the same as or different from each other, and each independently a substituted or unsubstituted alkyl group having 1 to 60 carbon atoms; or a substituted or unsubstituted aryl group having 6 to 60 carbon atoms.

According to one embodiment of the present specification, B11 to B13 are the same as or different from each other, and each independently a substituted or unsubstituted alkyl group having 1 to 30 carbon atoms; or a substituted or unsubstituted aryl group having 6 to 30 carbon atoms.

According to one embodiment of the present specification, B11 is a substituted or unsubstituted aryl group having 6 to 15 carbon atoms.

According to one embodiment of the present specification, B11 is a substituted or unsubstituted phenyl group.

According to one embodiment of the present specification, B11 is a phenyl group.

According to one embodiment of the present specification, B12 and B13 are the same as or different from each other, and each independently a substituted or unsubstituted alkyl group having 1 to 15 carbon atoms.

According to one embodiment of the present specification, B12 and B13 are a methyl group.

According to one embodiment of the present specification, b1 to b10 are 0 or 1.

According to one embodiment of the present specification, b1 to b10 are 0.

According to one embodiment of the present specification, at least two of Z1 to Z3 are N, and the rest is CR.

According to one embodiment of the present specification, Z1 to Z3 are N.

According to one embodiment of the present specification, L is a substituted or unsubstituted arylene group; or a substituted or unsubstituted divalent heterocyclic group.

According to one embodiment of the present specification, L is a substituted or unsubstituted arylene group having 6 to 60 carbon atoms; or a substituted or unsubstituted divalent heterocyclic group having 2 to 60 carbon atoms.

According to one embodiment of the present specification, L is a substituted or unsubstituted arylene group having 6 to 30 carbon atoms; or a substituted or unsubstituted divalent heterocyclic group having 2 to 30 carbon atoms.

According to one embodiment of the present specification, L is an aryl group unsubstituted or substituted with deuterium or an alkyl group; or a heterocyclic group unsubstituted or substituted with deuterium or an alkyl group.

According to one embodiment of the present specification, L is an aryl group having 6 to 30 carbon atoms unsubstituted or substituted with deuterium or an alkyl group having 1 to 20 carbon atoms; or a heterocyclic group having 2 to 30 carbon atoms unsubstituted or substituted with deuterium or an alkyl group having 1 to 20 carbon atoms.

According to one embodiment of the present specification, L is a substituted or unsubstituted phenylene group; a substituted or unsubstituted naphthylene group; a substituted or unsubstituted biphenylene group; a substituted or unsubstituted divalent carbazole group; a substituted or unsubstituted divalent fluorene group; a substituted or unsubstituted divalent dibenzofuran group; or a substituted or unsubstituted divalent dibenzothiophene group.

According to one embodiment of the present specification, L is a substituted or unsubstituted phenylene group; a substituted or unsubstituted naphthylene group; a substituted or unsubstituted biphenylene group; a substituted or unsubstituted divalent fluorene group; a substituted or unsubstituted divalent dibenzofuran group; or a substituted or unsubstituted divalent dibenzothiophene group.

According to one embodiment of the present specification, L is a phenylene group unsubstituted or substituted with deuterium or an alkyl group having 1 to 20 carbon atoms; a naphthylene group unsubstituted or substituted with deuterium or an alkyl group having 1 to 20 carbon atoms; a biphenylene group unsubstituted or substituted with deuterium or an alkyl group having 1 to 20 carbon atoms; a divalent fluorene group unsubstituted or substituted with deuterium or an alkyl group having 1 to 20 carbon atoms; a divalent dibenzofuran group unsubstituted or substituted with deuterium or an alkyl group having 1 to 20 carbon atoms; or a divalent dibenzothiophene group unsubstituted or substituted with deuterium or an alkyl group having 1 to 20 carbon atoms.

According to one embodiment of the present specification, L is a phenylene group unsubstituted or substituted with deuterium or a methyl group; a naphthylene group unsubstituted or substituted with deuterium or a methyl group; a biphenylene group unsubstituted or substituted with deuterium or a methyl group; a divalent fluorene group unsubstituted or substituted with deuterium or a methyl group; a divalent dibenzofuran group unsubstituted or substituted with deuterium or a methyl group; or a divalent dibenzothiophene group unsubstituted or substituted with deuterium or a methyl group.

According to one embodiment of the present specification, L is a phenylene group unsubstituted or substituted with deuterium; a naphthylene group; a biphenylene group; a divalent dimethylfluorene group; a divalent dibenzofuran group; or a divalent dibenzothiophene group.

According to one embodiment of the present specification, L is a phenylene group; a naphthylene group; a biphenylene group; a divalent dimethylfluorene group; a divalent dibenzofuran group; or a divalent dibenzothiophene group.

According to one embodiment of the present specification, L is any one selected from the group consisting of the following structures.

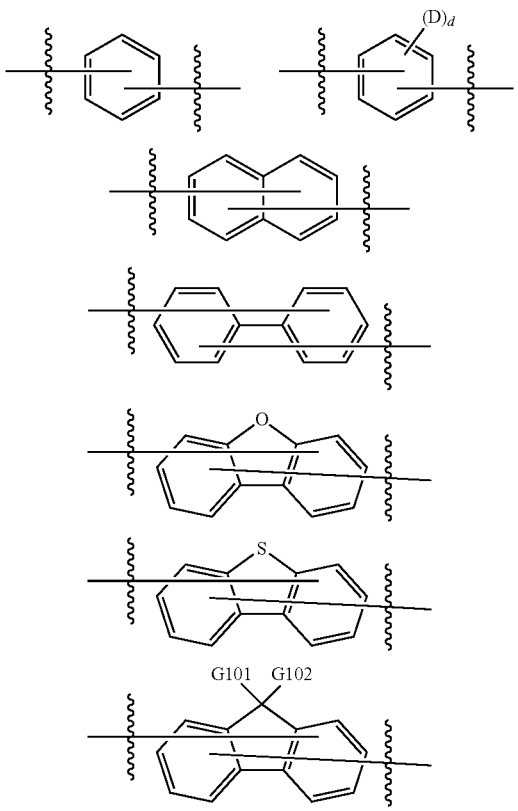

In the above structures, – is a bonding position, D is deuterium, G101 and G102 are a substituted or unsubstituted alkyl group, and d is an integer of 1 to 4.

According to one embodiment of the present specification, G101 and G102 are a substituted or unsubstituted alkyl group.

According to one embodiment of the present specification, G101 and G102 are an alkyl group having 1 to 10 carbon atoms.

According to one embodiment of the present specification, G101 and G102 are a methyl group.

According to one embodiment of the present specification, d is 4.

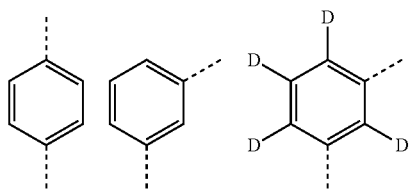

-continued

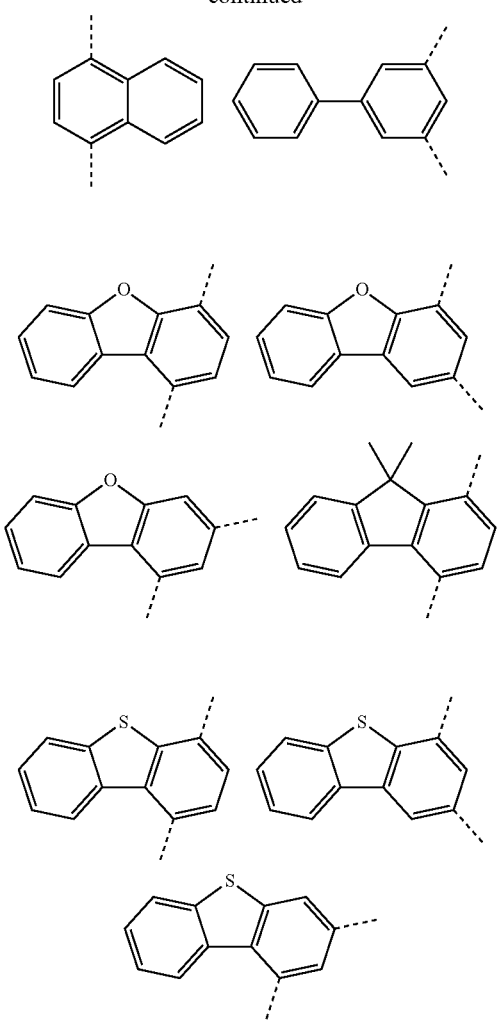

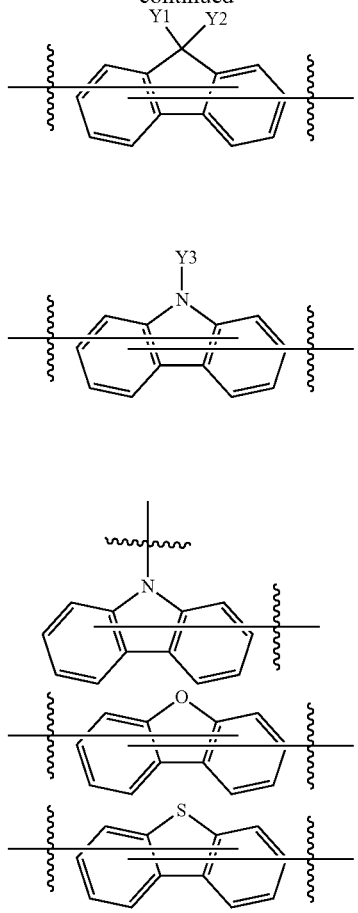

In the above structures, the dotted line is a bonding position.

According to one embodiment of the present specification, L may be any one selected from the group consisting of the following structures.

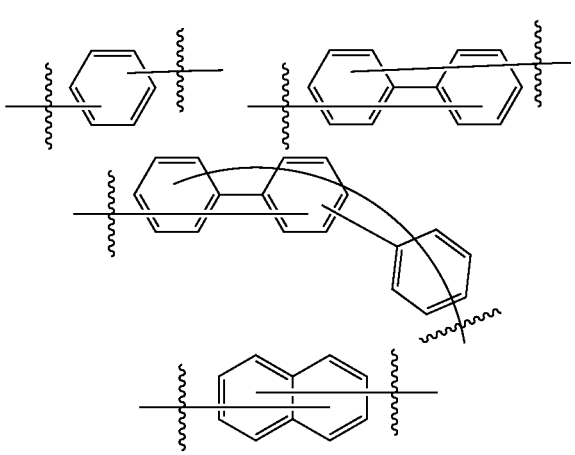

In the above structures,

Y1 to Y3 are the same as or different from each other, and each independently hydrogen; deuterium; a halogen group; a cyano group; a substituted or unsubstituted alkyl group; or a substituted or unsubstituted aryl group.

According to one embodiment of the present specification, Y1 to Y3 are the same as or different from each other, and each independently hydrogen; a substituted or unsubstituted alkyl group; or a substituted or unsubstituted aryl group.

According to one embodiment of the present specification, Y1 to Y3 are the same as or different from each other, and each independently a substituted or unsubstituted alkyl group; or a substituted or unsubstituted aryl group.

According to one embodiment of the present specification, Y1 to Y2 are the same as or different from each other, and each independently a substituted or unsubstituted alkyl group.

According to one embodiment of the present specification, Y1 and Y2 are a methyl group.

According to one embodiment of the present specification, Y3 is a substituted or unsubstituted aryl group.

According to one embodiment of the present specification, Y3 is a phenyl group.

According to one embodiment of the present specification, the compound of Chemical Formula 1 may be represented by the following Chemical Formula 6 or 7.

[Chemical Formula 6]

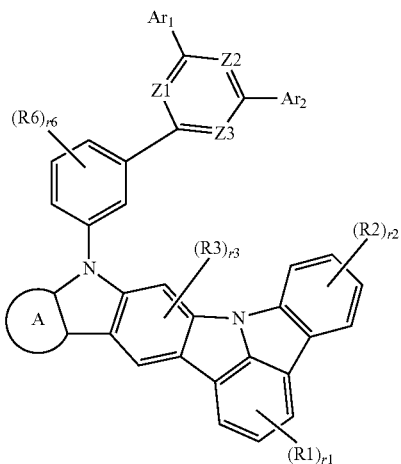

[Chemical Formula 7]

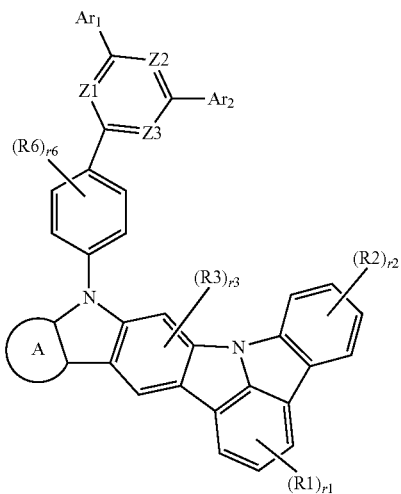

In Chemical Formula 6 and 7, $Ar_1, Ar_2$, Z1 to Z3, A, R1 to R3 and r1 to r3 have the same definitions as in Chemical Formula 1, R6 is hydrogen; deuterium; a halogen group; a cyano group; a substituted or unsubstituted alkyl group; a substituted or unsubstituted cycloalkyl group; a substituted or unsubstituted aryl group; or a substituted or unsubstituted heteroaryl group, or bonds to adjacent groups to form a substituted or unsubstituted hydrocarbon ring, or to form a substituted or unsubstituted heteroring, r6 is an integer of 0 to 4, and when r6 is 2 or greater, the groups of R6 are the same as or different from each other.

In the present specification, the "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

The hydrocarbon ring may be aromatic, aliphatic, or a fused ring of aromatic and aliphatic, and may be selected from among the examples of the cycloalkyl group or the aryl group except for those that are divalent.

In the present specification, the descriptions on the aryl group may be applied to the aromatic hydrocarbon ring except for those that are divalent.

In the present specification, the descriptions on the cycloalkyl group may be applied to the aliphatic hydrocarbon ring except for those that are divalent.

The descriptions on the heterocyclic group may be applied to the heteroring except for those that are divalent.

In one embodiment of the present specification, the group adjacent to R6 means other R6, Z1, Z3 or a hydrogen atom.

In one embodiment of the present specification, the group adjacent to R6 means other R6, Z1 or Z3.

In one embodiment of the present specification, the group adjacent to R6 means other R6.

According to one embodiment of the present specification, R6 is hydrogen; deuterium; or a substituted or unsubstituted aryl group, or bonds to adjacent groups to form a substituted or unsubstituted hydrocarbon ring, or to form a substituted or unsubstituted heteroring.

According to one embodiment of the present specification, R6 is hydrogen; deuterium; or a substituted or unsubstituted phenyl group, or bonds to adjacent groups to form a substituted or unsubstituted benzene ring; a substituted or unsubstituted indene ring; a substituted or unsubstituted benzofuran ring; or a substituted or unsubstituted benzothiophene ring.

According to one embodiment of the present specification, R6 is hydrogen; deuterium; or a substituted or unsubstituted phenyl group, or bonds to adjacent groups to form a substituted or unsubstituted naphthalene ring; a substituted or unsubstituted fluorene ring; a substituted or unsubstituted dibenzofuran ring; or a substituted or unsubstituted dibenzothiophene ring as a whole. Herein, forming a ring as a whole means forming a ring including a R6-substituted phenylene group.

According to one embodiment of the present specification, R6 is hydrogen; deuterium; or a phenyl group, or bonds to adjacent groups to form a naphthalene ring; a dimethylfluorene ring; a dibenzofuran ring; or a dibenzothiophene ring as a whole. Herein, forming a ring as a whole means forming a ring including a R6-substituted phenylene group.

According to one embodiment of the present specification, R6 is hydrogen; deuterium; or a phenyl group, or bonds to adjacent groups to form a naphthalene ring as a whole. Herein, forming a ring as a whole means forming a ring including a R6-substituted phenylene group.

According to one embodiment of the present specification, when R6 bonds to adjacent groups to form a ring, any one of the following structures may be formed.

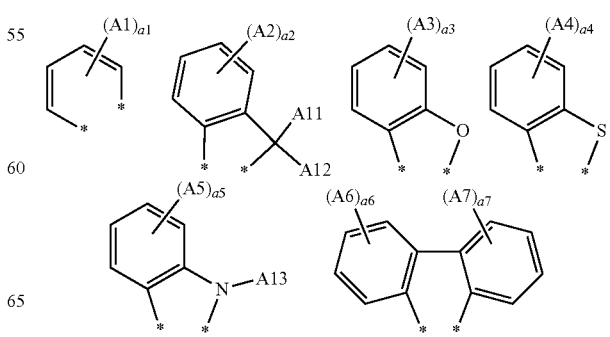

-continued

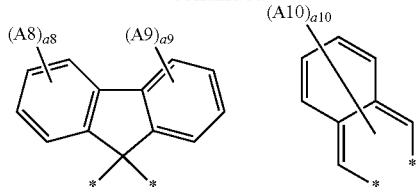

In the above structures,

A1 to A13 are the same as or different from each other, and each independently hydrogen; deuterium; a halogen group; a cyano group; a substituted or unsubstituted alkyl group; a substituted or unsubstituted cycloalkyl group; a substituted or unsubstituted aryl group; or a substituted or unsubstituted heterocyclic group, a1 to a9 are each an integer of 0 to 4, a10 is an integer of 0 to 6, and

* indicates a fused position.

According to one embodiment of the present specification, A1 is hydrogen; or a substituted or unsubstituted aryl group.

According to one embodiment of the present specification, A1 is hydrogen; or a substituted or unsubstituted aryl group having 6 to 30 carbon atoms.

According to one embodiment of the present specification, A1 is hydrogen; or a substituted or unsubstituted phenyl group.

According to one embodiment of the present specification, A1 is hydrogen or a phenyl group.

According to one embodiment of the present specification, A2 to A10 are hydrogen.

According to one embodiment of the present specification, A11 to A13 are the same as or different from each other, and each independently a substituted or unsubstituted alkyl group; or a substituted or unsubstituted aryl group.

According to one embodiment of the present specification, A11 to A13 are the same as or different from each other, and each independently a substituted or unsubstituted alkyl group having 1 to 30 carbon atoms; or a substituted or unsubstituted aryl group having 6 to 30 carbon atoms.

According to one embodiment of the present specification, A11 and A12 are a methyl group.

According to one embodiment of the present specification, Chemical Formula 1 may be represented by any one of the following Chemical Formulae 6-1 to 6-4, 7-1 and 7-2.

[Chemical Formula 6-1]

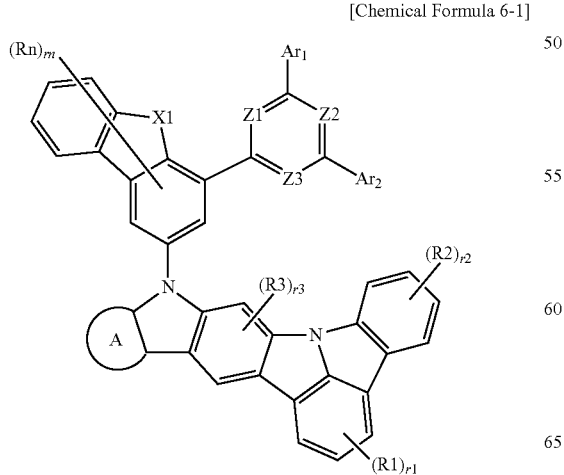

[Chemical Formula 6-2]

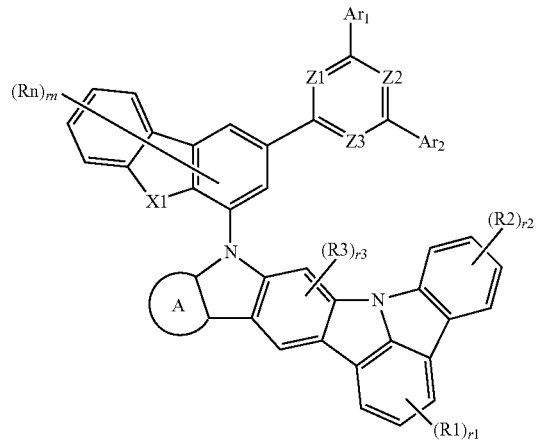

[Chemical Formula 6-3]

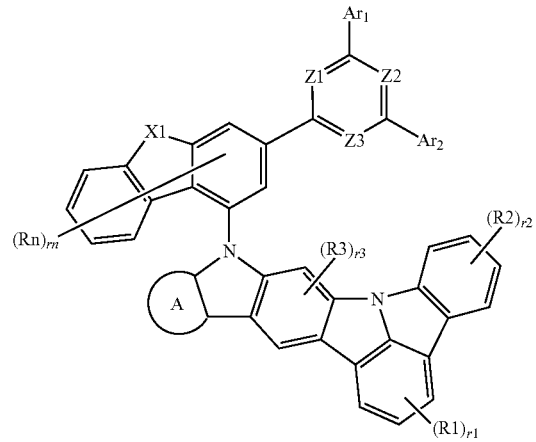

[Chemical Formula 6-4]

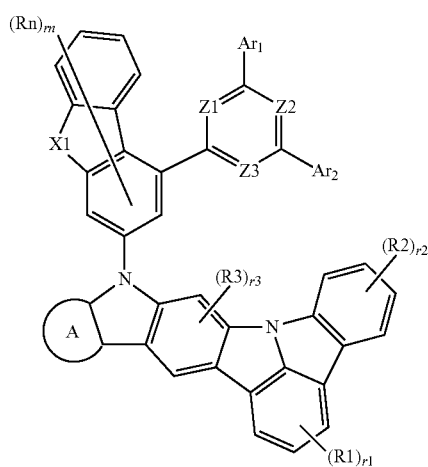

-continued

[Chemical Formula 7-1]

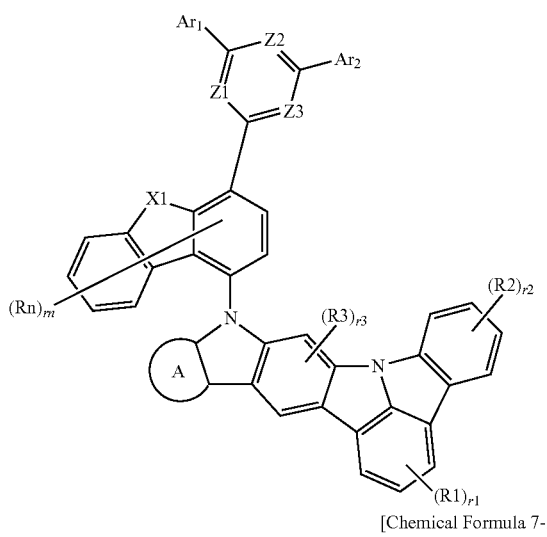

[Chemical Formula 7-2]

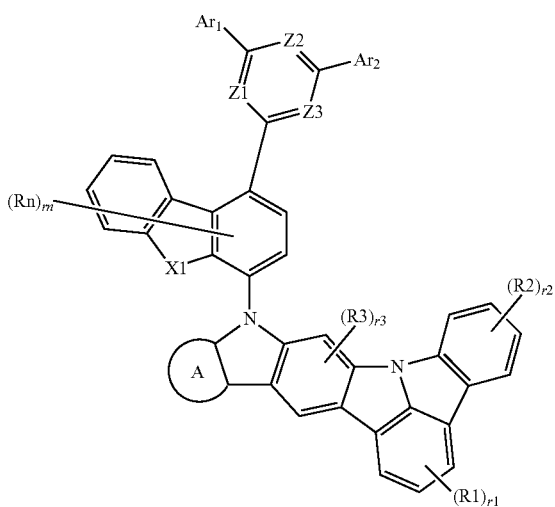

In Chemical Formulae 6-1 to 6-4, 7-1 and 7-2, $Ar_1$, $Ar_2$, Z1 to Z3, A, R1 to R3 and r1 to r3 have the same definitions as in Chemical Formula 1, X1 is CR101R102; O; or S, R101 and R102 are the same as or different from each other, and each independently a substituted or unsubstituted alkyl group, Rn is hydrogen; deuterium; a halogen group; a cyano group; a substituted or unsubstituted alkyl group; a substituted or unsubstituted cycloalkyl group; a substituted or unsubstituted aryl group; or a substituted or unsubstituted heteroaryl group, and rn is an integer of 0 to 6, and when rn is 2 or greater, each Rn is the same as or different from each other.

According to one embodiment of the present specification, X1 is CR101R102.

According to one embodiment of the present specification, X1 is O; or S.

According to one embodiment of the present specification, X1 is O.

According to one embodiment of the present specification, X1 is S.

According to one embodiment of the present specification, R101 and R102 are the same as or different from each other, and each independently a substituted or unsubstituted alkyl group having 1 to 30 carbon atoms.

According to one embodiment of the present specification, R101 and R102 are the same as or different from each other, and each independently a substituted or unsubstituted alkyl group having 1 to 15 carbon atoms.

According to one embodiment of the present specification, R101 and R102 are a methyl group.

According to one embodiment of the present specification, Rn is hydrogen; deuterium; a halogen group; a cyano group; a substituted or unsubstituted alkyl group having 1 to 30 carbon atoms; a substituted or unsubstituted cycloalkyl group having 3 to 60 carbon atoms; a substituted or unsubstituted aryl group having 6 to 60 carbon atoms; or a substituted or unsubstituted heteroaryl group having 2 to 60 carbon atoms.

According to one embodiment of the present specification, Rn is hydrogen; deuterium; a halogen group; a cyano group; a substituted or unsubstituted alkyl group having 1 to 15 carbon atoms; a substituted or unsubstituted cycloalkyl group having 3 to 30 carbon atoms; a substituted or unsubstituted aryl group having 6 to 30 carbon atoms; or a substituted or unsubstituted heteroaryl group having 2 to 30 carbon atoms.

According to one embodiment of the present specification, Rn is hydrogen; or deuterium.

According to one embodiment of the present specification, Rn is hydrogen.

According to one embodiment of the present specification, rn is 0 or 1.

According to one embodiment of the present specification, rn is 0.

According to one embodiment of the present specification, A is substituted or unsubstituted benzene, or substituted or unsubstituted naphthalene.

According to one embodiment of the present specification, A is benzene or naphthalene.

According to one embodiment of the present specification, A is substituted or unsubstituted benzene.

According to one embodiment of the present specification, A is benzene.

According to one embodiment of the present specification, A is substituted or unsubstituted naphthalene.

According to one embodiment of the present specification, A is naphthalene.

According to one embodiment of the present specification, the compound of Chemical Formula 1 may be represented by any one of the following Chemical Formulae 2 to 5.

[Chemical Formula 2]

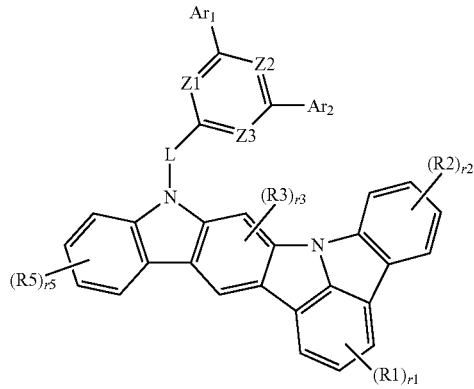

[Chemical Formula 3]

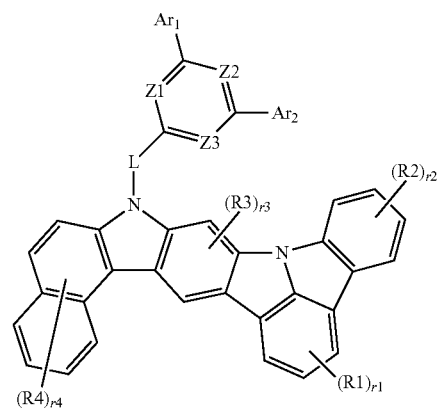

[Chemical Formula 4]

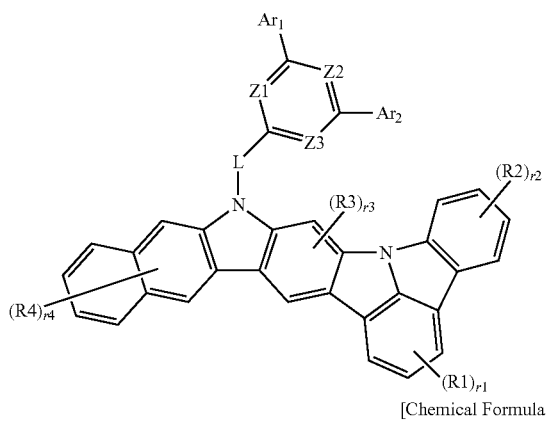

[Chemical Formula 5]

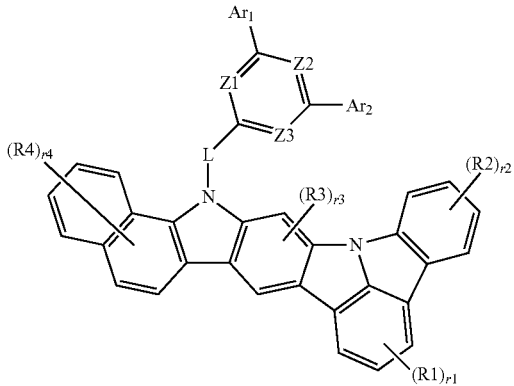

In Chemical Formulae 2 to 5, $Ar_1$, $Ar_2$, Z1 to Z3, L, R1 to R3 and r1 to r3 have the same definitions as in Chemical Formula 1, R4 and R5 are the same as or different from each other, and each independently hydrogen; deuterium; a halogen group; a cyano group; a substituted or unsubstituted alkyl group; a substituted or unsubstituted cycloalkyl group; a substituted or unsubstituted aryl group; or a substituted or unsubstituted heteroaryl group, r4 is an integer of 0 to 6, r5 is an integer of 0 to 4, and when r4 and r5 are 2 or greater, the two or more groups in parentheses are the same as or different from each other.

According to one embodiment of the present specification, R and R1 to R5 are the same as or different from each other, and each independently hydrogen; deuterium; a halogen group; a cyano group; a substituted or unsubstituted alkyl group; a substituted or unsubstituted cycloalkyl group; a substituted or unsubstituted aryl group; or a substituted or unsubstituted heteroaryl group.

According to one embodiment of the present specification, R and R1 to R5 are the same as or different from each other, and each independently hydrogen; deuterium; a halogen group; a cyano group; a substituted or unsubstituted alkyl group having 1 to 30 carbon atoms; a substituted or unsubstituted cycloalkyl group having 3 to 60 carbon atoms; a substituted or unsubstituted aryl group having 6 to 60 carbon atoms; or a substituted or unsubstituted heteroaryl group having 2 to 60 carbon atoms.

According to one embodiment of the present specification, R is hydrogen.

According to one embodiment of the present specification, R1 to R5 are the same as or different from each other, and each independently hydrogen; deuterium; a substituted or unsubstituted alkyl group; a substituted or unsubstituted aryl group; or a substituted or unsubstituted heteroaryl group.

According to one embodiment of the present specification, R1 to R5 are the same as or different from each other, and each independently hydrogen; deuterium; a substituted or unsubstituted alkyl group having 1 to 30 carbon atoms; a substituted or unsubstituted aryl group having 6 to 60 carbon atoms; or a substituted or unsubstituted heteroaryl group having 2 to 60 carbon atoms.

According to one embodiment of the present specification, R1 to R5 are the same as or different from each other, and each independently hydrogen; deuterium; a substituted or unsubstituted alkyl group having 1 to 15 carbon atoms; a substituted or unsubstituted aryl group having 6 to 30 carbon atoms; or a substituted or unsubstituted heteroaryl group having 2 to 30 carbon atoms.

According to one embodiment of the present specification, R1 to R5 are hydrogen; or deuterium.

According to one embodiment of the present specification, R1 to R5 are hydrogen.

According to one embodiment of the present specification, R1 to R3 are hydrogen; or deuterium.

According to one embodiment of the present specification, R1 to R3 are hydrogen.

According to one embodiment of the present specification, R4 and R5 are hydrogen; or deuterium.

According to one embodiment of the present specification, R4 and R5 are hydrogen.

According to one embodiment of the present specification, when r1 to r3 are 2 or greater, the groups in parentheses are the same as or different from each other.

According to one embodiment of the present specification, when r1 and r2 are 2 or greater and r3 is 2, the groups in parentheses are the same as or different from each other.

According to one embodiment of the present specification, when r1 is 2 or greater, the two or more groups of R1 are the same as or different from each other.

According to one embodiment of the present specification, when r2 is 2 or greater, the two or more groups of R2 are the same as or different from each other.

According to one embodiment of the present specification, when r4 and r5 are 2 or greater, the two or more groups in parentheses are the same as or different from each other.

According to one embodiment of the present specification, when r3 is 2, each R3 is the same as or different from each other.

According to one embodiment of the present specification, when r4 is 2 or greater, the two or more groups of R4 are the same as or different from each other.

According to one embodiment of the present specification, when r5 is 2 or greater, the two or more groups of R5 are the same as or different from each other.

According to one embodiment of the present specification, r1 to r5 are an integer of 0 or 1.

According to one embodiment of the present specification, r1 to r5 are 0.

According to one embodiment of the present specification, Chemical Formula 1 may be represented by any one of the following compounds.

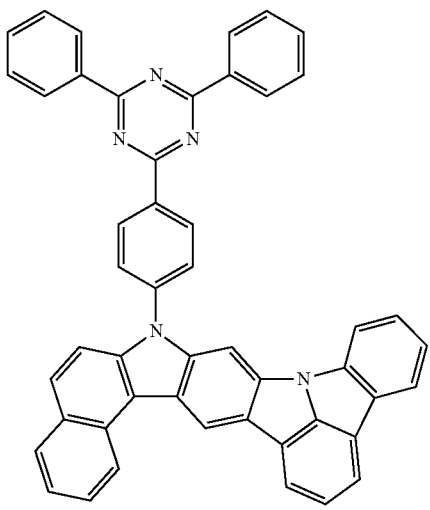

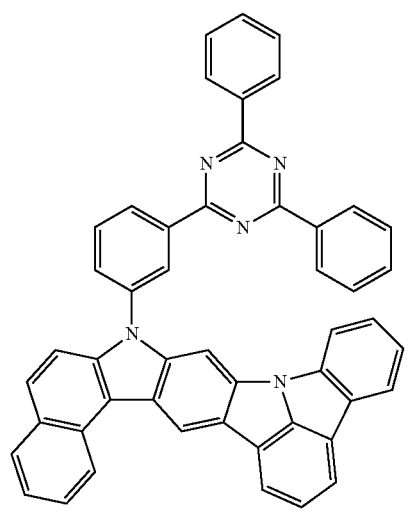

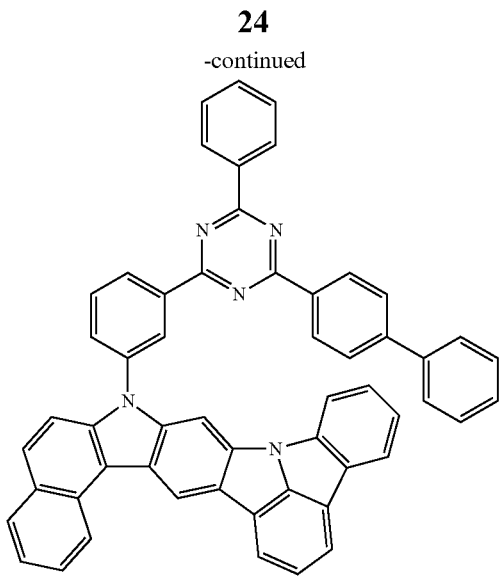

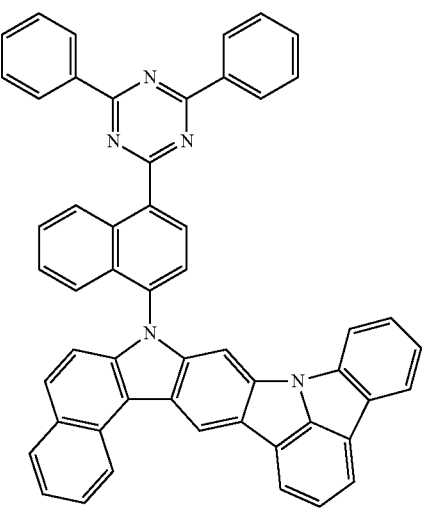

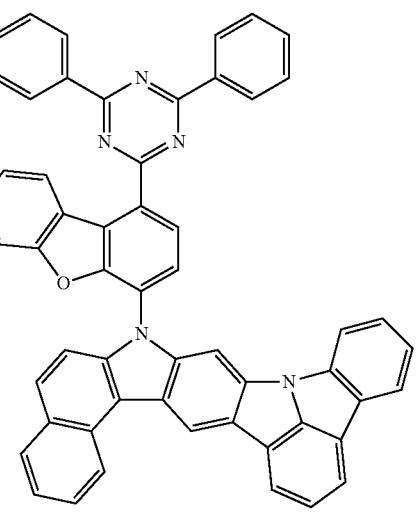

25
-continued
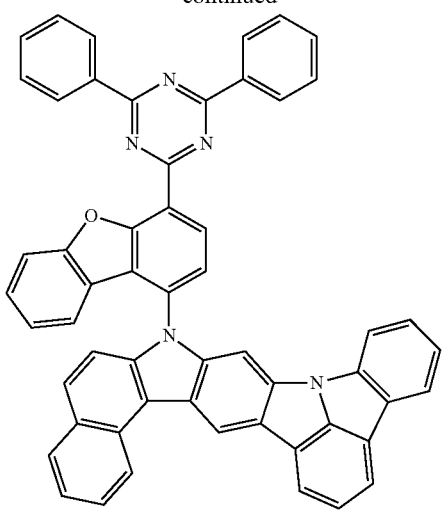
26
-continued
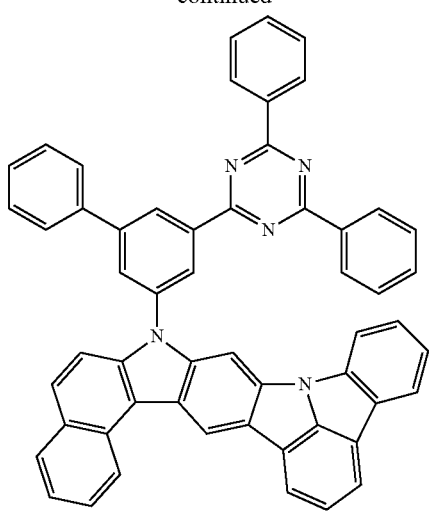
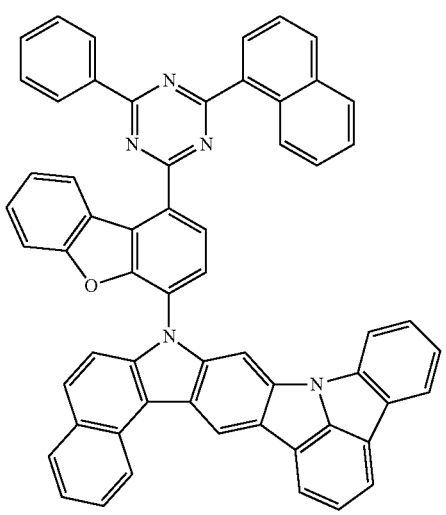
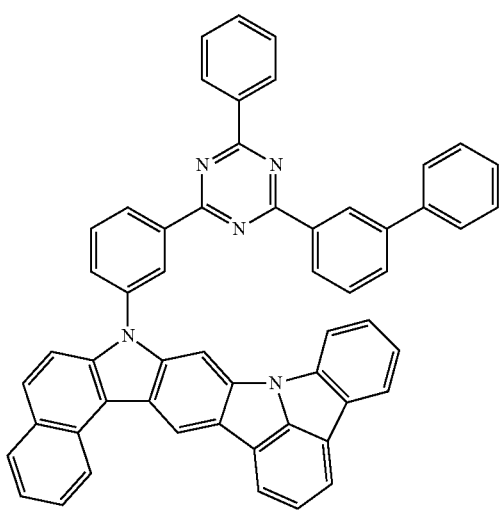
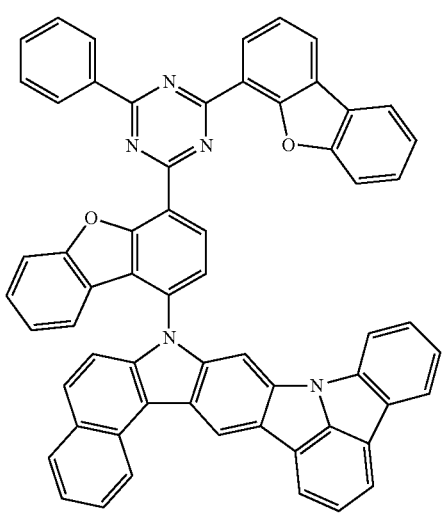
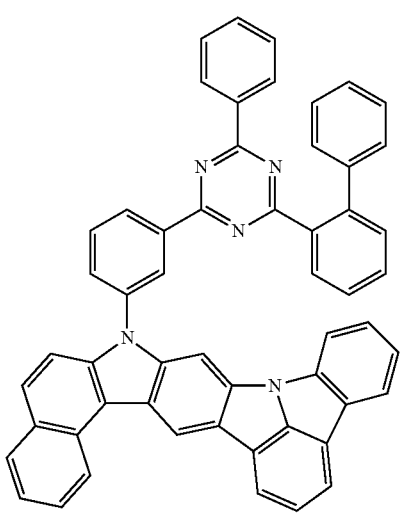

-continued
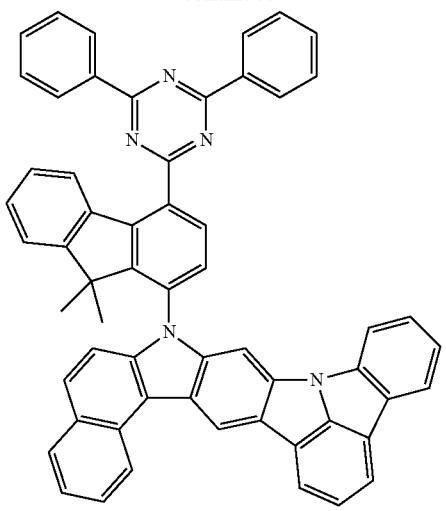
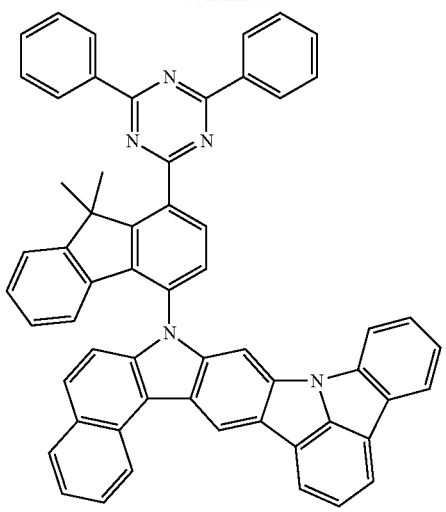
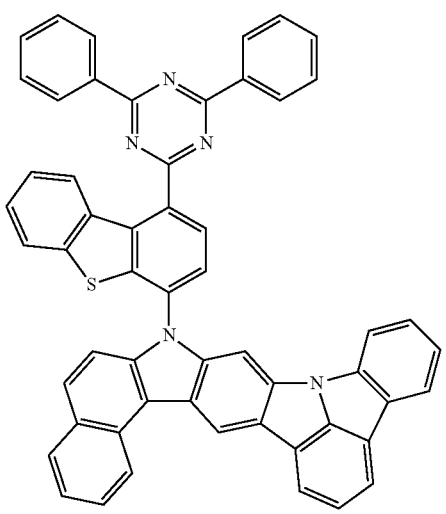
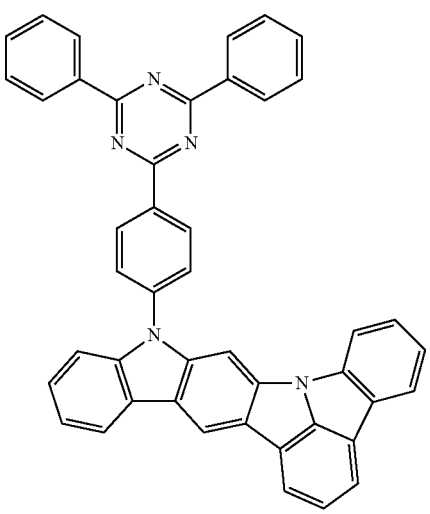
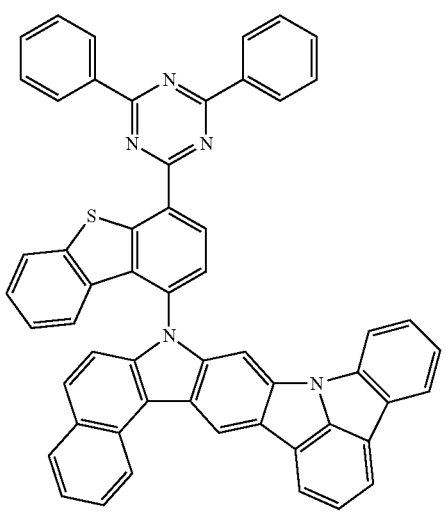
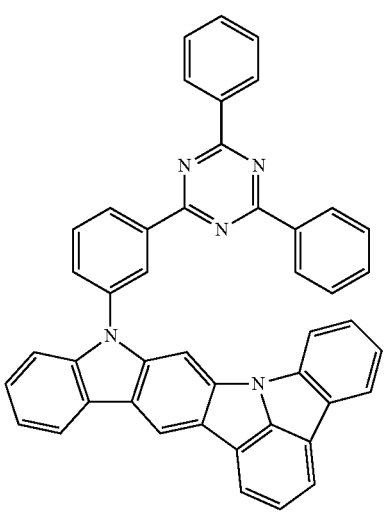

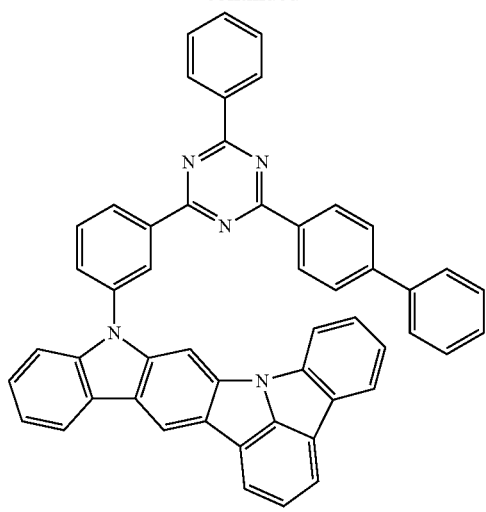
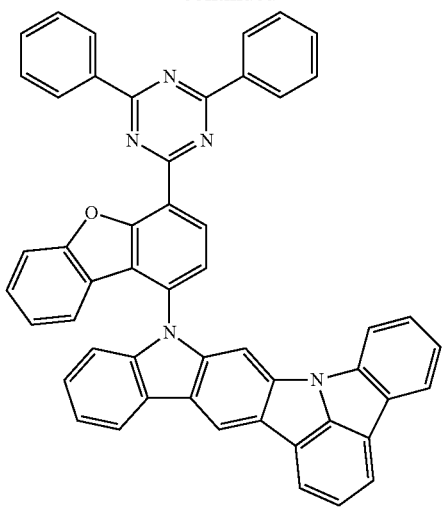
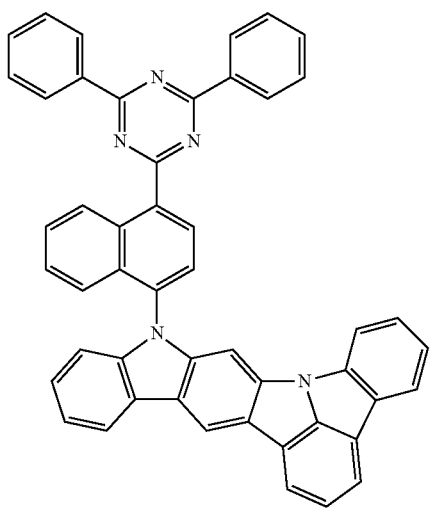
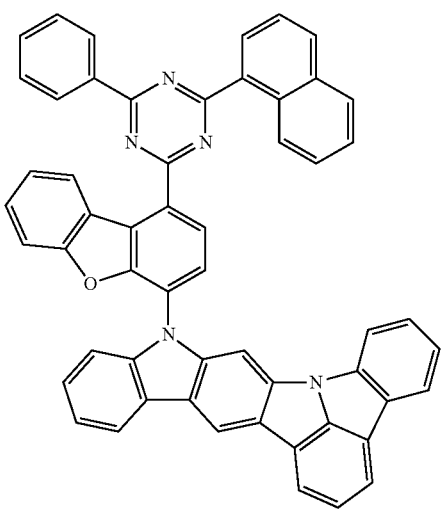
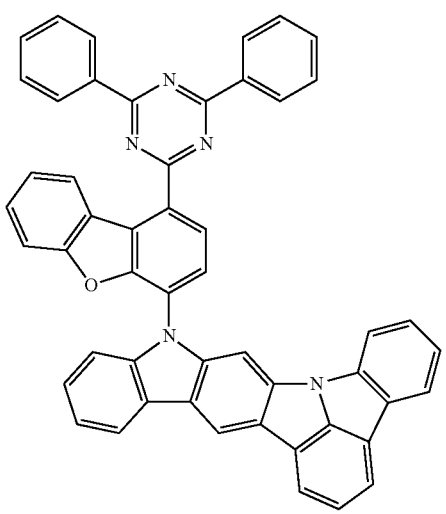
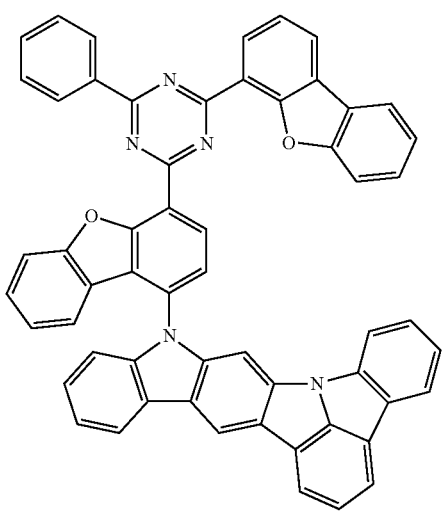

-continued
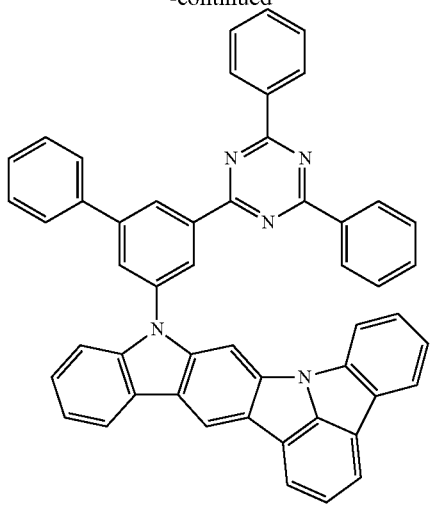
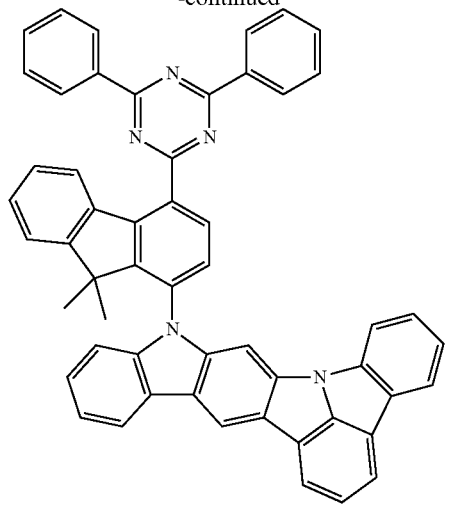
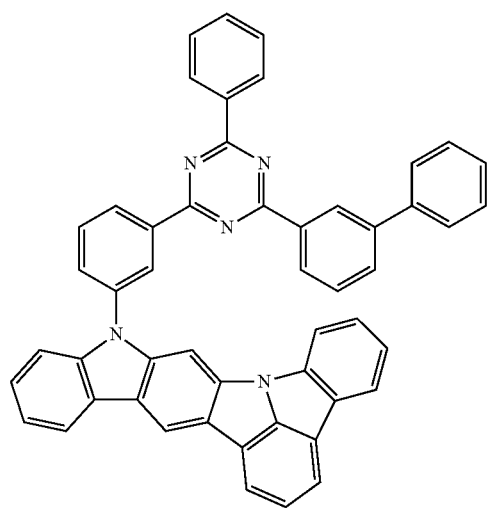
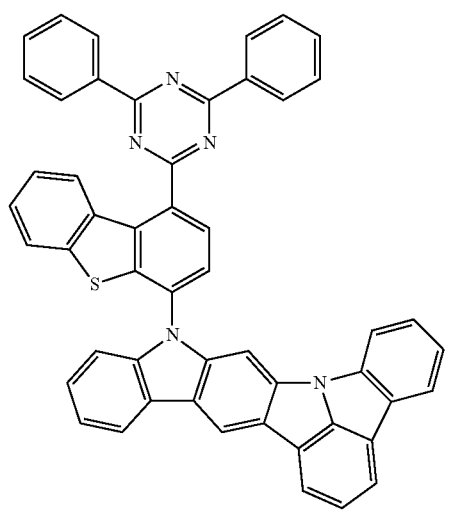
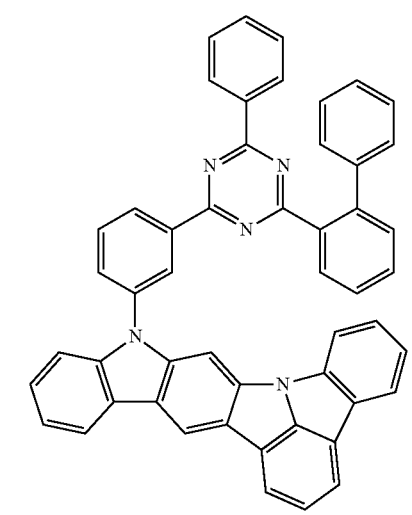
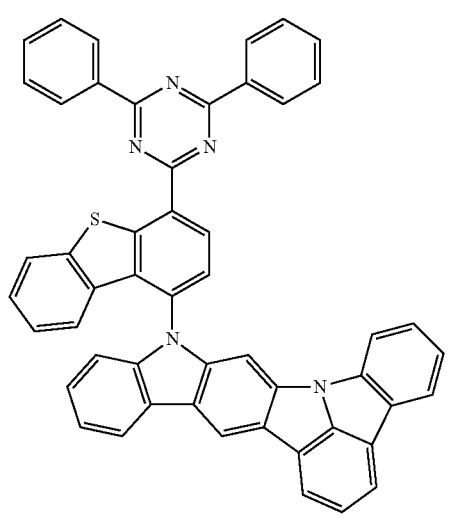

33
-continued
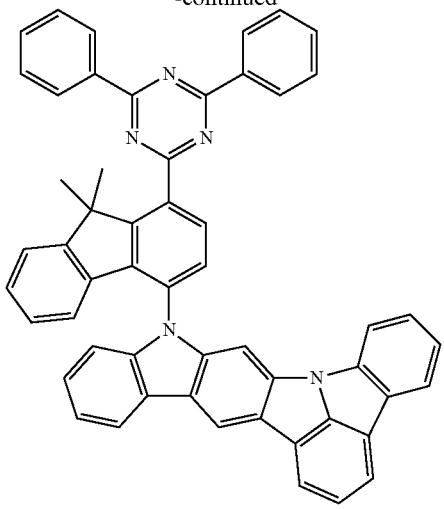
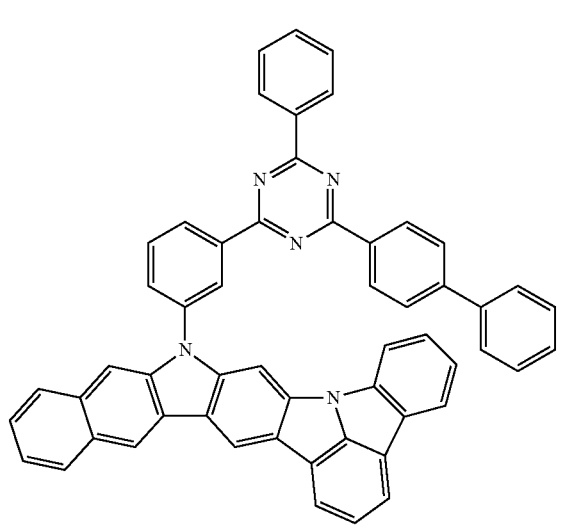
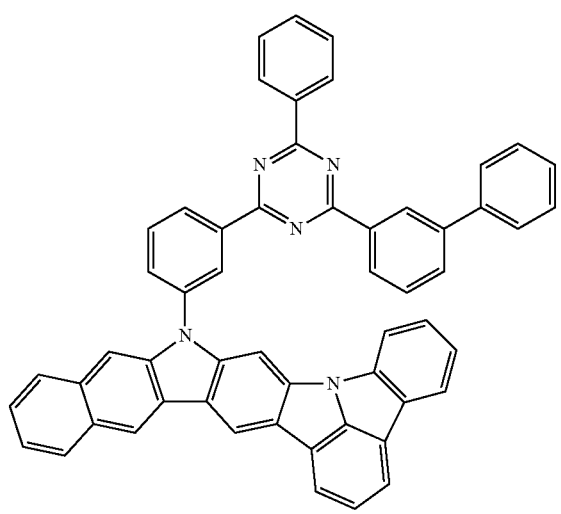
34
-continued
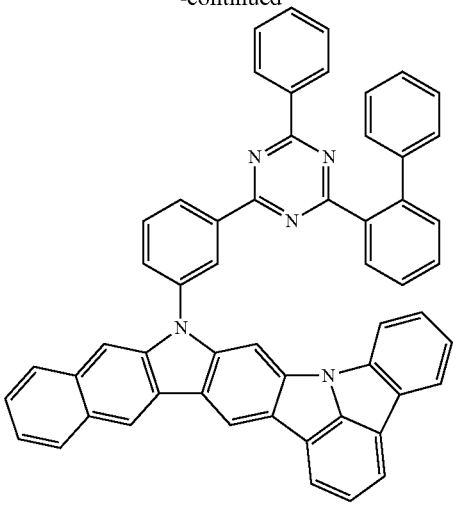
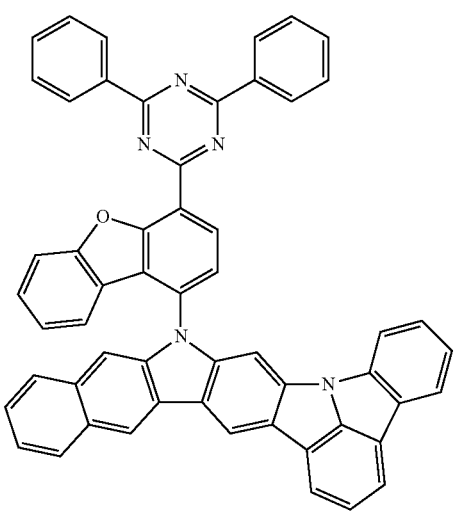
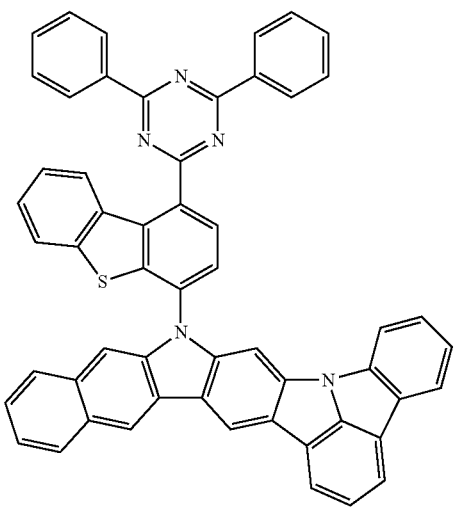

-continued
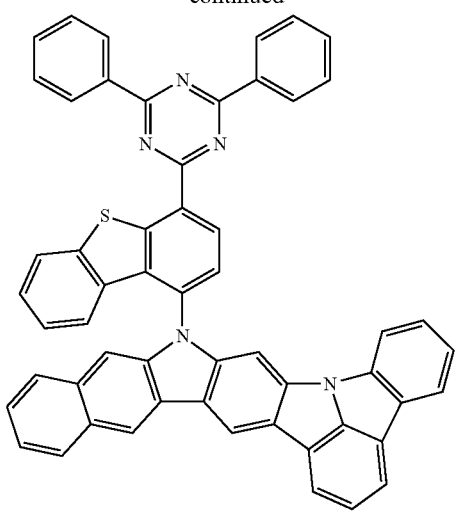 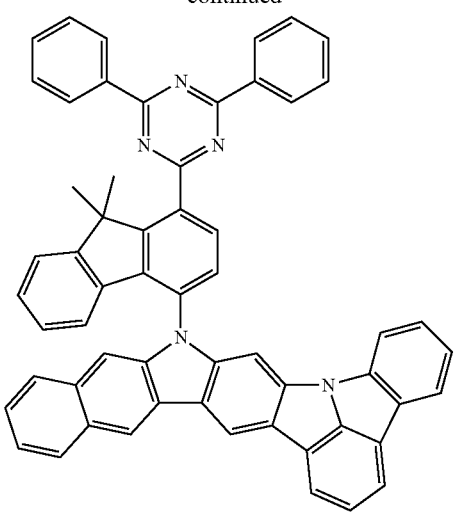
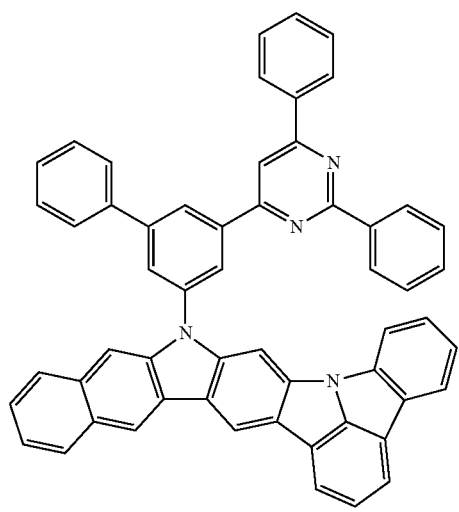 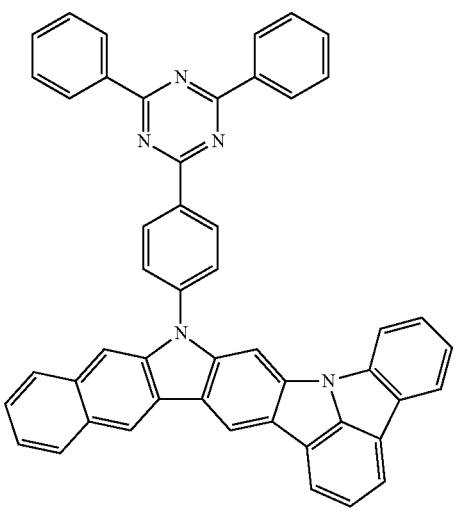
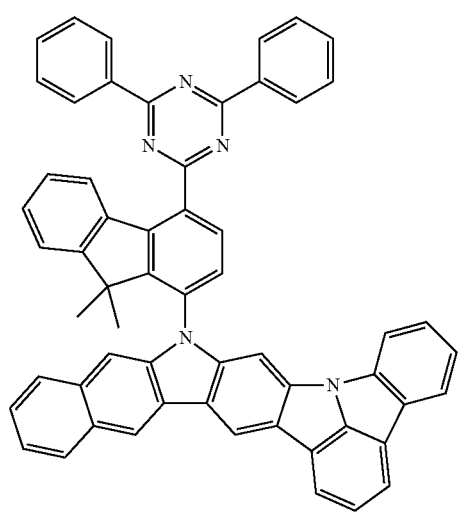 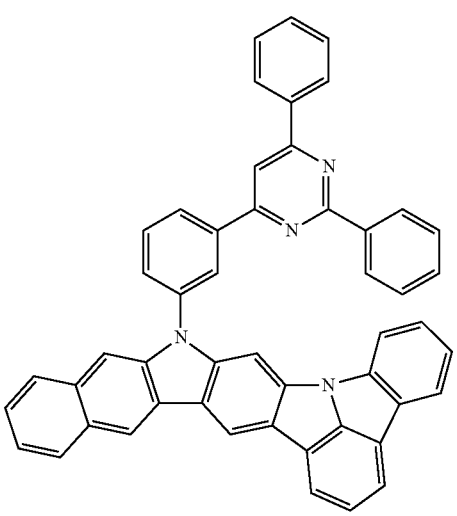

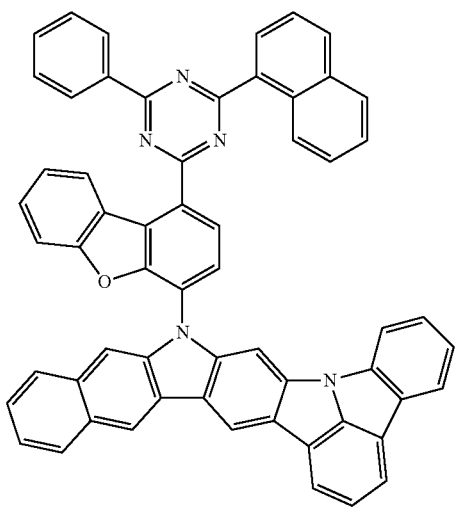
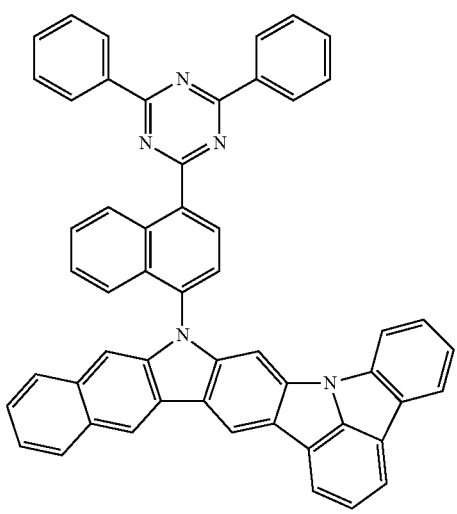
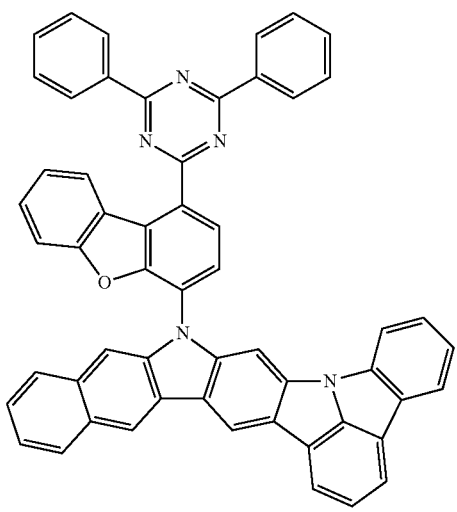
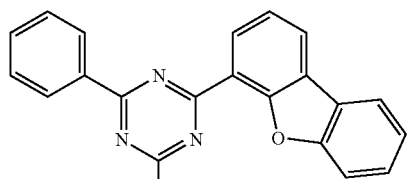
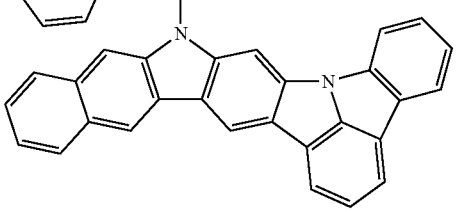
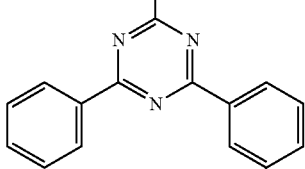
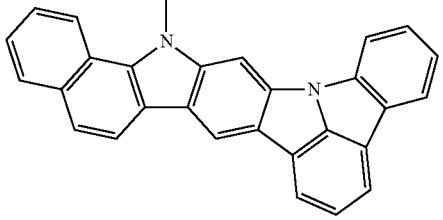
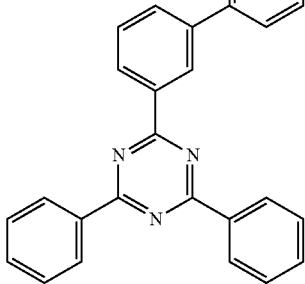
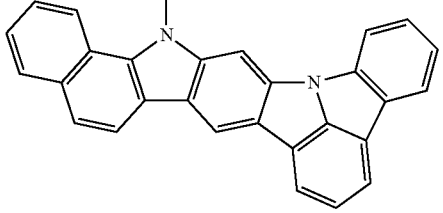

39
-continued
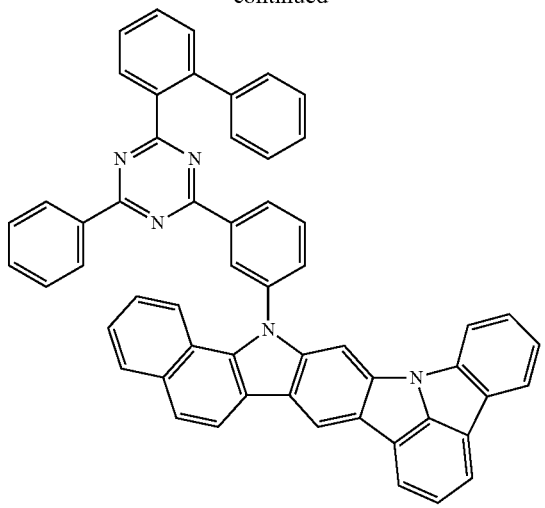
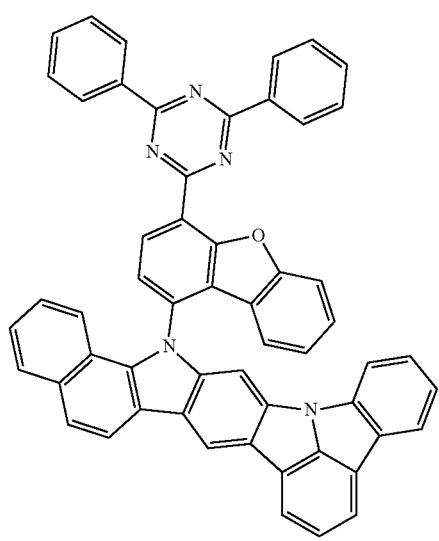
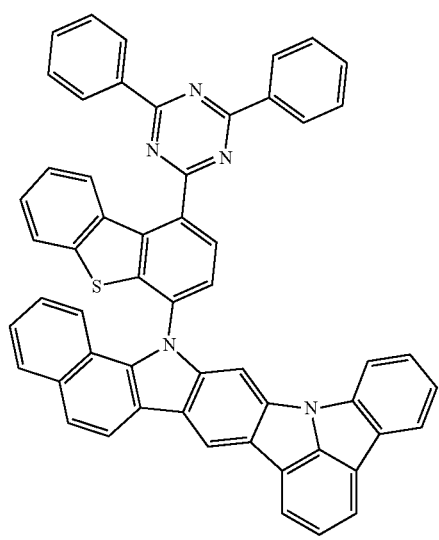
40
-continued
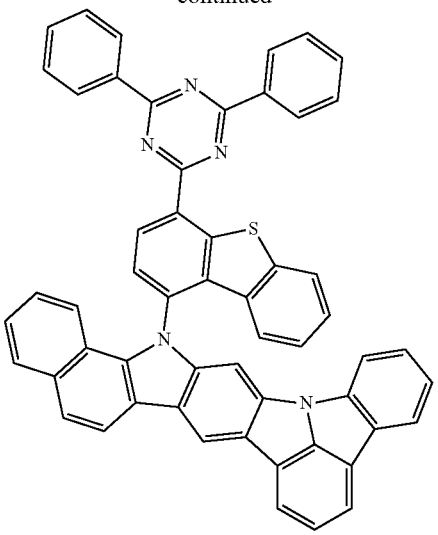
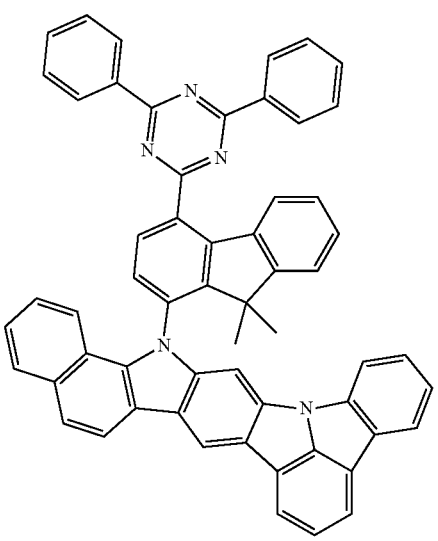

-continued
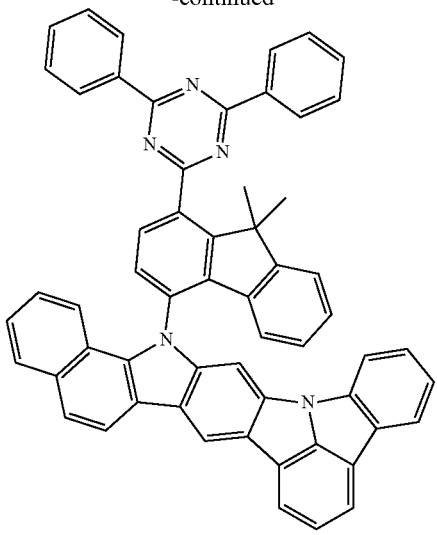
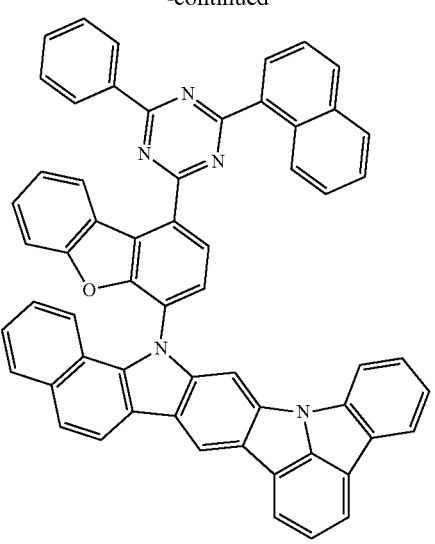
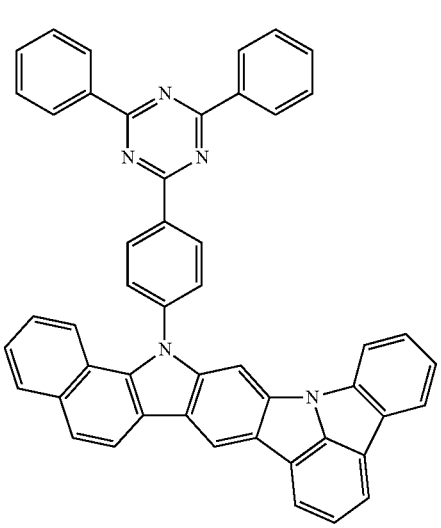
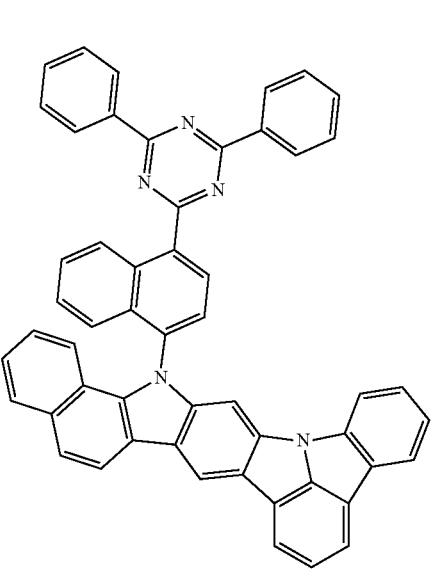
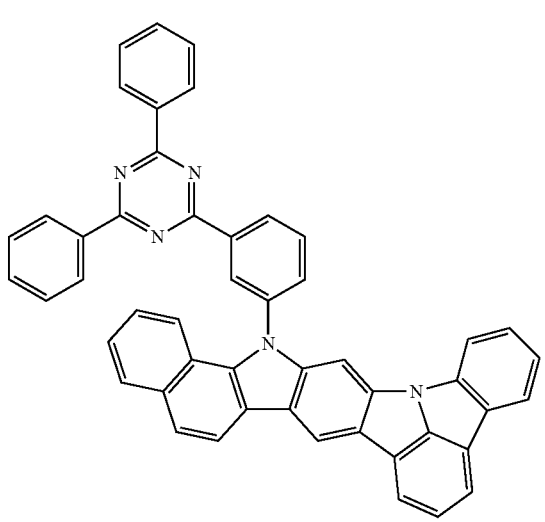
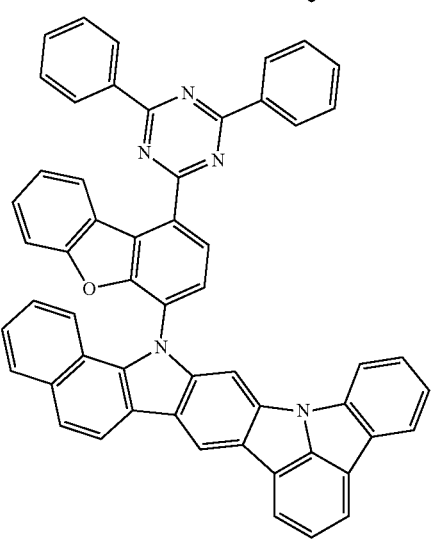

-continued
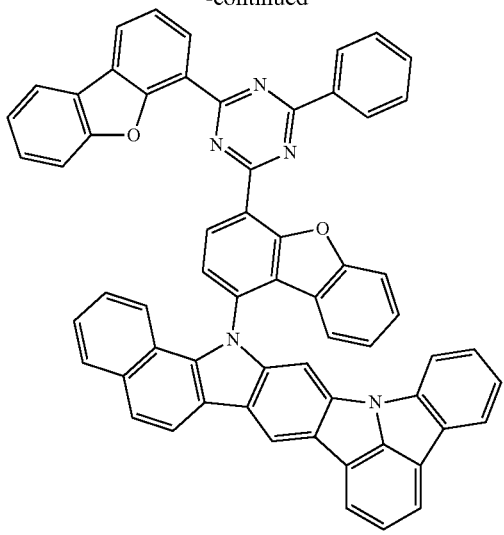
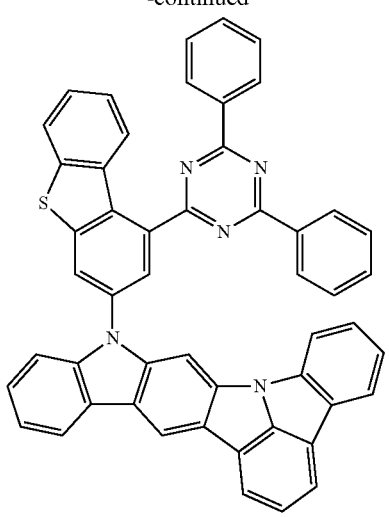
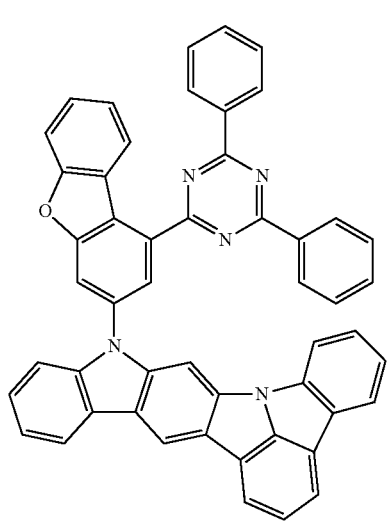
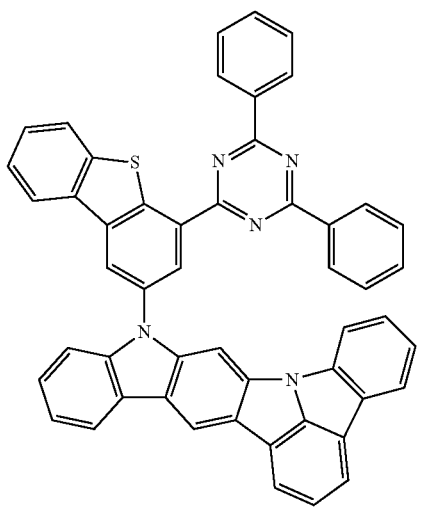
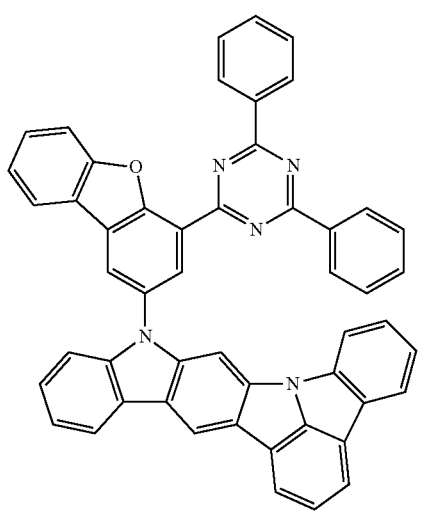
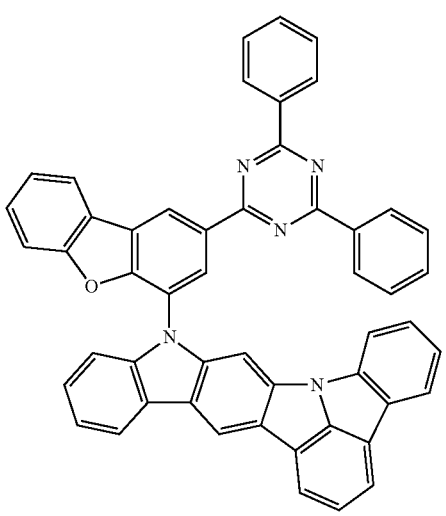

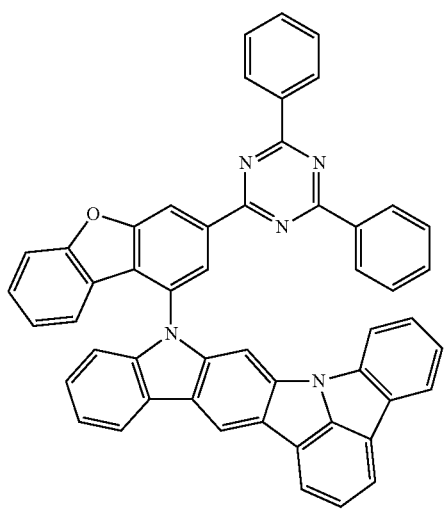
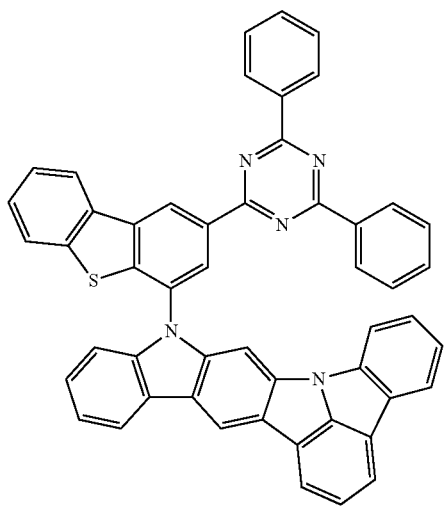
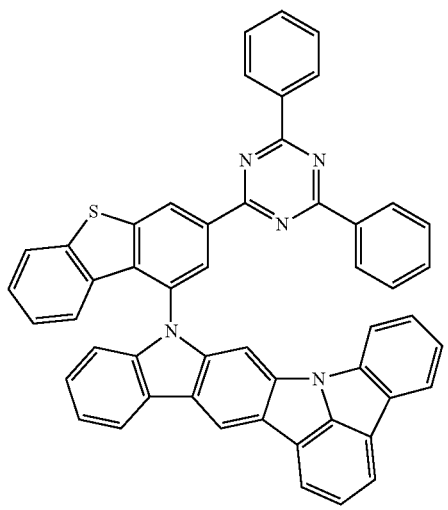
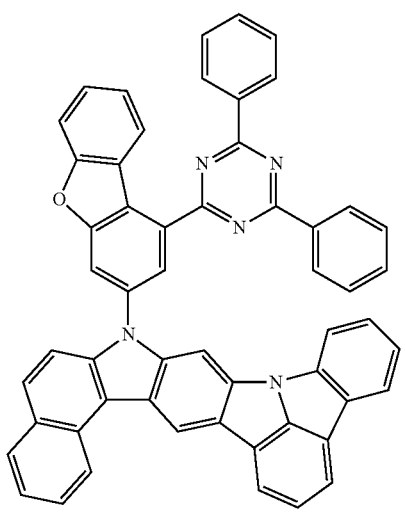
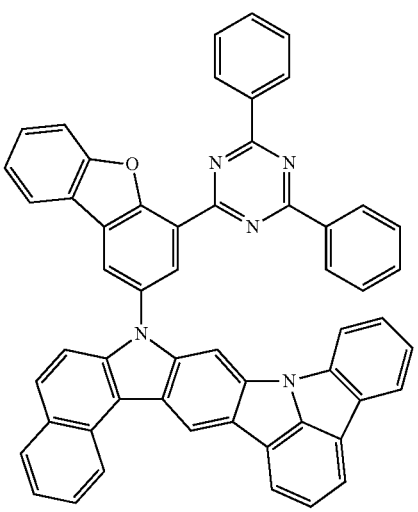
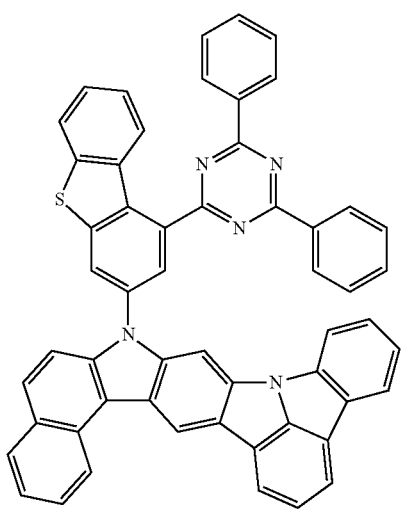

47
-continued
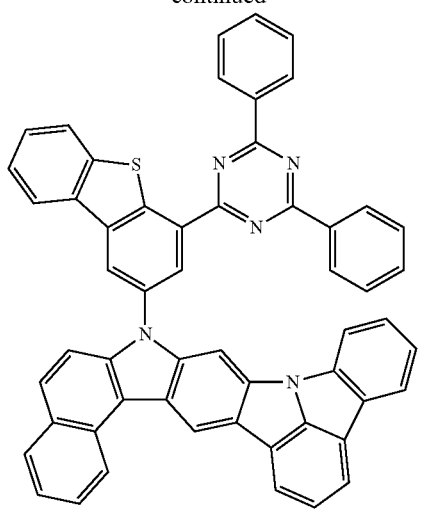
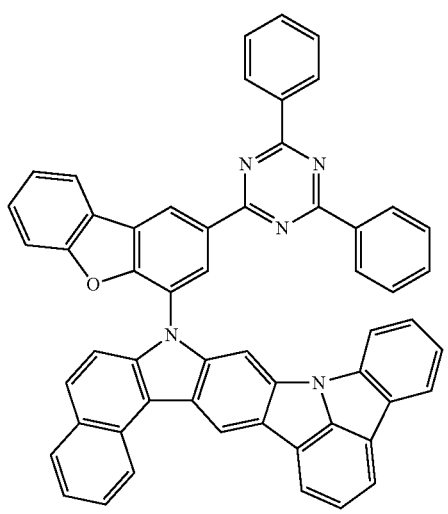
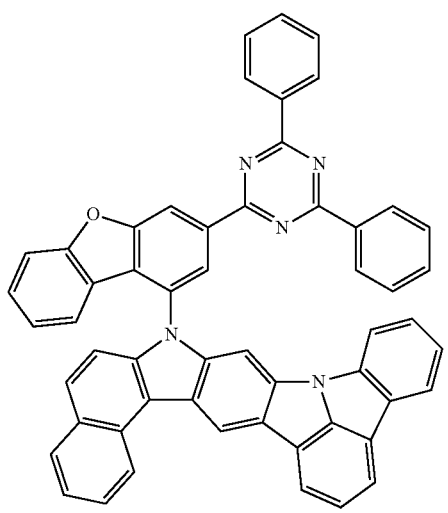
48
-continued
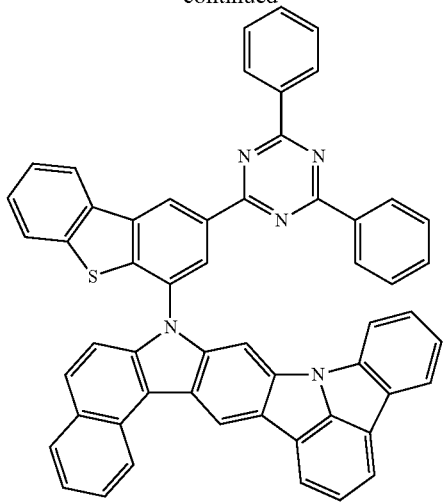
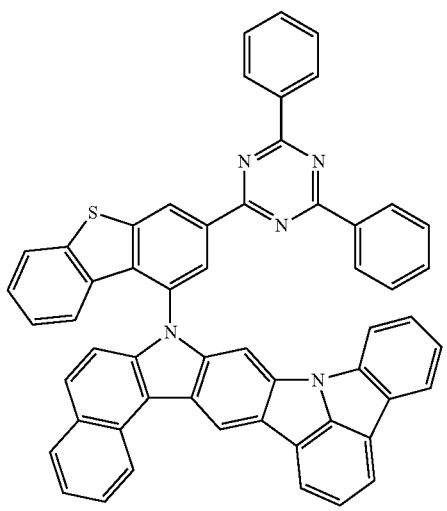
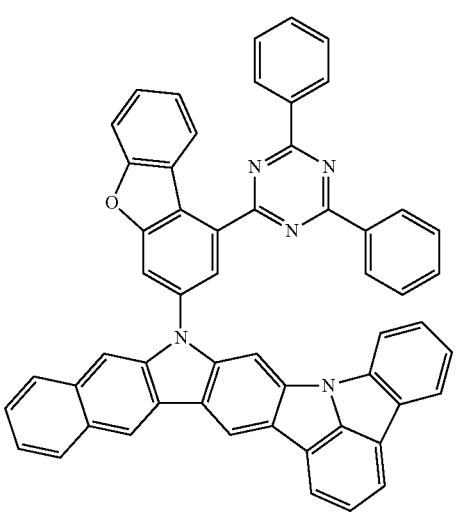

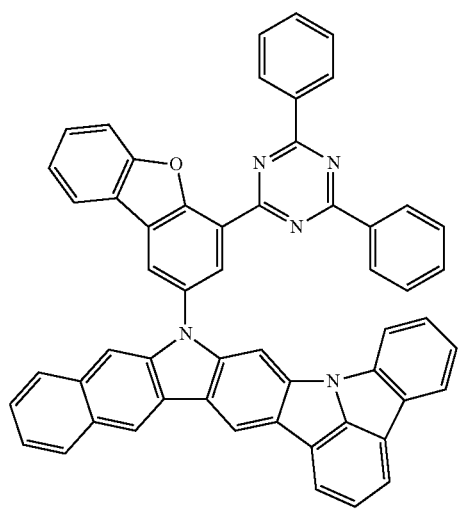
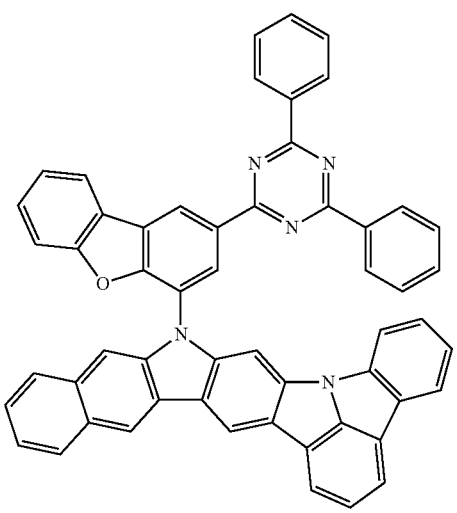
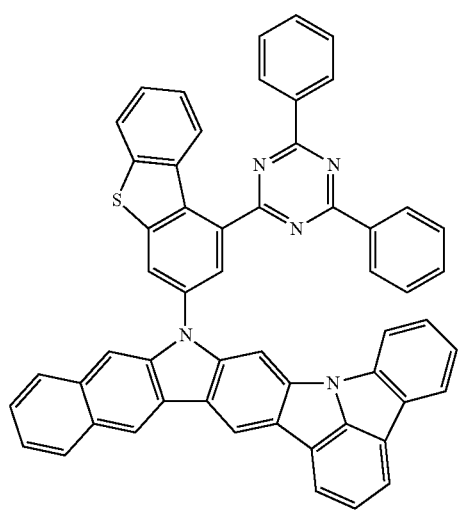
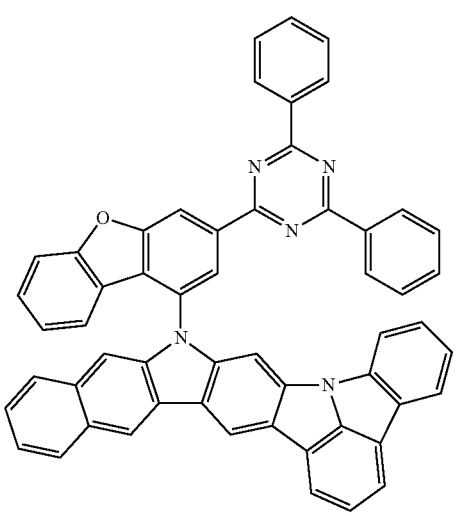
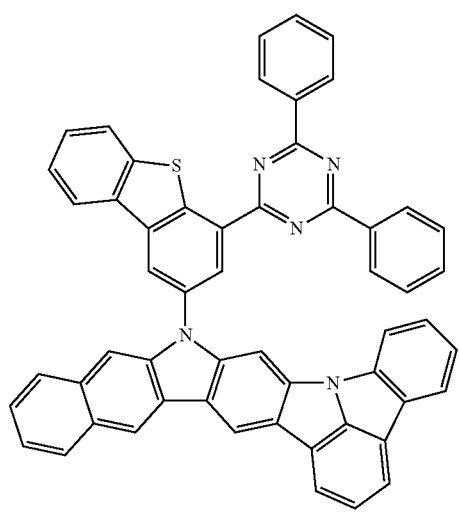
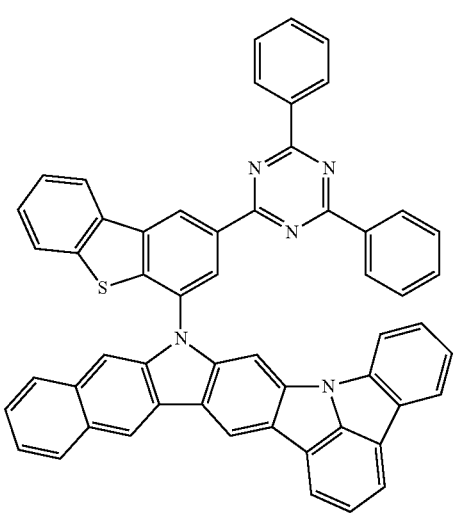

51
-continued
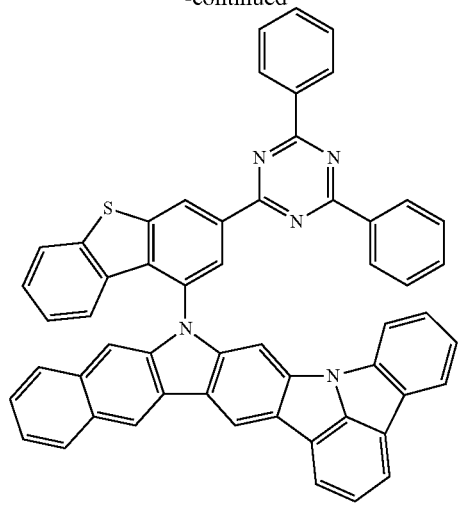
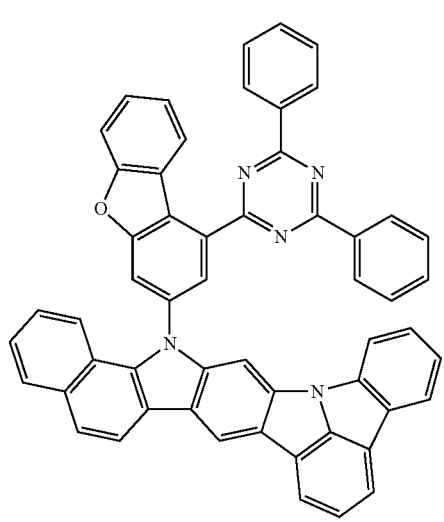
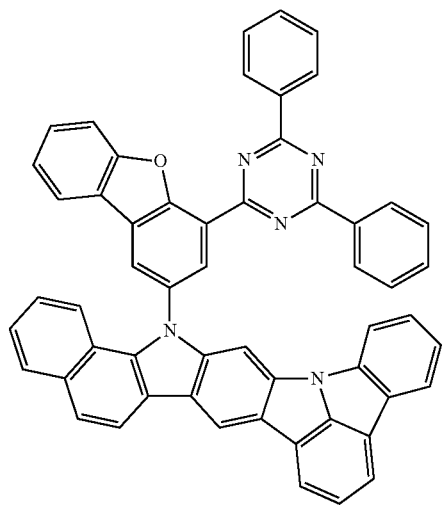
52
-continued
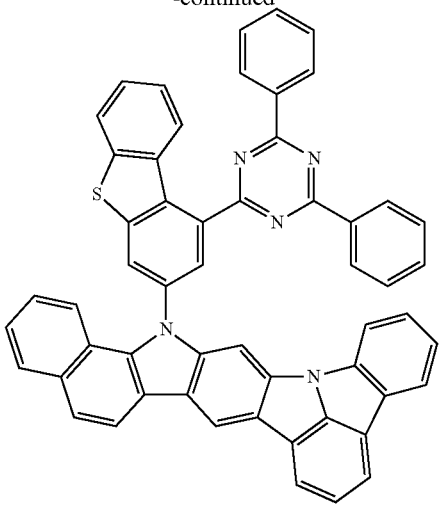
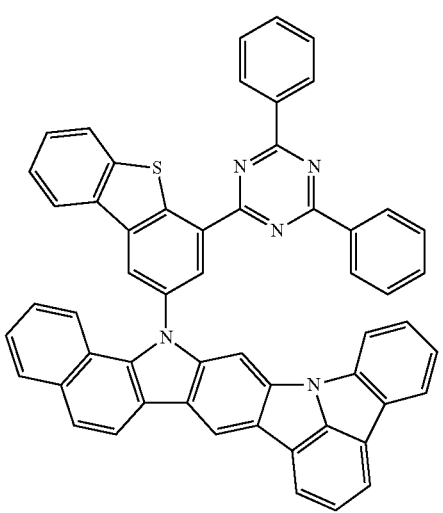
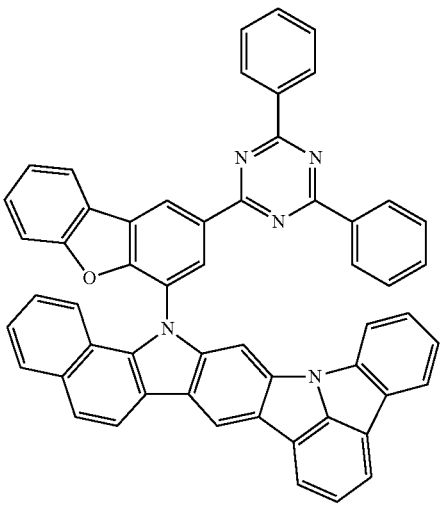

53
-continued
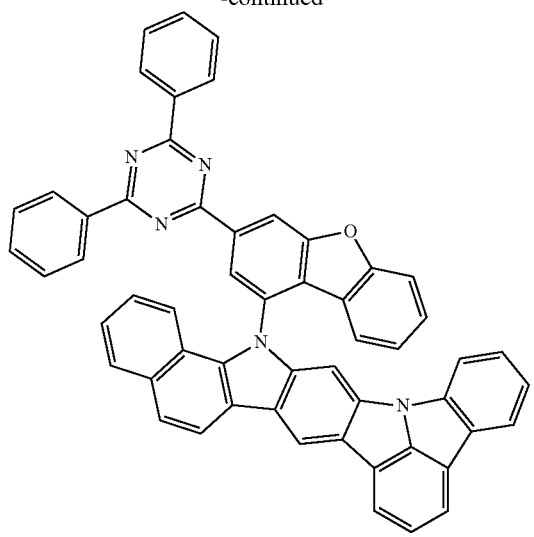
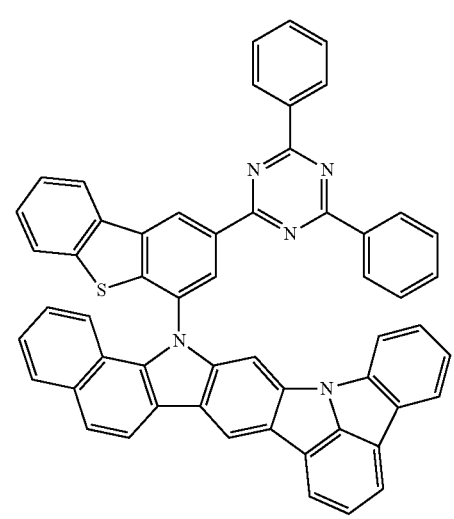
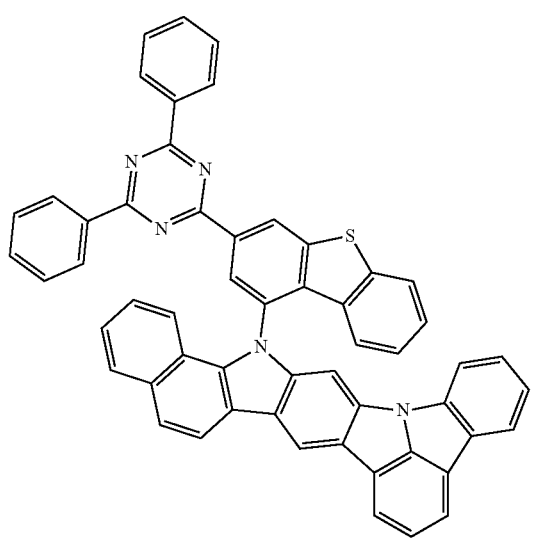
54
-continued
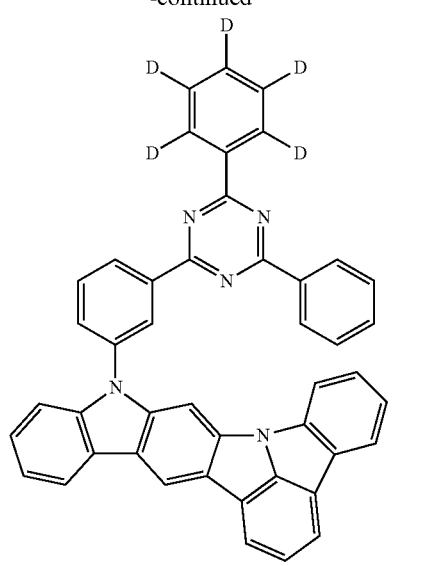
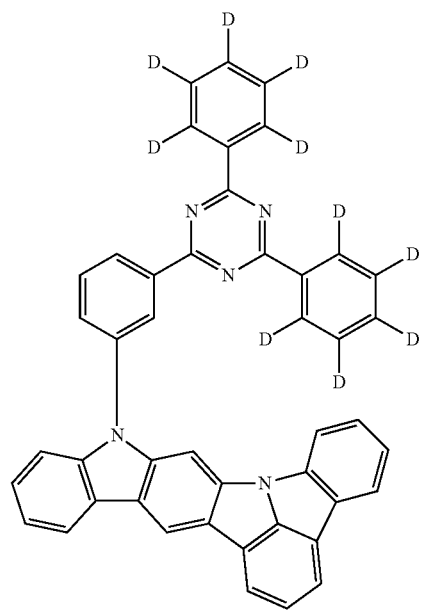
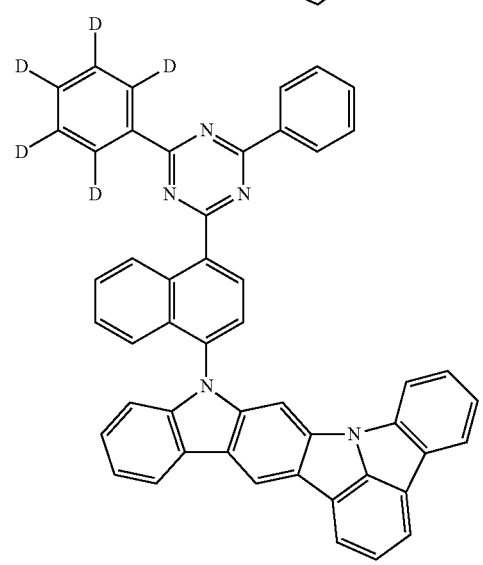

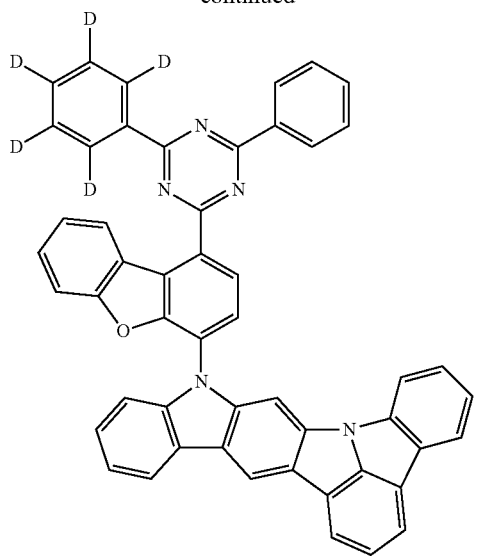
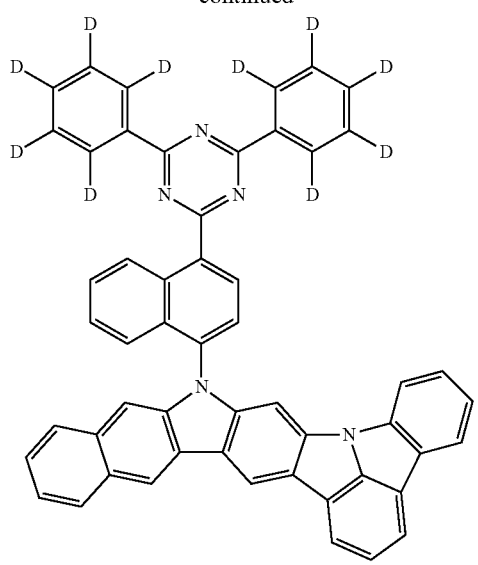
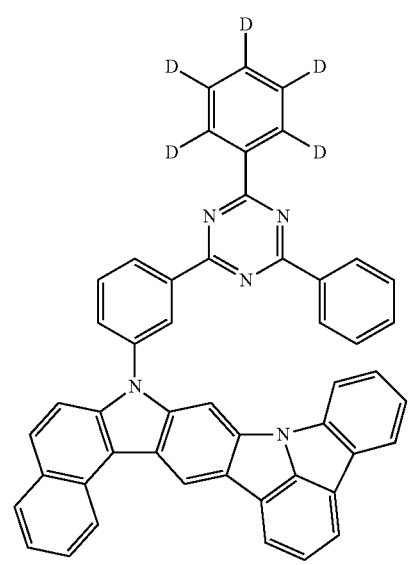
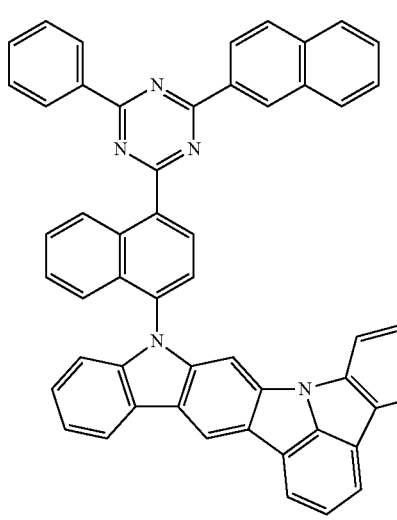
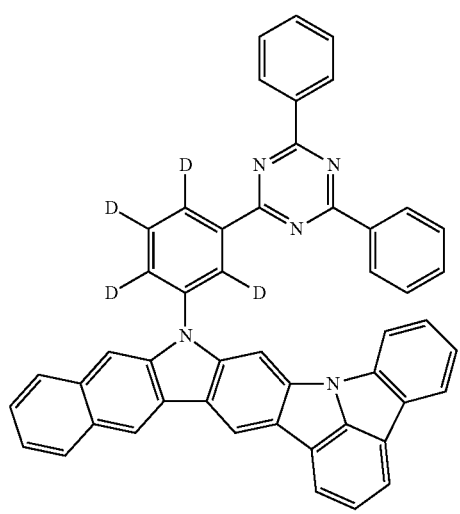
The compound represented by Chemical Formula 1 of the present specification may have its core structure prepared as in the following reaction formula. Substituents may bond using methods known in the art, and types, positions and the number of the substituents may vary depending on technologies known in the art.
<Reaction Formula>
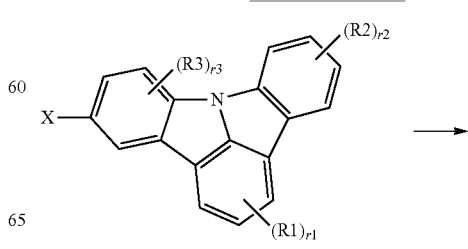

-continued

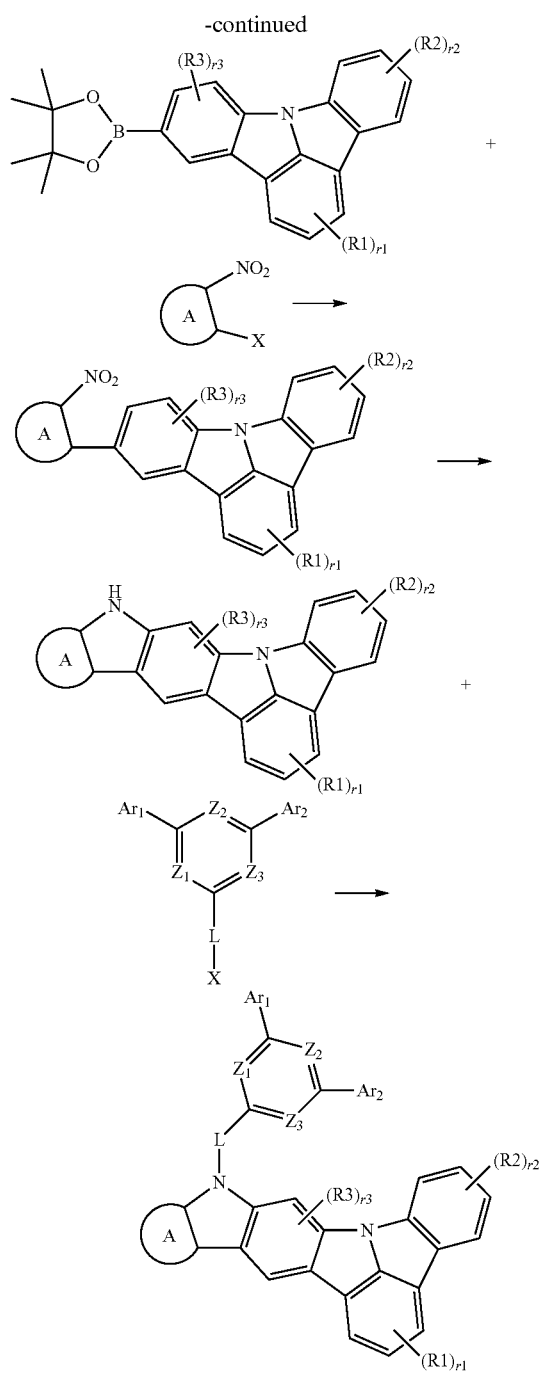

In the reaction formula,

R1 to R3, r1 to r3, A, L, Z1 to Z3 and $Ar_1$ to $Ar_2$ have the same definitions as in Chemical Formula 1, and X is each independently a halogen group.

In the present specification, compounds having various energy band gaps may be synthesized by introducing various substituents to the core structure as above. In addition, HOMO and LUMO energy levels of the compound may also be adjusted in the present specification by introducing various substituents to the core structure having a structure as above.

In addition, an organic light emitting device according to the present specification includes a first electrode; a second electrode provided to face the first electrode; and one or more organic material layers provided between the first electrode and the second electrode, wherein one or more layers of the organic material layers include the compound described above.

The organic light emitting device of the present specification may be manufactured using common organic light emitting device manufacturing methods and materials except that one or more organic material layers are formed using the compound represented by Chemical Formula 1 described above.

The organic material layer may be formed using a solution coating method as well as a vacuum deposition method when manufacturing the organic light emitting device having the organic material layer including the compound represented by Chemical Formula 1 formed therein. Herein, the solution coating method means spin coating, dip coating, inkjet printing, screen printing, a spray method, roll coating and the like, but is not limited thereto.

The organic material layer of the organic light emitting device of the present specification may be formed in a single layer structure, but may be formed in a multilayer structure in which two or more organic material layers are laminated. For example, the organic light emitting device of the present disclosure may have a structure including one or more of a hole transfer layer, a hole injection layer, an electron blocking layer, a layer carrying out hole transfer and hole injection at the same time, an electron transfer layer, an electron injection layer, a hole blocking layer, and a layer carrying out electron transfer and electron injection at the same time as the organic material layer. However, the structure of the organic light emitting device of the present specification is not limited thereto, and may include a smaller number or a larger number of organic material layers.

In the organic light emitting device of the present specification, the organic material layer includes a hole transfer layer or a hole injection layer, and the hole transfer layer or the hole injection layer may include the compound represented by Chemical Formula 1 described above.

In another organic light emitting device of the present specification, the organic material layer includes an electron transfer layer or an electron injection layer, and the electron transfer layer or the electron injection layer may include the compound represented by Chemical Formula 1 described above.

In another organic light emitting device of the present specification, the organic material layer includes a light emitting layer, and the light emitting layer may include the compound represented by Chemical Formula 1 described above.

According to another embodiment, the organic material layer includes a light emitting layer, and the light emitting layer may include the compound as a host of the light emitting layer.

In one embodiment of the present specification, the light emitting layer includes the compound represented by Chemical Formula 1 as a host of the light emitting layer, and may further include a dopant. Herein, a content of the dopant may be from 1 parts by weight to 60 parts by weight, and preferably from 1 parts by weight to 20 parts by weight based on 100 parts by weight of the host.

Herein, as the dopant, phosphorescent materials such as $(4,6-F2ppy)_2Irpic$, or fluorescent materials such as spiro-DPVBi, spiro-6P, distyrylbenzene (DSB), distyrylarylene (DSA), PFO-based polymers, PPV-based polymers, anthracene-based compounds, pyrene-based compounds and boron-based compounds may be used, however, the dopant is not limited thereto.

In one embodiment of the present specification, the first electrode is an anode, and the second electrode is a cathode.

According to another embodiment, the first electrode is a cathode, and the second electrode is an anode.

The organic light emitting device may have, for example, lamination structures as follows, however, the structure is not limited thereto.

(1) an anode/a hole transfer layer/a light emitting layer/a cathode (2) an anode/a hole injection layer/a hole transfer layer/a light emitting layer/a cathode (3) an anode/a hole transfer layer/a light emitting layer/an electron transfer layer/a cathode (4) an anode/a hole transfer layer/a light emitting layer/an electron transfer layer/an electron injection layer/a cathode (5) an anode/a hole injection layer/a hole transfer layer/a light emitting layer/an electron transfer layer/a cathode (6) an anode/a hole injection layer/a hole transfer layer/a light emitting layer/an electron transfer layer/an electron injection layer/a cathode (7) an anode/a hole transfer layer/an electron blocking layer/a light emitting layer/an electron transfer layer/a cathode (8) an anode/a hole transfer layer/an electron blocking layer/a light emitting layer/an electron transfer layer/an electron injection layer/a cathode (9) an anode/a hole injection layer/a hole transfer layer/an electron blocking layer/a light emitting layer/an electron transfer layer/a cathode

(10) an anode/a hole injection layer/a hole transfer layer/an electron blocking layer/a light emitting layer/an electron transfer layer/an electron injection layer/a cathode

(11) an anode/a hole transfer layer/a light emitting layer/a hole blocking layer/an electron transfer layer/a cathode

(12) an anode/a hole transfer layer/a light emitting layer/a hole blocking layer/an electron transfer layer/an electron injection layer/a cathode

(13) an anode/a hole injection layer/a hole transfer layer/a light emitting layer/a hole blocking layer/an electron transfer layer/a cathode

(14) an anode/a hole injection layer/a hole transfer layer/a light emitting layer/a hole blocking layer/an electron transfer layer/an electron injection layer/a cathode The organic light emitting device of the present specification may have structures as illustrated in FIG. 1 to FIG. 4, however, the structure is not limited thereto.

FIG. 1 illustrates a structure of the organic light emitting device in which an anode (2), a light emitting layer (3) and a cathode (4) are consecutively laminated on a substrate (1). In such a structure, the compound may be included in the light emitting layer (3).

FIG. 2 illustrates a structure of the organic light emitting device in which an anode (2), a hole injection layer (5), a hole transfer layer (6), a light emitting layer (7), an electron transfer layer (8) and a cathode (4) are consecutively laminated on a substrate (1). In such a structure, the compound may be included in the light emitting layer (7).

FIG. 3 illustrates a structure of the organic light emitting device in which an anode (2), a hole injection layer (5), a hole transfer layer (6), an electron blocking layer (9), a light emitting layer (7), an electron transfer and injection layer (10) and a cathode (4) are consecutively laminated on a substrate (1). In such a structure, the compound may be included in the light emitting layer (7).

FIG. 4 illustrates a structure of the organic light emitting device in which an anode (2), a hole transfer layer (6), an electron blocking layer (9), a light emitting layer (7), a hole blocking layer (11), an electron transfer and injection layer (10) and a cathode (4) are consecutively laminated on a substrate (1). In such a structure, the compound may be included in the light emitting layer (7).

For example, the organic light emitting device according to the present specification may be manufactured by forming an anode on a substrate by depositing a metal, a metal oxide having conductivity, or an alloy thereof using a physical vapor deposition (PVD) method such as sputtering or e-beam evaporation, forming an organic material layer including a hole injection layer, a hole transfer layer, a light emitting layer, an electron blocking layer, an electron transfer layer and an electron injection layer, and then depositing a material usable as a cathode thereon. In addition to such a method, the organic light emitting device may also be manufactured by consecutively depositing a cathode material, an organic material layer and an anode material on a substrate.

The organic material layer may have a multilayer structure including a hole injection layer, a hole transfer layer, a layer carrying out hole injection and hole transfer at the same time, an electron blocking layer, a light emitting layer, an electron transfer layer, an electron injection layer, a layer carrying out electron injection and electron transfer at the same time, and the like, but is not limited thereto, and may have a single layer structure. In addition, using various polymer materials, the organic material layer may be prepared to a smaller number of layers using a solvent process instead of a deposition method, for example, spin coating, dip coating, doctor blading, screen printing, inkjet printing, a thermal transfer method or the like.

The anode is an electrode injecting holes, and as the anode material, materials having large work function are normally preferred so that hole injection to an organic material layer is smooth. Specific examples of the anode material usable in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene] (PEDOT), polypyrrole and polyaniline, but are not limited thereto.

The cathode is an electrode injecting electrons, and as the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as $LiF/Al$ or $LiO_2/Al$, and the like, but are not limited thereto.

The hole injection layer is a layer performing a role of smoothly injecting holes from an anode to a light emitting layer, and the hole injection material is a material capable of favorably receiving holes from an anode at a low voltage. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto. The hole injection layer may have a thickness of 1 nm to 150 nm.

The hole injection layer having a thickness of 1 nm or greater has an advantage of preventing hole injection properties from declining, and the thickness being 150 nm or less has an advantage of preventing a driving voltage from increasing to enhance hole migration caused by the hole injection layer being too thick.

The hole transfer layer may perform a role of smoothly transferring holes. As the hole transfer material, materials capable of receiving holes from an anode or a hole injection layer, moving the holes to a light emitting layer, and having high mobility for the holes are suited. Specific examples thereof include arylamine-based organic materials, conductive polymers, block copolymers having conjugated parts and non-conjugated parts together, and the like, but are not limited thereto.

An electron blocking layer may be provided between the hole transfer layer and the light emitting layer. As the electron blocking layer, materials known in the art may be used.

The light emitting layer may emit red, green or blue, and may be formed with a phosphorescent material or a fluorescent material. The light emitting material is a material capable of emitting light in a visible region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxy-quinoline aluminum complexes (Alq$_3$); carbazole-based compounds; dimerized styryl compounds; BAlq; 10-hydroxybenzoquinoline-metal compounds; benzoxazole-, benzothiazole- and benzimidazole-based compounds; poly(p-phenylenevinylene) (PPV)-based polymers; spiro compounds; polyfluorene, rubrene, and the like, but are not limited thereto.

The light emitting layer may include the compound represented by Chemical Formula 1 of the present application, and specifically, may include the compound represented by Chemical Formula 1 of the present application as a host. More specifically, when the compound represented by Chemical Formula 1 of the present application is used as a host of the light emitting layer, the compound may be used as a phosphorescent material emitting red or green.

When the light emitting layer emits red light, phosphorescent materials such as bis(1-phenylisoquinoline)acetylacetonate iridium (PIQIr(acac)), bis(1-phenylquinoline)acetylacetonate iridium (PQIr(acac)), tris(1-phenylquinoline) iridium (PQIr) or octaethylporphyrin platinum (PtOEP), or fluorescent materials such as tris(8-hydroxyquinolino)aluminum (Alq$_3$) may be used as the light emitting dopant, however, the light emitting dopant is not limited thereto.

When the light emitting layer emits green light, phosphorescent materials such as fac tris(2-phenylpyridine)iridium (Ir(ppy)$_3$), or fluorescent materials such as tris(8-hydroxyquinolino)aluminum (Alq$_3$) may be used as the light emitting dopant, however, the light emitting dopant is not limited thereto.

The light emitting layer may further include a compound represented by the following Chemical Formula 8. Specifically, the light emitting layer may include a compound represented by the following Chemical Formula 8 as an additional host. Herein, the compound represented by Chemical Formula 1 may be included in 10 parts by weight to 70 parts by weight, and preferably in 20 parts by weight to 50 parts by weight based on 100 parts by weight of the whole host.

[Chemical Formula 8]

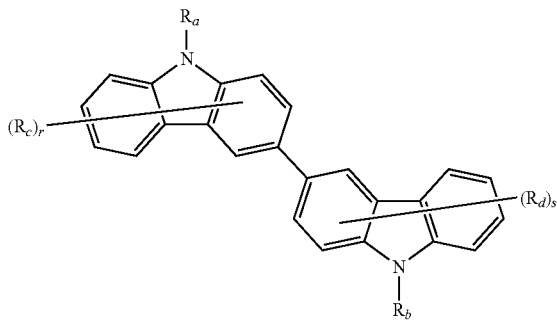

In Chemical Formula 8, $R_a$ and $R_b$ are the same as or different from each other, and each independently a substituted or unsubstituted aryl group; or a substituted or unsubstituted heteroaryl group, $R_c$ and $R_d$ are the same as or different from each other, and each independently hydrogen; deuterium; a halogen group; a cyano group; a nitro group; an amino group; a substituted or unsubstituted alkyl group having 1 to 60 carbon atoms; a substituted or unsubstituted cycloalkyl group having 3 to 60 carbon atoms; a substituted or unsubstituted alkenyl group having 2 to 60 carbon atoms; a substituted or unsubstituted aryl group having 6 to 60 carbon atoms; or a substituted or unsubstituted heteroaryl group having 2 to 60 carbon atoms including any one or more heteroatoms selected from the group consisting of N, O and S, and r and s are each an integer of 0 to 7, and when r is 2 or greater, each $R_c$ is the same as or different from each other, and when s is 2 or greater, each $R_d$ is the same as or different from each other.

According to one embodiment of the present specification, $R_c$ and $R_d$ are the same as or different from each other, and each independently hydrogen; deuterium; a halogen group; a cyano group; a nitro group; an amino group; a substituted or unsubstituted alkyl group having 1 to 30 carbon atoms; a substituted or unsubstituted cycloalkyl group having 3 to 30 carbon atoms; a substituted or unsubstituted alkenyl group having 2 to 30 carbon atoms; a substituted or unsubstituted aryl group having 6 to 30 carbon atoms; or a substituted or unsubstituted heteroaryl group having 2 to 30 carbon atoms including any one or more heteroatoms selected from the group consisting of N, O and S.

According to one embodiment of the present specification, $R_c$ and $R_d$ are hydrogen.

According to one embodiment of the present specification, $R_a$ and $R_b$ are the same as or different from each other, and each independently a substituted or unsubstituted aryl group having 6 to 60 carbon atoms; or a substituted or unsubstituted heteroaryl group having 2 to 60 carbon atoms.

According to one embodiment of the present specification, $R_a$ and $R_b$ are the same as or different from each other, and each independently a substituted or unsubstituted aryl group having 6 to 30 carbon atoms; or a substituted or unsubstituted heteroaryl group having 2 to 30 carbon atoms.

According to one embodiment of the present specification, $R_a$ and $R_b$ are the same as or different from each other, and each independently a substituted or unsubstituted phenyl group; a substituted or unsubstituted biphenyl group; a substituted or unsubstituted terphenyl group; a substituted or unsubstituted naphthyl group; a substituted or unsubstituted carbazole group; a substituted or unsubstituted fluorene group; a substituted or unsubstituted dibenzofuran group; a substituted or unsubstituted dibenzothiophene group; or a substituted or unsubstituted benzothiazole group.

According to one embodiment of the present specification, $R_a$ and $R_b$ are the same as or different from each other, and each independently a phenyl group unsubstituted or substituted with an alkyl group or an aryl group; a biphenyl group unsubstituted or substituted with an alkyl group or an aryl group; a terphenyl group unsubstituted or substituted with an alkyl group or an aryl group; a naphthyl group unsubstituted or substituted with an alkyl group or an aryl group; a fluorene group unsubstituted or substituted with an alkyl group or an aryl group; a dibenzofuran group unsubstituted or substituted with an alkyl group or an aryl group; or a dibenzothiophene group unsubstituted or substituted with an alkyl group or an aryl group.

According to one embodiment of the present specification, $R_a$ and $R_b$ are the same as or different from each other, and each independently a phenyl group unsubstituted or substituted with a methyl group, a phenyl group or a naphthyl group; a biphenyl group unsubstituted or substituted with a methyl group, a phenyl group or a naphthyl group; a terphenyl group unsubstituted or substituted with a methyl group, a phenyl group or a naphthyl group; a naphthyl group unsubstituted or substituted with a methyl group, a phenyl group or a naphthyl group; a fluorene group unsubstituted or substituted with a methyl group, a phenyl group or a naphthyl group; a dibenzofuran group unsubstituted or substituted with a methyl group, a phenyl group or a naphthyl group; or a dibenzothiophene group unsubstituted or substituted with a methyl group, a phenyl group or a naphthyl group. According to one embodiment of the present specification, $R_a$ and $R_b$ are the same as or different from each other, and each independently a phenyl group unsubstituted or substituted with a phenyl group or a naphthyl group; a biphenyl group; a terphenyl group; a naphthyl group unsubstituted or substituted with a phenyl group; a dimethylfluorene group; a dibenzofuran group; or a dibenzothiophene group.

According to one embodiment of the present specification, $R_a$ and $R_b$ may each be represented by any one of the following structures.

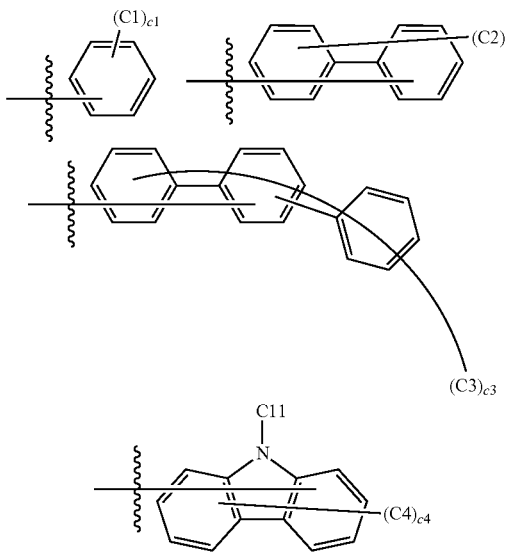

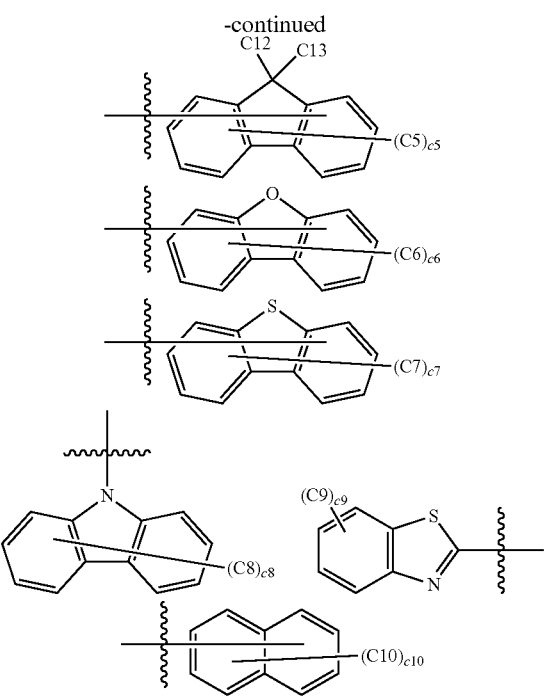

In the above structures,

C1 to C13 are each independently hydrogen; deuterium; a halogen group; a cyano group; a substituted or unsubstituted alkyl group; or a substituted or unsubstituted aryl group, c1 is an integer of 0 to 5,
c2 is an integer of 0 to 9,
c3 is an integer of 0 to 13,
c4 to c7 are each an integer of 0 to 7,
c8 is an integer of 0 to 8,
c9 is an integer of 0 to 4,
c10 is an integer of 0 to 7, and when c1 to c10 are 2 or greater, the two or more groups in parentheses are the same as or different from each other.

According to one embodiment of the present specification, C1 to C10 are hydrogen.

According to one embodiment of the present specification, C11 to C13 are each independently a substituted or unsubstituted alkyl group; or a substituted or unsubstituted aryl group.

According to one embodiment of the present specification, C11 to C13 are each independently a substituted or unsubstituted alkyl group having 1 to 60 carbon atoms; or a substituted or unsubstituted aryl group having 6 to 60 carbon atoms.

According to one embodiment of the present specification, C11 to C13 are each independently a substituted or unsubstituted alkyl group having 1 to 30 carbon atoms; or a substituted or unsubstituted aryl group having 6 to 30 carbon atoms.

According to one embodiment of the present specification, C11 is a substituted or unsubstituted aryl group having 6 to 15 carbon atoms.

According to one embodiment of the present specification, C11 is a substituted or unsubstituted phenyl group.

According to one embodiment of the present specification, C11 is a phenyl group.

According to one embodiment of the present specification, C12 and C13 are each independently a substituted or unsubstituted alkyl group having 1 to 15 carbon atoms.

According to one embodiment of the present specification, C12 and C13 are a methyl group.

According to one embodiment of the present specification, $R_a$ and $R_b$ may each be represented by any one of the following structures.

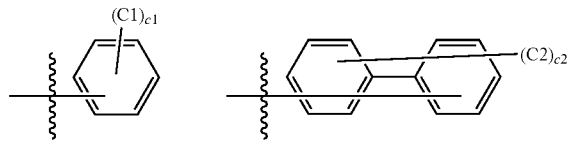

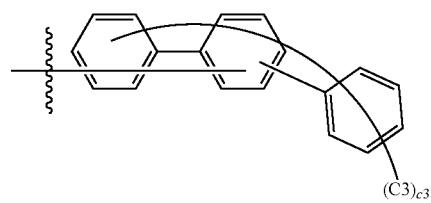

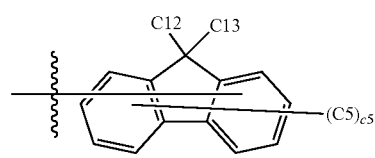

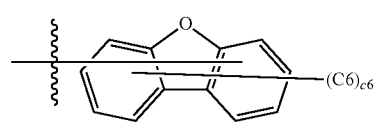

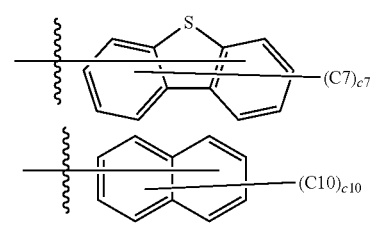

C1 to C3, C5 to C7, C10, C12, C13, c1 to c3, c5 to c7 and c10 have the same definitions as above.

According to one embodiment of the present specification, r and s are each an integer of 0 to 7.

According to one embodiment of the present specification, r and s are each 0 or 1.

The compound of Chemical Formula 8 may be any one selected from the group consisting of the following compounds.

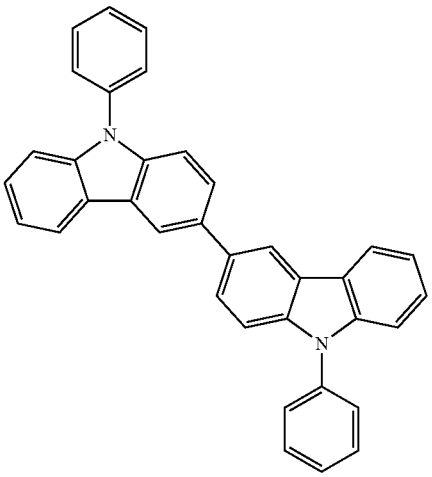

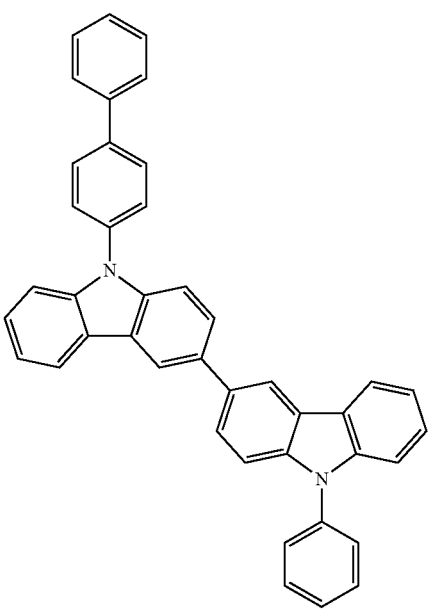

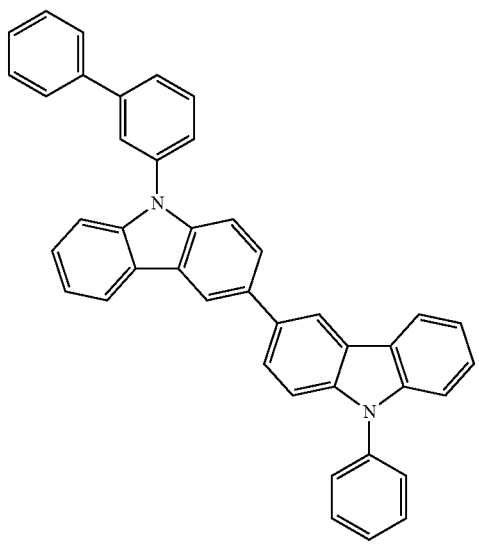

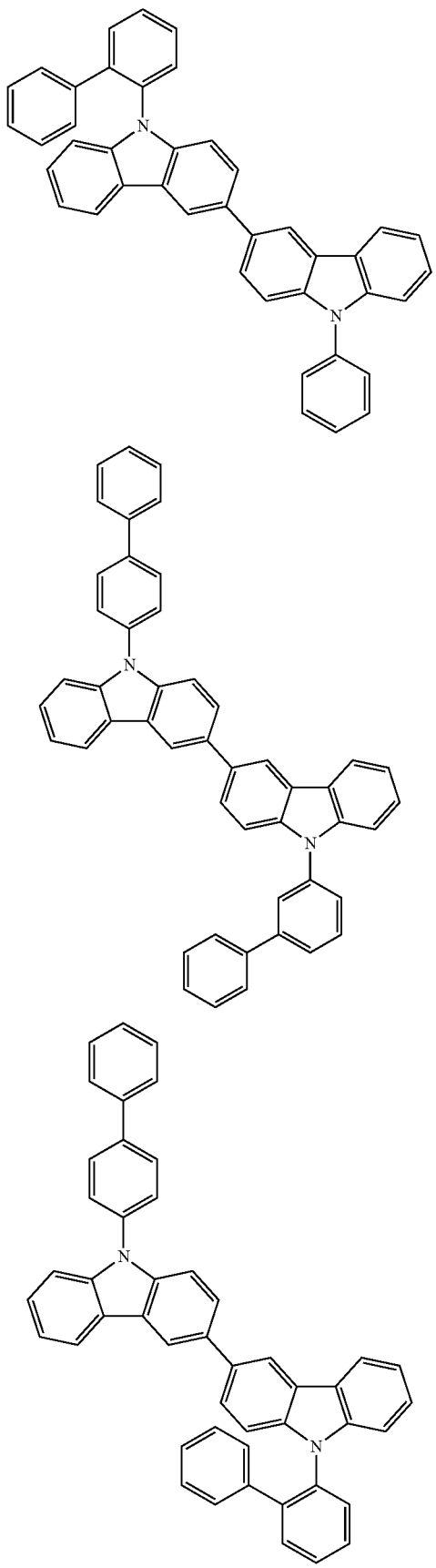 [SMILES: c1ccc(-c2ccccc2-n2c3ccccc3c3cc(-c4ccc5c(c4)c4ccccc4n5-c4ccccc4)ccc32)cc1 ; c1ccc(-c2ccc(-n3c4ccccc4c4cc(-c5ccc6c(c5)c5ccccc5n6-c5cccc(-c6ccccc6)c5)ccc43)cc2)cc1 ; c1ccc(-c2ccc(-n3c4ccccc4c4cc(-c5ccc6c(c5)c5ccccc5n6-c5ccccc5-c5ccccc5)ccc43)cc2)cc1]
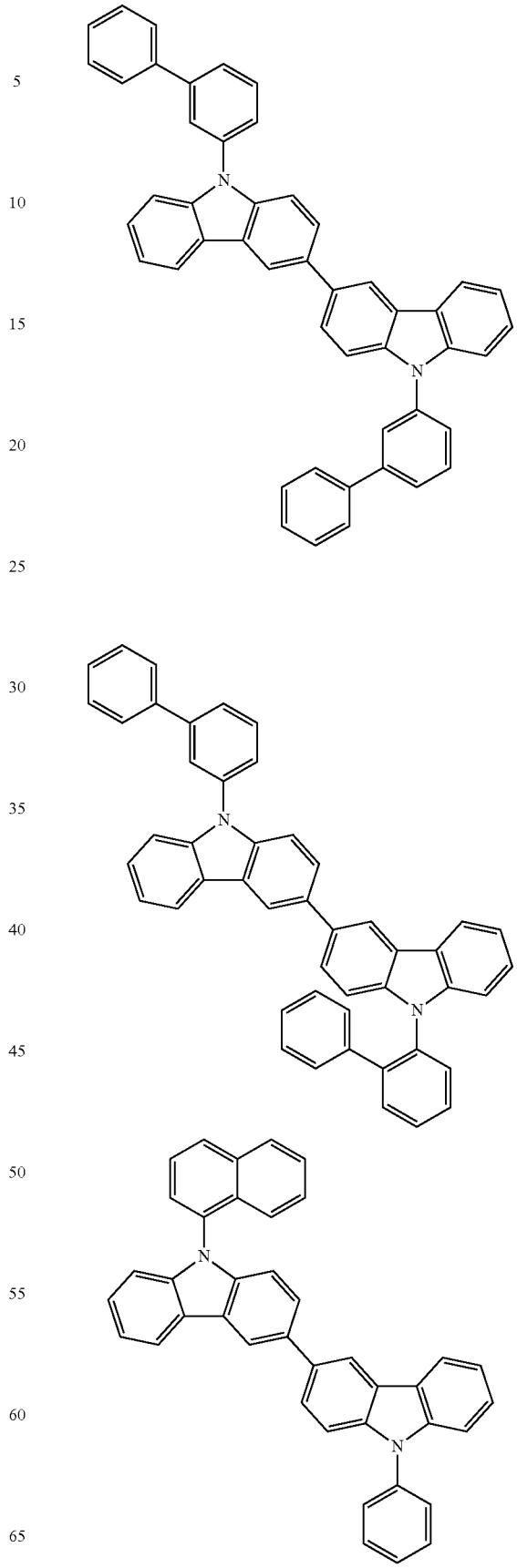

-continued
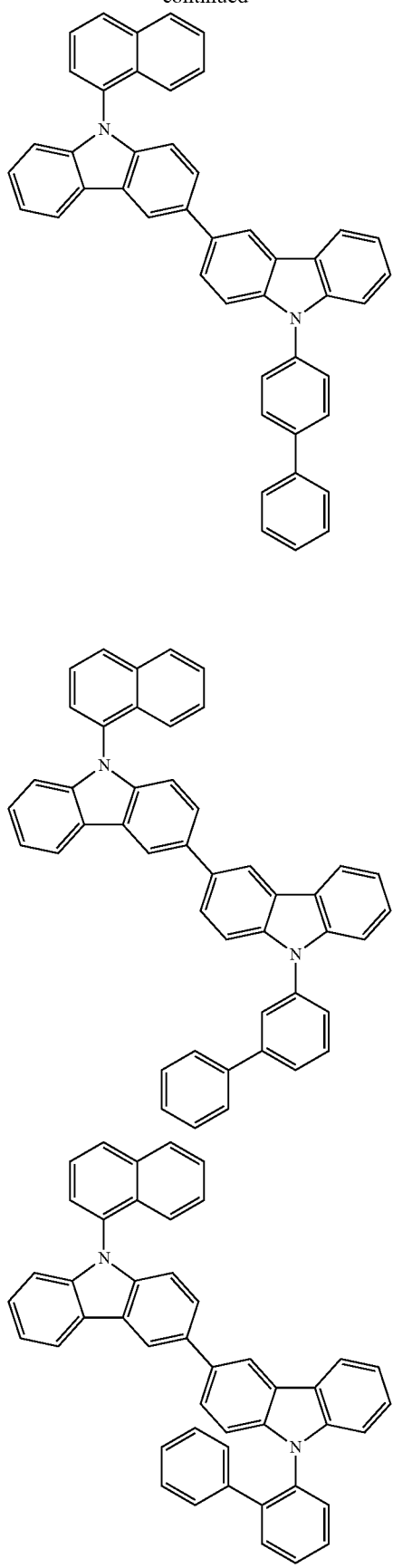
-continued
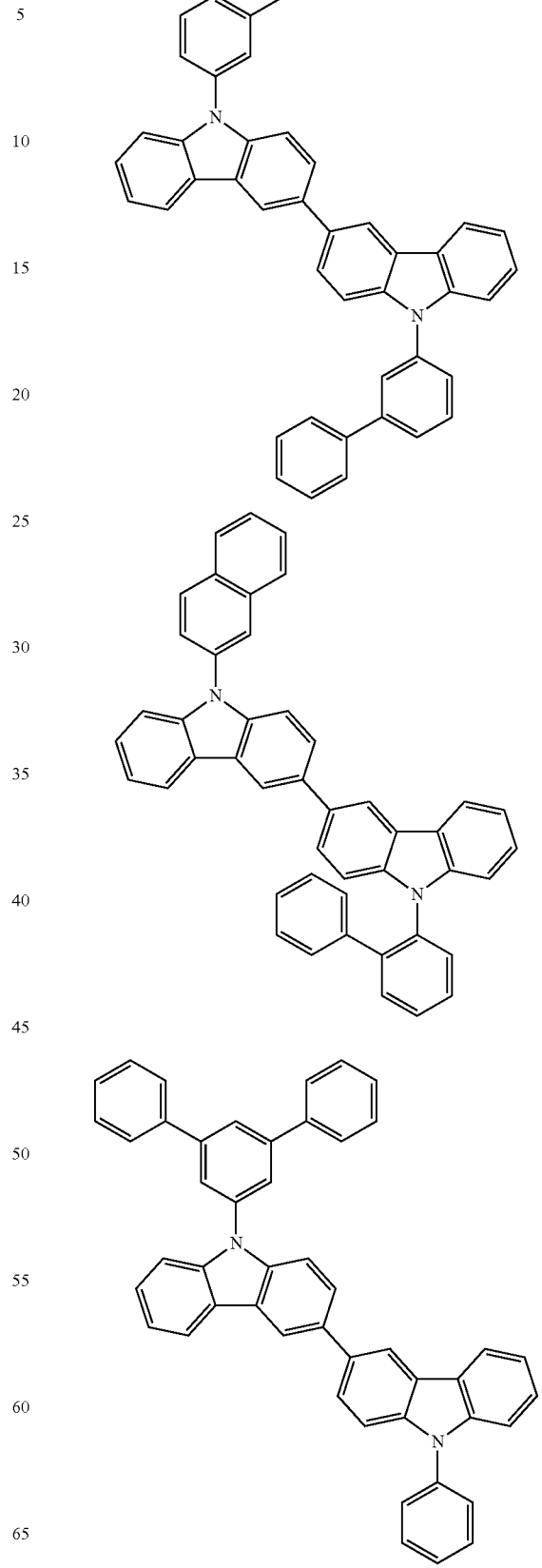

71
-continued
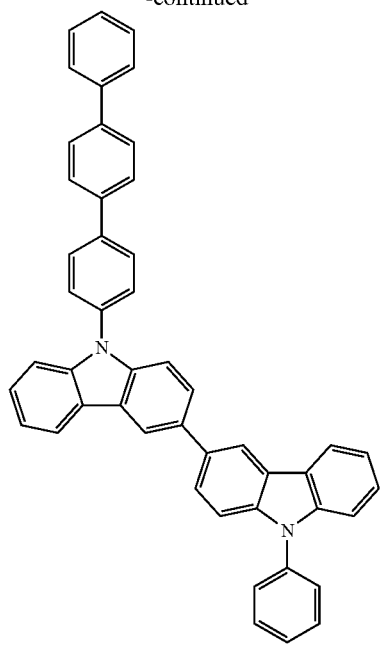
72
-continued
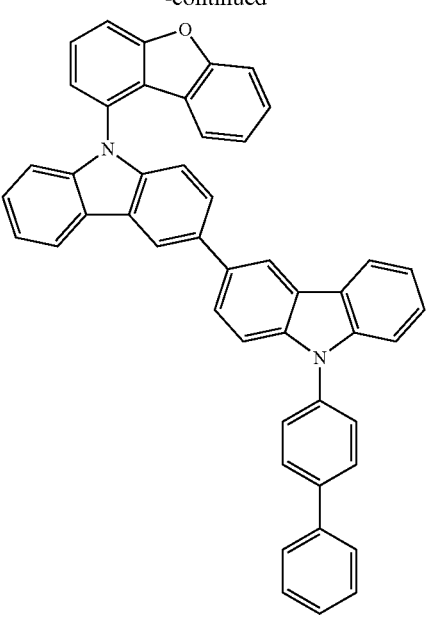
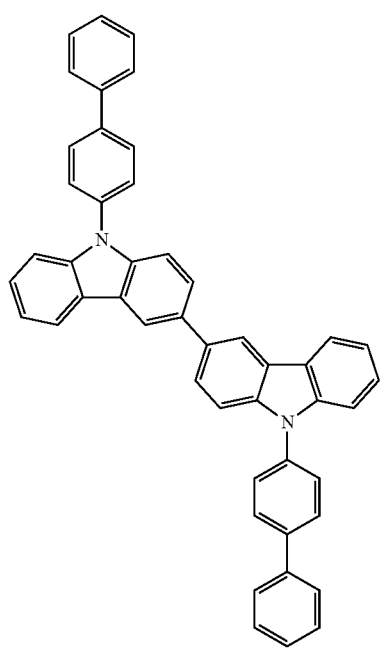
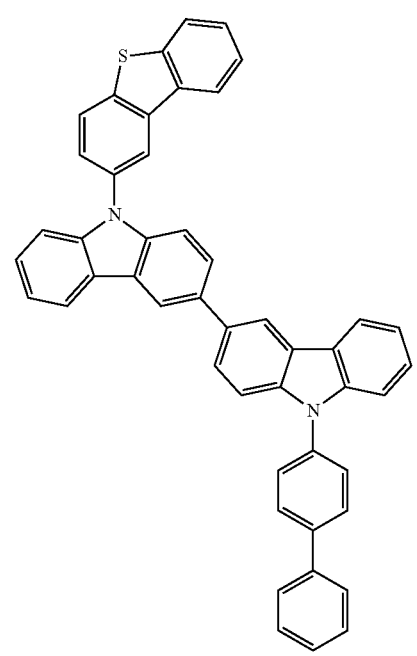

73
-continued
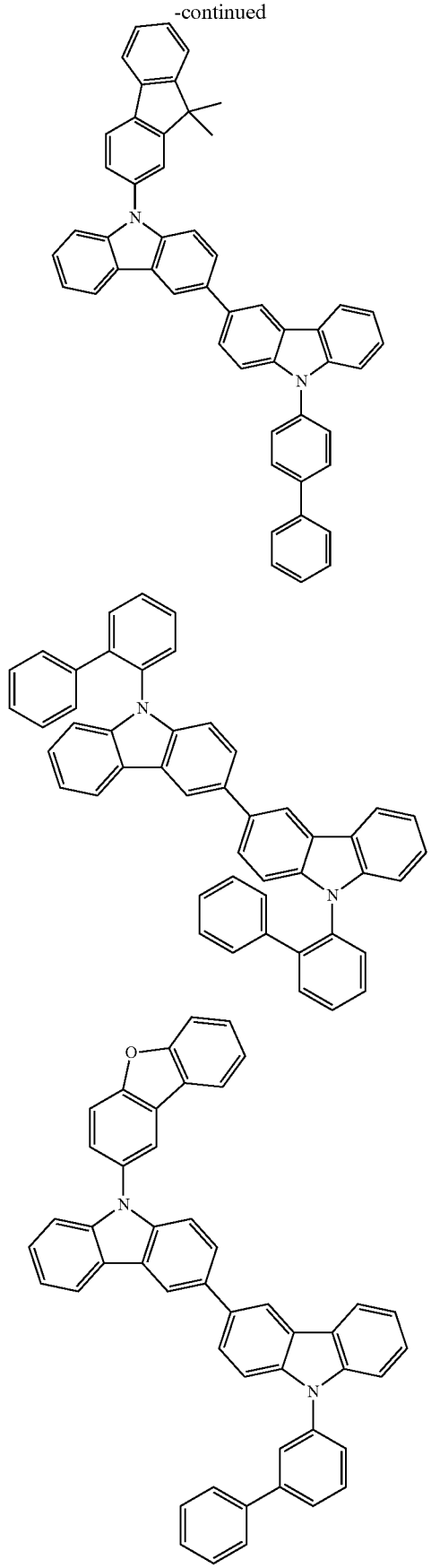
74
-continued
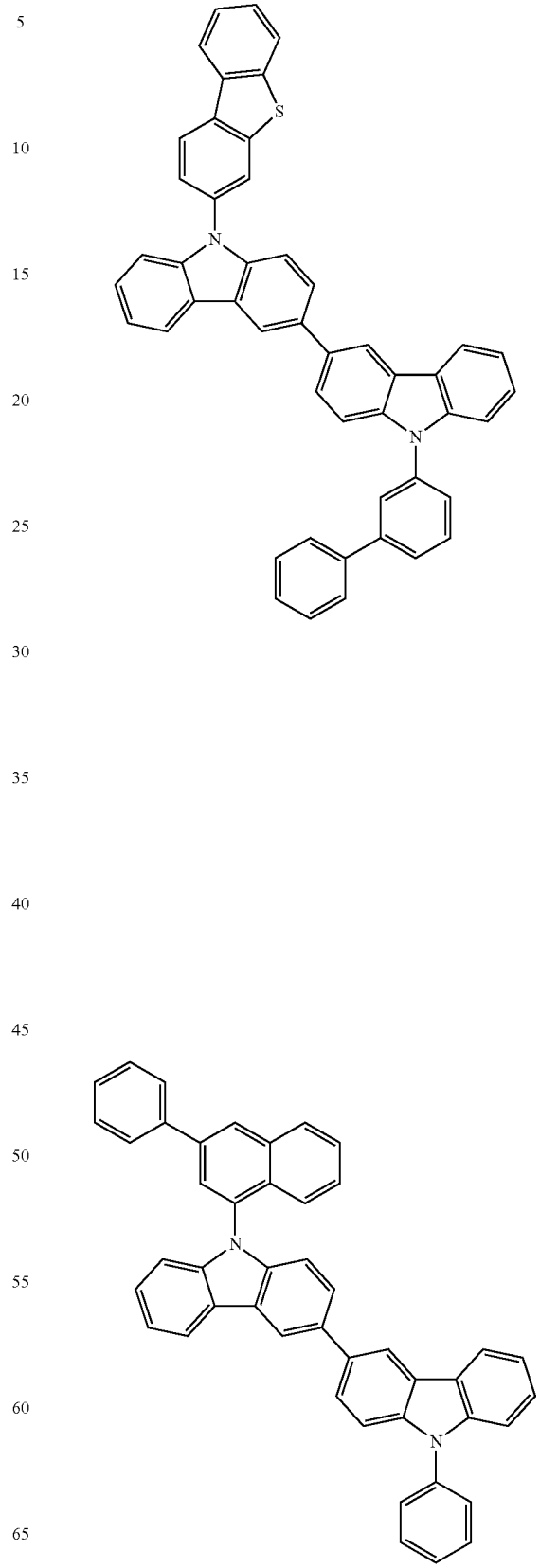

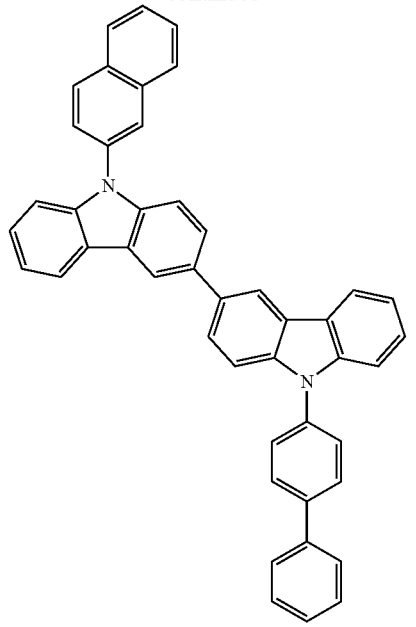
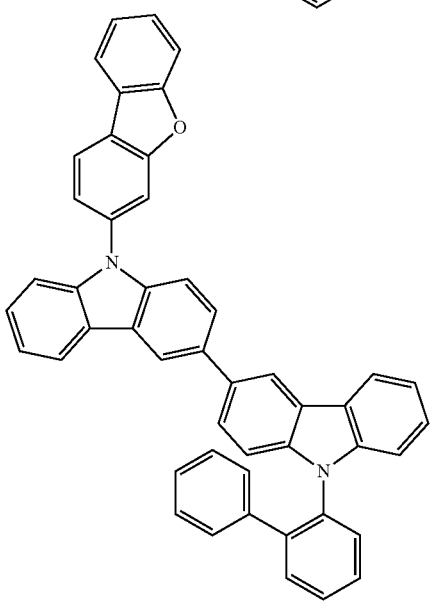
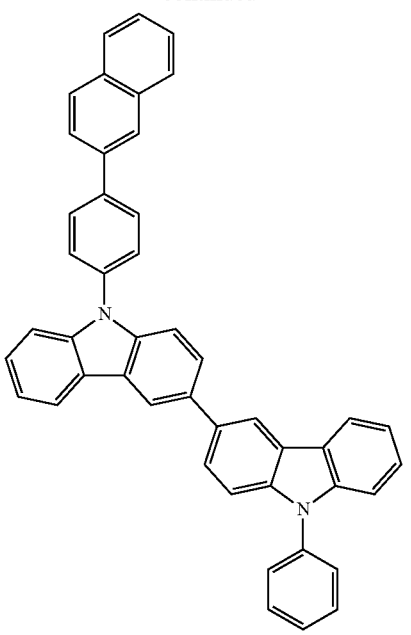
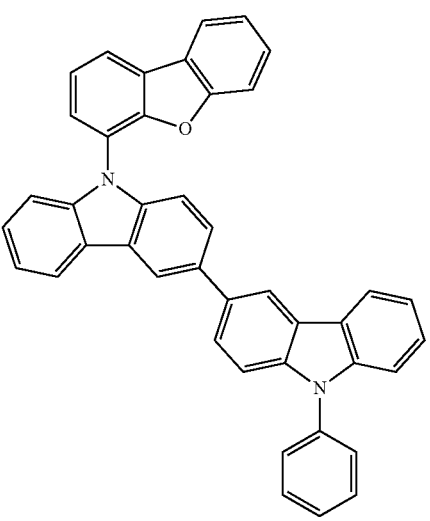
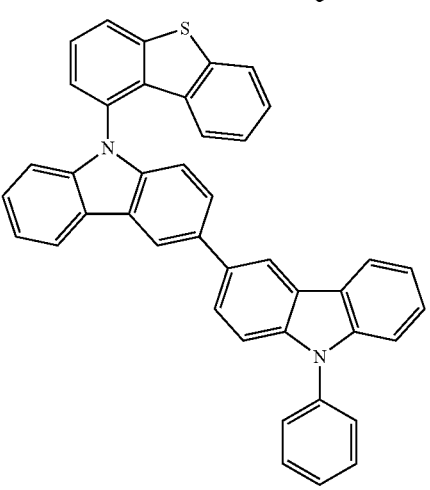

77
-continued
78
-continued
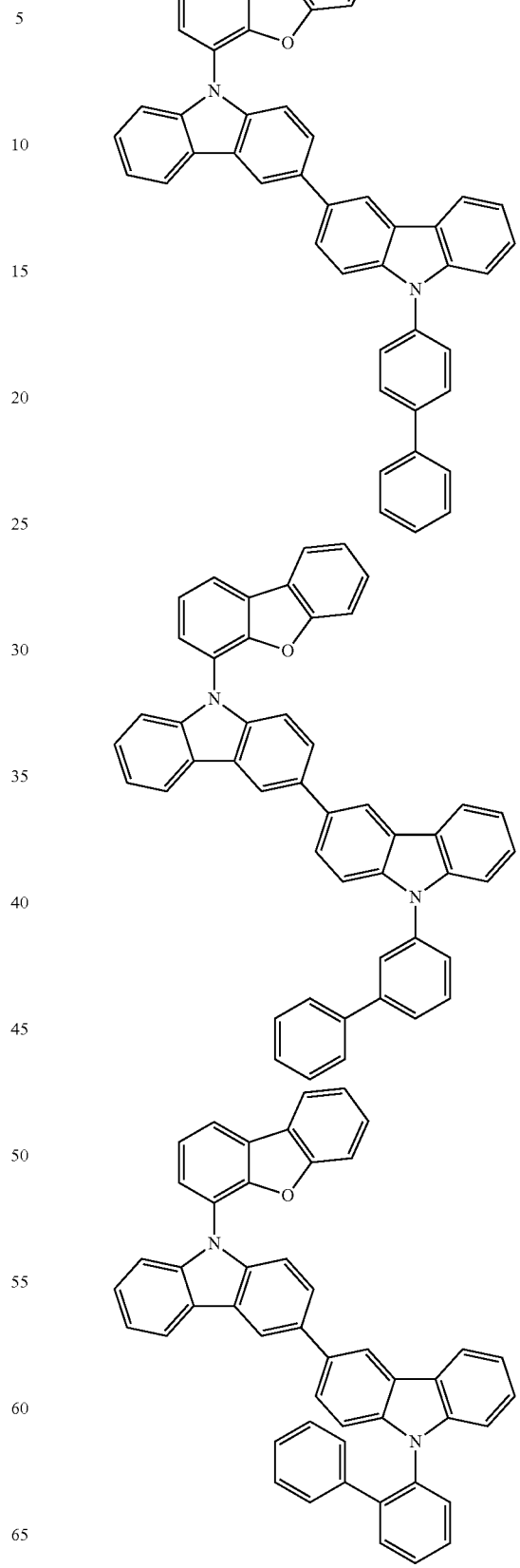

79
-continued
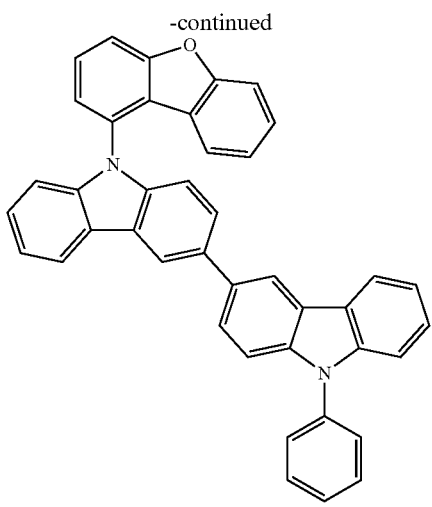
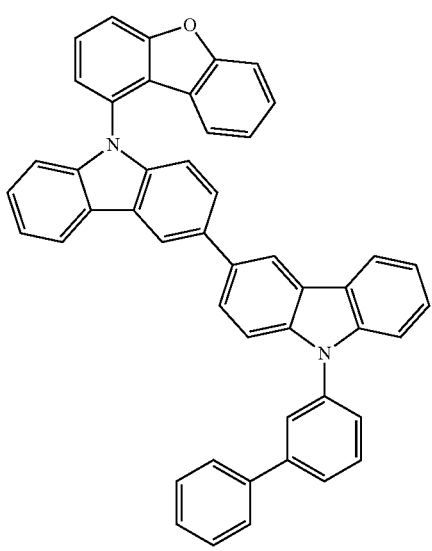
80
-continued
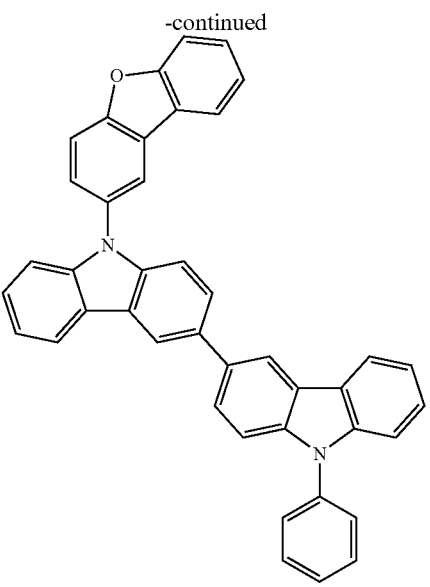
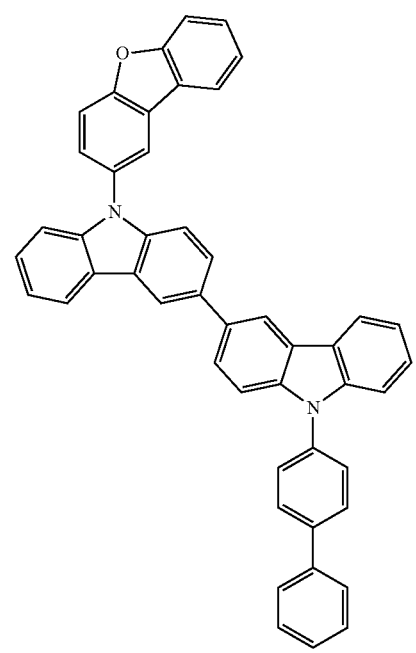

-continued
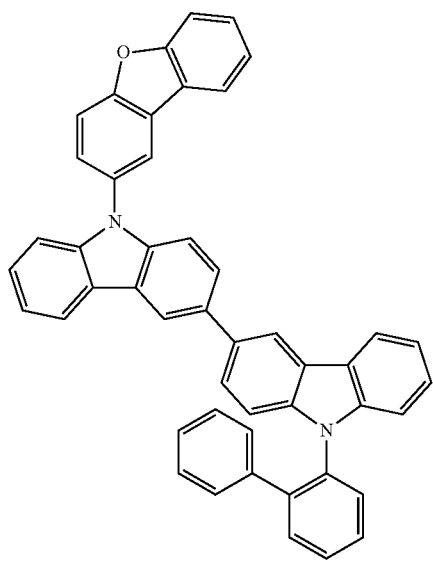
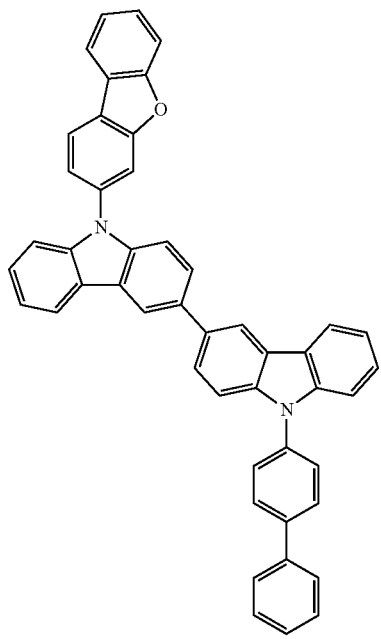
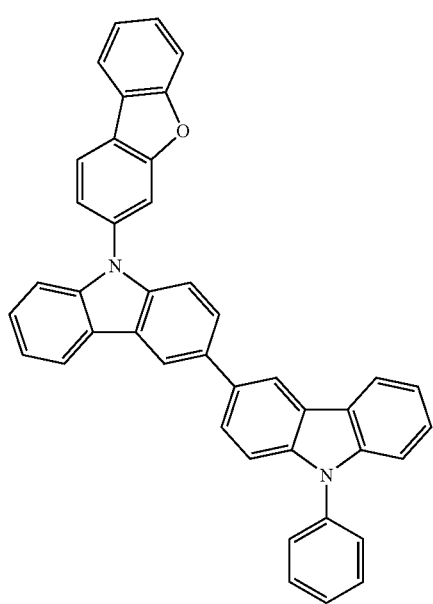
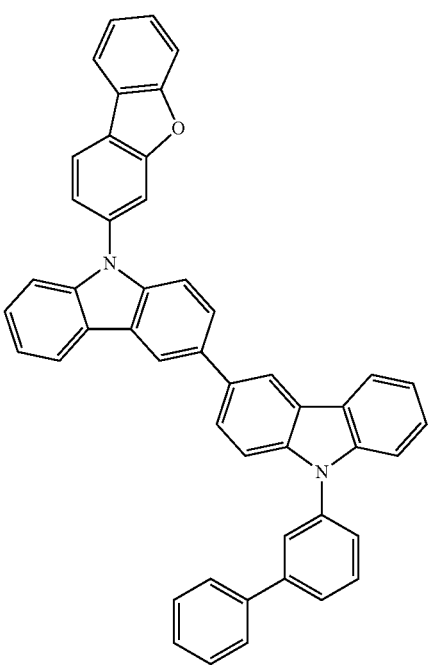

-continued
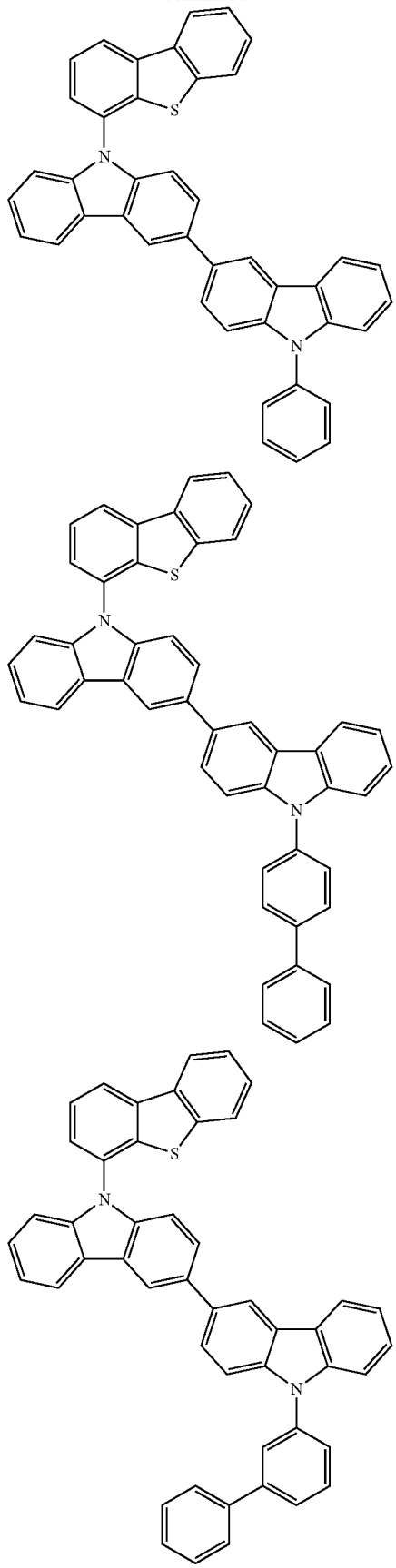
-continued
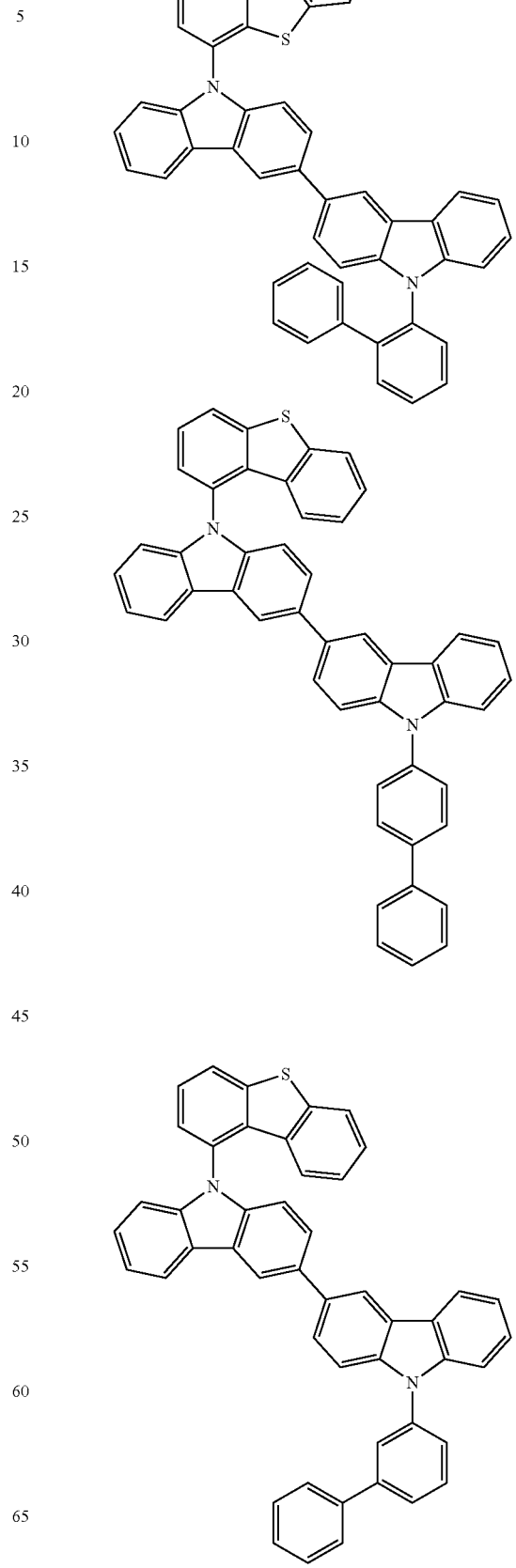

85
-continued
86
-continued
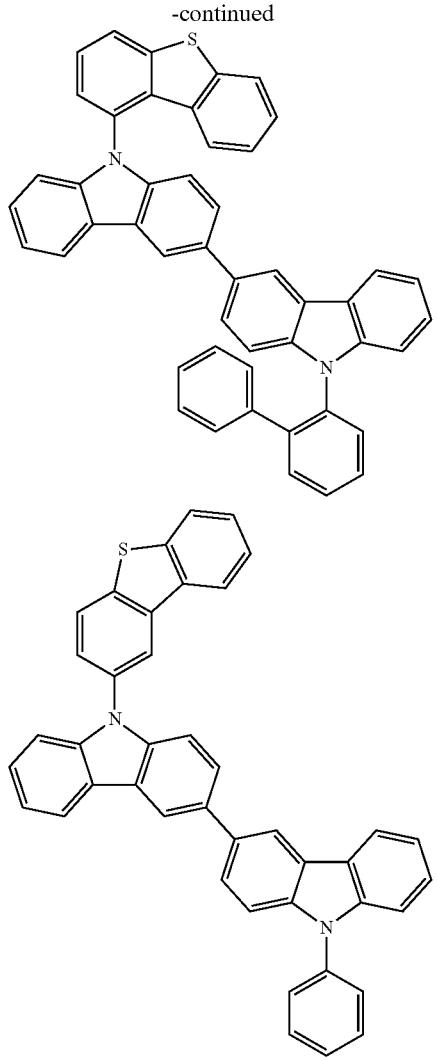
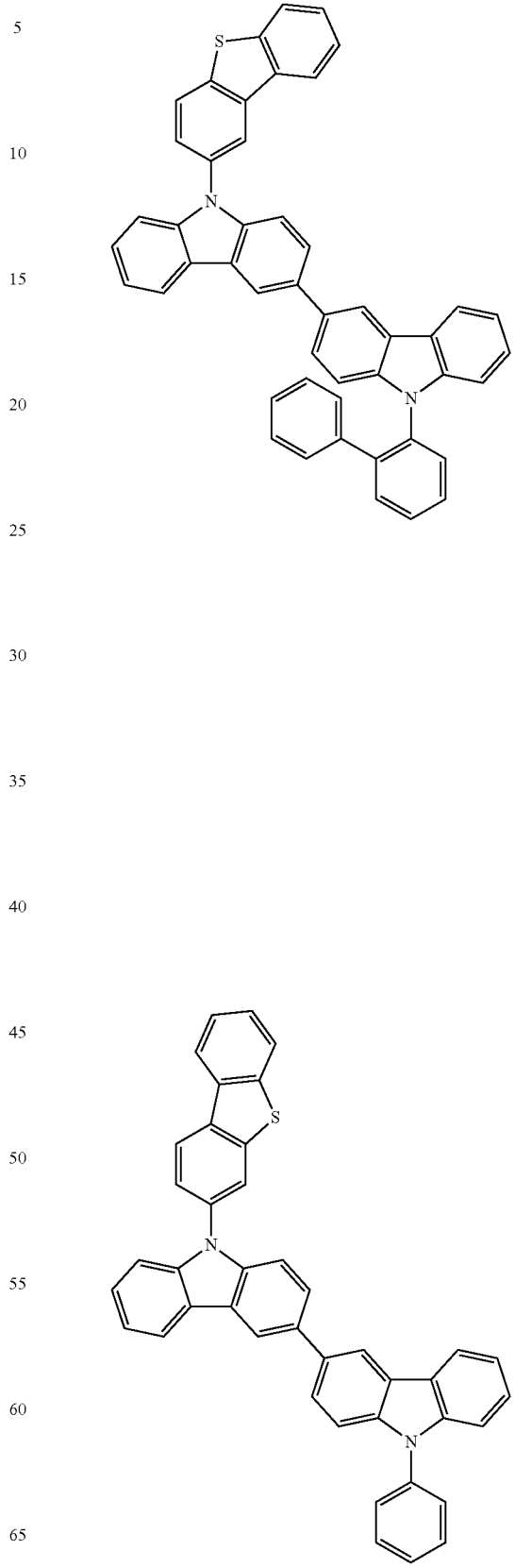

87
-continued
88
-continued
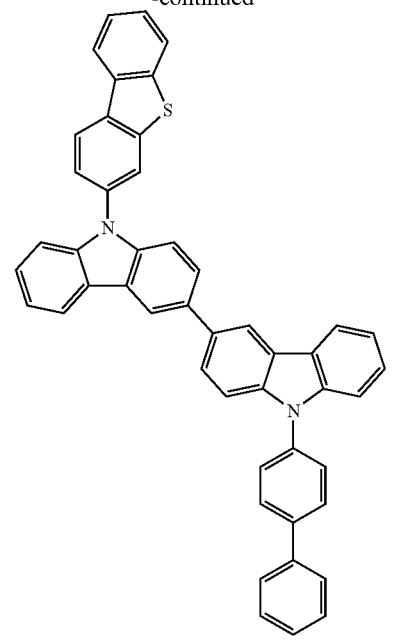
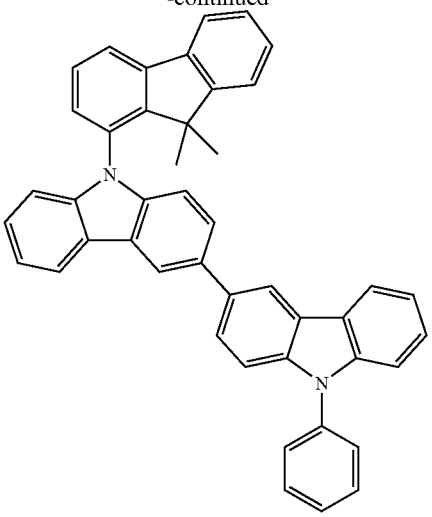
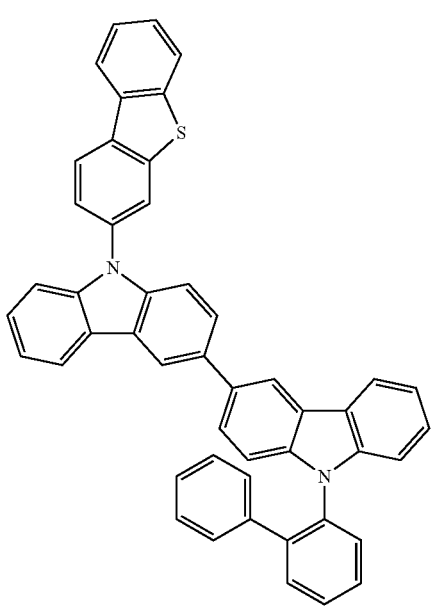

89
-continued
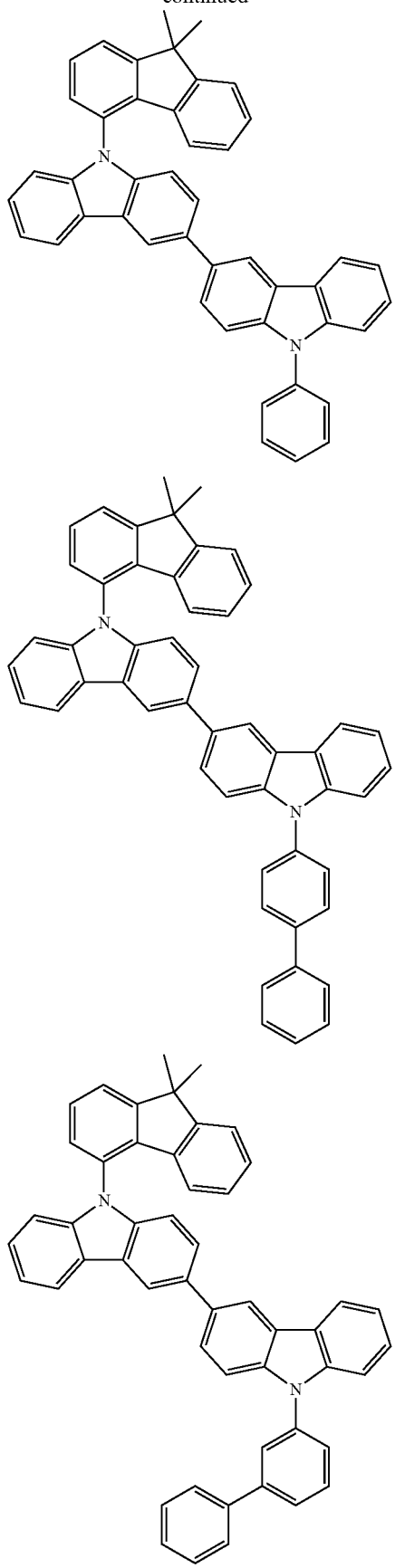
90
-continued
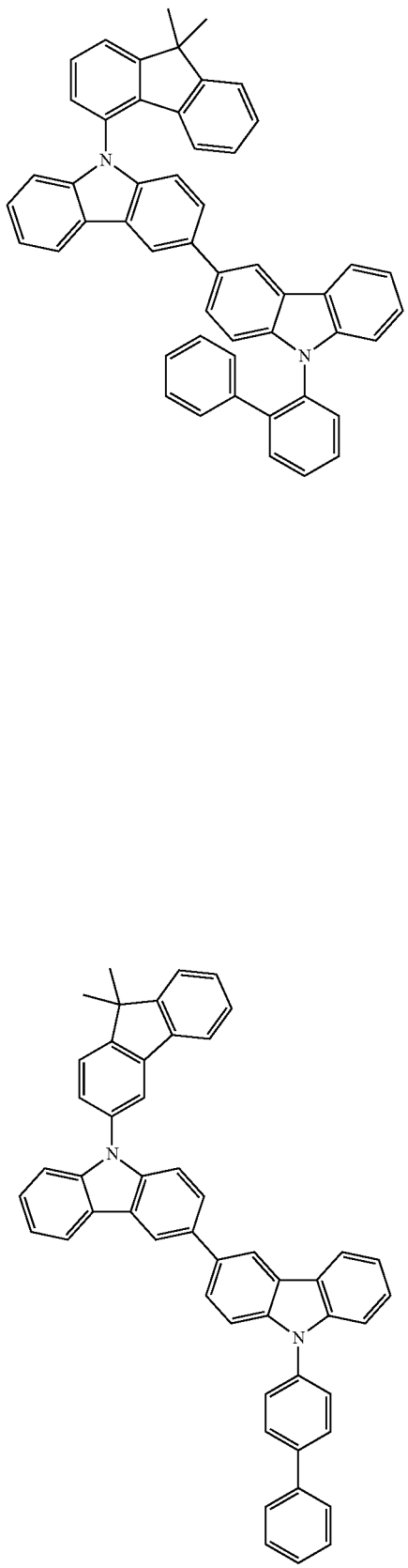

91
-continued
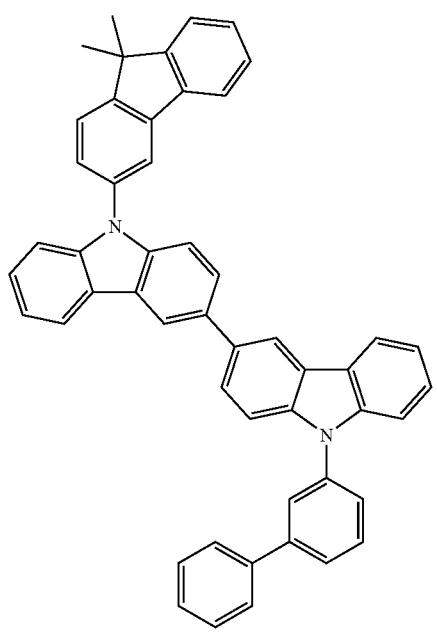
92
-continued
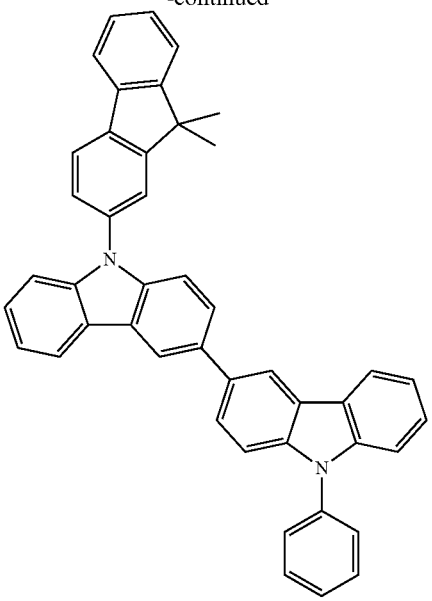
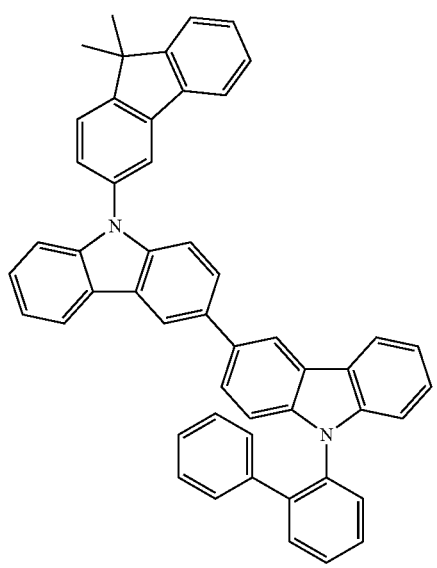
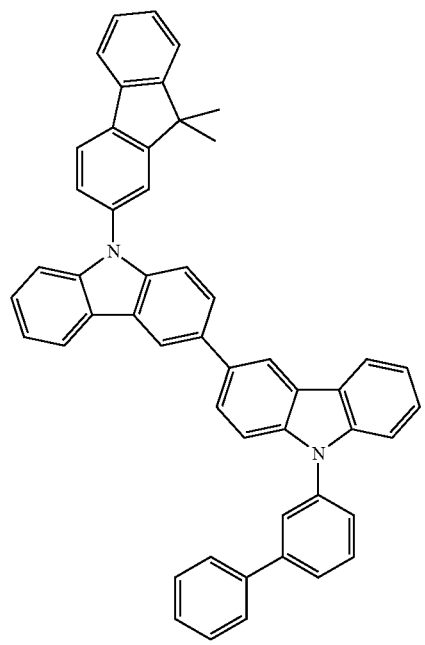

93
-continued
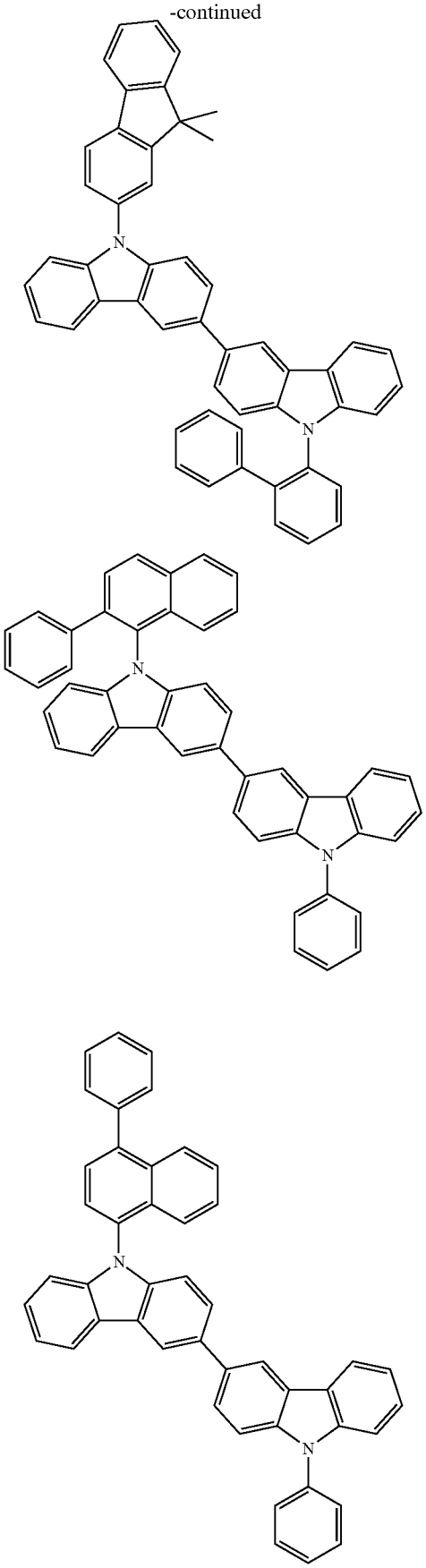
94
-continued
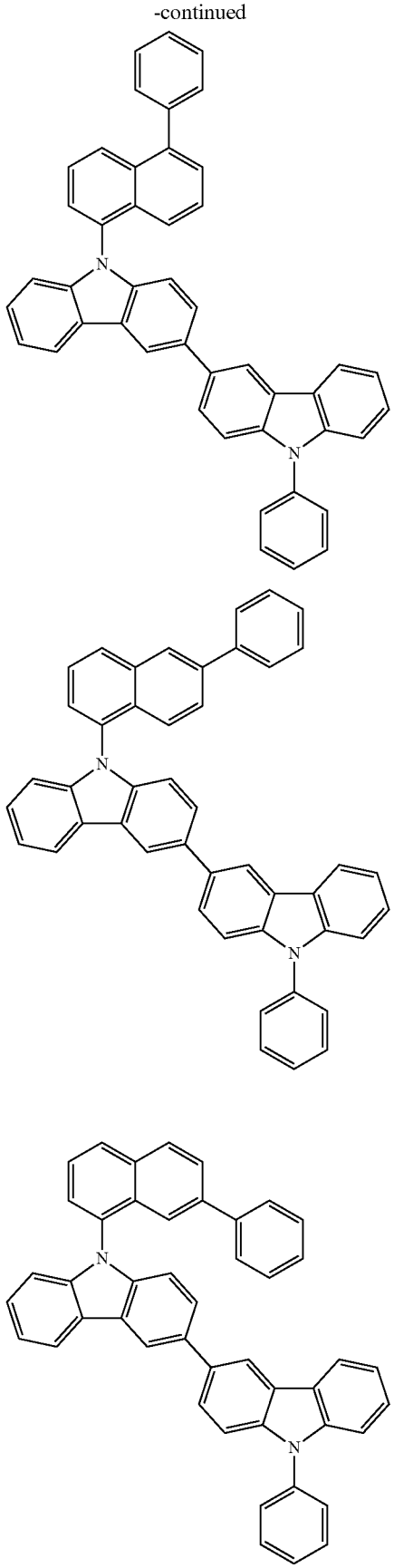

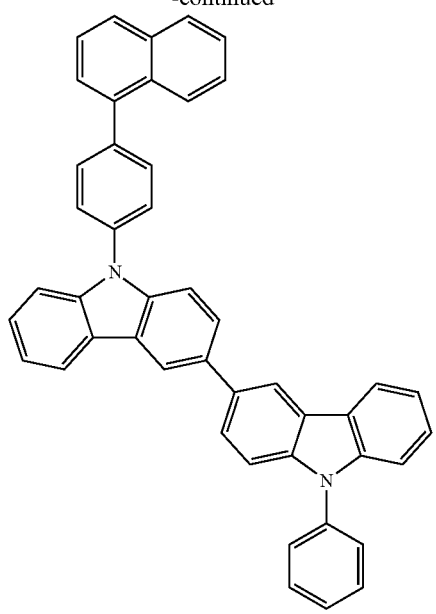
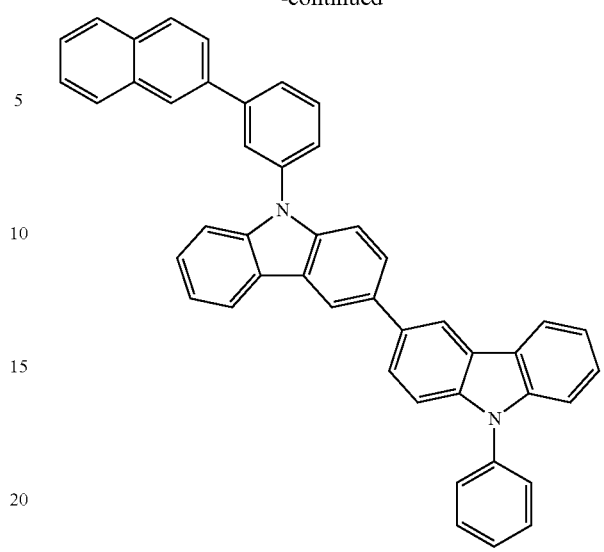
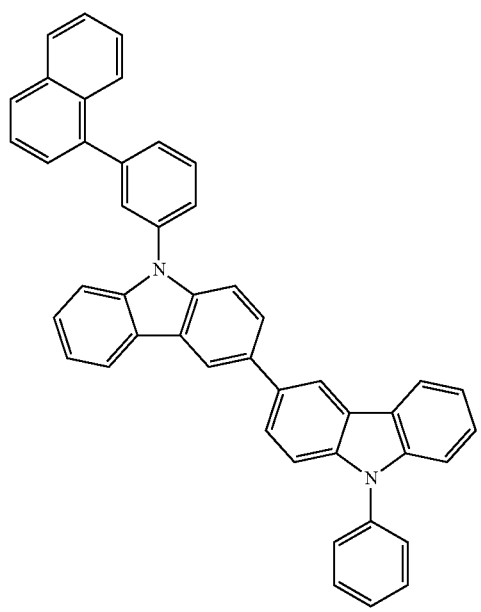

97
-continued
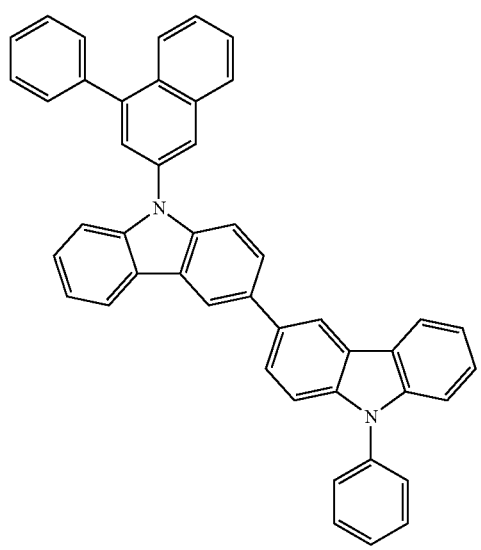
98
-continued
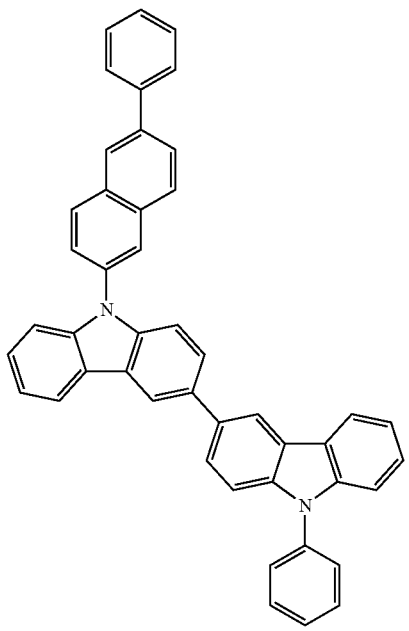
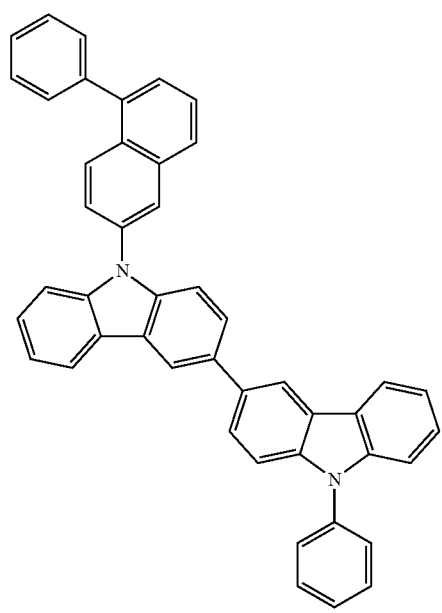
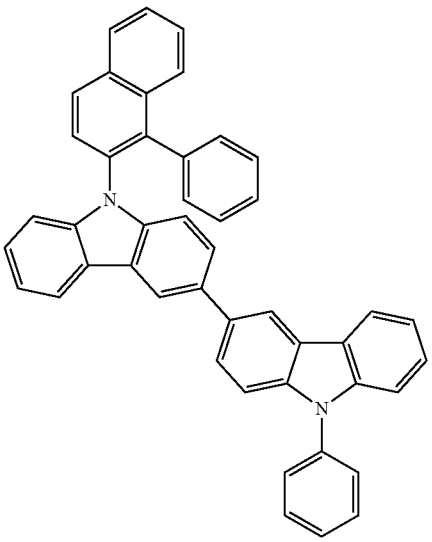

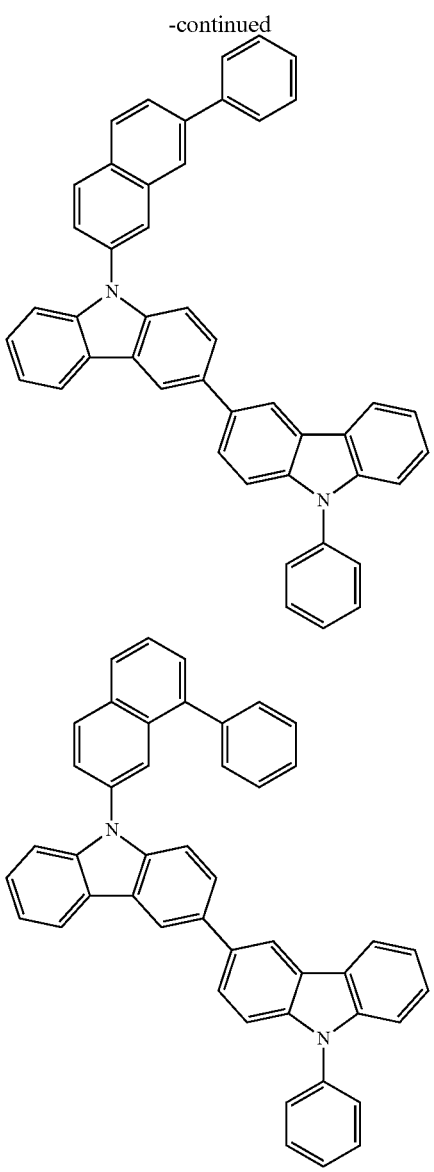

The electron transfer layer may perform a role of smoothly transferring electrons. As the electron transfer material, materials capable of favorably receiving electrons from a cathode, moving the electrons to a light emitting layer, and having high mobility for the electrons are suited. Specific examples thereof include Al complexes of 8-hydroxyquinoline; complexes including Alq$_3$; organic radical compounds; hydroxyflavon-metal complexes, and the like, but are not limited thereto. The electron transfer layer may have a thickness of 1 nm to 50 nm. The electron transfer layer having a thickness of 1 nm or greater has an advantage of preventing electron transfer properties from declining, and the thickness being 50 nm or less has an advantage of preventing a driving voltage from increasing to enhance electron migration caused by the electron transfer layer being too thick.

The electron injection layer may perform a role of smoothly injecting electrons. As the electron injection material, compounds having an electron transferring ability, having an electron injection effect from a cathode, having an excellent electron injection effect for a light emitting layer or light emitting material, and preventing excitons generated in the light emitting layer from moving to a hole injection layer, and in addition thereto, having an excellent thin film forming ability are preferred. Specific examples thereof may include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato) (O-cresolato)gallium, bis(2-methyl-8-quinolinato) (1-naphtholato)aluminum, bis(2-methyl-8-quinolinato) (2-naphtholato)gallium and the like, but is not limited thereto.

The hole blocking layer is a layer blocking holes from reaching a cathode, and may be generally formed under the same condition as the hole injection layer. Specific examples thereof may include oxadiazole derivatives, triazole derivatives, phenanthroline derivatives, BCP, aluminum complexes and the like, but are not limited thereto.

The organic light emitting device according to the present disclosure may be a top-emission type, a bottom-emission type or a dual-emission type depending on the materials used.

Hereinafter, the present specification will be described in detail with reference to examples. However, the examples according to the present specification may be modified to various other forms, and the scope of the present application is not to be construed as being limited to the examples described below. Examples of the present application are provided in order to more fully describe the present specification to those having average knowledge in the art.

SYNTHESIS EXAMPLES

Preparation Example 1: Synthesis of Intermediate A

1) Synthesis of Intermediate A-1

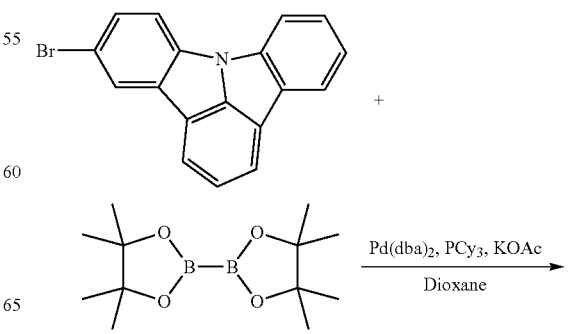

-continued

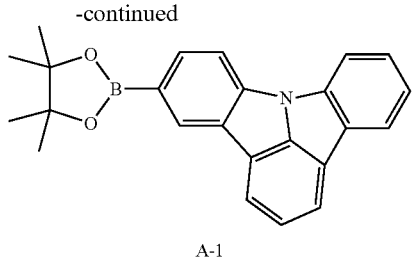

A-1

To a 3-neck flask, 11-bromoindolo[3,2,1-jk]carbazole (20.0 g, 62.5 mmol), bis(pinacolato)diboron (19.0 g, 75.0 mmol), bis(dibenzylideneacetone)palladium(0) (Pd(dba)$_2$) (0.7 g, 1.2 mmol) and tricyclohexylphosphine (PCy$_3$) (0.7 g, 2.5 mmol), potassium acetate (KOAc) (12.3 g, 124.9 mmol) and 1,4-dioxane (300 ml) were introduced, and the result was stirred for 12 hours under an argon atmosphere reflux condition. When the reaction was finished, the reaction solution was cooled to room temperature, then transferred to a separatory funnel, and extracted with ethyl acetate after adding water (200 mL) thereto. The extract was dried with MgSO$_4$, then filtered and concentrated, and the sample was purified by silica gel column chromatography to obtain Intermediate A-1 (16.3 g). (Yield 71%, MS: [M+H]+=367)

2) Synthesis of Intermediate A-2

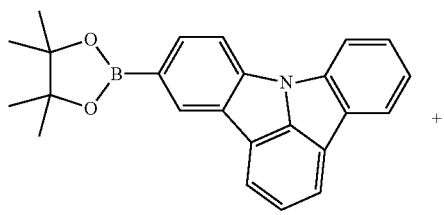

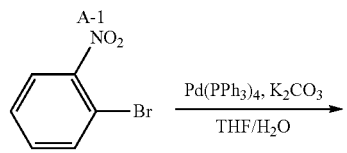

A-2

In a 3-neck flask, Intermediate A-1 (16.0 g, 43.6 mmol) and 1-bromo-2-nitrobenzene (9.7 g, 47.9 mmol) were dissolved in tetrahydrofuran (THF) (240 ml), and potassium carbonate (K$_2$CO$_3$) (24.1 g, 174.3 mmol) dissolved in H$_2$O (80 ml) was introduced thereto. Tetrakis(triphenylphosphine)palladium(0) (Pd(PPh$_3$)$_4$) (2.5 g, 2.2 mmol) was introduced thereto, and the result was stirred for 8 hours under an argon atmosphere reflux condition. When the reaction was finished, the reaction solution was cooled to room temperature, then transferred to a separatory funnel, and extracted with ethyl acetate. The extract was dried with MgSO$_4$, then filtered and concentrated, and the sample was purified by silica gel column chromatography to obtain Intermediate A-2 (10.7 g). (Yield 68%, MS[M+H]+=362)

3) Synthesis of Intermediate A

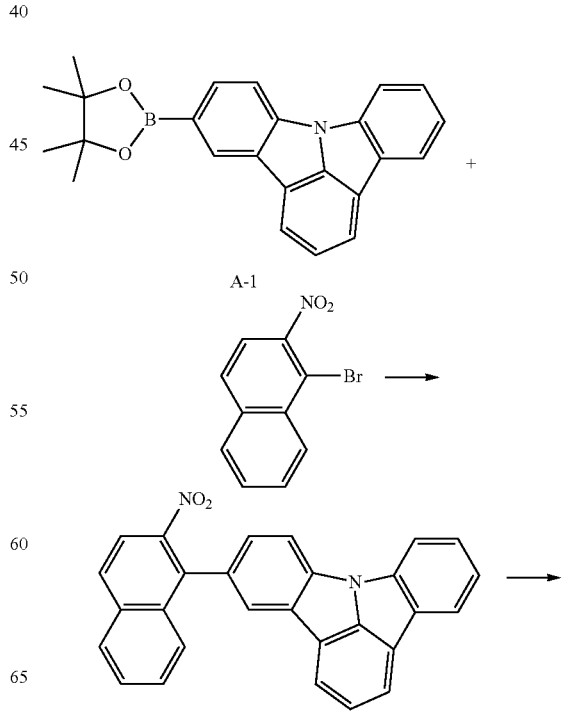

To a 2-neck flask, Intermediate A-2 (10.0 g, 27.6 mmol), triphenylphosphine (PPh$_3$) (5.7 g, 41.4 mmol) and o-dichlorobenzene (o-DCB) (100 ml) were introduced, and the result was stirred for 24 hours under a reflux condition. When the reaction was finished, the result was cooled to room temperature, and, after removing the solvent by vacuum distillation, extracted with CH$_2$Cl$_2$. The extract was dried with MgSO$_4$, then filtered and concentrated, and the sample was purified by silica gel column chromatography to obtain Intermediate A (4.8 g). (yield 53%, MS[M+H]$^+$=330)

Preparation Example 2: Synthesis of Intermediate B

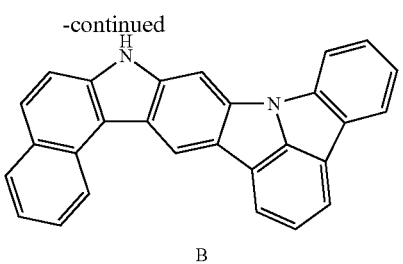

B

Intermediate B was prepared in the same manner as in Preparation of Intermediate A of Preparation Example 1 except that 1-bromo-2-nitrobenzene was changed to 1-bromo-2-nitronaphthalene. (MS[M+H]⁺=380)

Preparation Example 3: Synthesis of Intermediate C

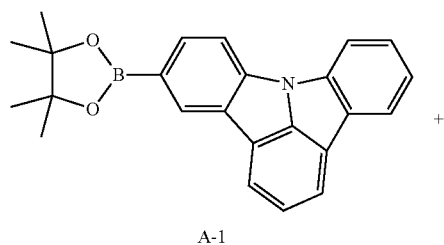

A-1

↓

↓

C

Intermediate C was prepared in the same manner as in Preparation of Intermediate A of Preparation Example 1 except that 1-bromo-2-nitrobenzene was changed to 2-bromo-3-nitronaphthalene. (MS[M+H]⁺=380)

Preparation Example 4: Synthesis of Intermediate D

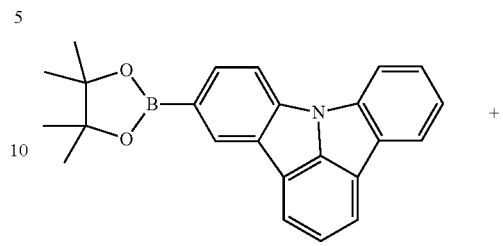

A-1 +

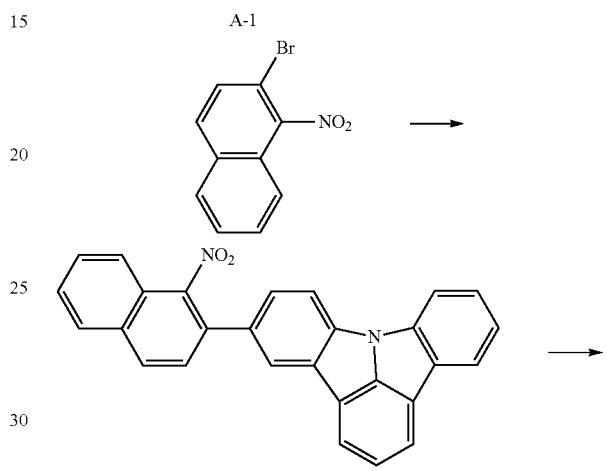

D

Intermediate D was prepared in the same manner as in Preparation of Intermediate A of Preparation Example 1 except that 1-bromo-2-nitrobenzene was changed to 2-bromo-1-nitronaphthalene. (MS[M+H]⁺=380)

Synthesis Example 1: Synthesis of Compound 1

A +

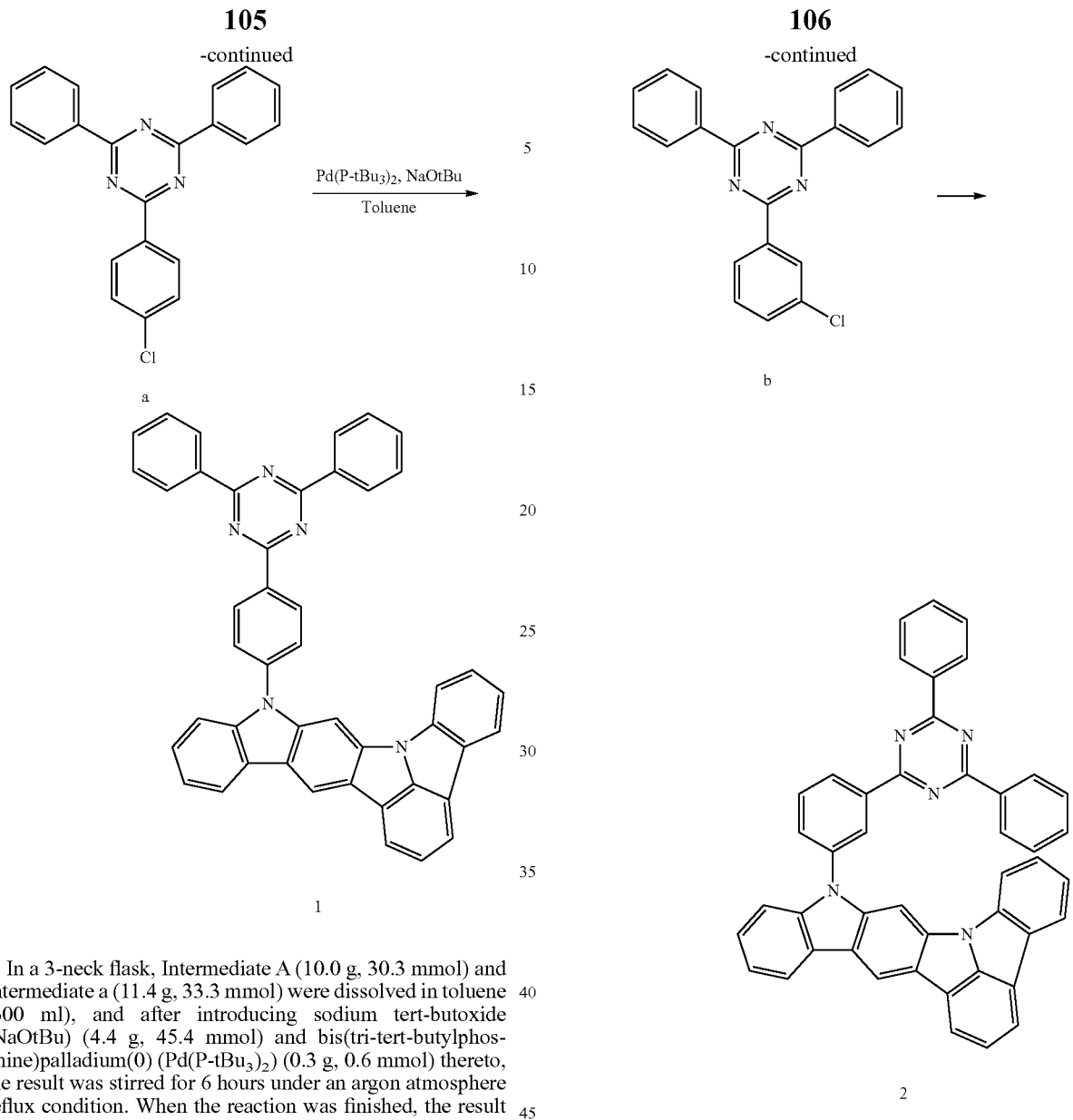

In a 3-neck flask, Intermediate A (10.0 g, 30.3 mmol) and Intermediate a (11.4 g, 33.3 mmol) were dissolved in toluene (300 ml), and after introducing sodium tert-butoxide (NaOtBu) (4.4 g, 45.4 mmol) and bis(tri-tert-butylphosphine)palladium(0) (Pd(P-tBu$_3$)$_2$) (0.3 g, 0.6 mmol) thereto, the result was stirred for 6 hours under an argon atmosphere reflux condition. When the reaction was finished, the result was cooled to room temperature, H$_2$O was introduced thereto, and the reaction solution was transferred to a separatory funnel and extracted. The extract with dried with MgSO$_4$, concentrated, and the sample was purified by silica gel column chromatography, and then sublimation purified to obtain Compound 1 (5.8 g). (Yield 30%, MS[M+H]$^+$=637)

Synthesis Example 2: Synthesis of Compound 2

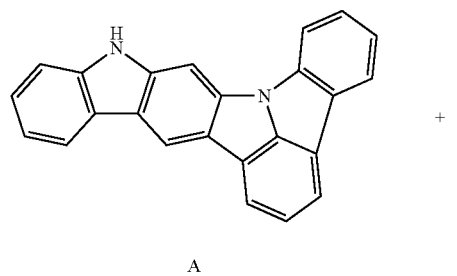

Compound 2 was prepared in the same manner as in Preparation of Compound 1 of Synthesis Example 1 except that Intermediate a was changed to Intermediate b. (MS[M+H]$^+$=637)

Synthesis Example 3: Synthesis of Compound 3

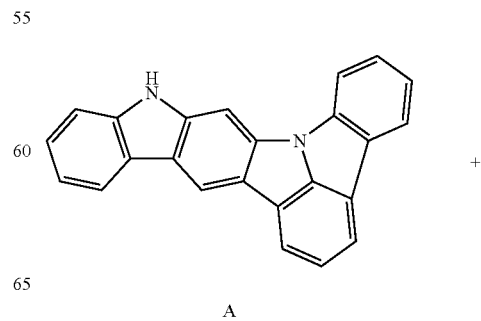

107
-continued

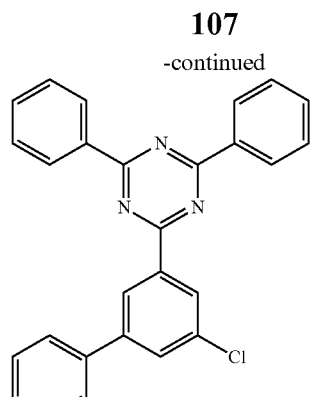

c

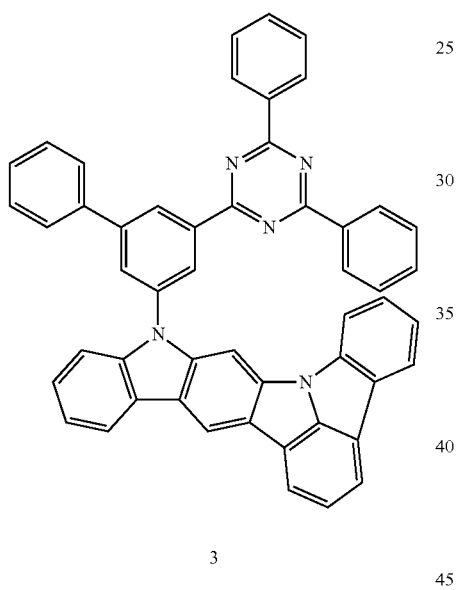

3

Compound 3 was prepared in the same manner as in Preparation of Compound 1 of Synthesis Example 1 except that Intermediate a was changed to Intermediate c. (MS[M+H]⁺=713)

Synthesis Example 4: Synthesis of Compound 4

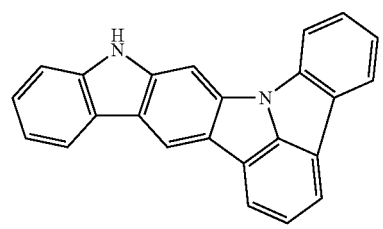

A

108
-continued

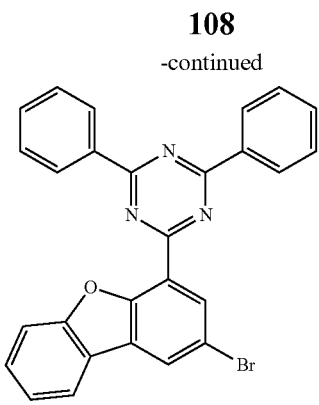

d

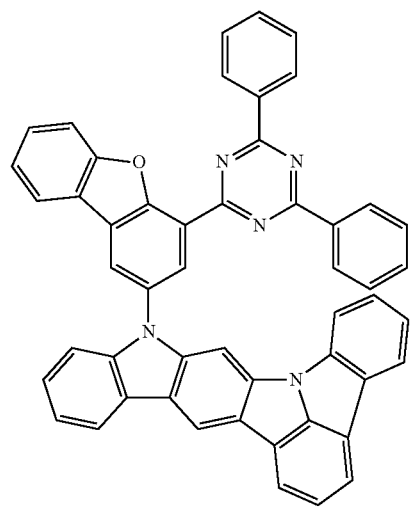

4

Compound 4 was prepared in the same manner as in Preparation of Compound 1 of Synthesis Example 1 except that Intermediate a was changed to Intermediate d. (MS[M+H]+=727)

Synthesis Example 5: Synthesis of Compound 5

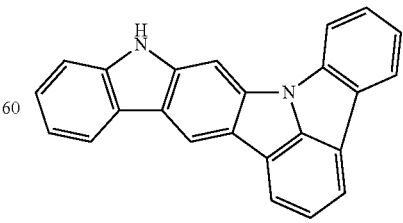

A

+

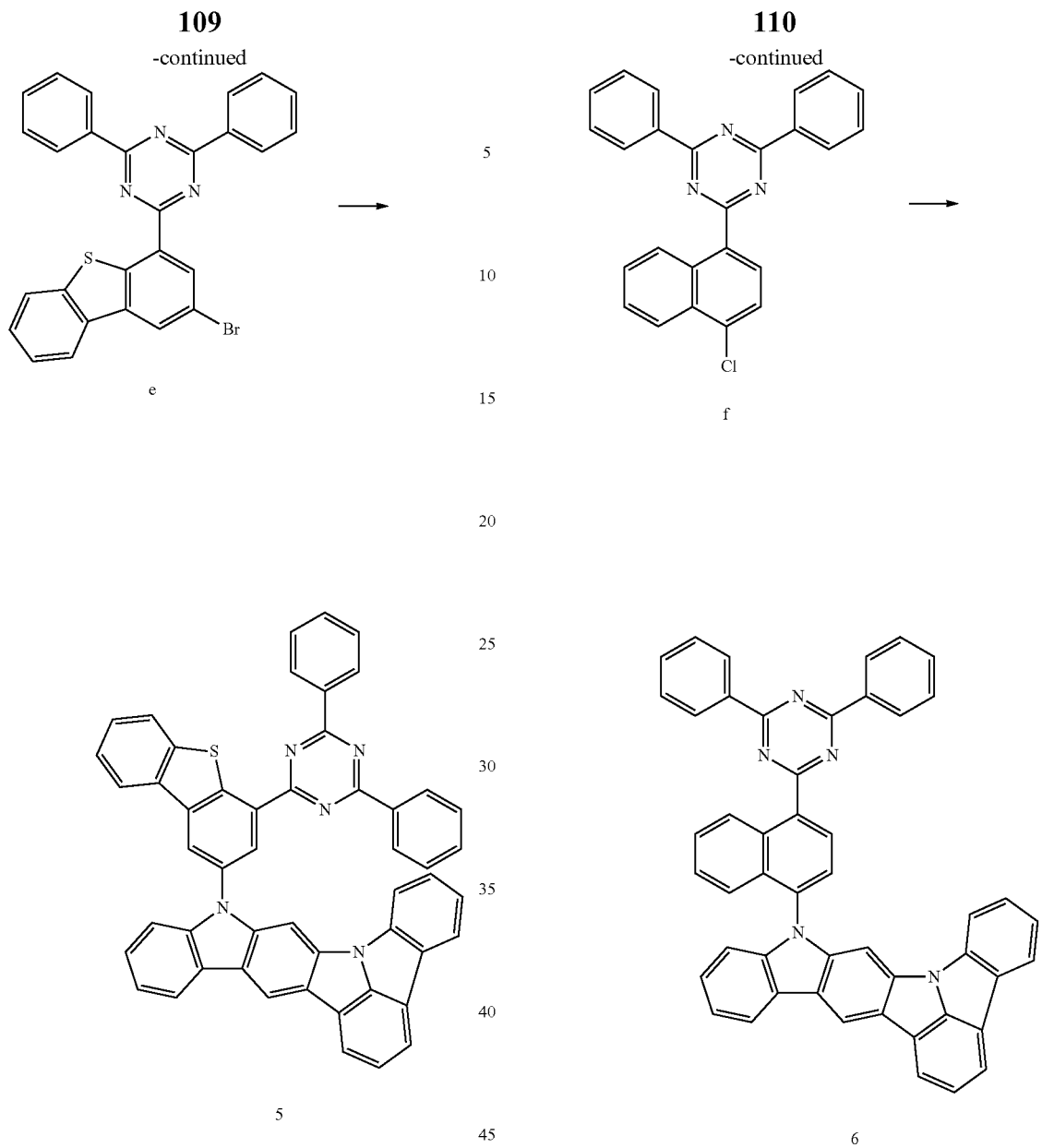

Compound 5 was prepared in the same manner as in Preparation of Compound 1 of Synthesis Example 1 except that Intermediate a was changed to Intermediate e. (MS[M+H]$^+$=743)

Synthesis Example 6: Synthesis of Compound 6

Compound 6 was prepared in the same manner as in Preparation of Compound 1 of Synthesis Example 1 except that Intermediate a was changed to Intermediate f. (MS[M+H]$^+$=687)

Synthesis Example 7: Synthesis of Compound 7

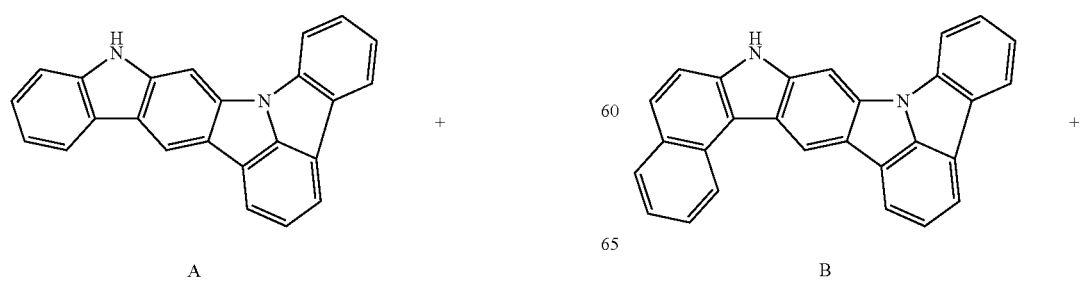

111 -continued

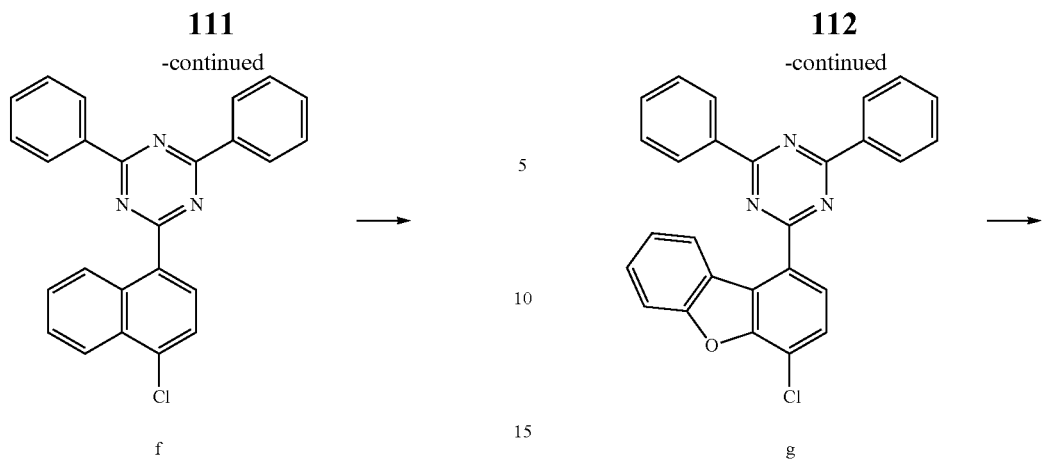

f

112 -continued g

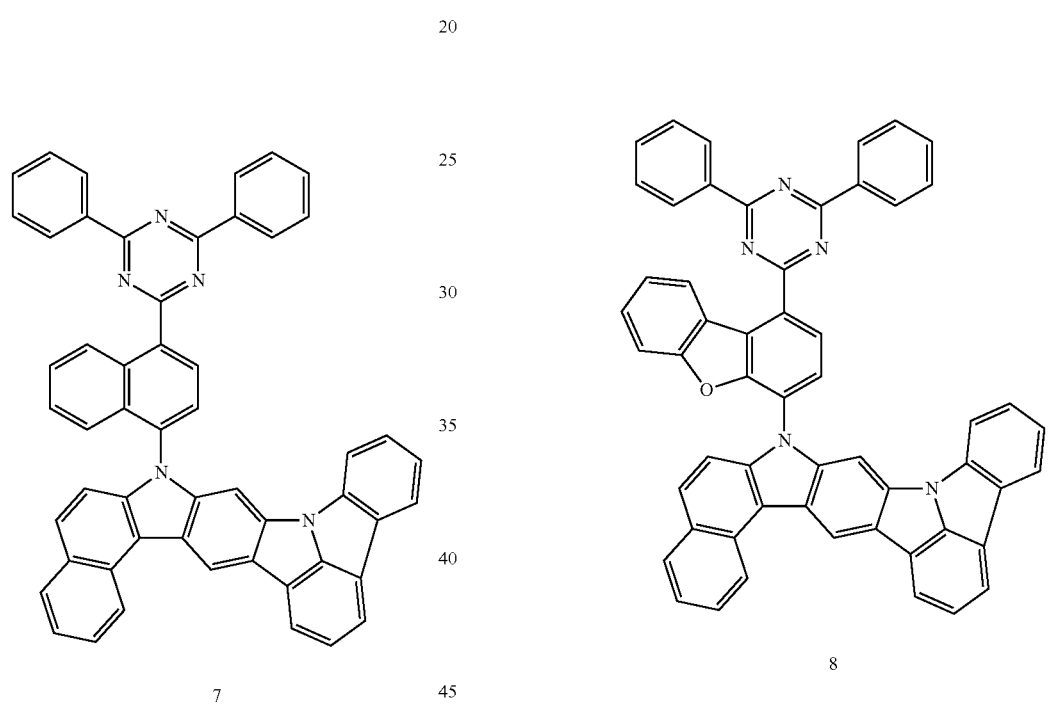

7

Compound 7 was prepared in the same manner as in Preparation of Compound 1 of Synthesis Example 1 except that Intermediate A was changed to Intermediate B, and Intermediate a was changed to Intermediate f. (MS[M+H]⁺= 737)

Synthesis Example 8: Synthesis of Compound 8

8

Compound 8 was prepared in the same manner as in Preparation of Compound 1 of Synthesis Example 1 except that Intermediate A was changed to Intermediate B, and Intermediate a was changed to Intermediate g. (MS[M+H]⁺= 777)

Synthesis Example 9: Synthesis of Compound 9

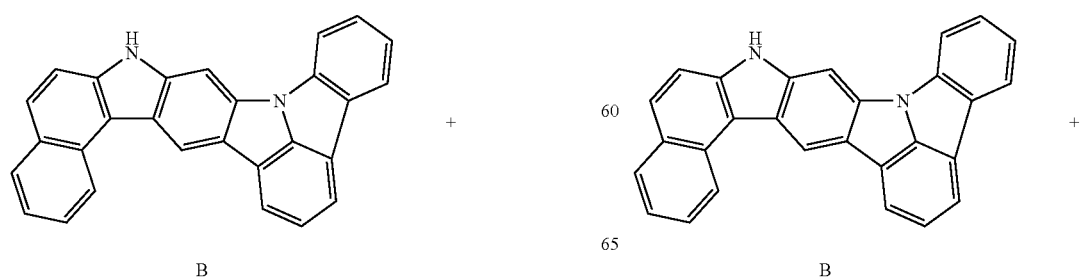

B                +                B                +

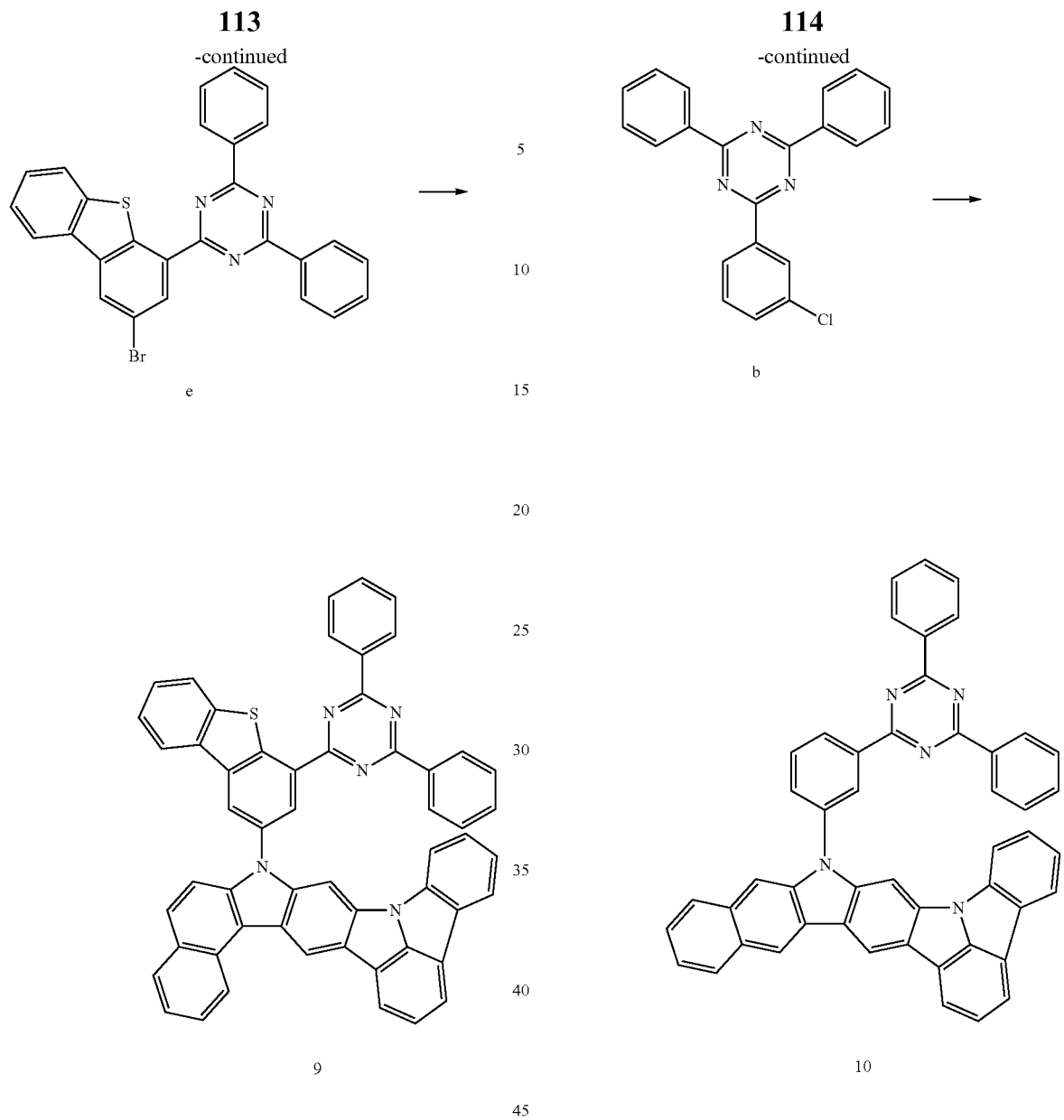

Compound 9 was prepared in the same manner as in Preparation of Compound 1 of Synthesis Example 1 except that Intermediate A was changed to Intermediate B, and Intermediate a was changed to Intermediate e. (MS[M+H]⁺= 793)

Compound 10 was prepared in the same manner as in Preparation of Compound 1 of Synthesis Example 1 except that Intermediate A was changed to Intermediate C, and Intermediate a was changed to Intermediate b. (MS[M+H]⁺= 687)

Synthesis Example 10: Synthesis of Compound 10

Synthesis Example 11: Synthesis of Compound 11

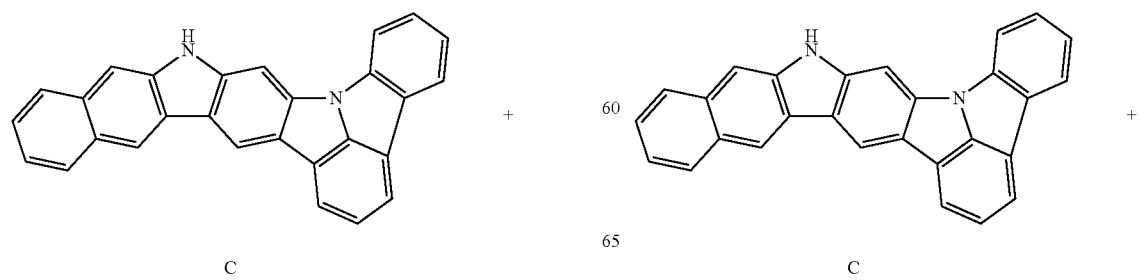

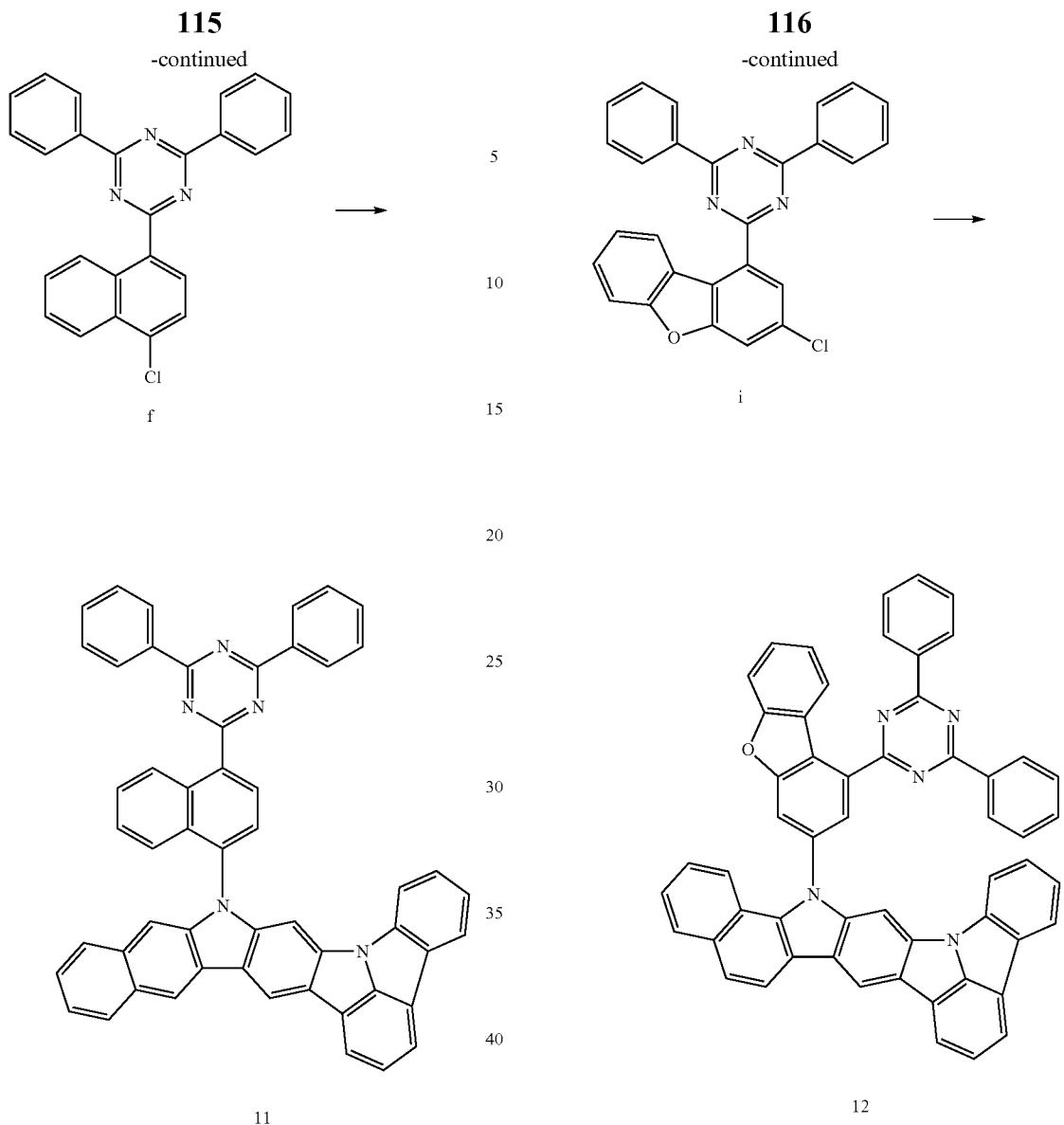

Compound 11 was prepared in the same manner as in Preparation of Compound 1 of Synthesis Example 1 except that Intermediate A was changed to Intermediate C, and Intermediate a was changed to Intermediate f. (MS[M+H]⁺= 737)

Compound 12 was prepared in the same manner as in Preparation of Compound 1 of Synthesis Example 1 except that Intermediate A was changed to Intermediate D, and Intermediate a was changed to Intermediate i. (MS[M+H]⁺= 777)

Synthesis Example 12: Synthesis of Compound 12

Synthesis Example 13: Synthesis of Compound 13

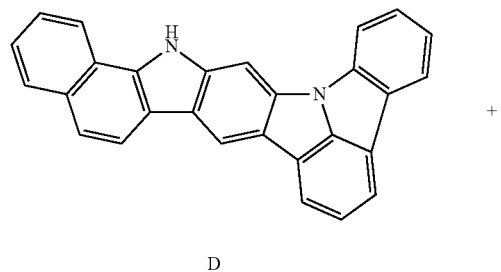

D +

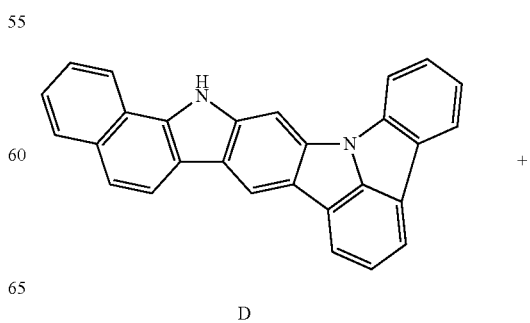

D +

-continued

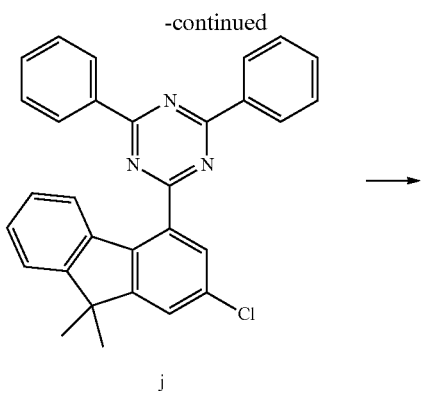

j

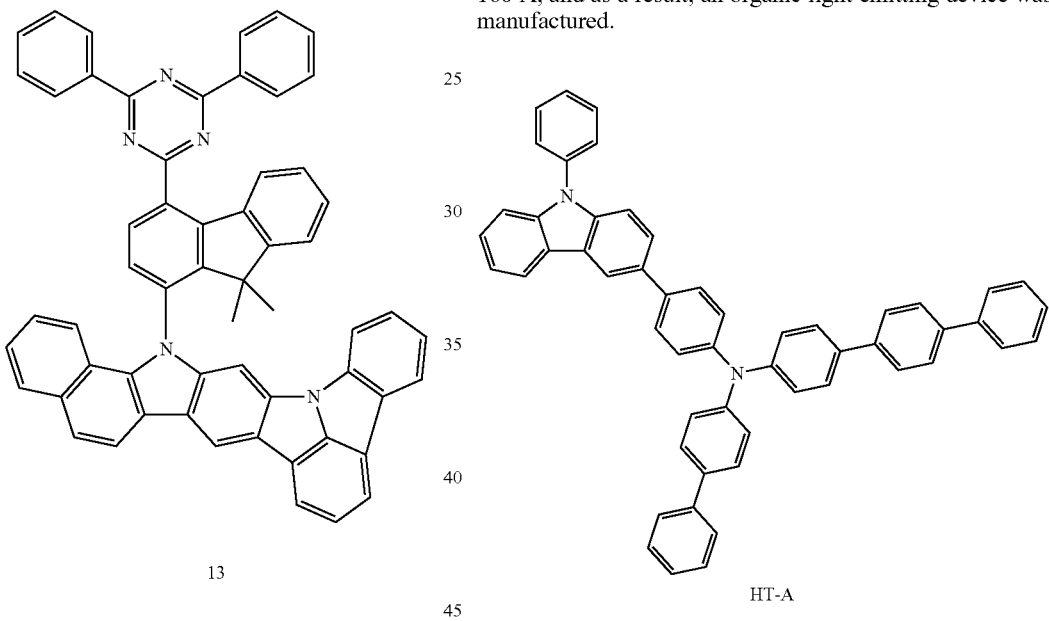

13

Compound 13 was prepared in the same manner as in Preparation of Compound 1 of Synthesis Example 1 except that Intermediate A was changed to Intermediate D, and Intermediate a was changed to Intermediate j. (MS[M+H]$^+$= 803)

EXPERIMENTAL EXAMPLES

Example 1-1

A glass substrate on which a thin film of indium tin oxide (ITO) coated in a thickness of 1,400 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum deposition apparatus.

On the transparent ITO electrode prepared as above, a hole transfer layer was formed by thermal vacuum depositing the following HT-A and 5% by weight of PD to a thickness of 100 Å and then depositing just a HT-A material to a thickness of 1150 Å. The following EB-A was thermal vacuum deposited to a thickness of 450 Å thereon as an electron blocking layer. Subsequently, a light emitting layer was vacuum deposited to a thickness of 400 Å using Compound 1 and 15% by weight (based on 100 parts by weight of Compound 1) of GD as a dopant. Then, the following HB-A was vacuum deposited to a thickness of 50 Å as a hole blocking layer. Subsequently, as an electron transfer and injection layer, the following ET-A and Liq in a ratio of 2:1 were thermal vacuum deposited to a thickness of 250 Å, and then LiF and magnesium in a ratio of 1:1 were vacuum deposited to a thickness of 30 Å. On the electron transfer and injection layer, a cathode was formed by depositing magnesium and silver in a ratio of 1:4 to a thickness of 160 Å, and as a result, an organic light emitting device was manufactured.

HT-A

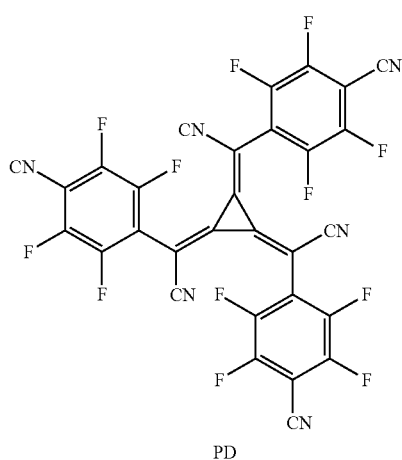

PD

119
-continued

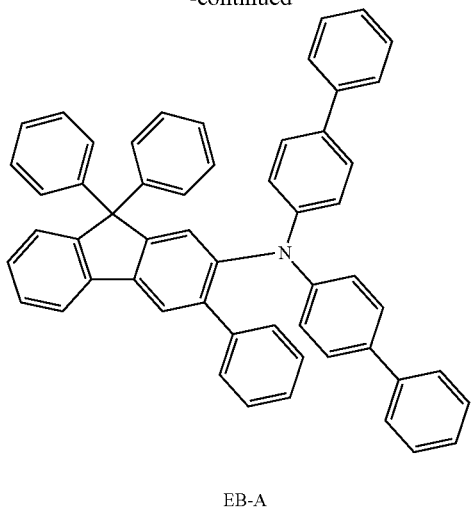

EB-A

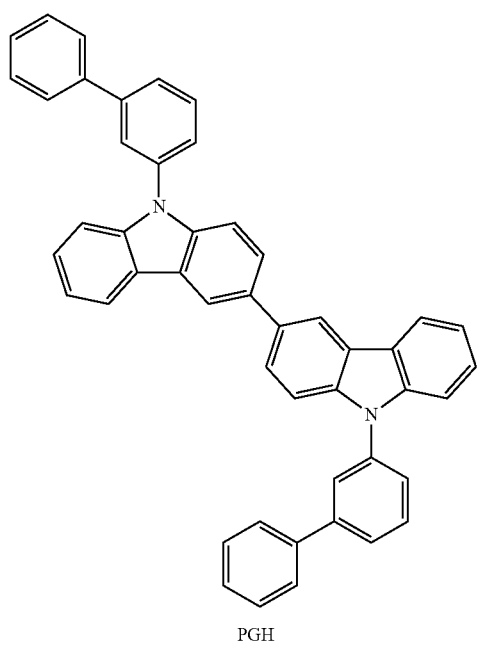

PGH

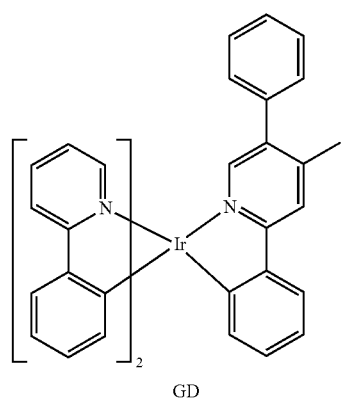

GD

120
-continued

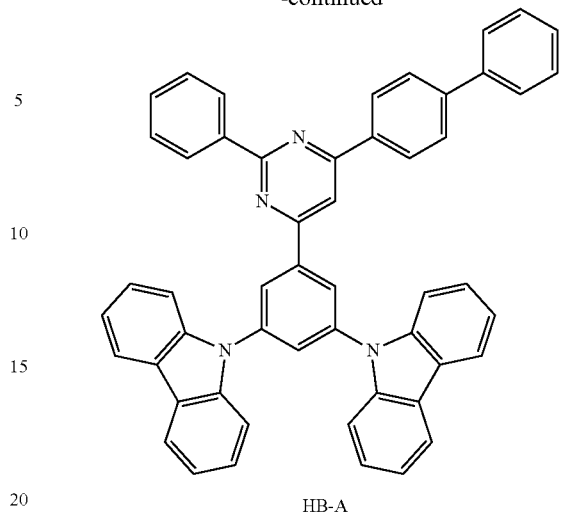

HB-A

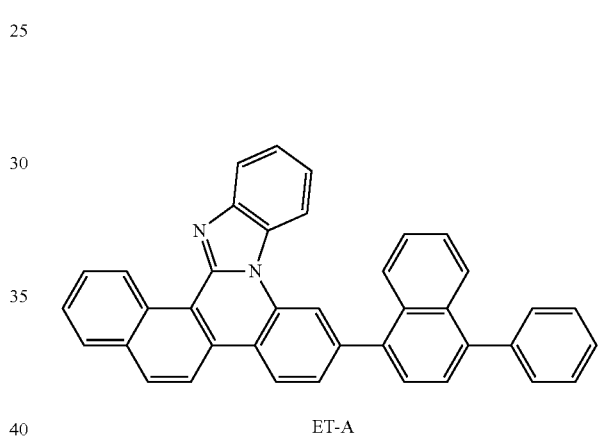

ET-A

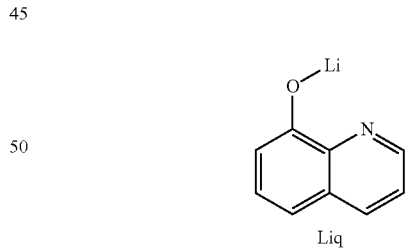

Liq

Example 1-2 to Example 1-7 and Comparative Example 1-1 to Comparative Example 1-5

Organic light emitting devices of Example 1-2 to Example 1-7 and Comparative Example 1-1 to Comparative Example 1-5 were each manufactured in the same manner as in Example 1-1 except that the host material was changed as in the following Table 1. Herein, when using a mixture of two types of compounds as the host, numbers in the parenthesis mean a weight ratio between the host compounds.

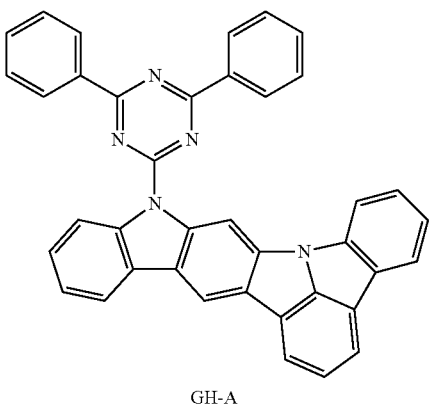

GH-A

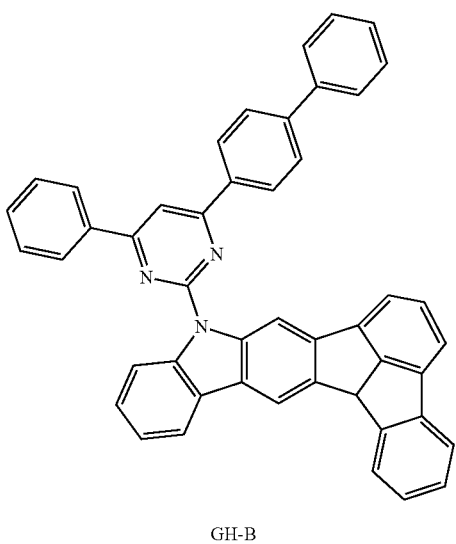

GH-B

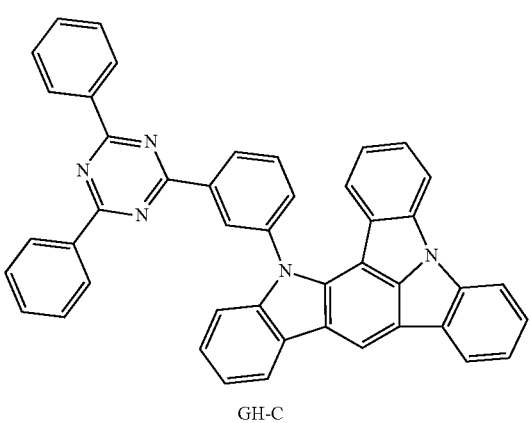

GH-C

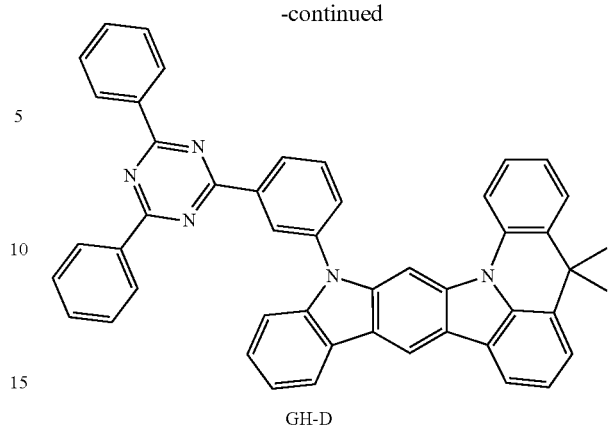

GH-D

Voltage, efficiency and lifetime ($LT_{95}$) were measured by applying a current to each of the organic light emitting devices manufactured in Example 1-1 to Example 1-7 and Comparative Example 1-2 to Comparative Example 1-5, and the results are shown in the following Table 1. Herein, the voltage and the efficiency were measured by applying current density of 10 mA/cm$^2$, and $LT_{95}$ means time taken for initial luminance decreasing to 95% at current density of 20 mA/cm$^2$.

TABLE 1

| | | @10 mA/cm$^2$ | | @20 mA/cm$^2$ |
|---|---|---|---|---|
| | Host Material | Voltage (V) | Efficiency (cd/A) | Lifetime ($LT_{95}$, hr) |
| Example 1-1 | Compound 1 | 4.58 | 49.5 | 100 |
| Example 1-2 | Compound 2 | 4.49 | 51.0 | 123 |
| Example 1-3 | Compound 3 | 4.59 | 49.9 | 105 |
| Example 1-4 | Compound 4 | 4.55 | 50.2 | 108 |
| Example 1-5 | Compound 5 | 4.50 | 50.8 | 117 |
| Example 1-6 | PGH:Compound 1 (60:40) | 4.37 | 56.5 | 145 |
| Example 1-7 | PGH:Compound 5 (60:40) | 4.38 | 56.1 | 140 |
| Comparative Example 1-1 | GH-A | 6.57 | 37.8 | 51 |
| Comparative Example 1-2 | GH-B | 8.10 | 32.1 | 35 |
| Comparative Example 1-3 | GH-C | 5.51 | 43.0 | 62 |
| Comparative Example 1-4 | GH-D | 4.63 | 44.5 | 58 |
| Comparative Example 1-5 | PGH:GH-A (60:40) | 5.82 | 32.0 | 64 |

The compound represented by Chemical Formula 1 has a structure in which a monocyclic nitrogen-containing heteroring unit having strong electron acceptor properties and a unit having strong electron donor properties by including two nitrogen atoms acting as an electron donor in the ring are linked through L. When strong two units with very different properties like GH-A or GH-B directly bond, internal charge transfer becomes too strong losing an ability to transfer other charges. The compound represented by Chemical Formula 1 mitigates internal charge transfer by introducing L between the two units and thereby separating the electron donor unit and the electron acceptor unit, which is advantageous for both hole and electron transfer, and as seen in Table 1, suitable properties as a light emitting layer host are obtained.

In addition, the nitrogen atoms of the electron donor unit are fused so as to be located in a meta position to each other, and, whereas the ortho position does not properly push electrons to the nitrogen atom linked to L and the para position as in GH-B pushes too excessively, the meta position allows a proper electron donor role and thereby performs a role of balancing hole and electron transfer.

Even with the same meta position, structural interference is severe when fused as in GH-C leading to a distorted structure or a broken conjugation due to rotation of the phenyl group used as a linker. On the other hand, when fused to be structurally separated from other units including L linked to the nitrogen atom as in the compound of Chemical Formula 1, structural interference is low and stability is high due to a flat structure, and as a result, properties of long lifetime are obtained when used in an organic electroluminescent device.

In addition, when having a structure in which an electron donor unit is linked through another element instead of a direct bond as in GH-D, bonding on both sides becomes weak around the corresponding element resulting in decreased material stability, and as a result, a shorter lifetime is obtained compared to the compound of Chemical Formula 1 of the present application.

As a result, it was seen that properties of low voltage, high efficiency and long lifetime were obtained when using the compound of Chemical Formula 1 as a host of the organic electroluminescent device.

Particularly, the effects were more significant when mixing with the compound of Chemical Formula 8 such as PGH, and more superior effects were obtained compared to when mixing compounds having different structures with the compound of Chemical Formula 8.

Example 2-1

A glass substrate on which indium tin oxide (ITO) was coated as a thin film to a thickness of 1,400 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum deposition apparatus.

On the transparent ITO electrode prepared as above, a hole injection layer was formed by consecutively thermal vacuum depositing the following HI-B and hexanitrile hexaazatriphenylene (HAT-CN) to thicknesses of 800 Å and 50 Å, respectively. The following HT-B was vacuum deposited to a thickness of 800 Å thereon as a hole transfer layer, and then the following EB-B was thermal vacuum deposited to a thickness of 600 Å thereon as an electron blocking layer. Subsequently, Compound 6 and 2% by weight (based on 100 parts by weight of Compound 6) of dopant RD were vacuum deposited to a thickness of 400 Å as a light emitting layer. Then, as an electron transfer and injection layer, the following ET-B and Liq in a ratio of 1:1 were thermal vacuum deposited to a thickness of 360 Å, and then Liq was vacuum deposited to a thickness of 5 Å.

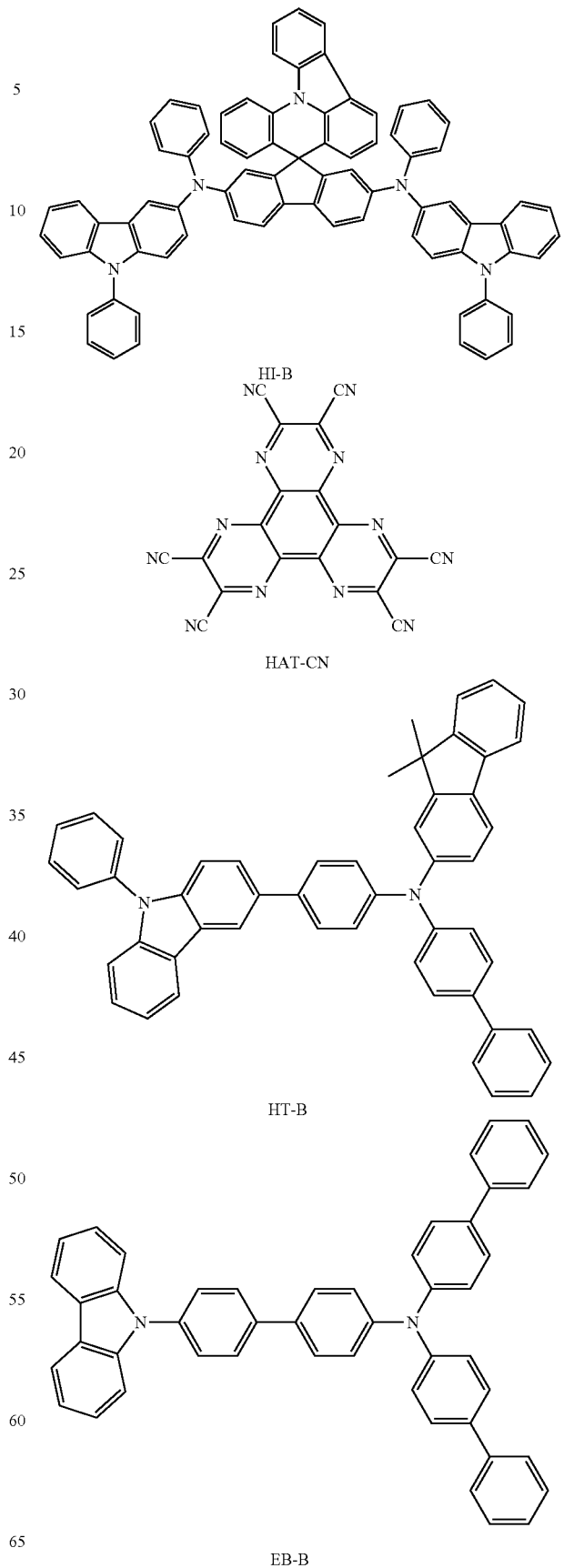

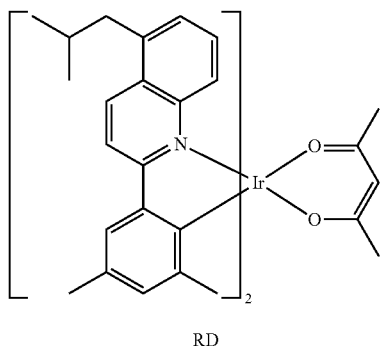

RD

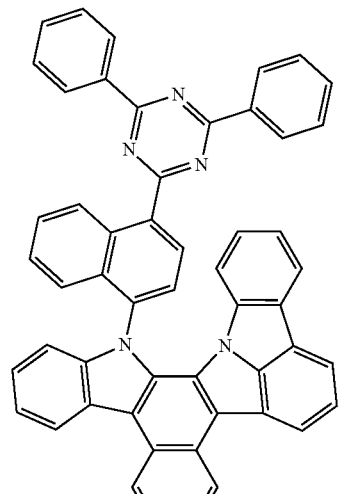

RH-A

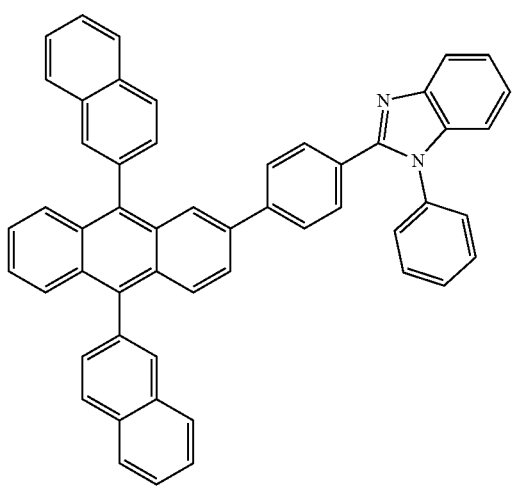

ET-B

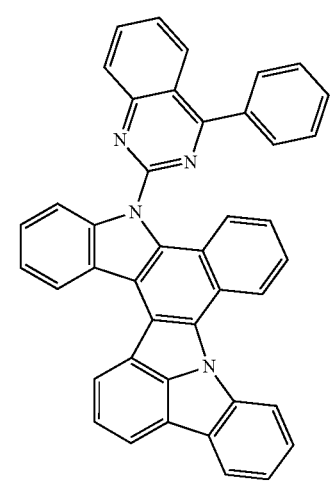

RH-B

On the electron transfer and injection layer, a cathode was formed by consecutively depositing magnesium and silver in a ratio of 10:1 to a thickness of 220 Å, and depositing aluminum to a thickness of 1000 Å, and as a result, an organic light emitting device was manufactured.

Example 2-2 to Example 2-8 and Comparative Example 2-1 to Comparative Example 2-3

Organic light emitting devices of Example 2-2 to Example 2-8 and Comparative Example 2-1 to Comparative Example 2-3 were each manufactured in the same manner as in Example 2-1 except that the host material was changed as in the following Table 2.

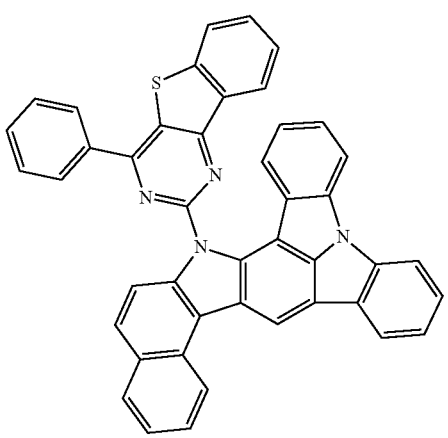

RH-C

Voltage, efficiency and lifetime were measured by applying a current to each of the organic light emitting devices manufactured in Example 2-1 to Example 2-8 and Comparative Example 2-1 to Comparative Example 2-3, and the results are shown in the following Table 2. Herein, the voltage and the efficiency were measured by applying current density of 10 mA/cm$^2$, and $LT_{97}$ means time taken for initial luminance decreasing to 97% at current density of 20 mA/cm$^2$.

TABLE 2

| | | @10 mA/cm$^2$ | | @20 mA/cm$^2$ |
|---|---|---|---|---|
| | Host Material | Voltage (V) | Efficiency (cd/A) | Lifetime ($LT_{97}$, hr) |
| Example 2-1 | Compound 6 | 4.75 | 22.5 | 100 |
| Example 2-2 | Compound 7 | 4.74 | 22.3 | 107 |
| Example 2-3 | Compound 8 | 4.76 | 22.0 | 101 |
| Example 2-4 | Compound 9 | 4.71 | 22.8 | 106 |
| Example 2-5 | Compound 10 | 4.78 | 22.1 | 100 |
| Example 2-6 | Compound 11 | 4.82 | 22.3 | 96 |
| Example 2-7 | Compound 12 | 4.96 | 21.6 | 96 |
| Example 2-8 | Compound 13 | 4.96 | 21.2 | 95 |
| Comparative Example 2-1 | RH-A | 5.23 | 18.1 | 62 |
| Comparative Example 2-2 | RH-B | 6.03 | 14.1 | 63 |
| Comparative Example 2-3 | RH-C | 5.12 | 17.2 | 43 |

Structures in which the compound represented by Chemical Formula 1 of the present disclosure includes a naphthalene ring have lower triplet energy while retaining properties as a light emitting layer host, and properties advantageous for energy transfer to a red phosphorescent dopant are added.

Herein, it is advantageous as the naphthalene ring is closer to the position linked to the nitrogen-containing heterring acting as an electron acceptor, and rather than being located between two nitrogen atoms as in RH-A or RH-B, being located at position A or position L of Chemical Formula 1 is advantageous as a host. When an electron donor unit and an electron acceptor unit are linked as in Chemical Formula 1, it is likely to be in a charge transfer state internally, and involving the naphthalene ring, a unit having low triplet energy, thereto is advantageous in stabilizing the triplet state.

Even when naphthalene is located in L as in RH-A or naphthalene is located in the A ring as in RH-C, the structure is distorted or a dihedral angle between the electron donor and the electron acceptor increases when there are severe structural interference in the fused structure, and as a result, the conjugation is broken, which is disadvantageous for energy transfer.

Accordingly, as seen in Table 2, properties of low voltage, high efficiency and long lifetime are obtained even when the compound is used as a host of a red light emitting layer, and thereby an optimum device may be obtained.

The invention claimed is:

1. A compound of the following Chemical Formula 1:

[Chemical Formula 1]

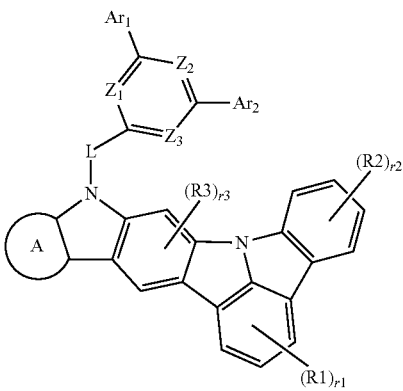

wherein, in Chemical Formula 1,

Ar$_1$ and Ar$_2$ are the same as or different from each other, and are each independently an aryl group having 6 to 30 carbon atoms that is unsubstituted or substituted with deuterium, or a heterocyclic group having 2 to 30 carbon atoms that is unsubstituted or substituted with deuterium, Z1 to Z3 are N, L is an arylene group having 6 to 30 carbon atoms that is unsubstituted or substituted with deuterium, or a divalent heterocyclic group having 2 to 30 carbon atoms that is unsubstituted or substituted with deuterium, A is a benzene or a naphthalene, R1 to R3 are the same as or different from each other, and are each independently hydrogen or deuterium, r1 is an integer of 0 to 3, r2 is an integer of 0 to 4, r3 is an integer of 0 to 2, when r1 and r2 are 2 or greater, the two or more groups in parentheses are the same as or different from each other, and when r3 is 2, the two groups in parentheses are the same as or different from each other.

2. The compound of claim 1, wherein the compound of Chemical Formula 1 is any one of the following Chemical Formulae 2 to 5:

[Chemical Formula 2]

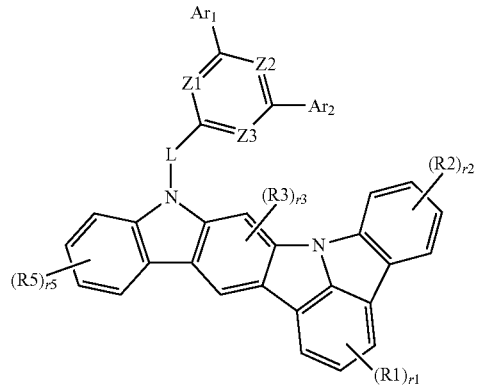

[Chemical Formula 3]

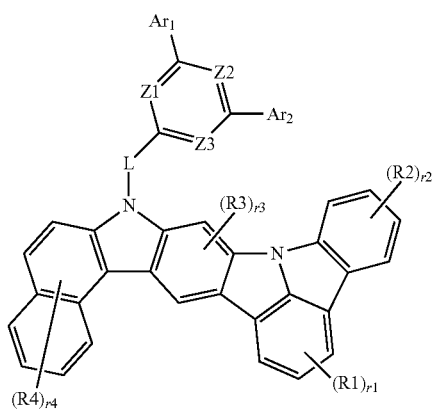

[Chemical Formula 4]

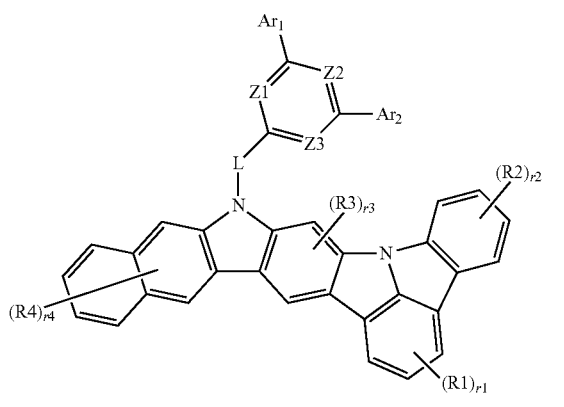

[Chemical Formula 5]

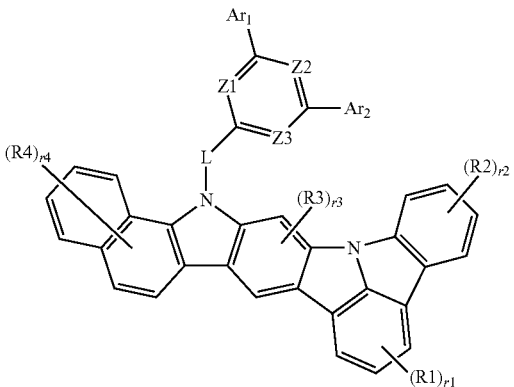

wherein, in Chemical Formulae 2 to 5,

Ar$_1$, Ar$_2$, Z1 to Z3, L, R1 to R3 and r1 to r3 are the same as defined in Chemical Formula 1, R4 and R5 are the same as or different from each other, and are each independently hydrogen or deuterium, r4 is an integer of 0 to 6, r5 is an integer of 0 to 4, and when r4 and r5 are 2 or greater, the two or more groups in parentheses are the same as or different from each other.

3. The compound of claim 1, wherein L is any one of the following structures:

wherein,

Y1 to Y3 are the same as or different from each other, and are each independently hydrogen, deuterium, a halogen group, a cyano group, an alkyl group having 1 to 20 carbon atoms that is unsubstituted or substituted with deuterium, an aryl group having 6 to 30 carbon atoms that is unsubstituted or substituted with deuterium.

4. The compound of claim 1, wherein Ar$_1$ and Ar$_2$ are the same as or different from each other, and are each independently any one of the following structures:

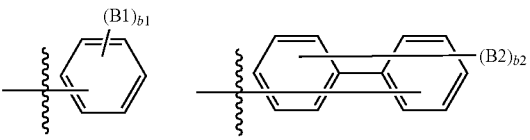

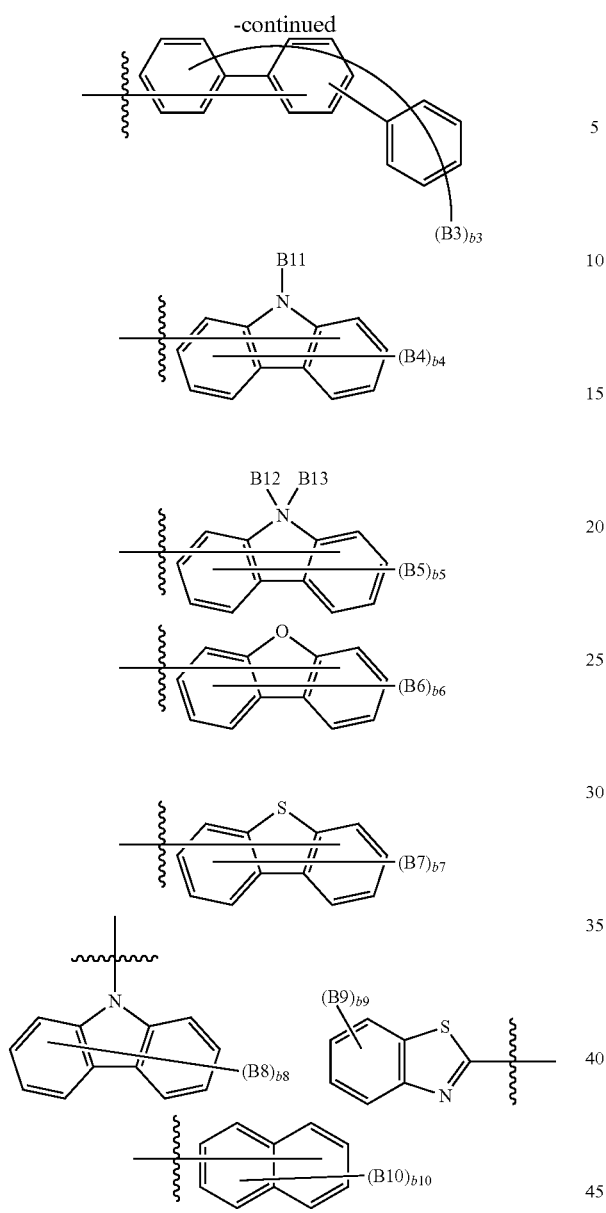

wherein,

B1 to B13 are the same as or different from each other, and are each independently hydrogen or deuterium, b1 is an integer of 0 to 5, b2 is an integer of 0 to 9, b3 is an integer of 0 to 13, b4 to b7 are each an integer of 0 to 7, b8 is an integer of 0 to 8, b9 is an integer of 0 to 4, b10 is an integer of 0 to 7, and when b1 to b10 are 2 or greater, the two or more groups in parentheses are the same as or different from each other.

5. The compound of claim 1, wherein the compound of Chemical Formula 1 is any one compound selected from the group consisting of the following compounds:

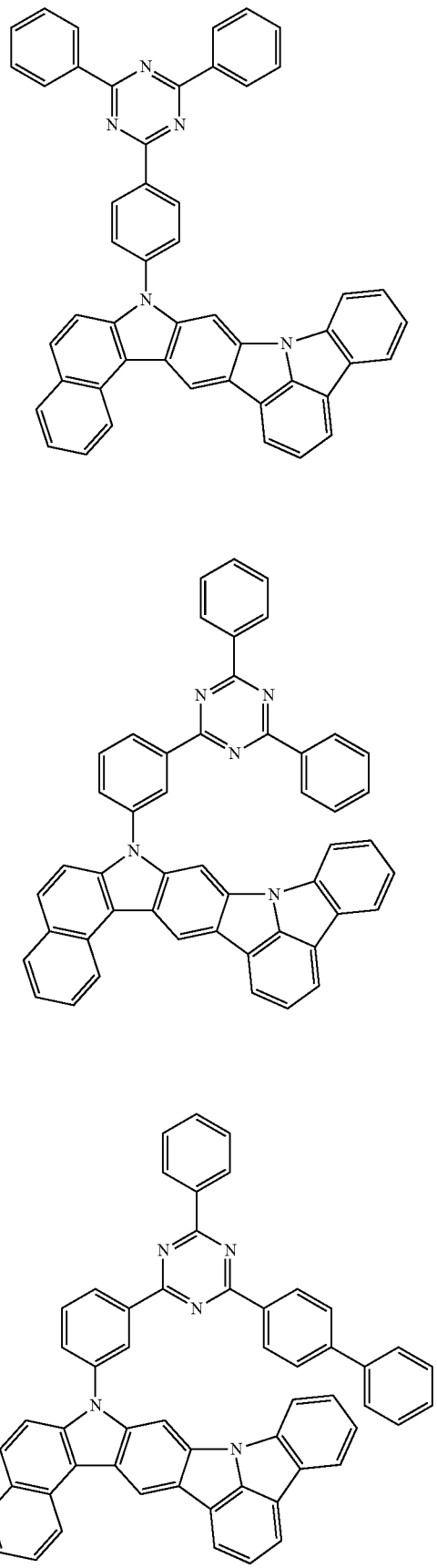

133
-continued
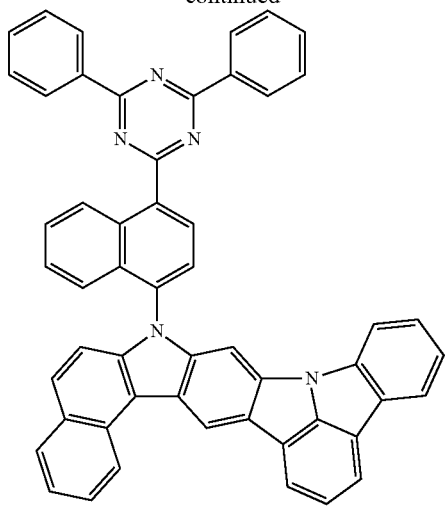
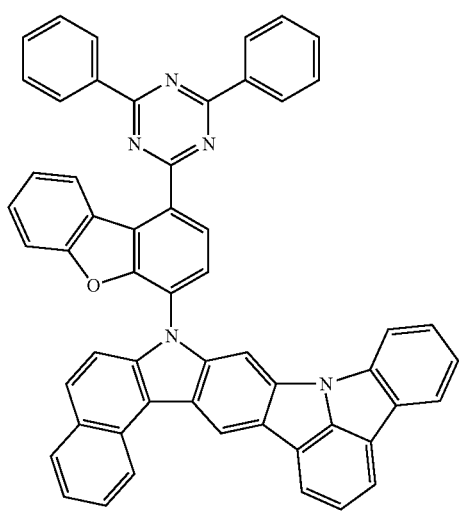
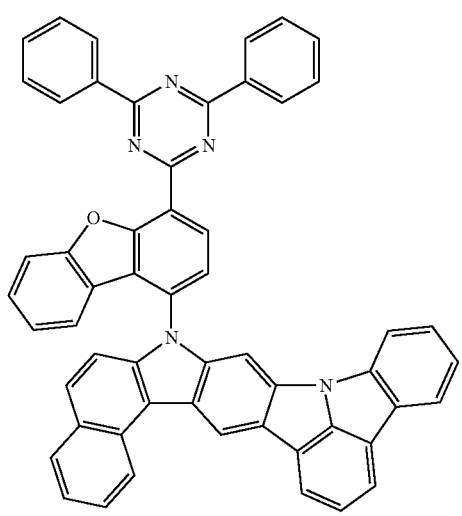
134
-continued
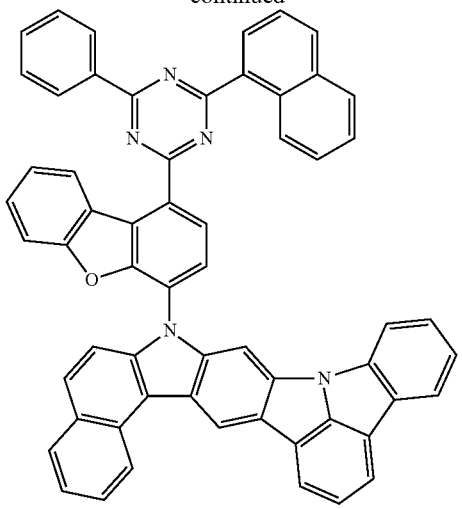
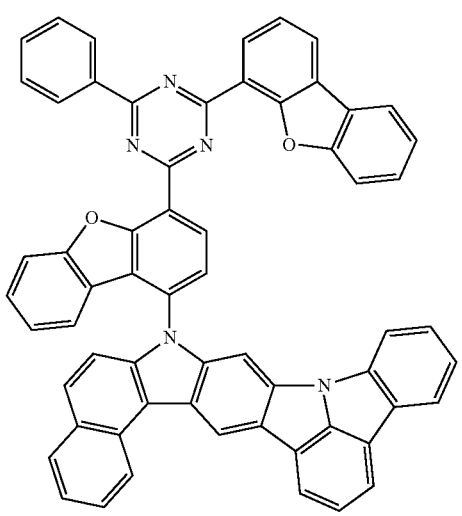
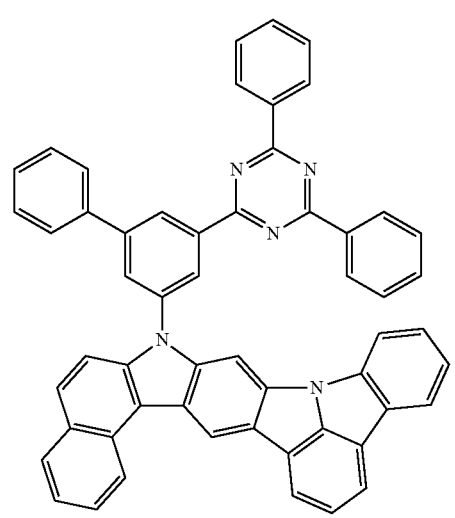

135
-continued
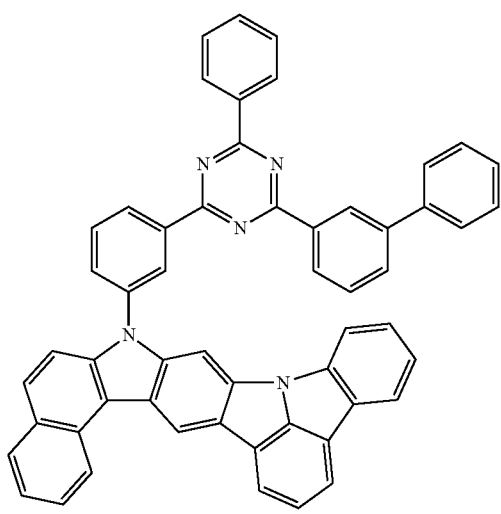
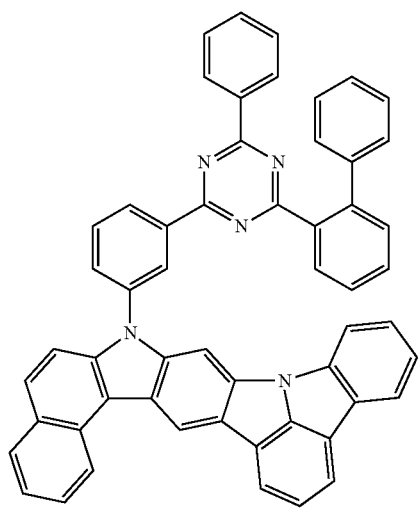
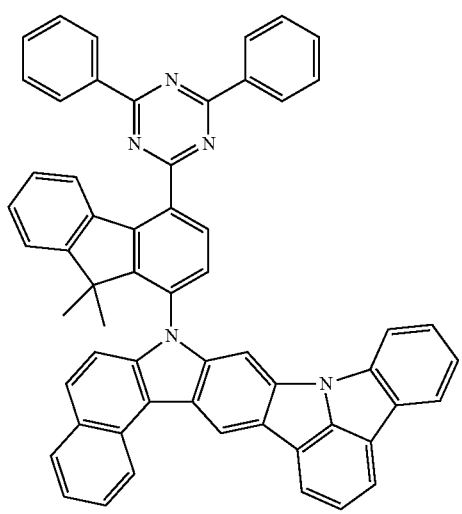
136
-continued
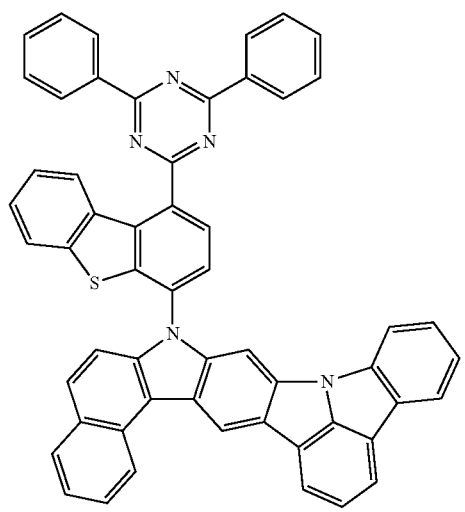
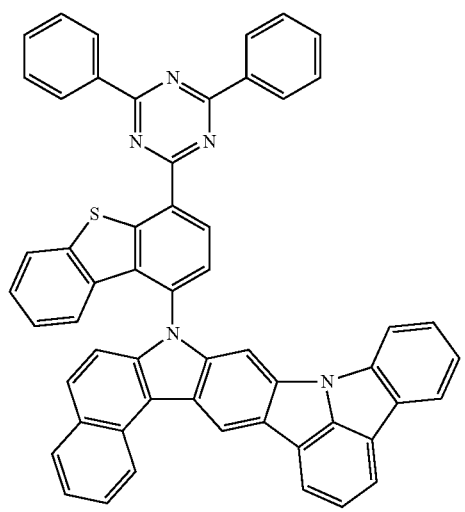
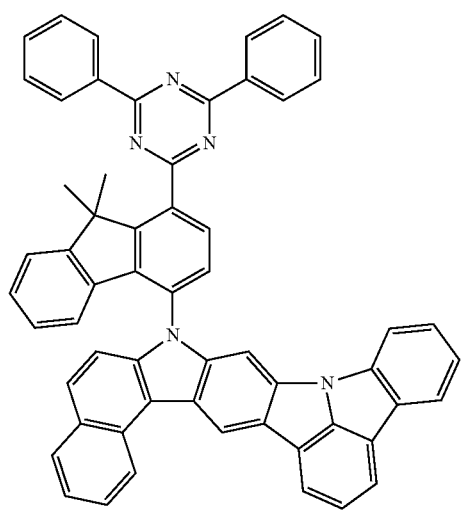

137
-continued
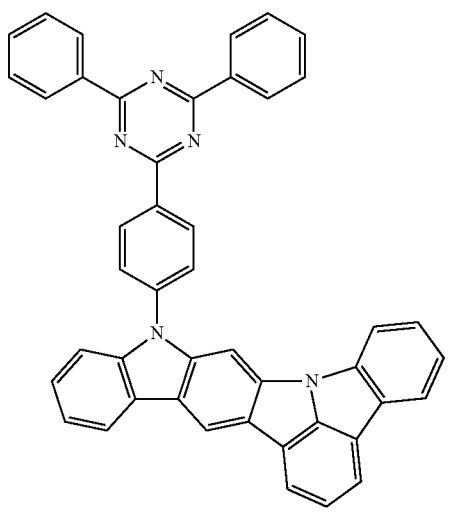
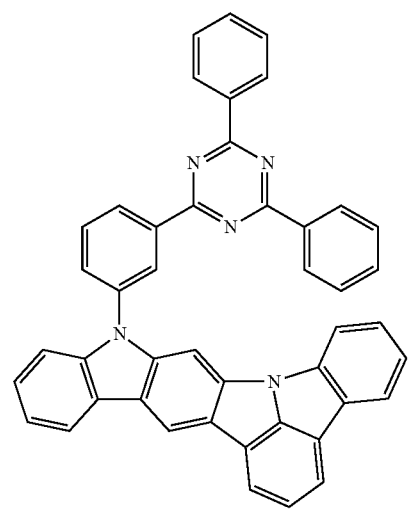
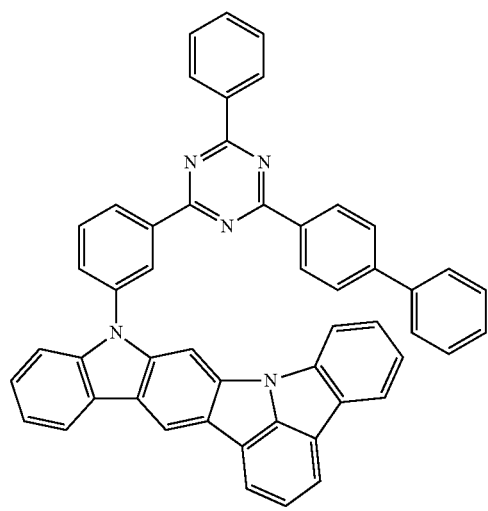
138
-continued
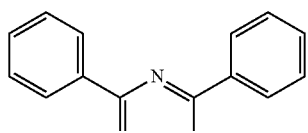
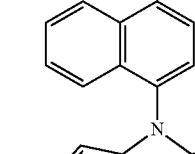
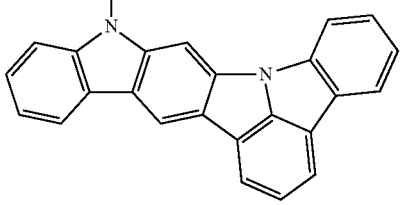
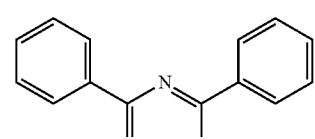
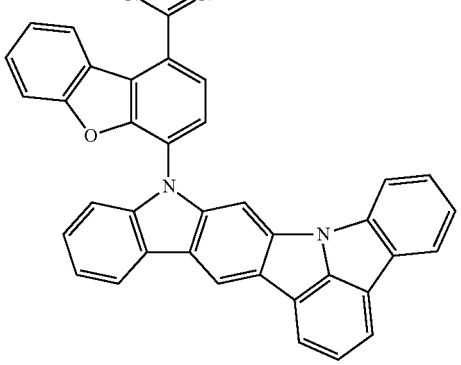
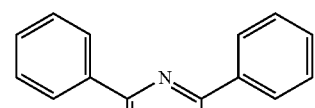
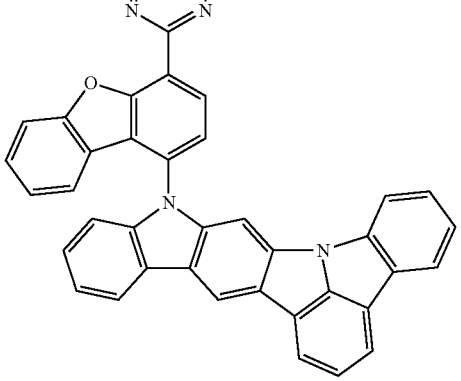

139
-continued
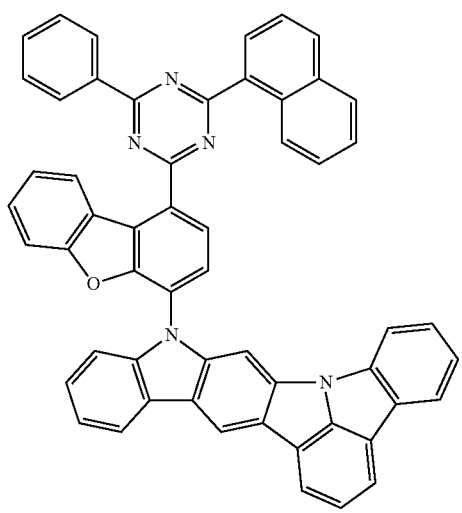
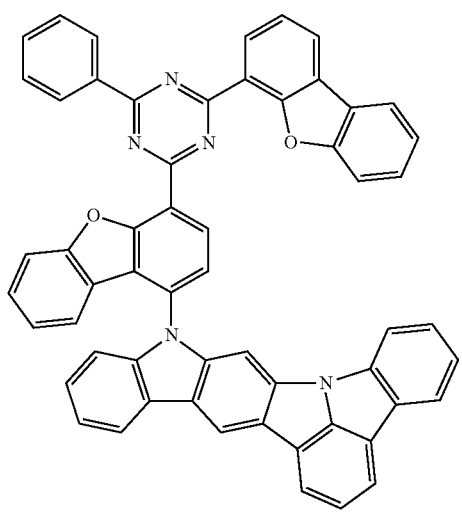
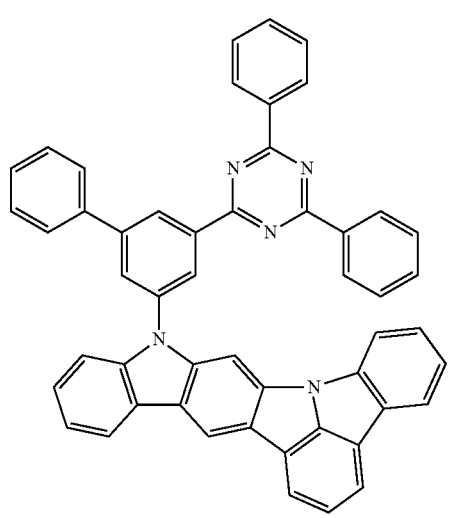
140
-continued
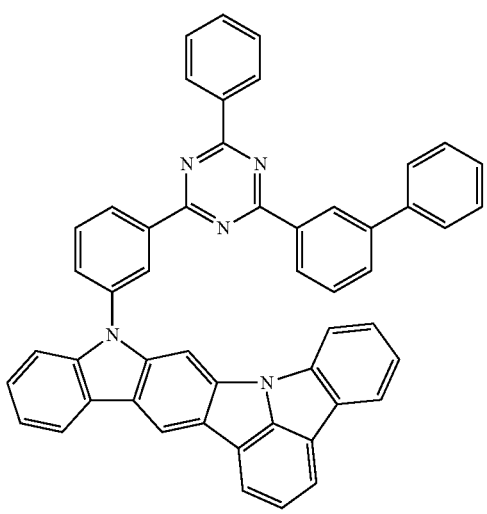
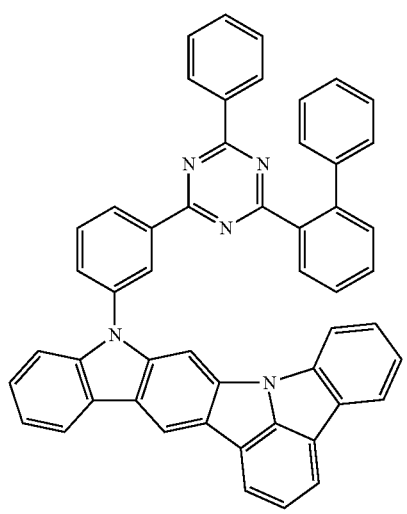
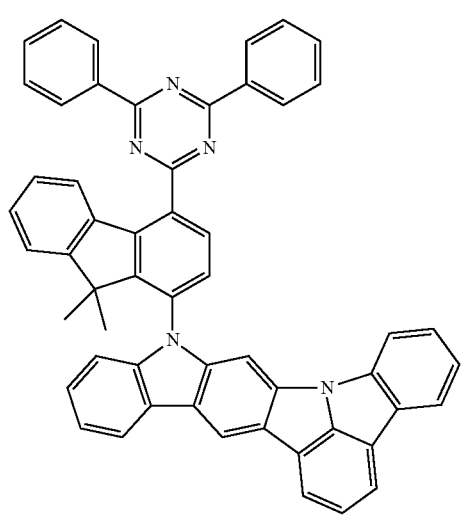

141
-continued
142
-continued
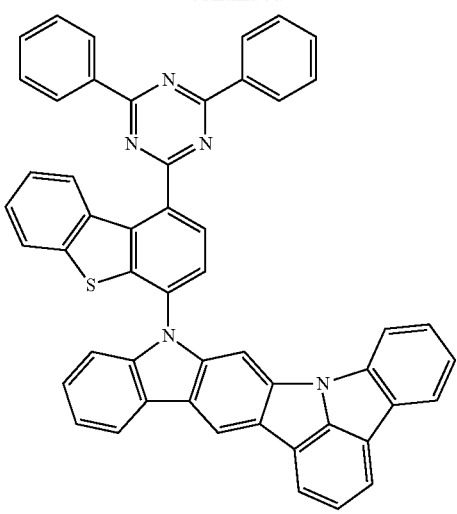
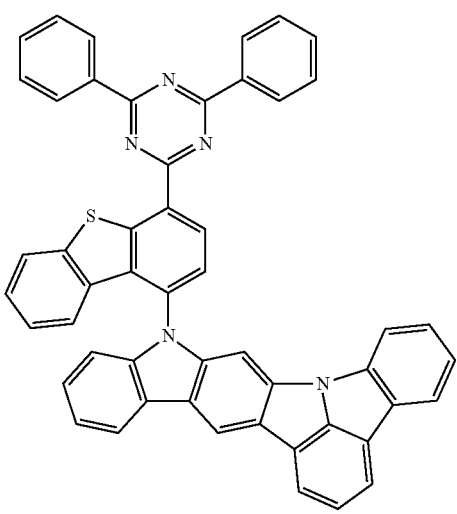
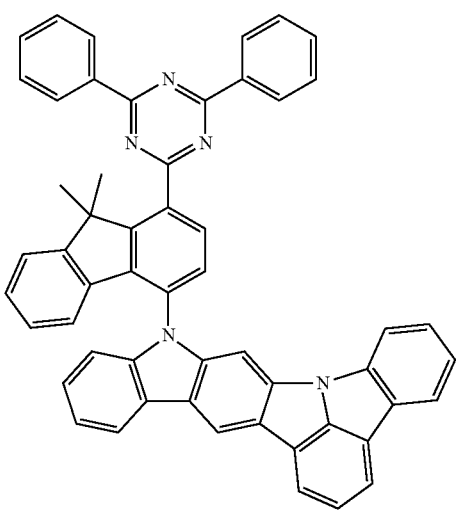
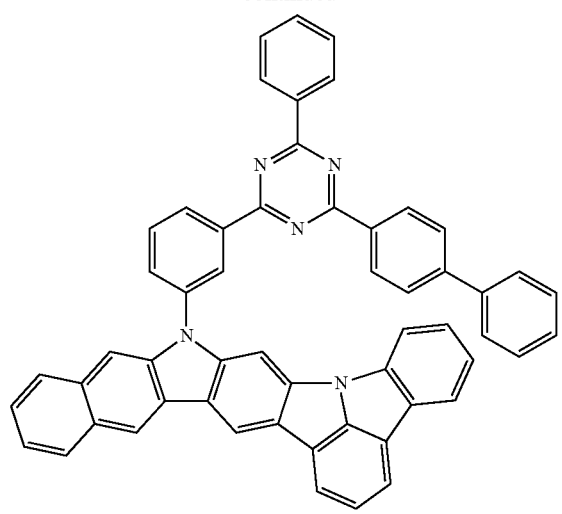
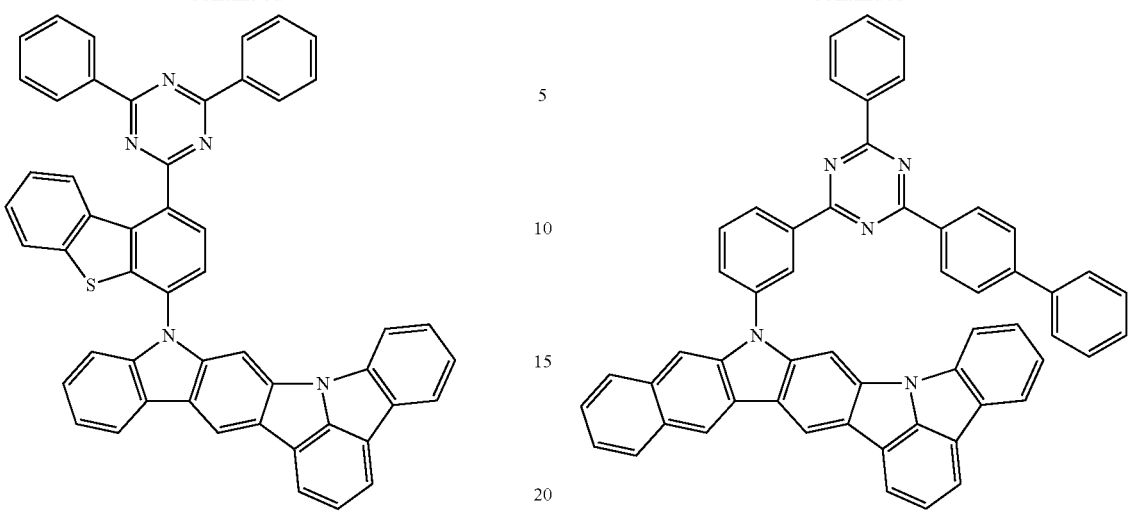
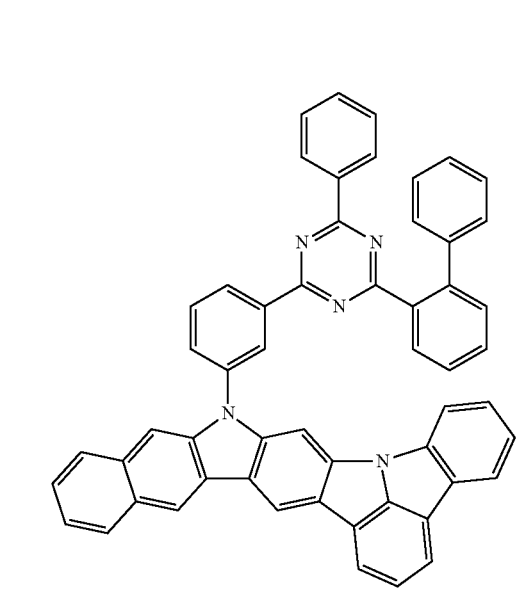

143
-continued
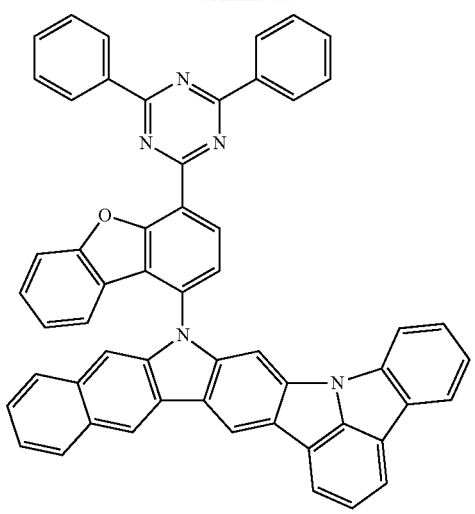
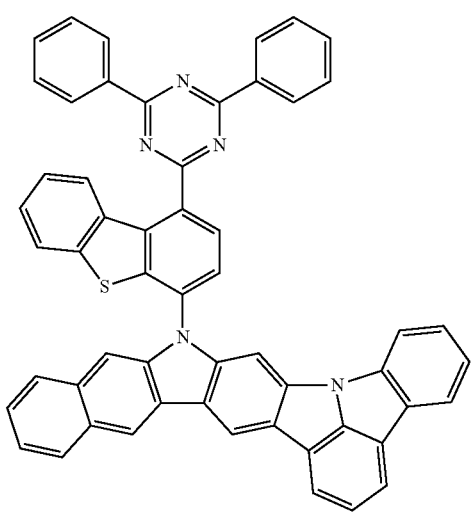
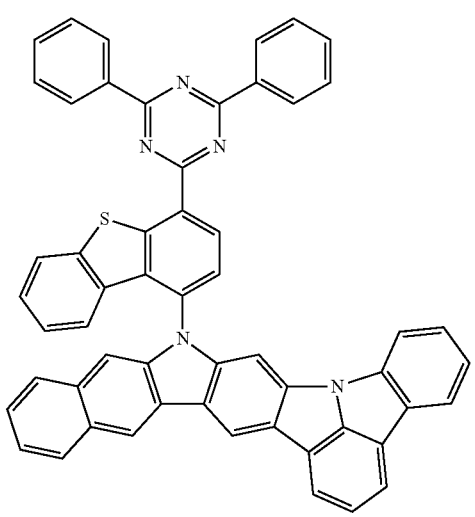
144
-continued
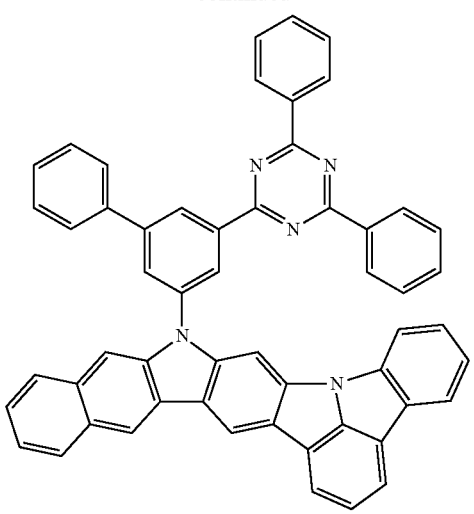
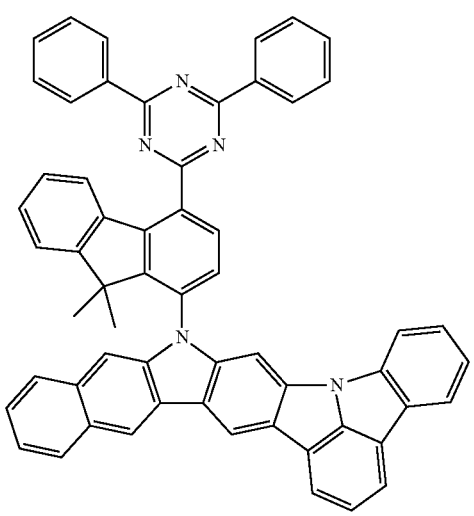
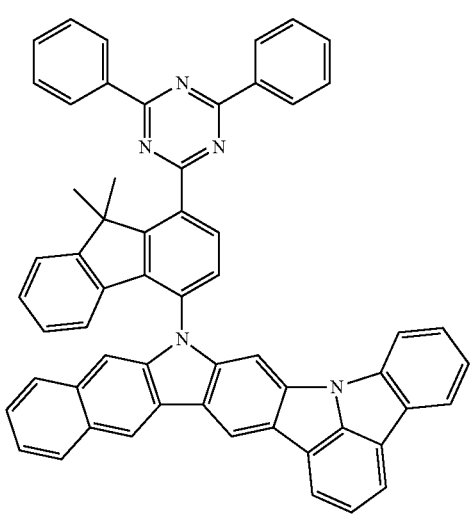

145
-continued
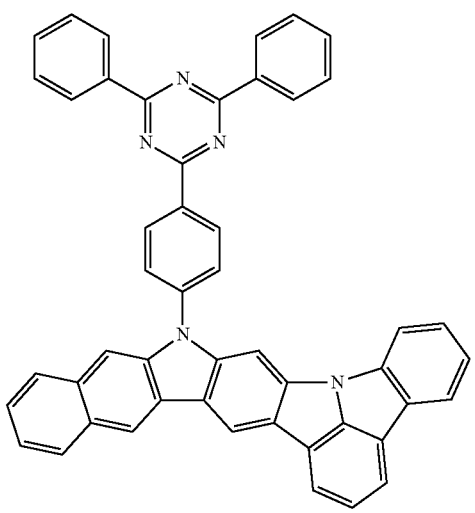
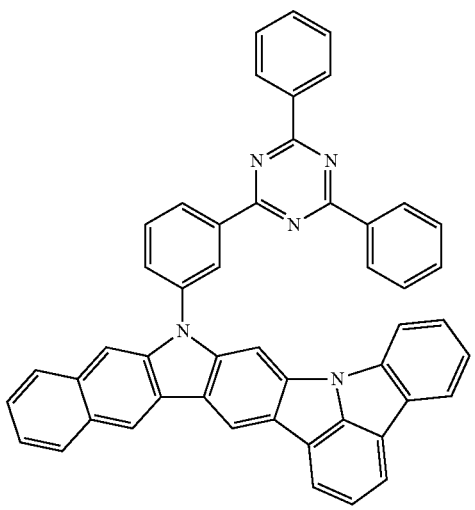
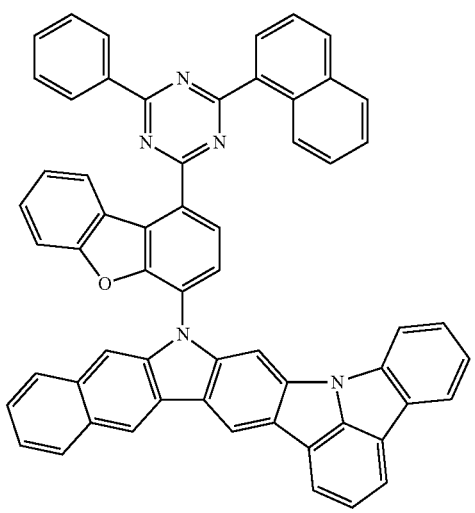
146
-continued
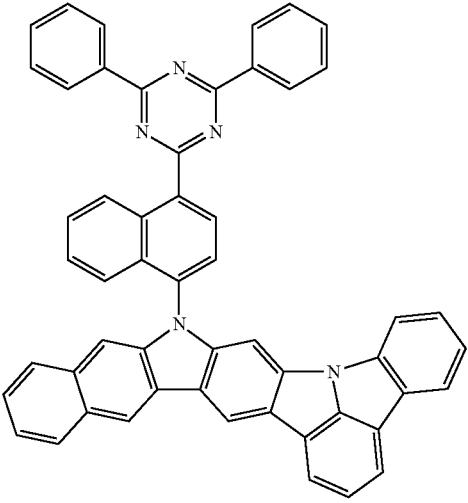
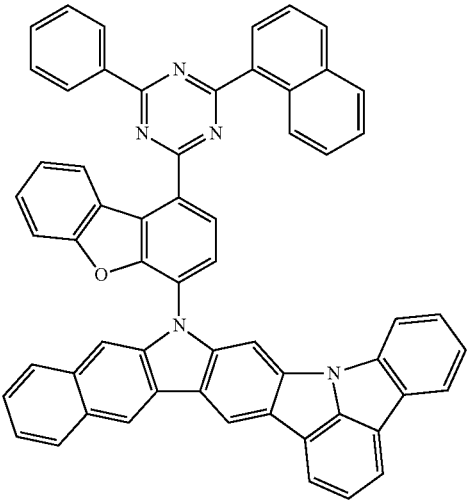

147
-continued
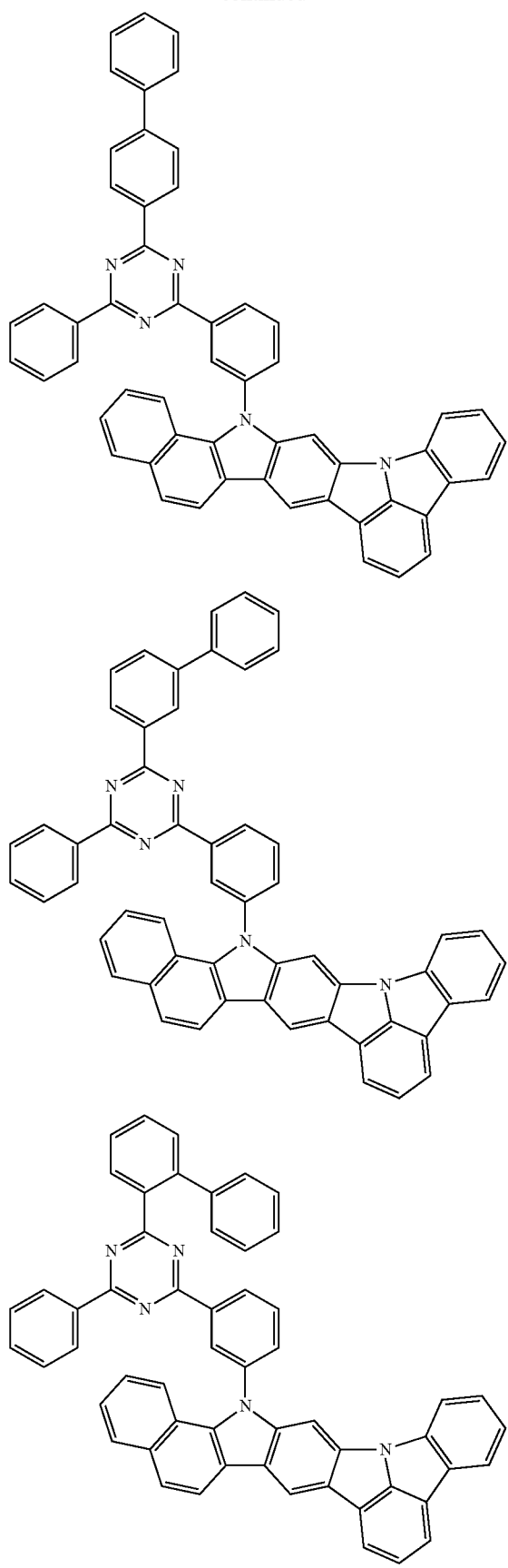
148
-continued
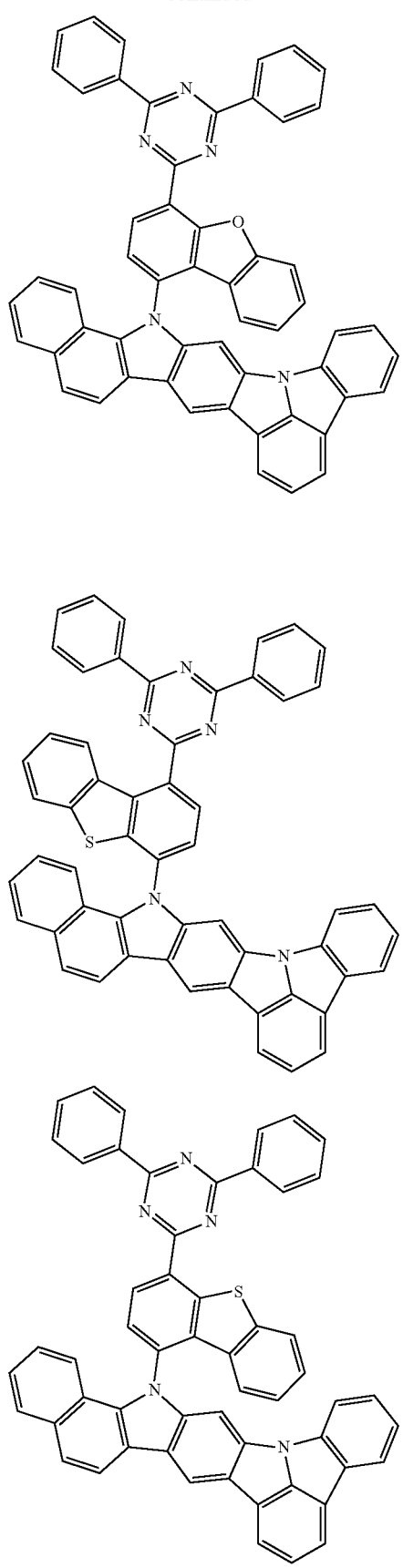

149
-continued
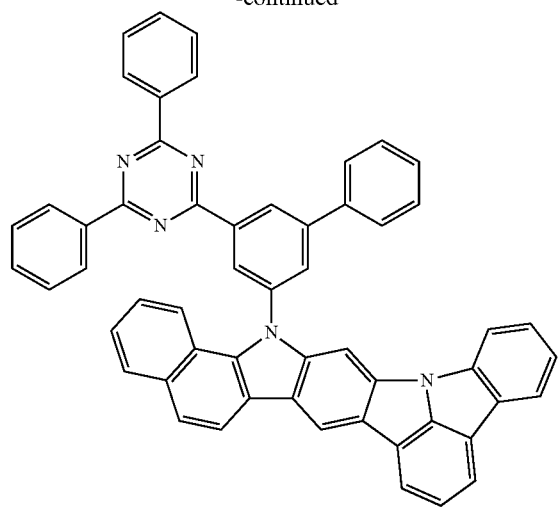
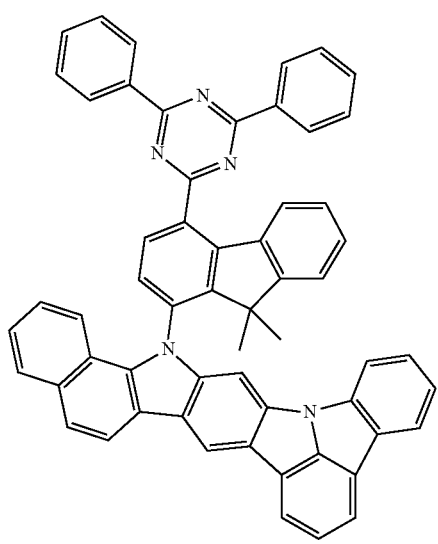
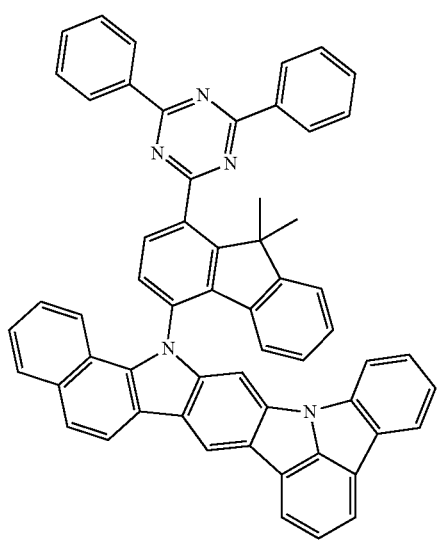
150
-continued
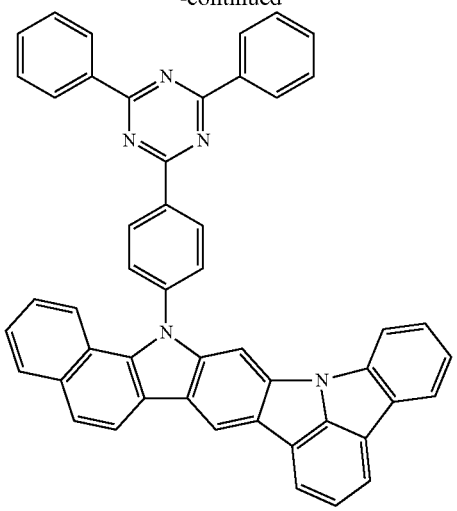
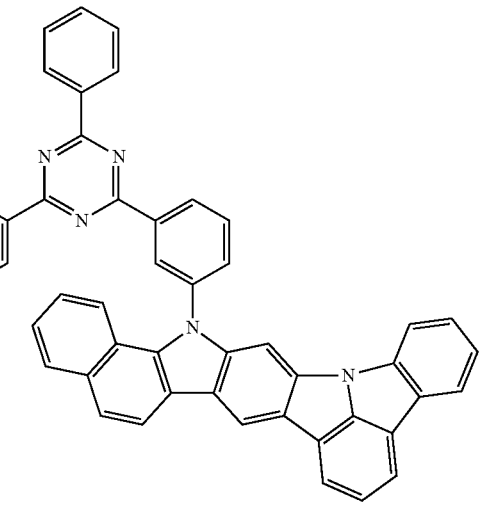
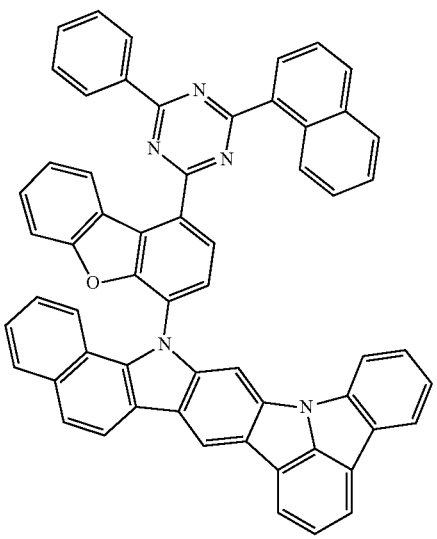

151
-continued
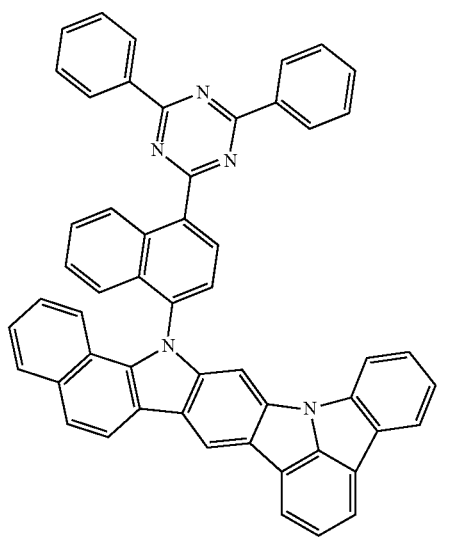
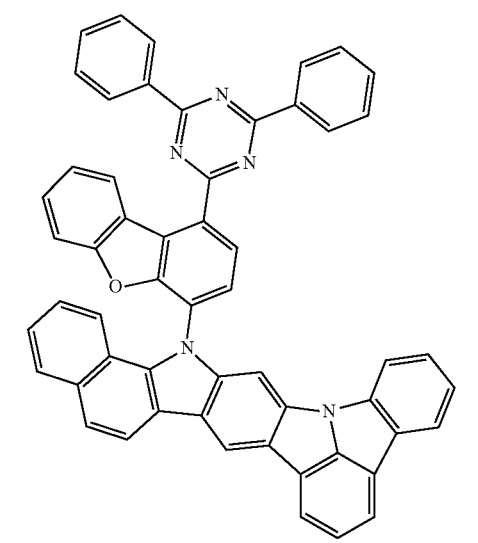
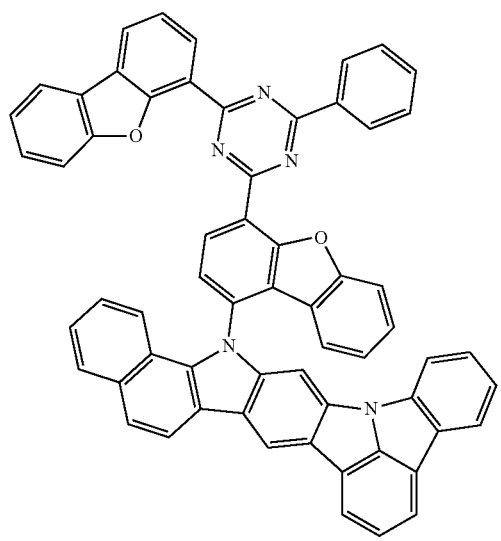
152
-continued
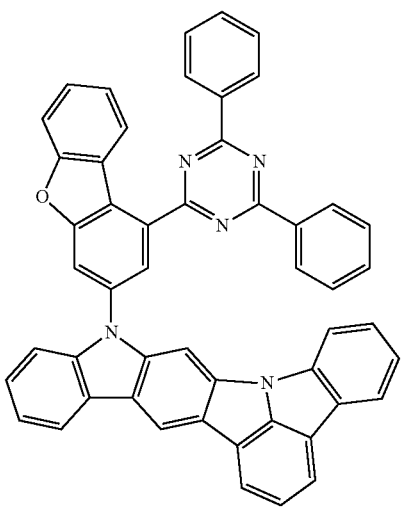
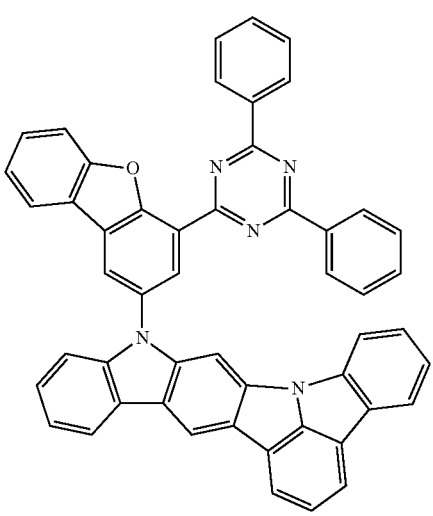
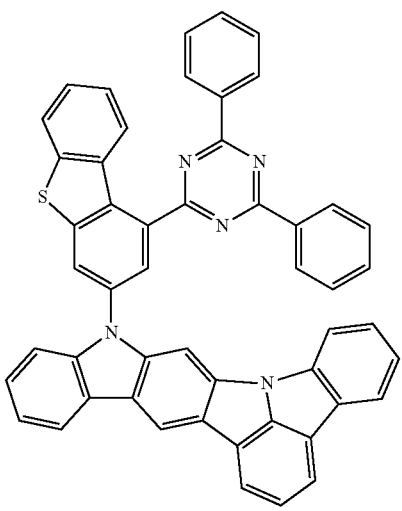

153
-continued
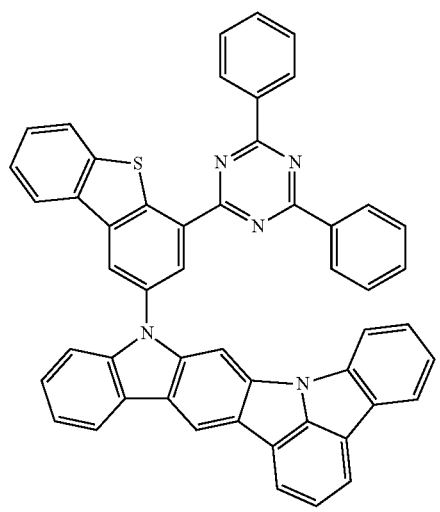 [SMILES: c1ccc(-c2nc(-c3ccccc3)nc(-c3cc(-n4c5ccccc5c5cc6c7cccc8c9ccccc9n(c6cc54)c87)cc4c3sc3ccccc34)n2)cc1]
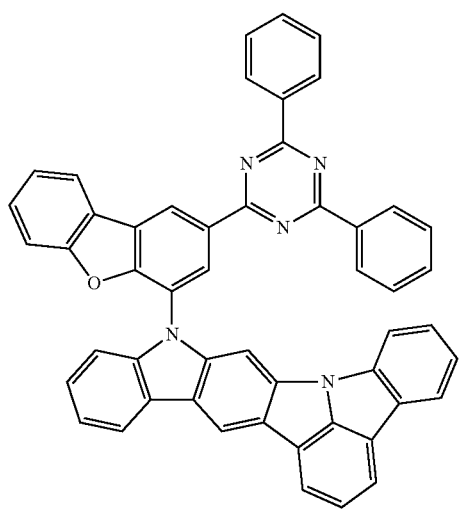
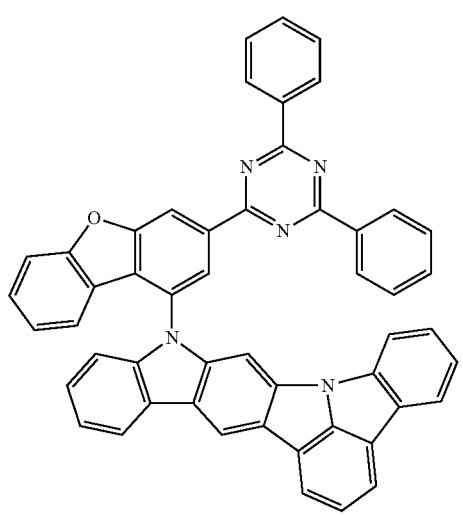
154
-continued
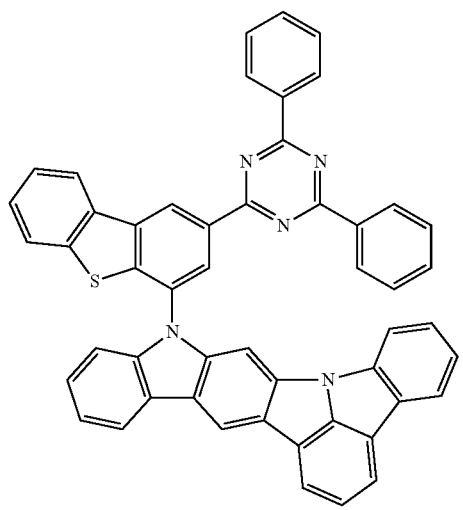
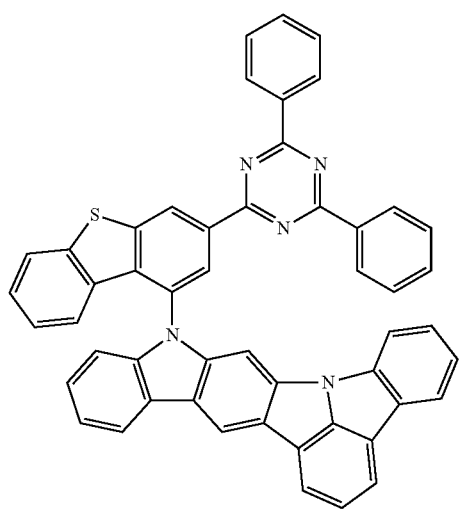
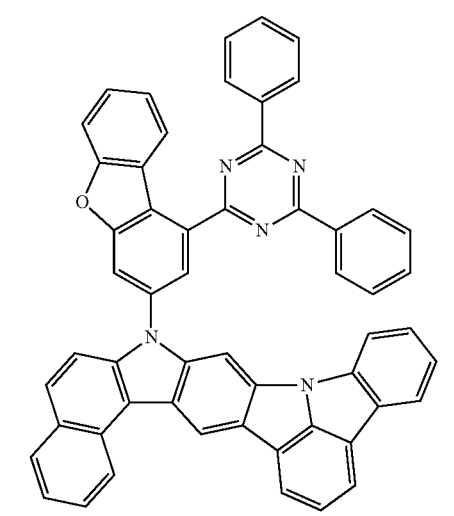

155
-continued
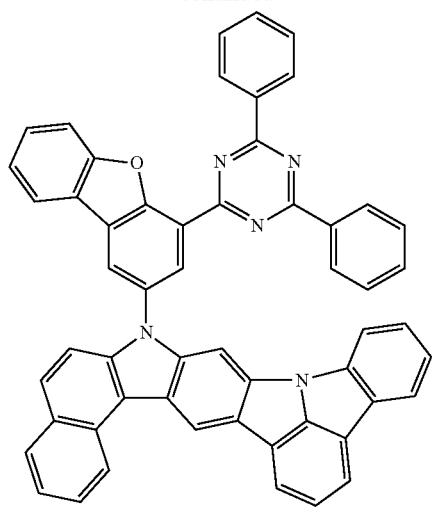
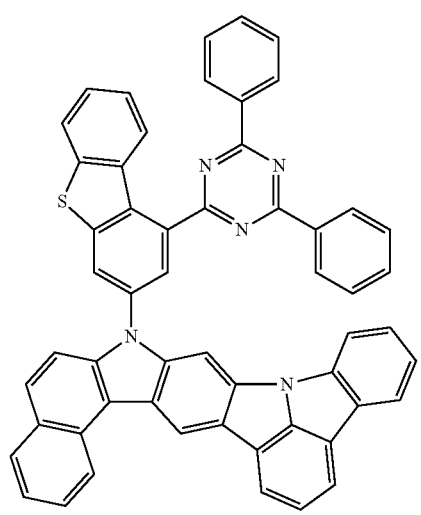
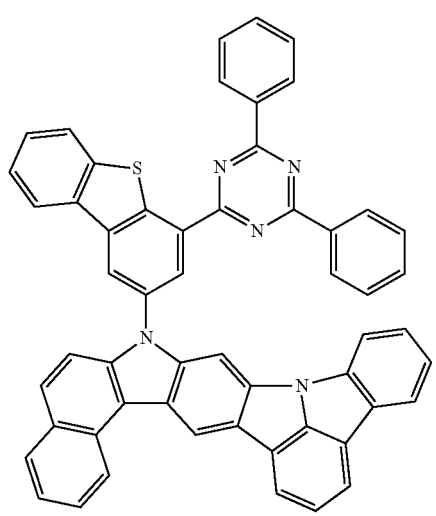
156
-continued
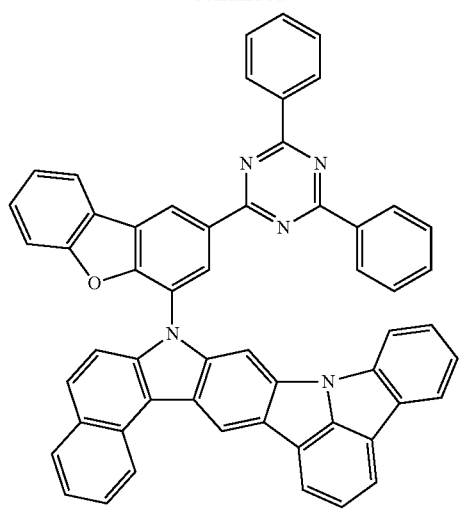
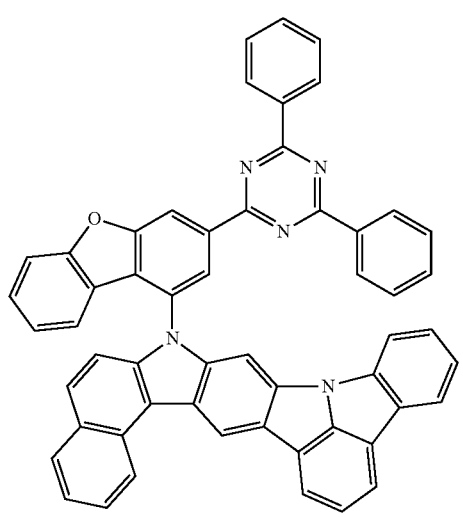
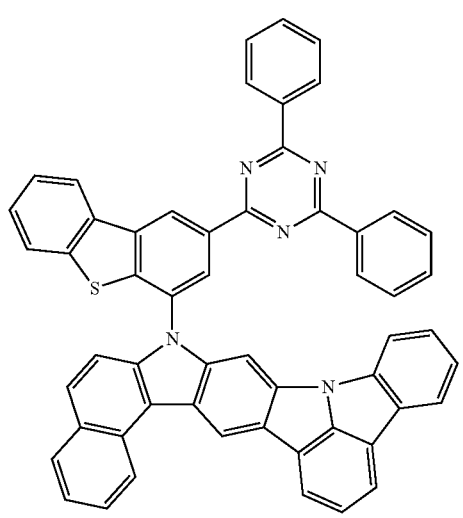

157
-continued
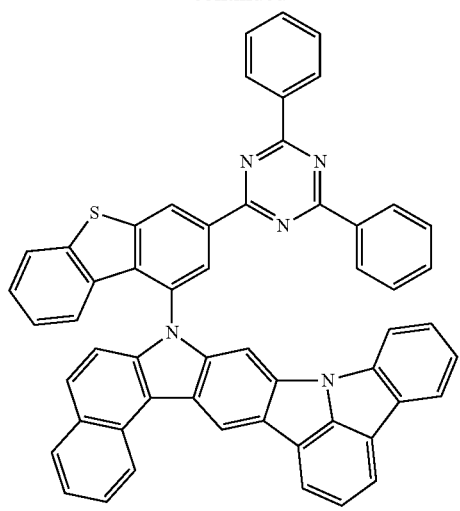
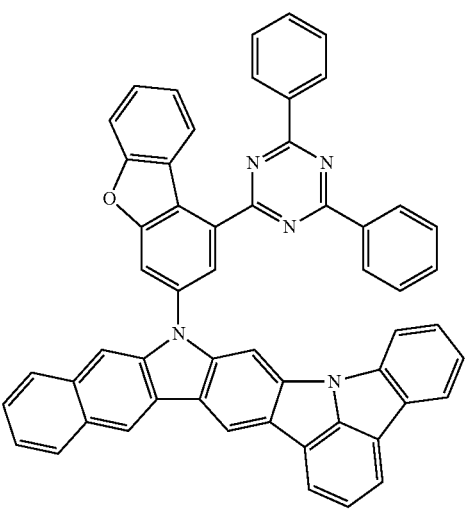
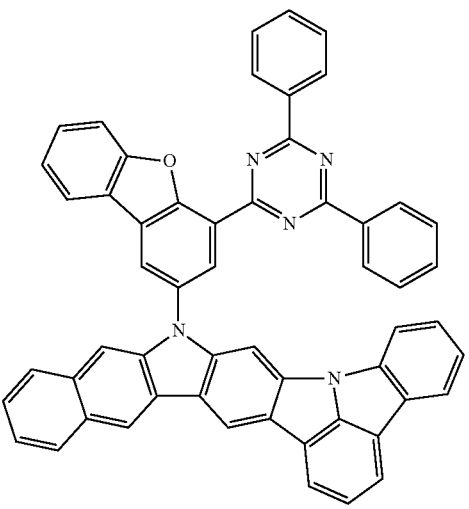
158
-continued
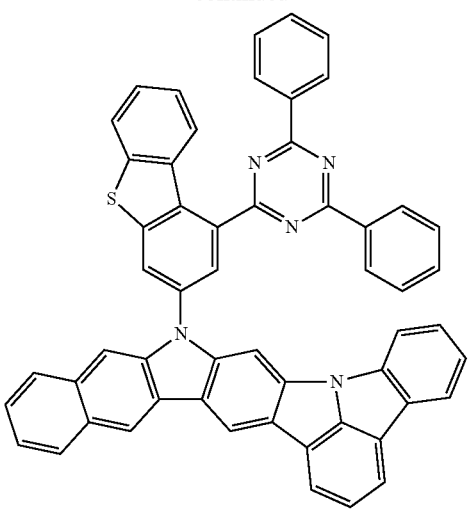
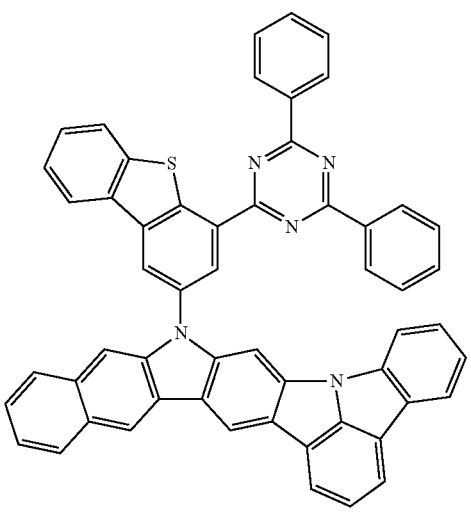
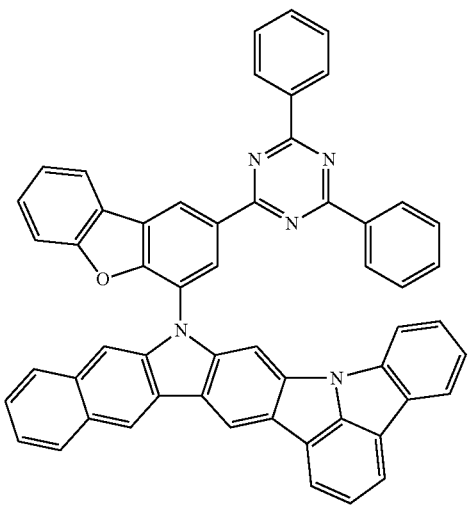

159
-continued
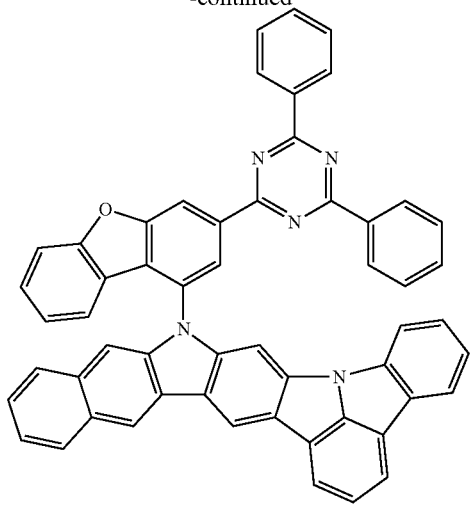
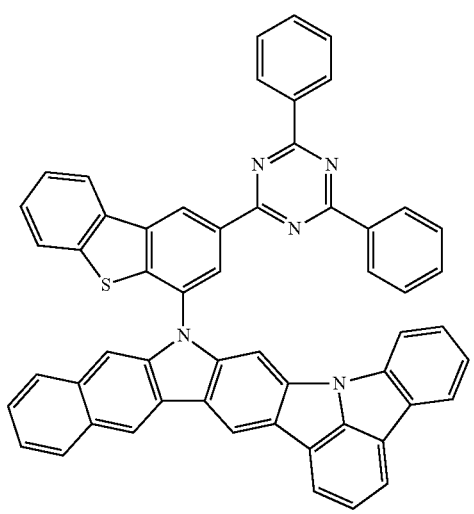
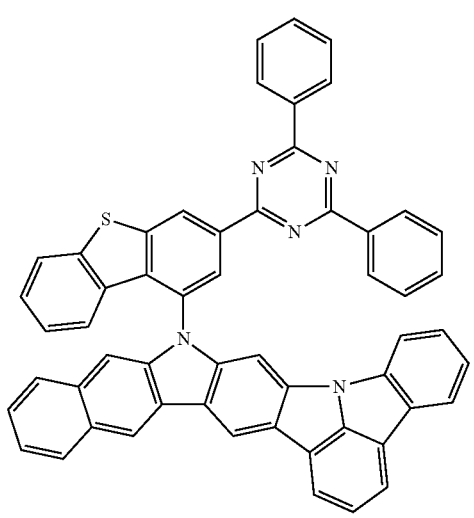
160
-continued
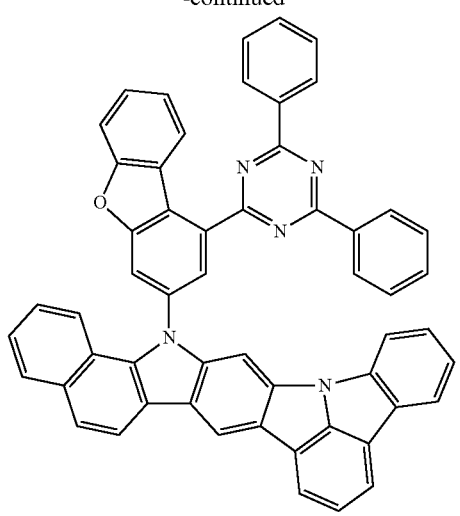
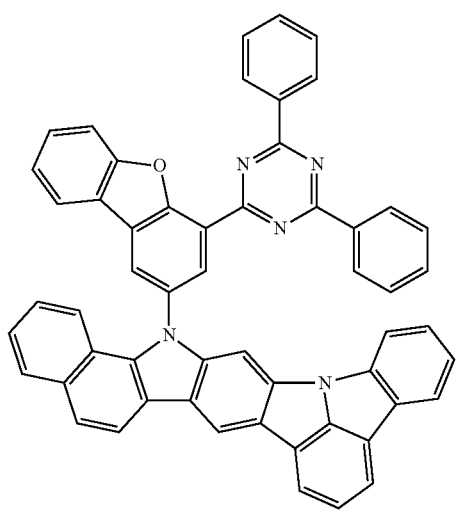 [SMILES: c1ccc(-c2nc(-c3ccccc3)nc(-c3cc(-n4c5cc6c(cc5c5ccc7ccccc7c54)c4cccc5c7ccccc7n6c54)cc4c3oc3ccccc34)n2)cc1]
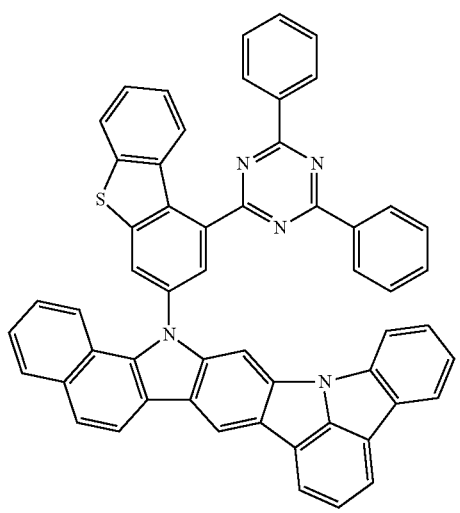

161
-continued
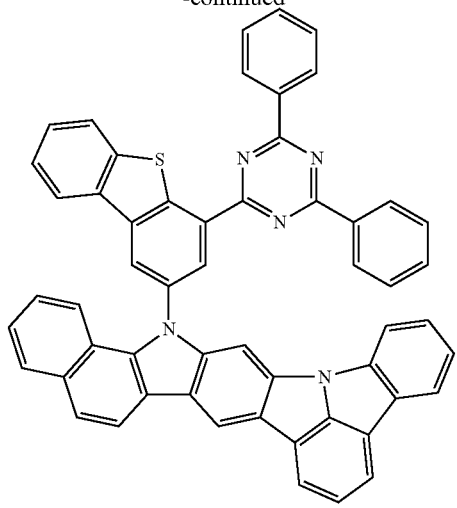
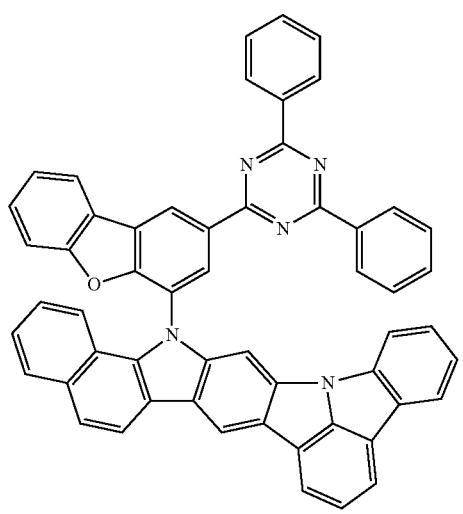
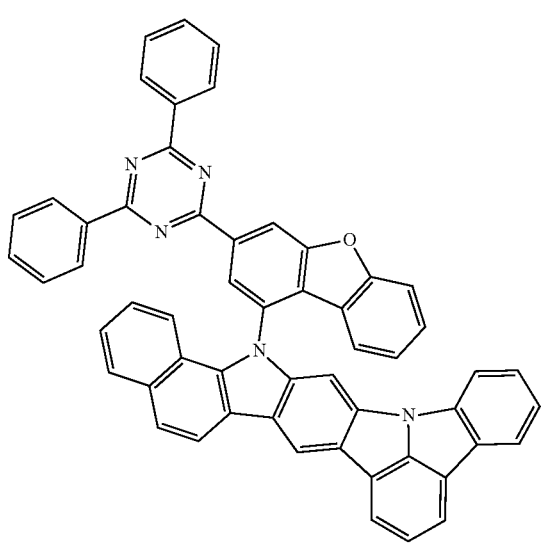
162
-continued
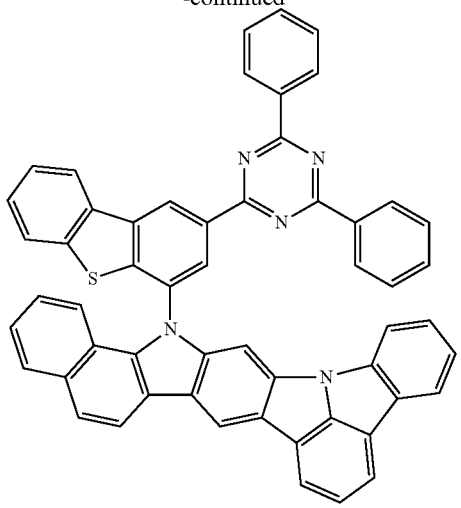
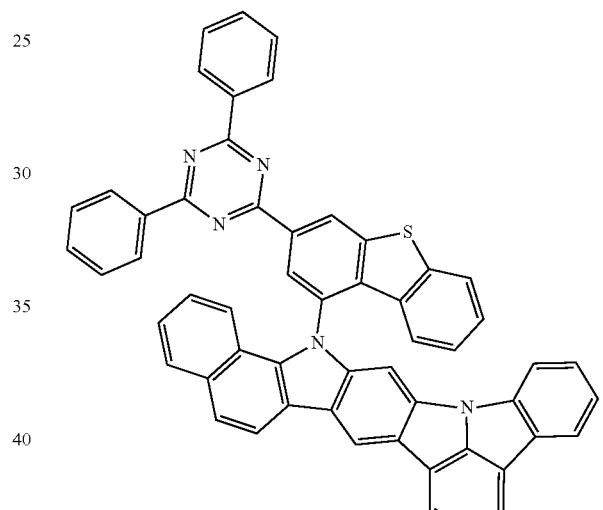
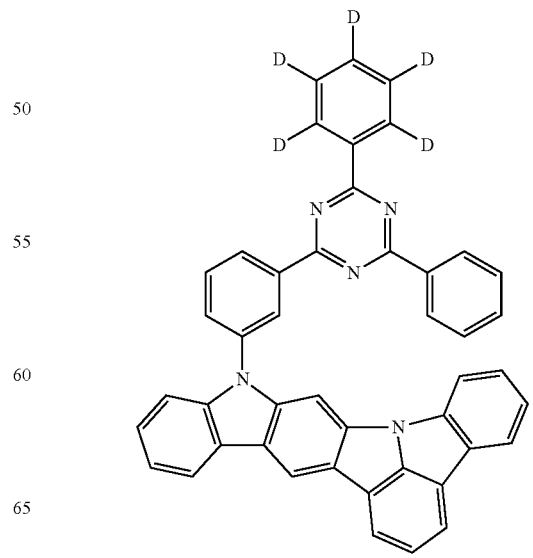

-continued
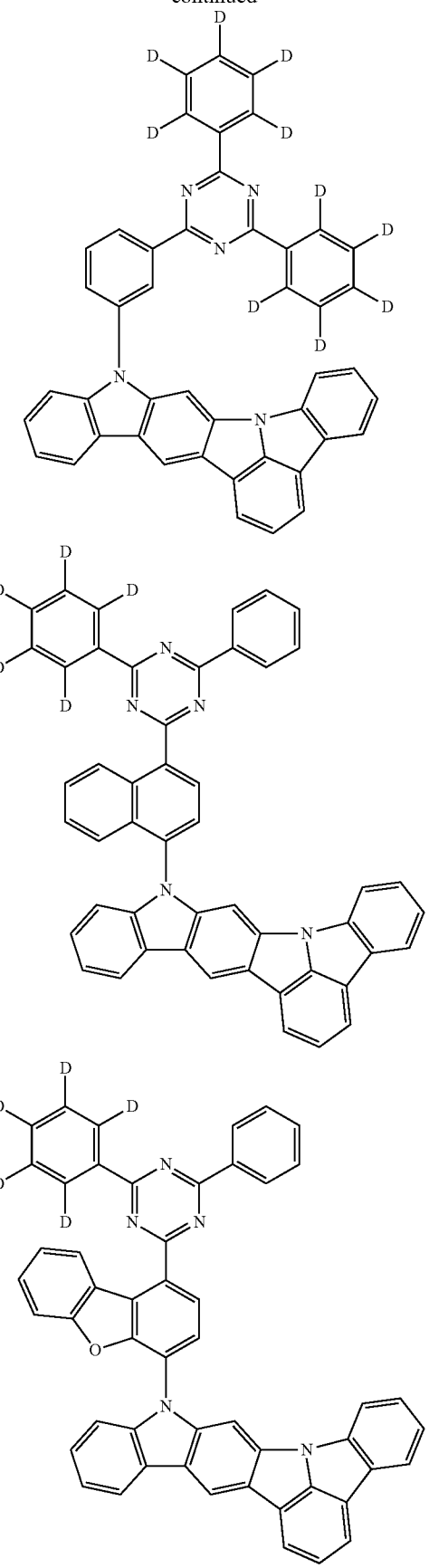
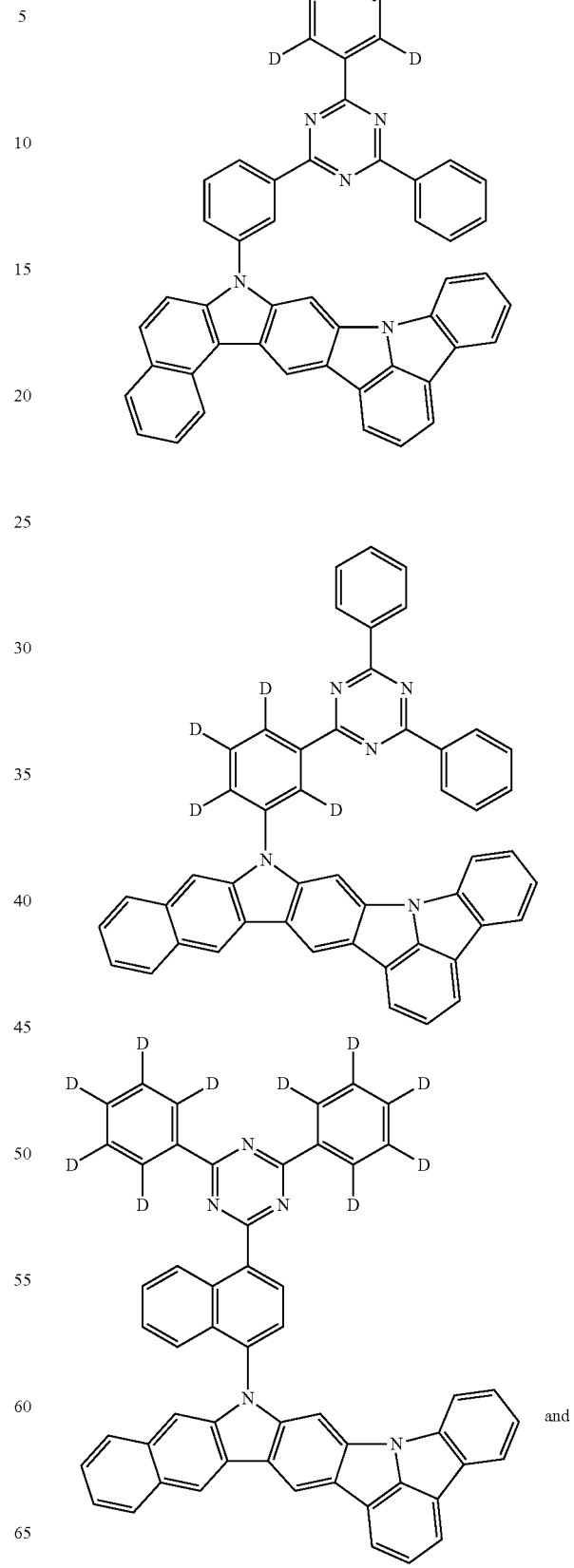
and

-continued

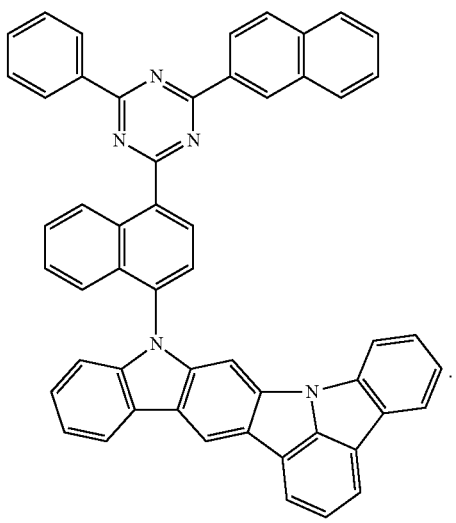

6. An organic light emitting device comprising:
a first electrode;
a second electrode provided to face the first electrode; and
one or more organic material layers provided between the first electrode and the second electrode,
wherein one or more layers of the organic material layers include the compound of claim 1.

7. The organic light emitting device of claim 6, wherein the one or more organic material layers include a light emitting layer, and the light emitting layer includes the compound.

8. The organic light emitting device of claim 6, wherein the one or more organic material layers include a light emitting layer, and the light emitting layer includes the compound as a host of the light emitting layer.

9. A compound of Chemical Formulae 6 or 7:

[Chemical Formula 6]

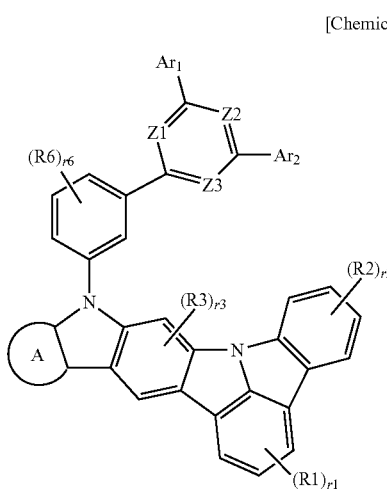

-continued

[Chemical Formula 7]

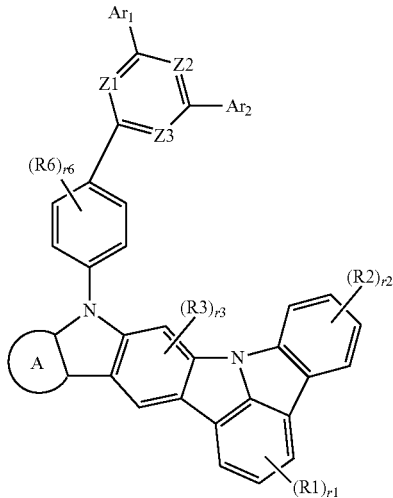

wherein, in Chemical Formulae 6 and 7:
$Ar_1$ and $Ar_2$ are the same as or different from each other, and are each independently a substituted or unsubstituted aryl group or a substituted or unsubstituted heterocyclic group;
at least two of Z1 to Z3 are N, and the rest is CR;
L is a substituted or unsubstituted arylene group or a substituted or unsubstituted divalent heterocyclic group;
A is substituted or unsubstituted benzene or substituted or unsubstituted naphthalene;
R1 to R3 are the same as or different from each other, and are each independently hydrogen, deuterium, a halogen group, a cyano group, a substituted or unsubstituted alkyl group, a substituted or unsubstituted cycloalkyl group, a substituted or unsubstituted aryl group, or a substituted or unsubstituted heteroaryl group;
r1 is an integer of 0 to 3;
r2 is an integer of 0 to 4;
r3 is an integer of 0 to 2;
when r1 and r2 are 2 or greater, the two or more groups in parentheses are the same as or different from each other, and
when r3 is 2, the two groups in parentheses are the same as or different from each other;
r6 is an integer of 2 to 4; and
R6 is hydrogen, deuterium, a halogen group, a cyano group, a substituted or unsubstituted alkyl group, a substituted or unsubstituted cycloalkyl group, a substituted or unsubstituted aryl group, or a substituted or unsubstituted heteroaryl group, or bonds to adjacent groups to form a substituted or unsubstituted hydrocarbon ring,
wherein at least two adjacent R6 groups bond together to form a ring selected from the group consisting of the following:

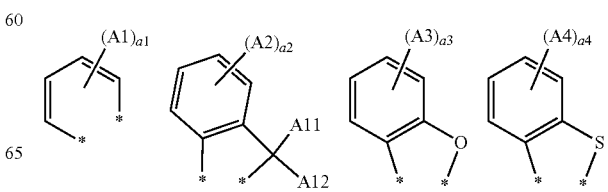

-continued

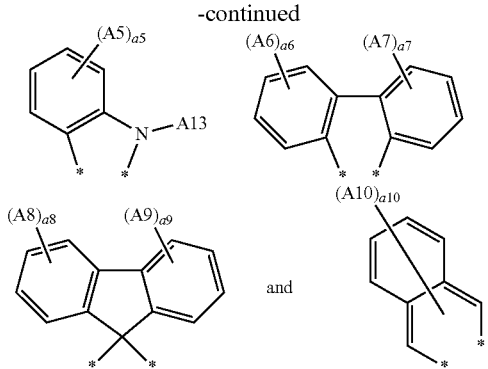

and wherein,

A1 to A13 are each independently hydrogen, deuterium, a halogen group, a cyano group, a substituted or unsubstituted alkyl group, a substituted or unsubstituted cycloalkyl group, a substituted or unsubstituted aryl group, or a substituted or unsubstituted heterocyclic group, a1 to a9 are each an integer of 0 to 4, a10 is an integer of 0 to 6, when a1 to a10 are 2 or greater, the two or more groups in parentheses are the same as or different from each other, and

* indicates a fused position.

10. An organic light emitting device comprising:
a first electrode;
a second electrode provided to face the first electrode; and
one or more organic material layers provided between the first electrode and the second electrode,
wherein one or more layers of the organic material layers include the compound of any one of Chemical Formulae 6 and 7 of claim 5.

11. The organic light emitting device of claim 10, wherein the one or more organic material layers include a light emitting layer, and the light emitting layer includes the compound.

12. The organic light emitting device of claim 10, wherein the one or more organic material layers include a light emitting layer, and the light emitting layer includes the compound as a host of the light emitting layer.

13. The organic light emitting device of claim 10, wherein the light emitting layer further includes a compound of Chemical Formula 8:

[Chemical Formula 8]

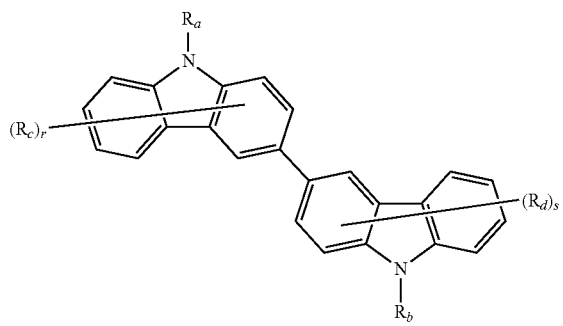

wherein, in Chemical Formula 8:

$R_a$ and $R_b$ are the same as or different from each other, and are each independently a substituted or unsubstituted aryl group or a substituted or unsubstituted heteroaryl group;

$R_c$ and $R_d$ are the same as or different from each other, and are each independently hydrogen, deuterium, a halogen group, a cyano group, a nitro group, an amino group, a substituted or unsubstituted alkyl group having 1 to 60 carbon atoms, a substituted or unsubstituted cycloalkyl group having 3 to 60 carbon atoms, a substituted or unsubstituted alkenyl group having 2 to 60 carbon atoms, a substituted or unsubstituted aryl group having 6 to 60 carbon atoms, or a substituted or unsubstituted heteroaryl group having 2 to 60 carbon atoms including one or more heteroatoms selected from the group consisting of N, O and S; and r and s are each an integer of 0 to 7, and when r is 2 or greater, each $R_c$ is the same as or different from each other, and when s is 2 or greater, each $R_d$ is the same as or different from each other.

14. A compound of any one of the following Chemical Formulae 6-1 to 6-4, 7-1 and 7-2:

[Chemical Formula 6-1]

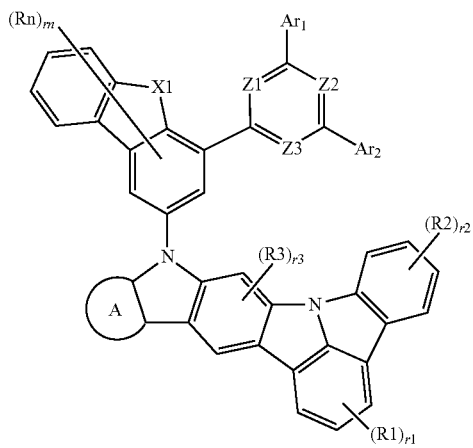

[Chemical Formula 6-2]

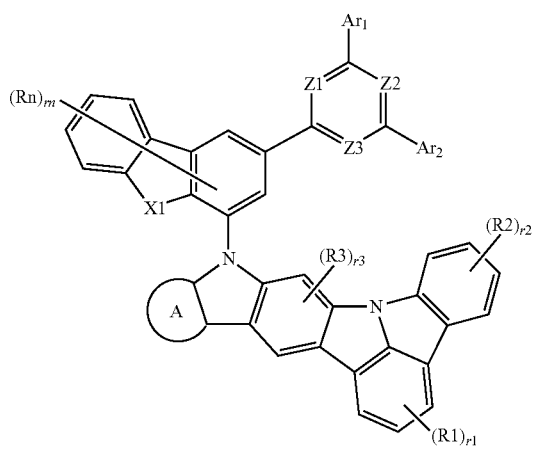

[Chemical Formula 6-3]

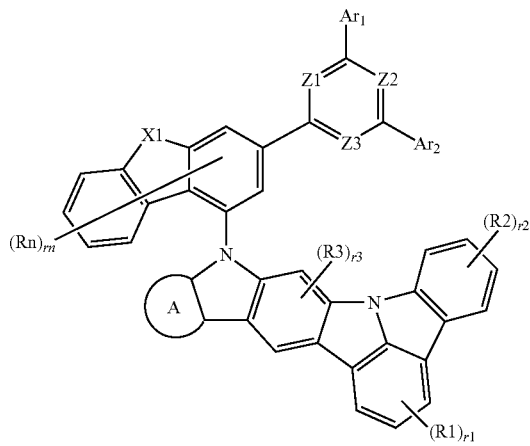

[Chemical Formula 6-4]

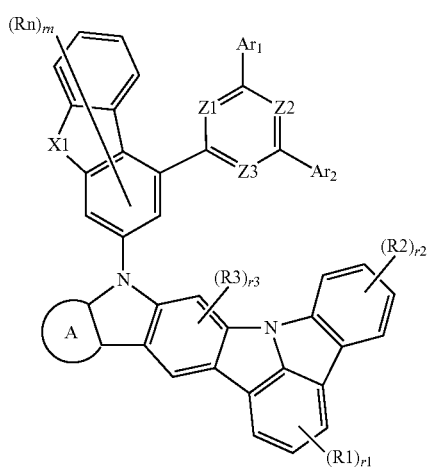

[Chemical Formula 7-1]

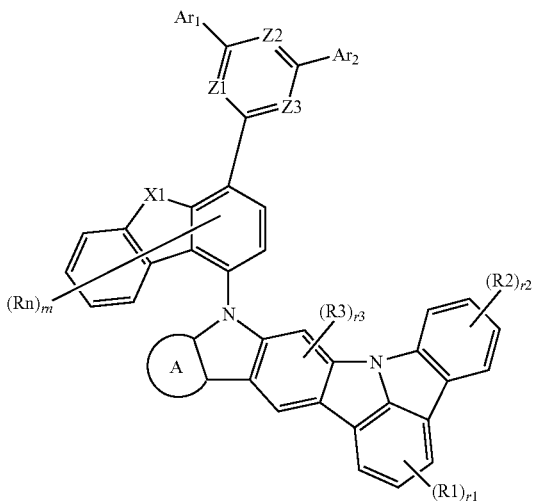

[Chemical Formula 7-2]

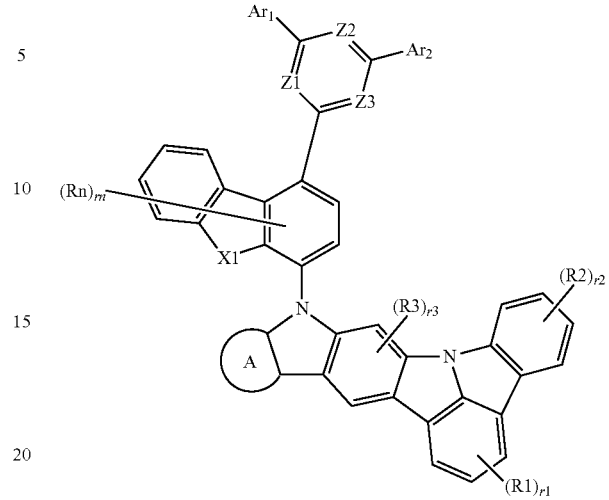

wherein, in Chemical Formulae 6-1 to 6-4, 7-1 and 7-2:

$Ar_1$ and $Ar_2$ are the same as or different from each other, and are each independently a substituted or unsubstituted aryl group or a substituted or unsubstituted heterocyclic group;

at least two of Z1 to Z3 are N, and the rest is CR;

L is a substituted or unsubstituted arylene group or a substituted or unsubstituted divalent heterocyclic group;

A is substituted or unsubstituted benzene or substituted or unsubstituted naphthalene;

R1 to R3 are the same as or different from each other, and are each independently hydrogen, deuterium, a halogen group, a cyano group, a substituted or unsubstituted alkyl group, a substituted or unsubstituted cycloalkyl group, a substituted or unsubstituted aryl group, or a substituted or unsubstituted heteroaryl group;

r1 is an integer of 0 to 3;

r2 is an integer of 0 to 4;

r3 is an integer of 0 to 2;

when r1 and r2 are 2 or greater, the two or more groups in parentheses are the same as or different from each other, and when r3 is 2, the two groups in parentheses are the same as or different from each other;

X1 is $CR101R102$, O, or S, S;

R101 and R102 are the same as or different from each other, and each independently a substituted or unsubstituted alkyl group;

Rn is hydrogen, deuterium, a halogen group, a cyano group, a substituted or unsubstituted alkyl group, a substituted or unsubstituted cycloalkyl group, a substituted or unsubstituted aryl group, or a substituted or unsubstituted heteroaryl group, and rn is an integer of 0 to 6, and each Rn is the same as or different from each other when rn is 2 or greater.

15. An organic light emitting device comprising:
a first electrode;
a second electrode provided to face the first electrode; and
one or more organic material layers provided between the first electrode and the second electrode,
wherein one or more layers of the organic material layers include the compound of any one of Chemical Formulae 6-1 to 6-4, 7-1 and 7-2 of claim 14.

16. The organic light emitting device of claim 15, wherein the one or more organic material layers include a light emitting layer, and the light emitting layer includes the compound.

17. The organic light emitting device of claim 15, wherein the one or more organic material layers include a light emitting layer, and the light emitting layer includes the compound as a host of the light emitting layer.

18. The organic light emitting device of claim 15, wherein the light emitting layer further includes a compound of Chemical Formula 8:

[Chemical Formula 8]

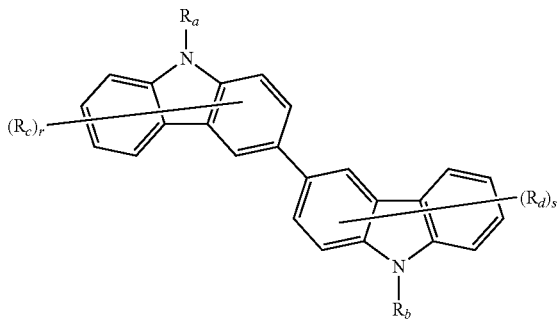

wherein, in Chemical Formula 8:

$R_a$ and $R_b$ are the same as or different from each other, and are each independently a substituted or unsubstituted aryl group or a substituted or unsubstituted heteroaryl group;

$R_c$ and $R_d$ are the same as or different from each other, and are each independently hydrogen, deuterium, a halogen group, a cyano group, a nitro group, an amino group, a substituted or unsubstituted alkyl group having 1 to 60 carbon atoms, a substituted or unsubstituted cycloalkyl group having 3 to 60 carbon atoms, a substituted or unsubstituted alkenyl group having 2 to 60 carbon atoms, a substituted or unsubstituted aryl group having 6 to 60 carbon atoms, or a substituted or unsubstituted heteroaryl group having 2 to 60 carbon atoms including one or more heteroatoms selected from the group consisting of N, O and S; and r and s are each an integer of 0 to 7, and when r is 2 or greater, each $R_c$ is the same as or different from each other, and when s is 2 or greater, each $R_d$ is the same as or different from each other.

19. An organic light emitting device comprising:

a first electrode;

a second electrode provided to face the first electrode; and one or more organic material layers provided between the first electrode and the second electrode, wherein one or more layers of the one or more organic material layers include a light emitting layer, and the light emitting layer includes a compound of the following Chemical Formula 1, and wherein the light emitting layer further includes a compound of the following Chemical Formula 8:

[Chemical Formula 1]

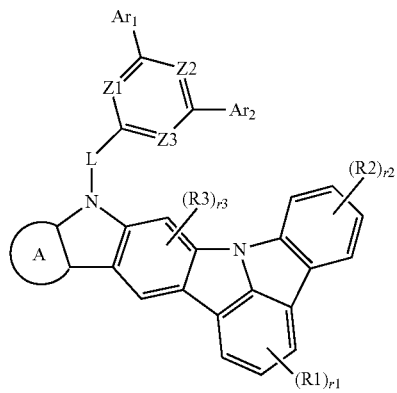

wherein, in Chemical Formula 1:

$Ar_1$ and $Ar_2$ are the same as or different from each other, and are each independently a substituted or unsubstituted aryl group or a substituted or unsubstituted heterocyclic group;

at least two of Z1 to Z3 are N, and the rest is CR;

L is a substituted or unsubstituted arylene group or a substituted or unsubstituted divalent heterocyclic group;

A is substituted or unsubstituted benzene or substituted or unsubstituted naphthalene;

R and R1 to R3 are the same as or different from each other, and are each independently hydrogen, deuterium, a halogen group, a cyano group, a substituted or unsubstituted alkyl group, a substituted or unsubstituted cycloalkyl group, a substituted or unsubstituted aryl group, or a substituted or unsubstituted heteroaryl group;

r1 is an integer of 0 to 3;

r2 is an integer of 0 to 4;

r3 is an integer of 0 to 2;

when r1 and r2 are 2 or greater, the two or more groups in parentheses are the same as or different from each other, and when r3 is 2, the two groups in parentheses are the same as or different from each other;

[Chemical Formula 8]

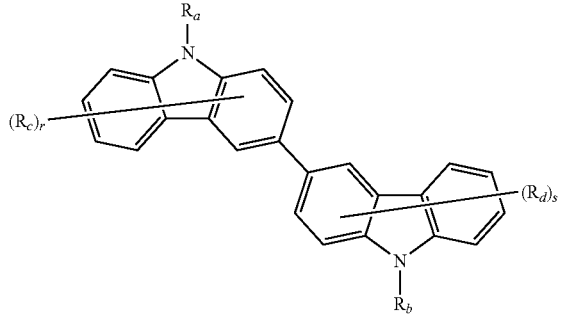

wherein, in Chemical Formula 8:

$R_a$ and $R_b$ are the same as or different from each other, and are each independently a substituted or unsubstituted aryl group or a substituted or unsubstituted heteroaryl group;

$R_c$ and $R_d$ are the same as or different from each other, and are each independently hydrogen, deuterium, a halogen group, a cyano group, a nitro group, an amino group, a substituted or unsubstituted alkyl group having 1 to 60 carbon atoms, a substituted or unsubstituted cycloalkyl group having 3 to 60 carbon atoms, a substituted or unsubstituted alkenyl group having 2 to 60 carbon atoms, a substituted or unsubstituted aryl group having 6 to 60 carbon atoms, or a substituted or unsubstituted heteroaryl group having 2 to 60 carbon atoms including one or more heteroatoms selected from the group consisting of N, O and S; and r and s are each an integer of 0 to 7, and when r is 2 or greater, each $R_c$ is the same as or different from each other, and when s is 2 or greater, each $R_d$ is the same as or different from each other.

20. The organic light emitting device of claim 19, wherein the compound of Chemical Formula 8 is any one compound selected from the group consisting of the following compounds:

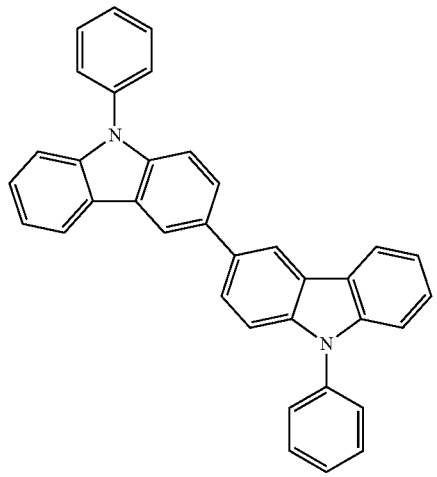

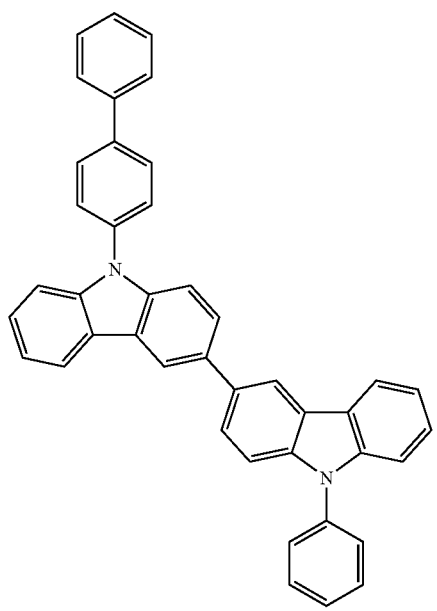

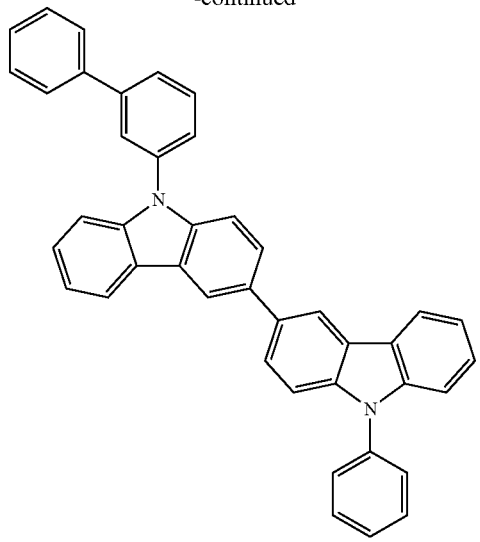

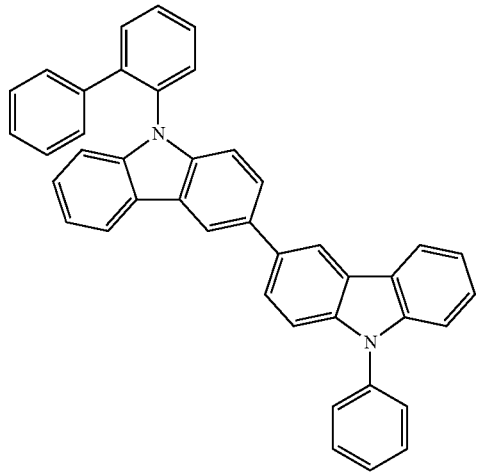

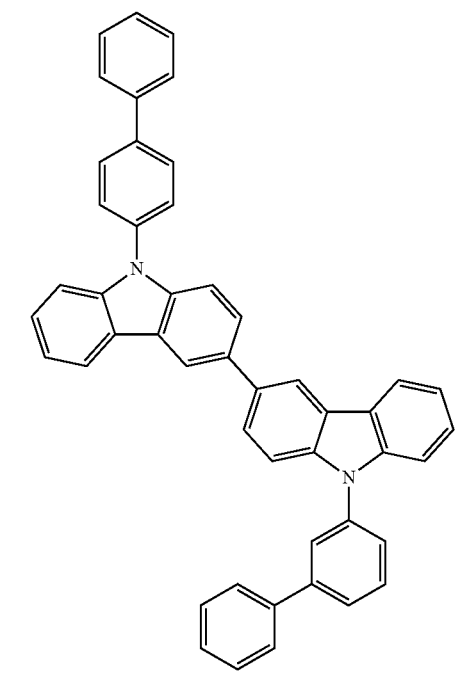

175
-continued
176
-continued
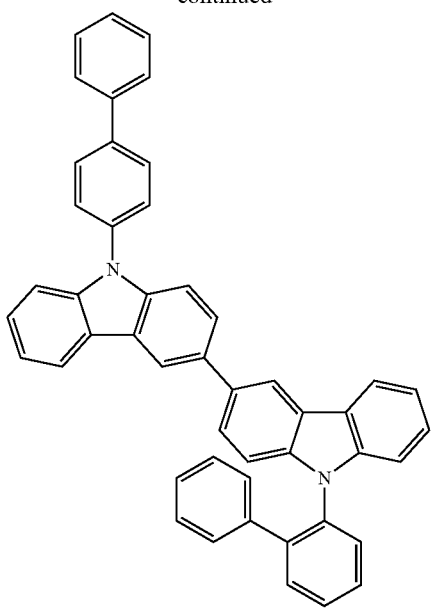
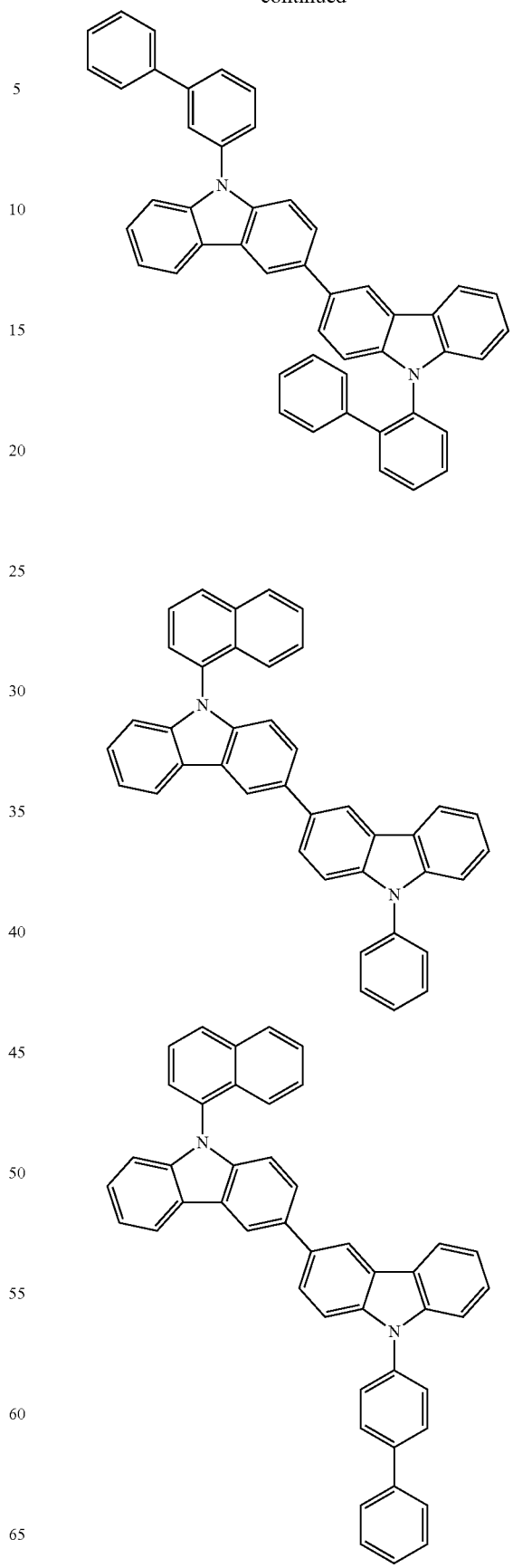

177
-continued
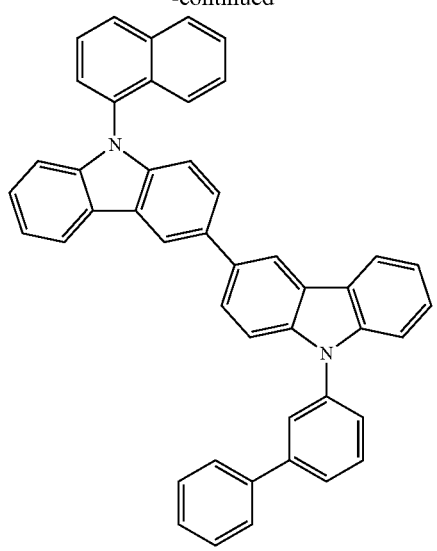
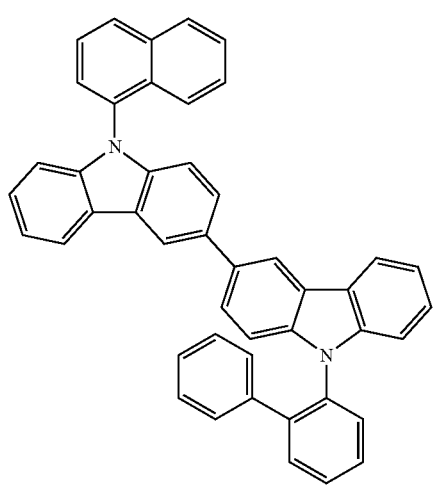
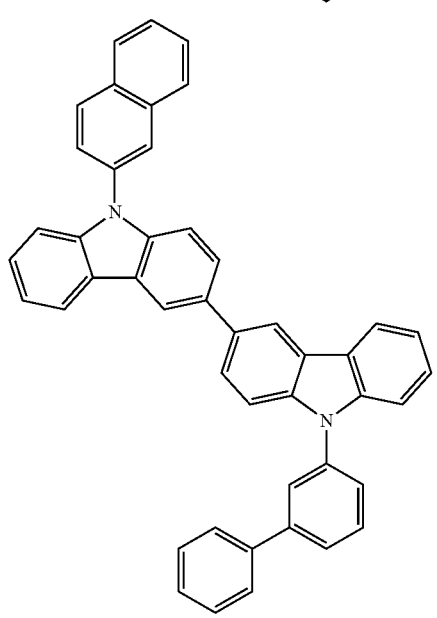
178
-continued
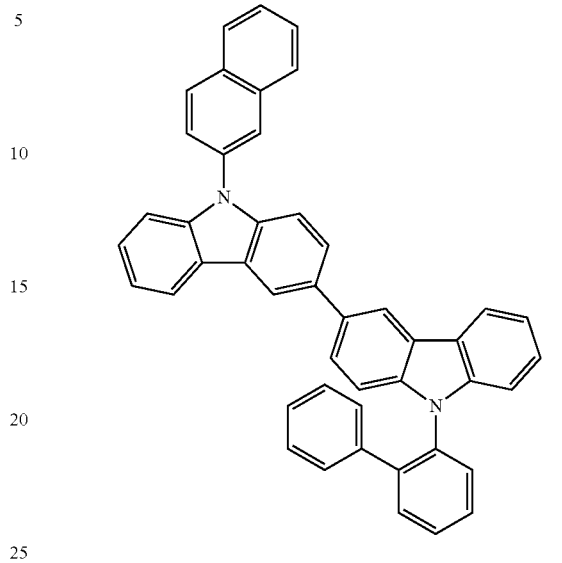
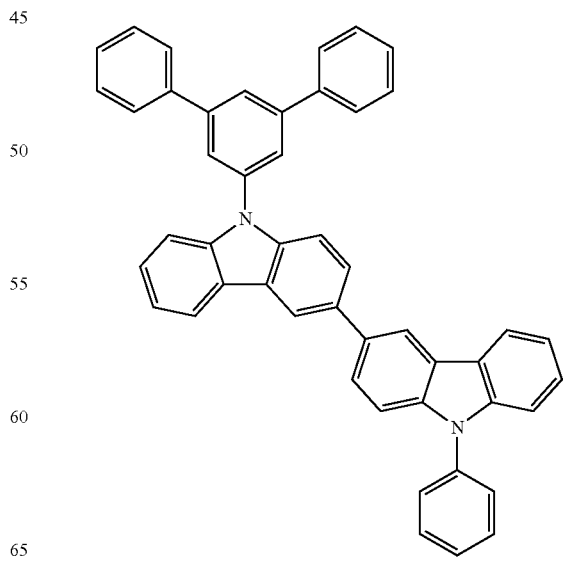

179
-continued
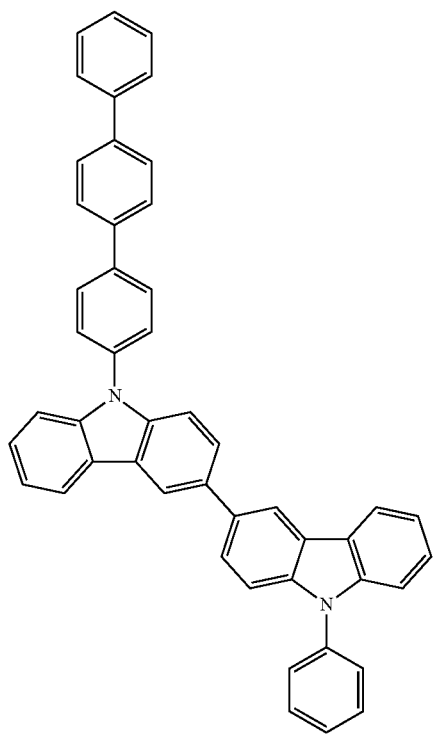
180
-continued
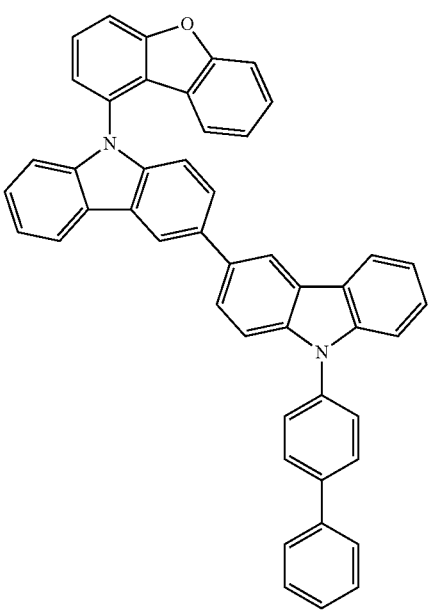
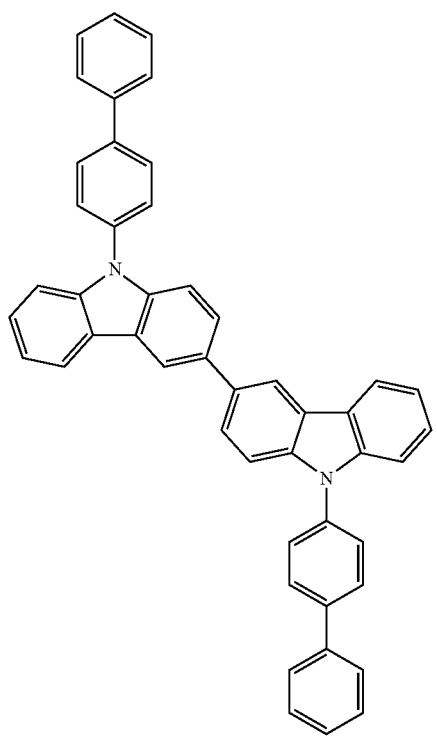
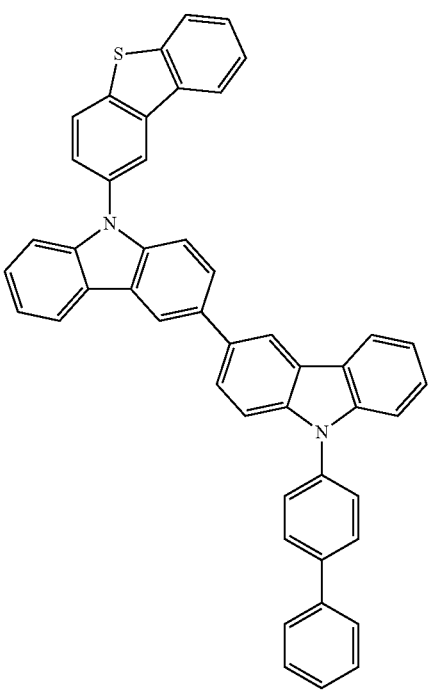

181
-continued
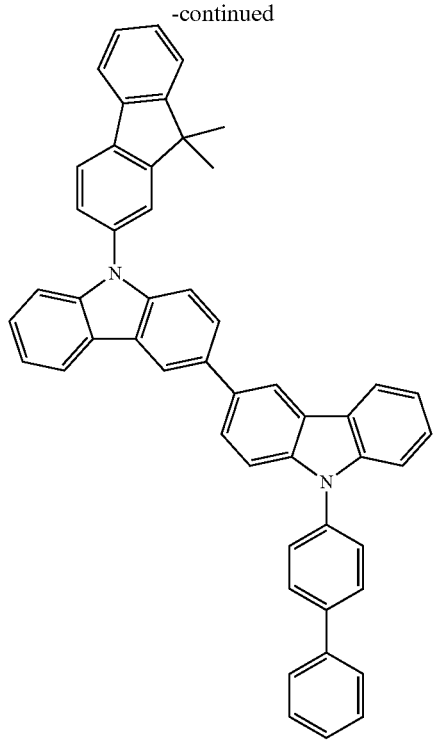
182
-continued
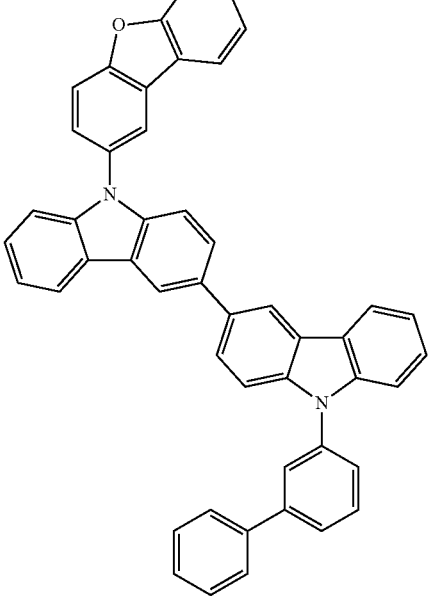
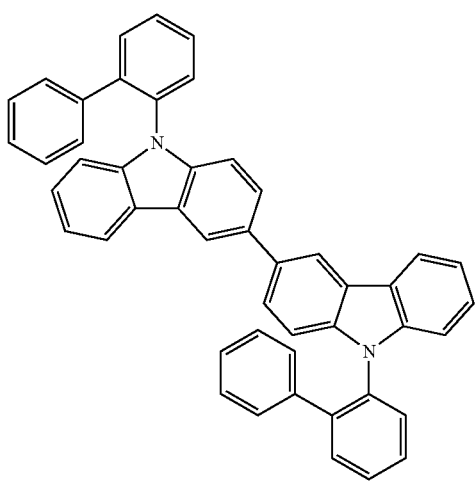
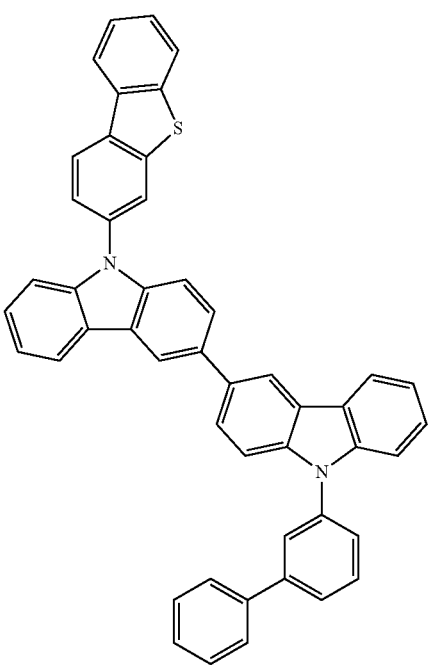

183
-continued
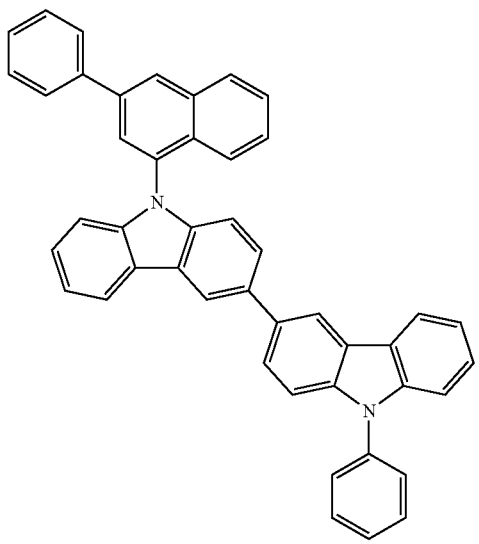
184
-continued
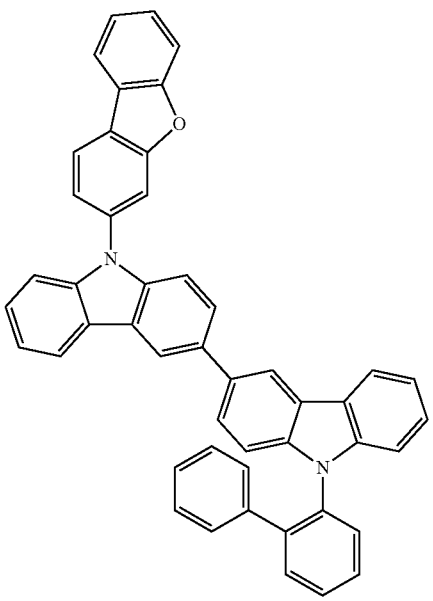
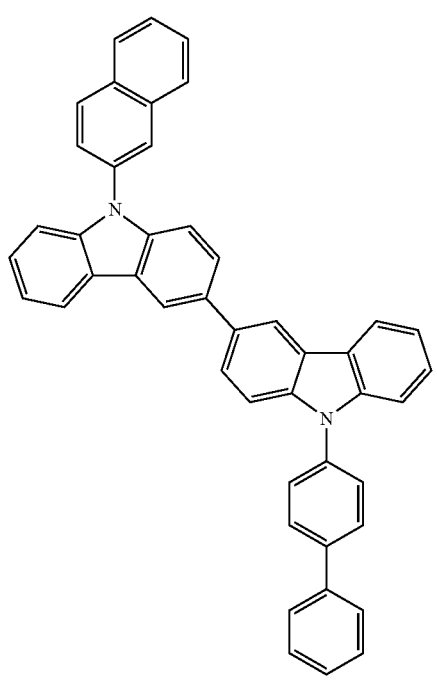

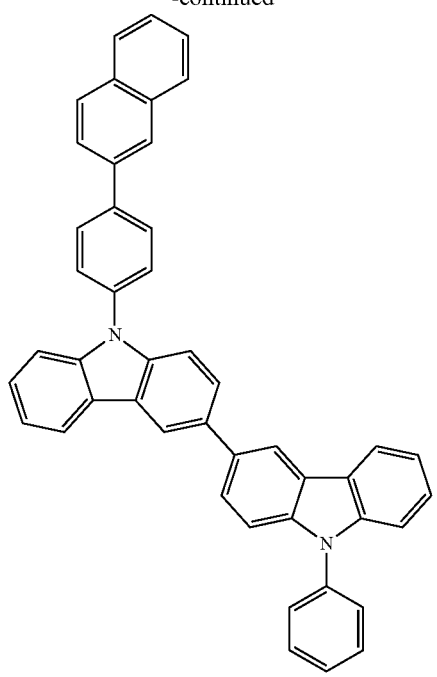
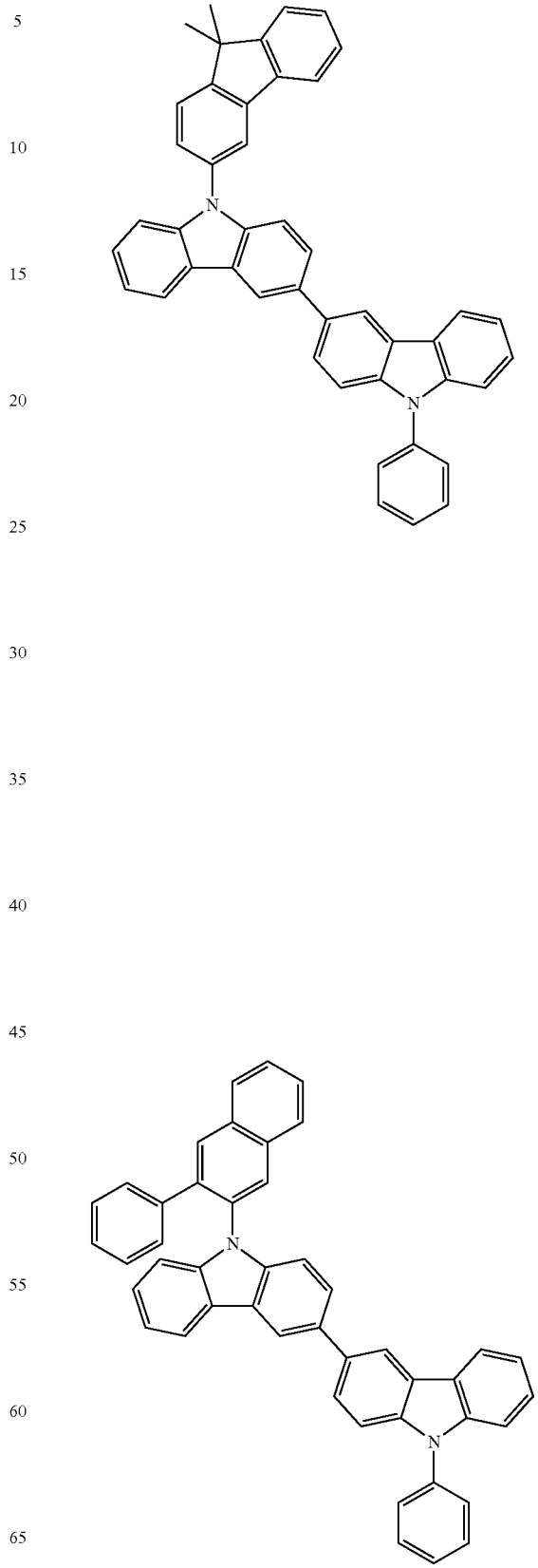

187
-continued
188
-continued
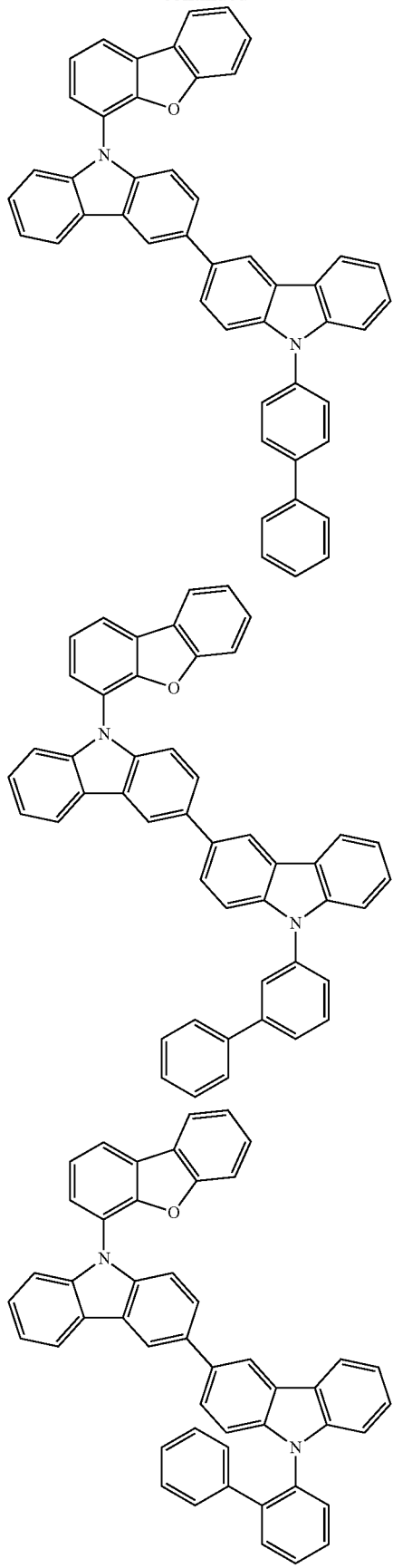
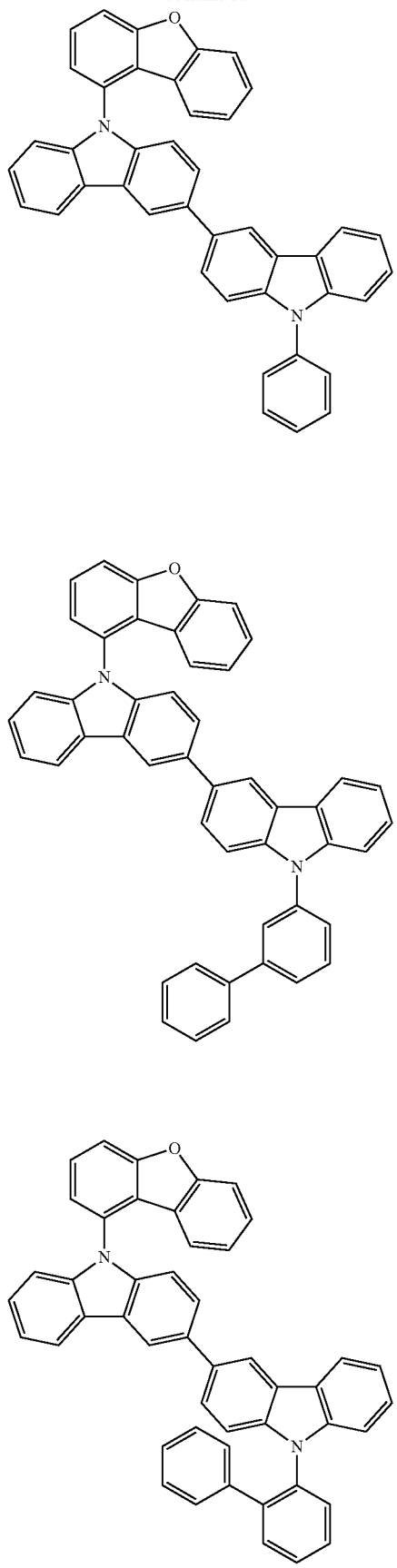

189
-continued
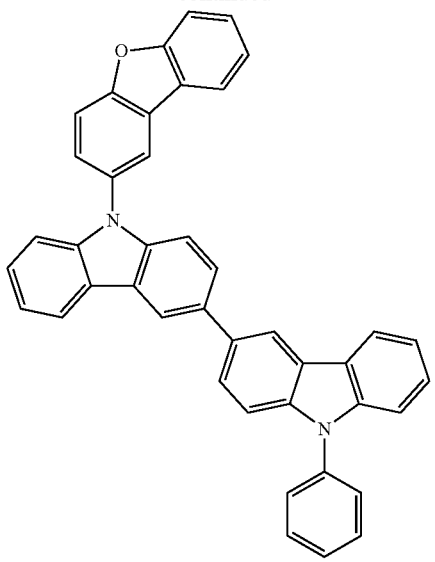 [SMILES: c1ccc(-n2c3ccccc3c3cc(-c4ccc5c(c4)c4ccccc4n5-c4ccc5oc6ccccc6c5c4)ccc32)cc1]
190
-continued
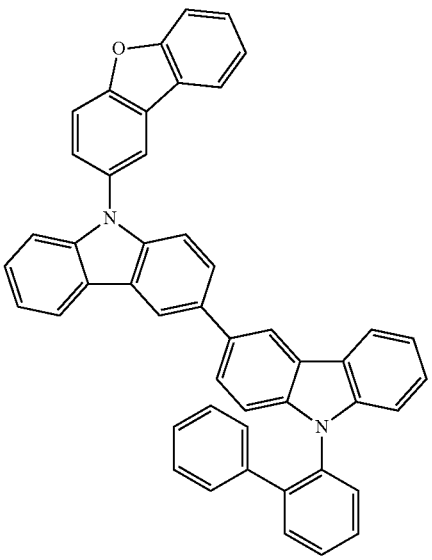
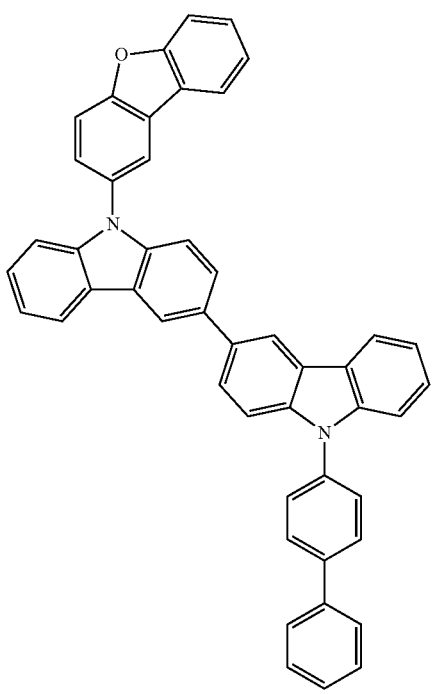
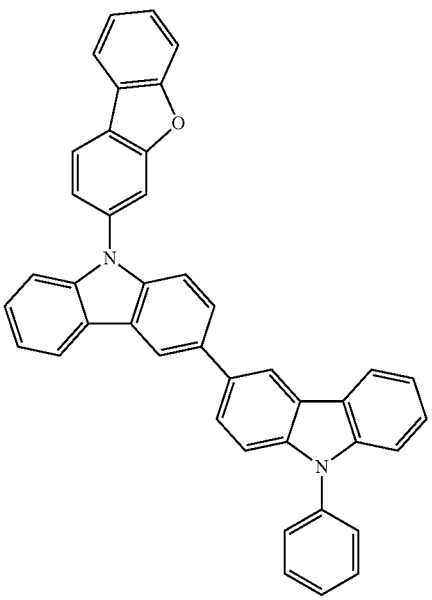

191
-continued
192
-continued
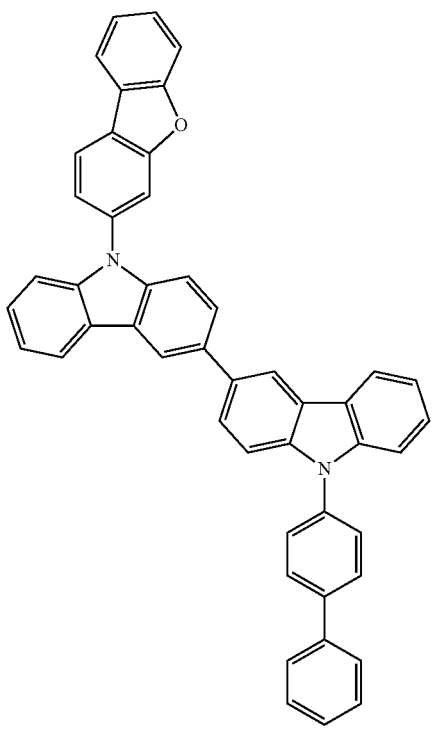
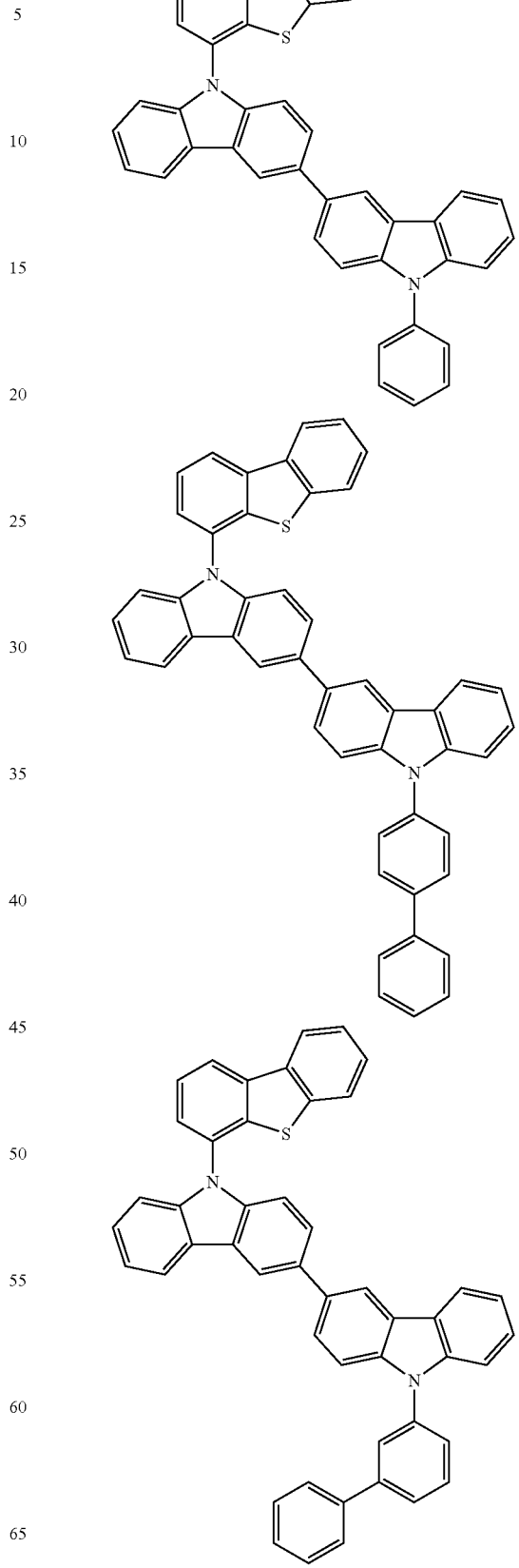
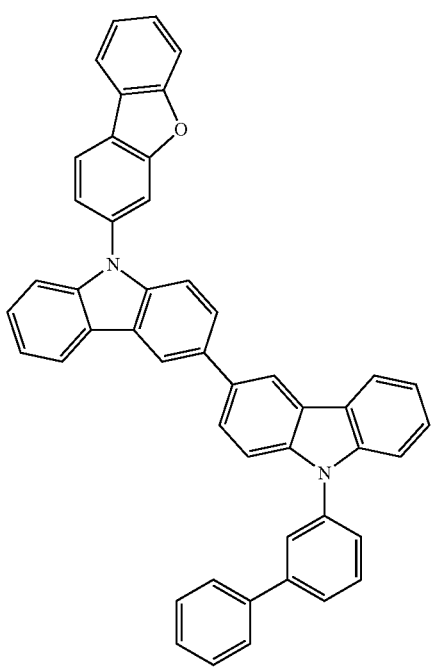

193
-continued
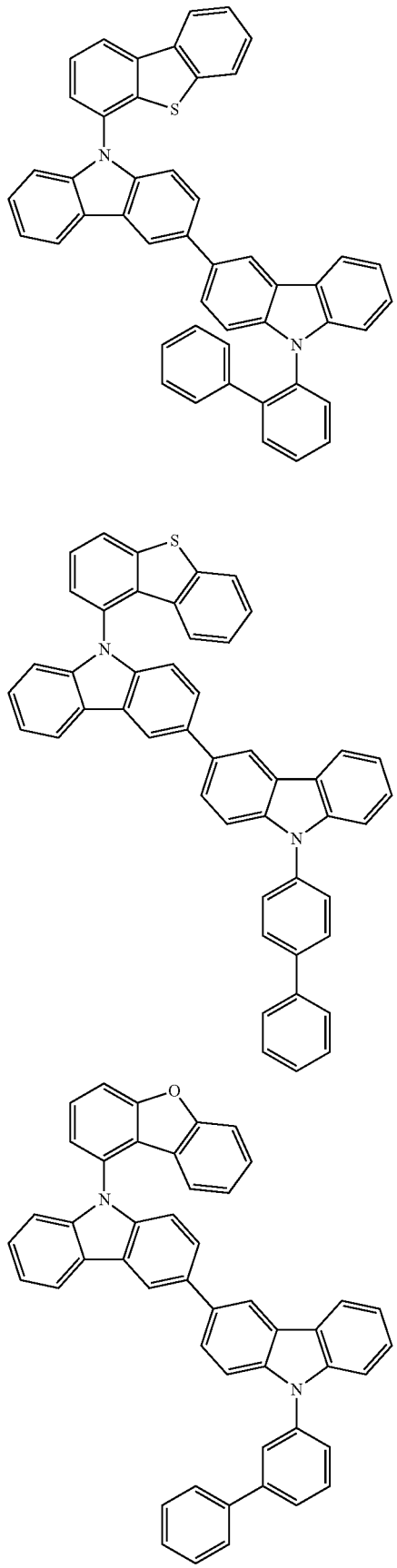
194
-continued
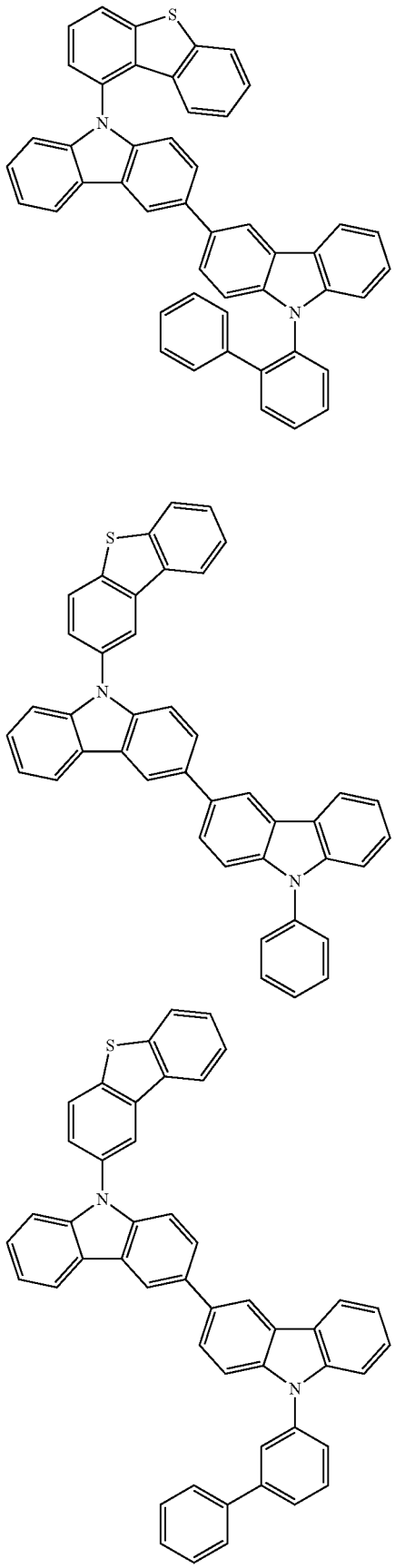

195
-continued
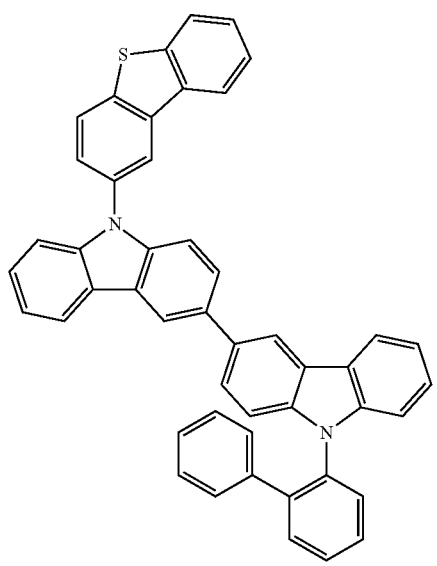
196
-continued
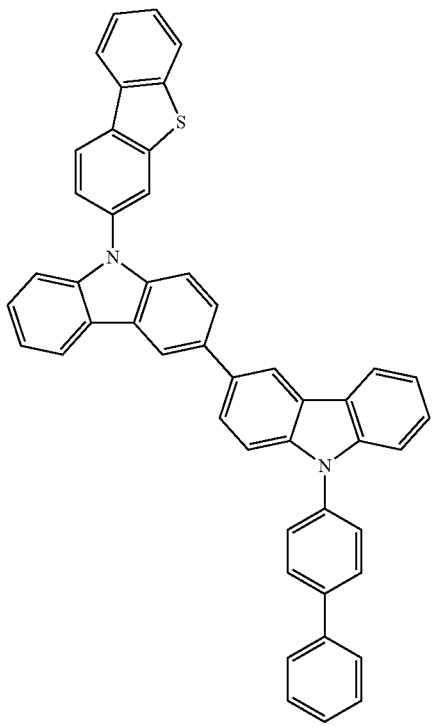
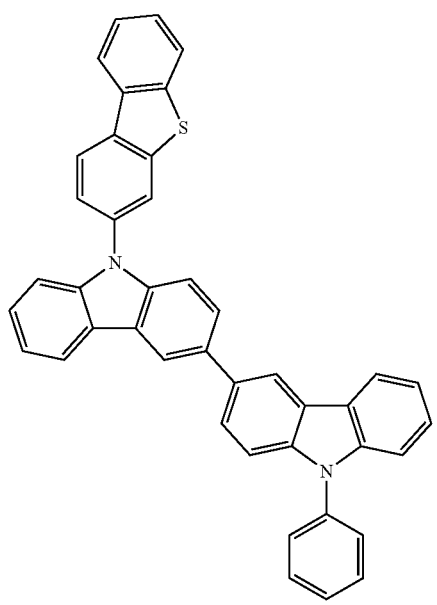
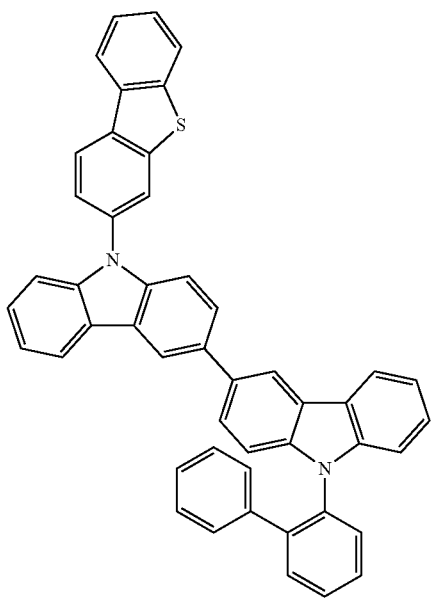

197
-continued
198
-continued
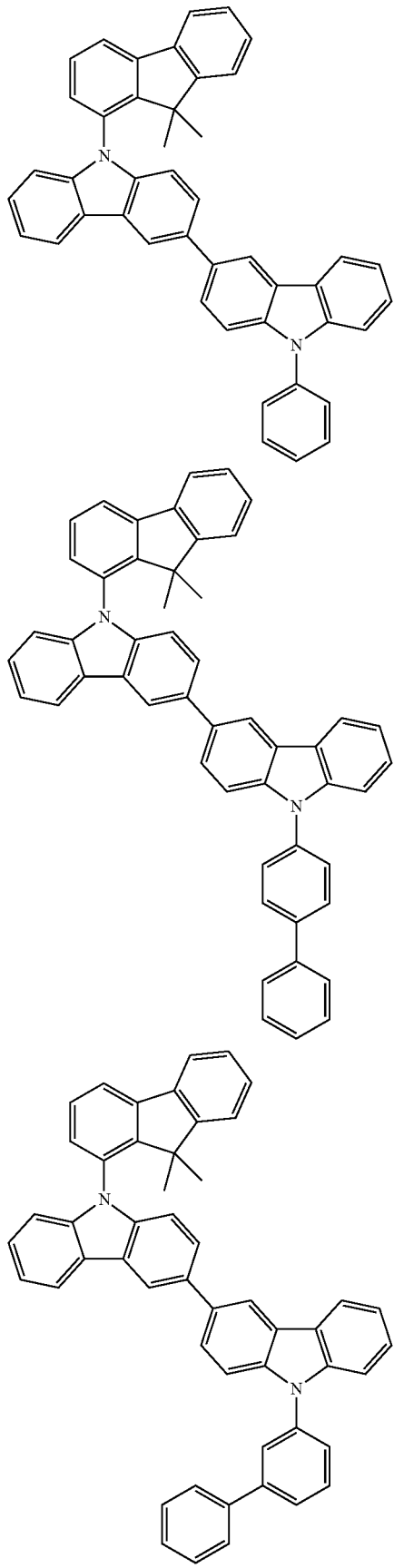
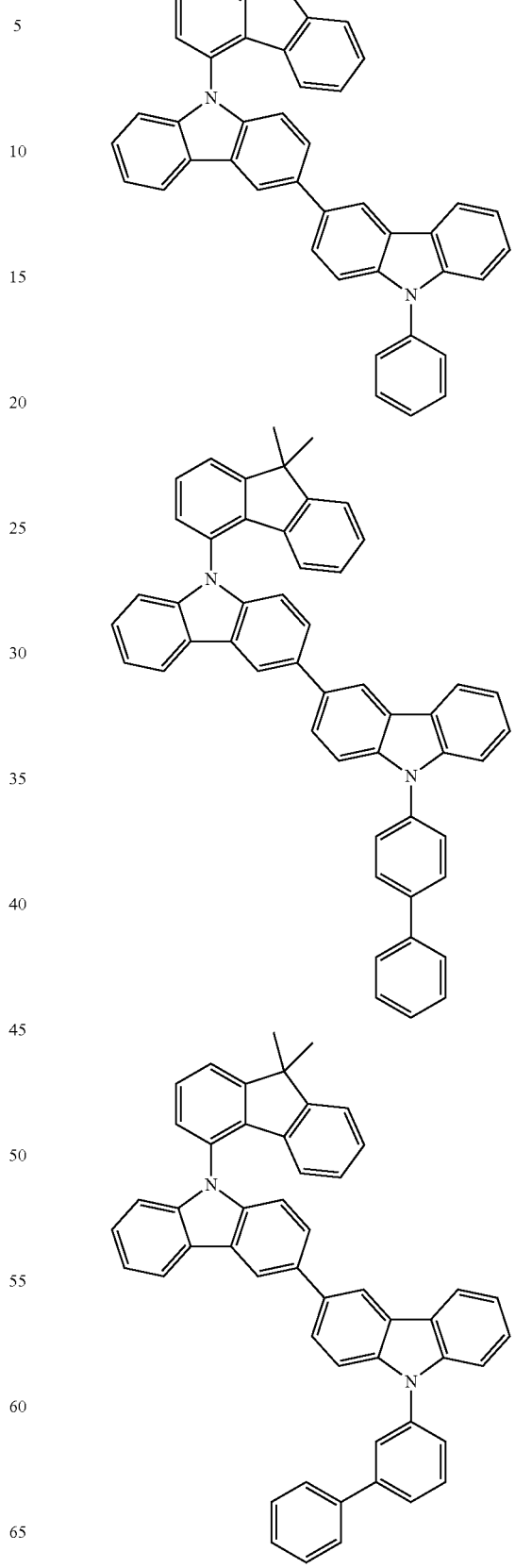

199
-continued
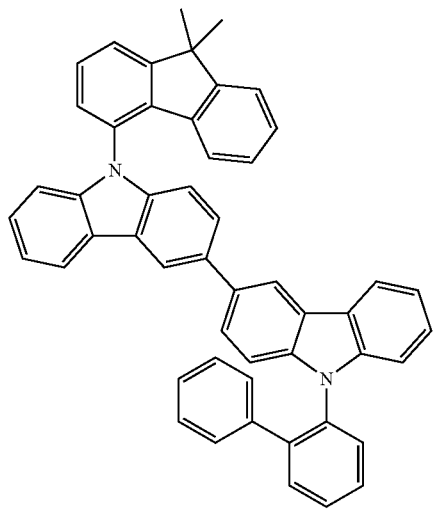
200
-continued
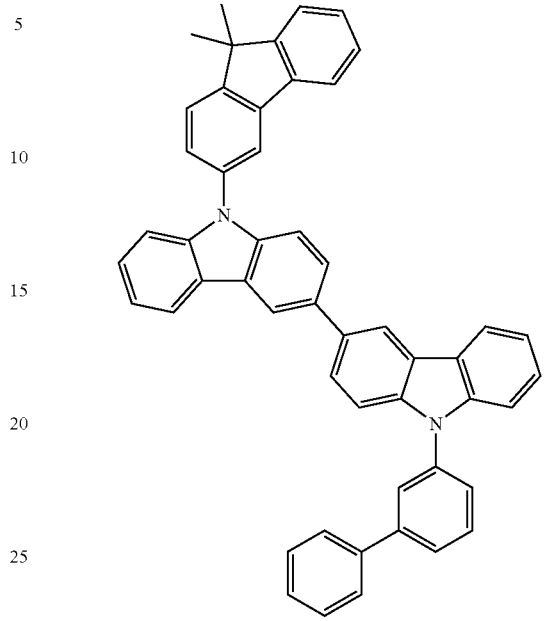
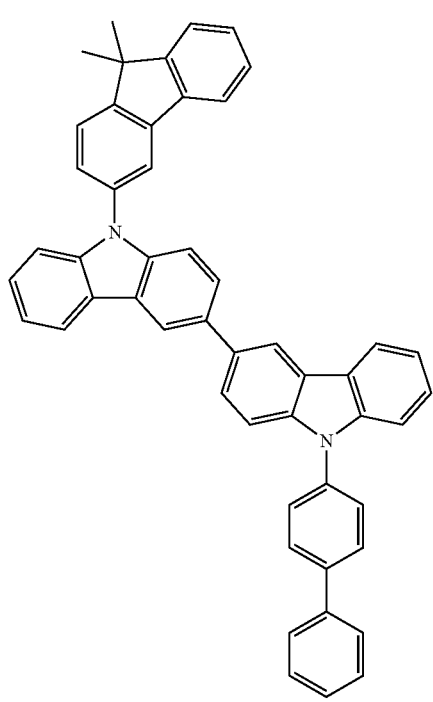
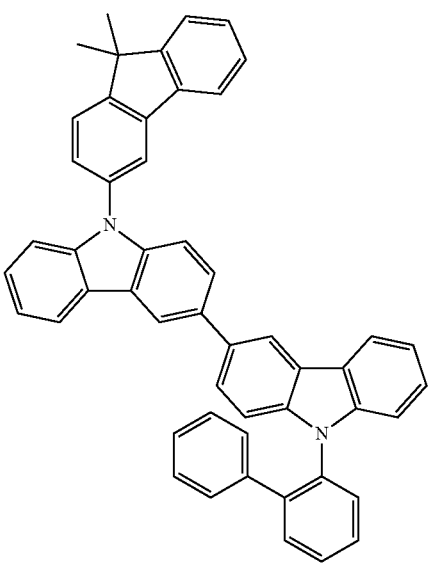

201
-continued
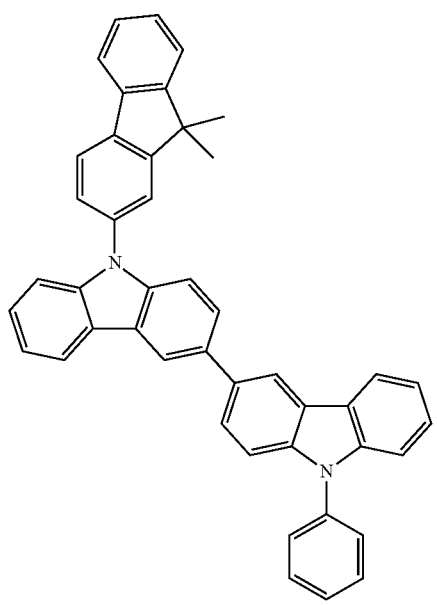
202
-continued
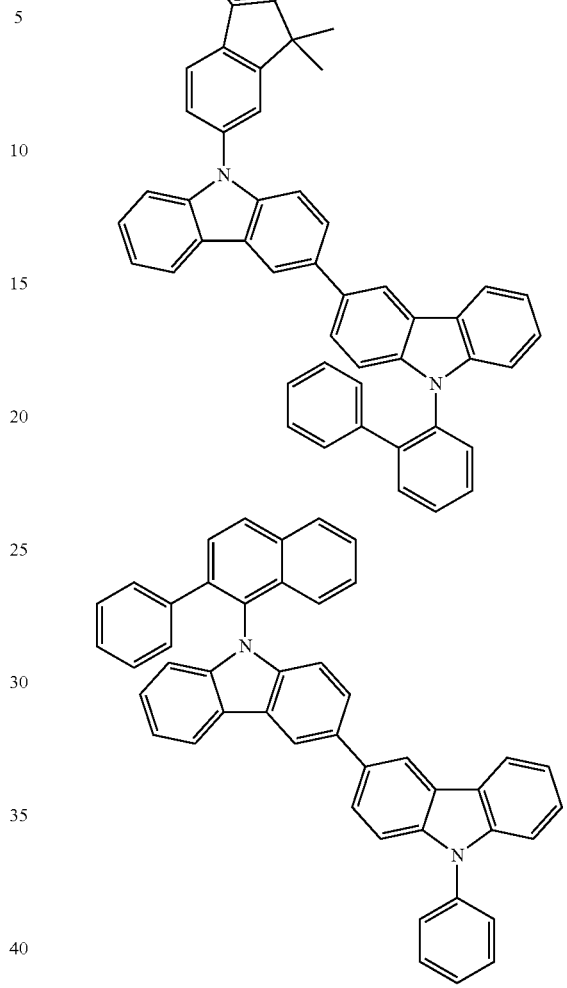
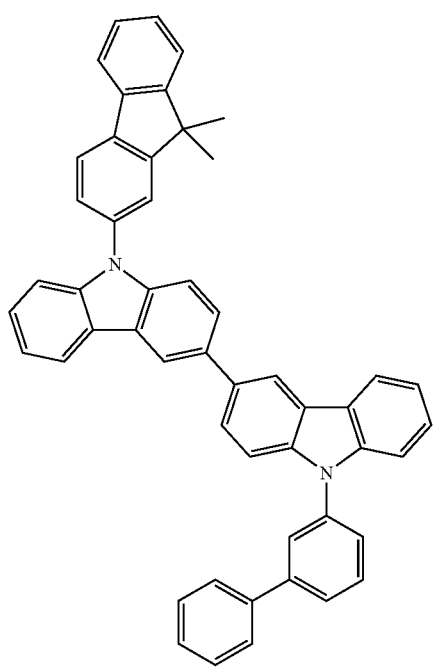
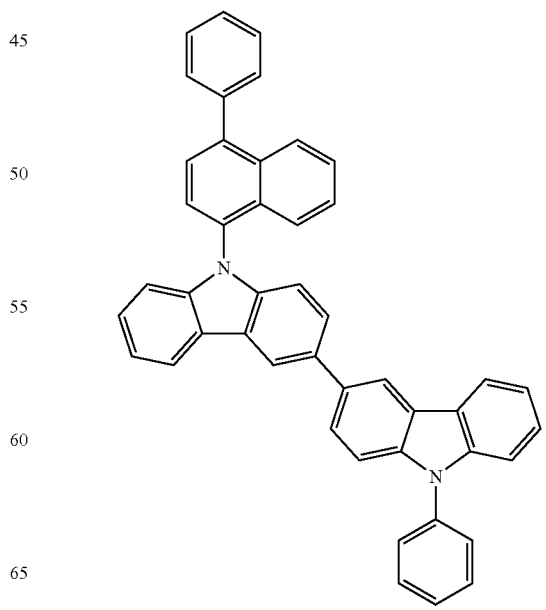

203
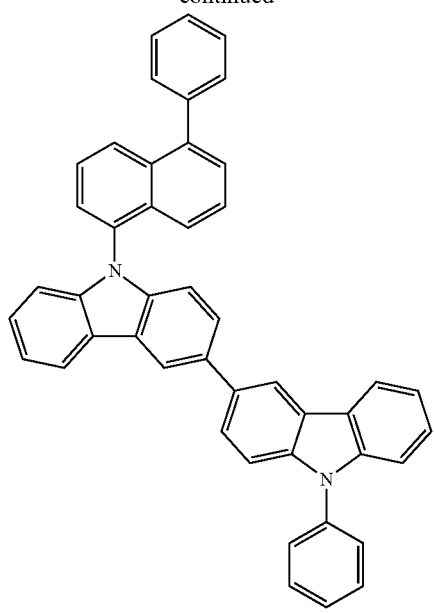
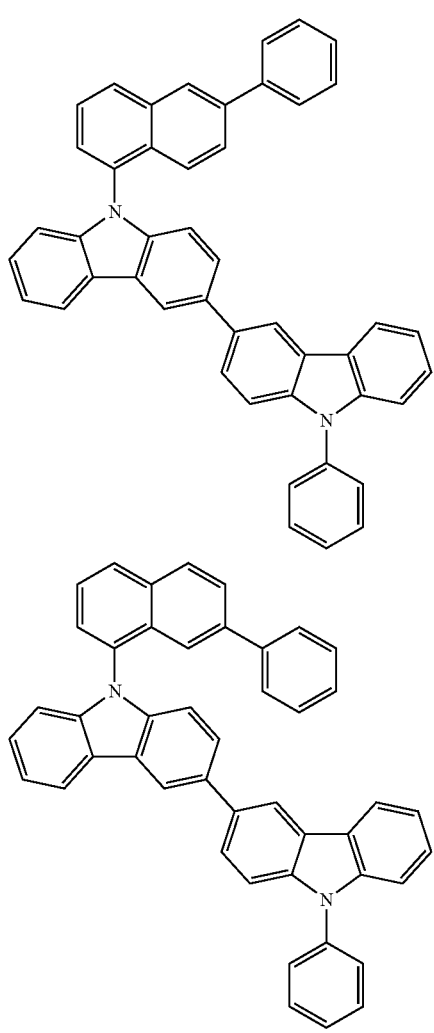
204
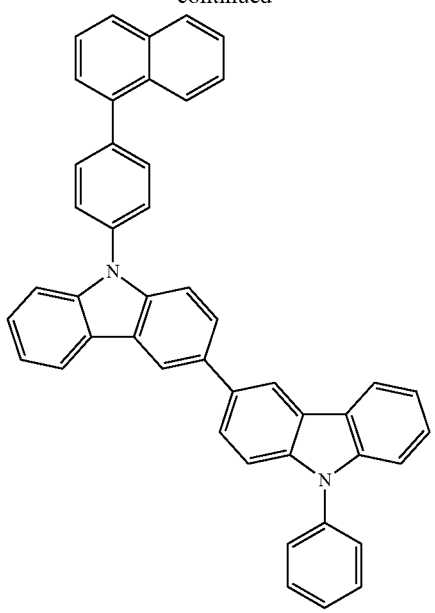
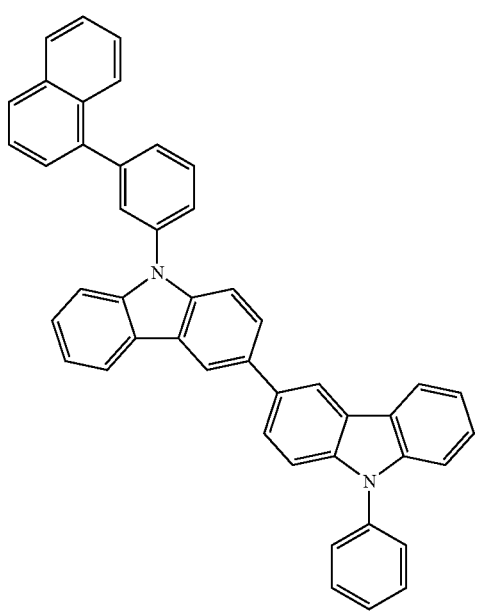

205
-continued
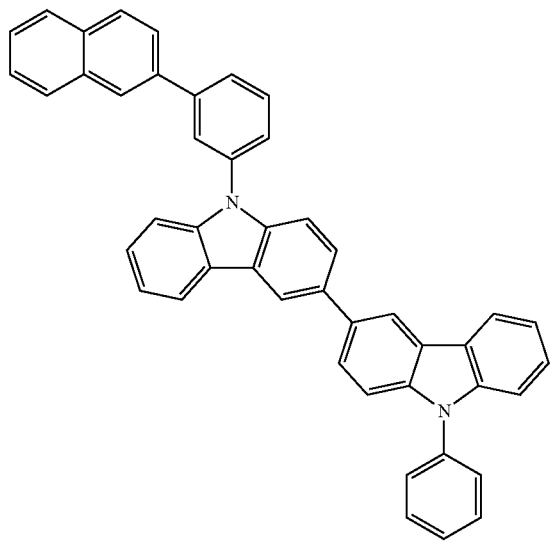
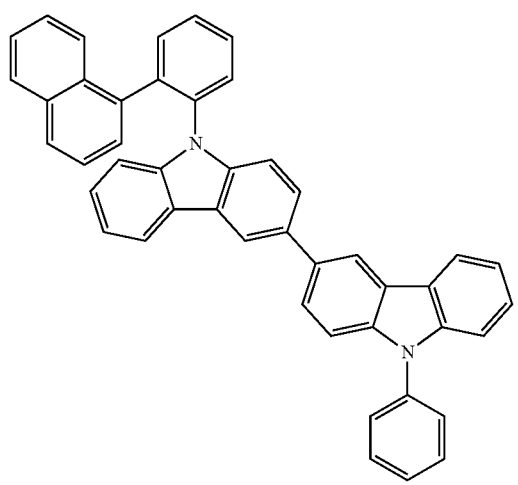
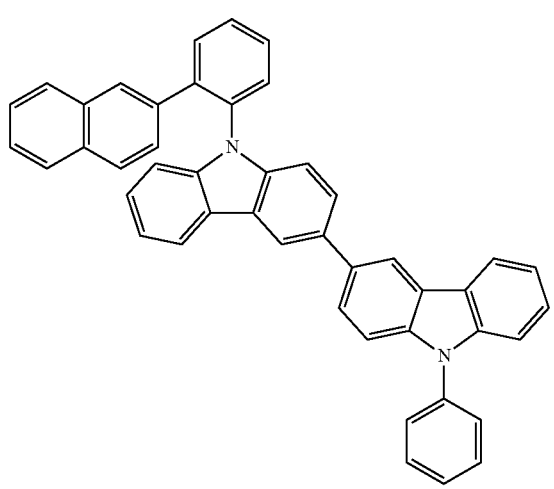
206
-continued
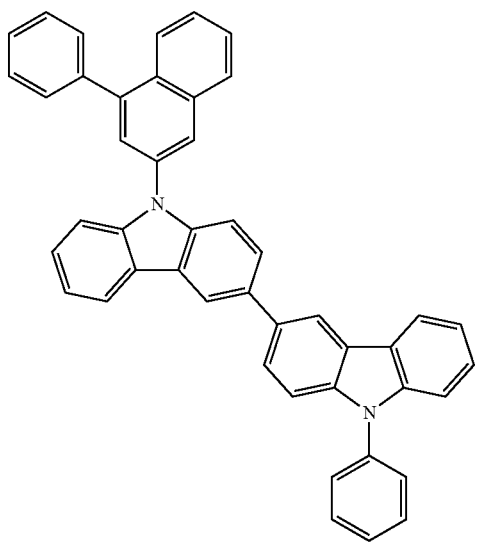
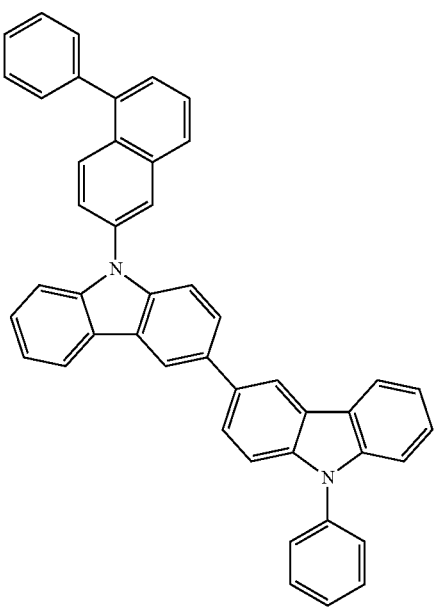

207
-continued
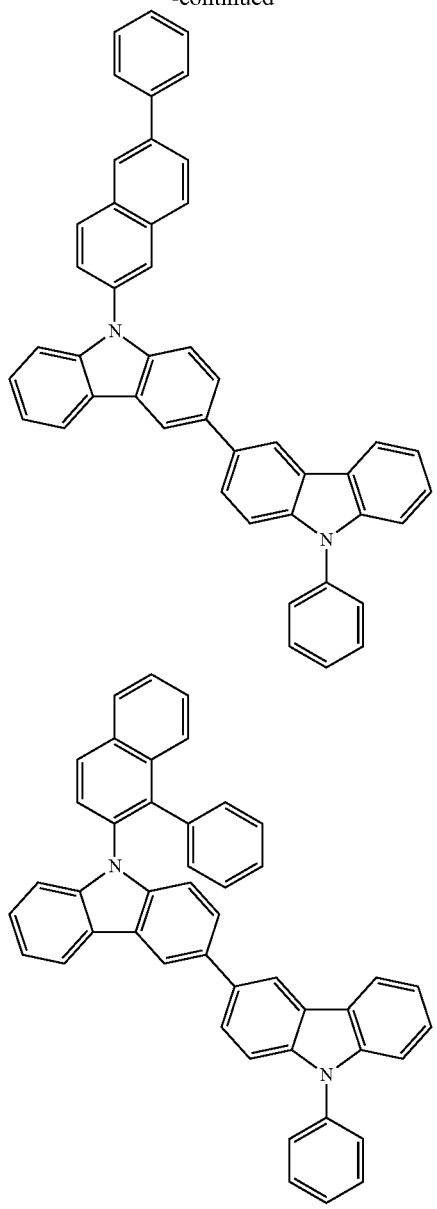
208
-continued
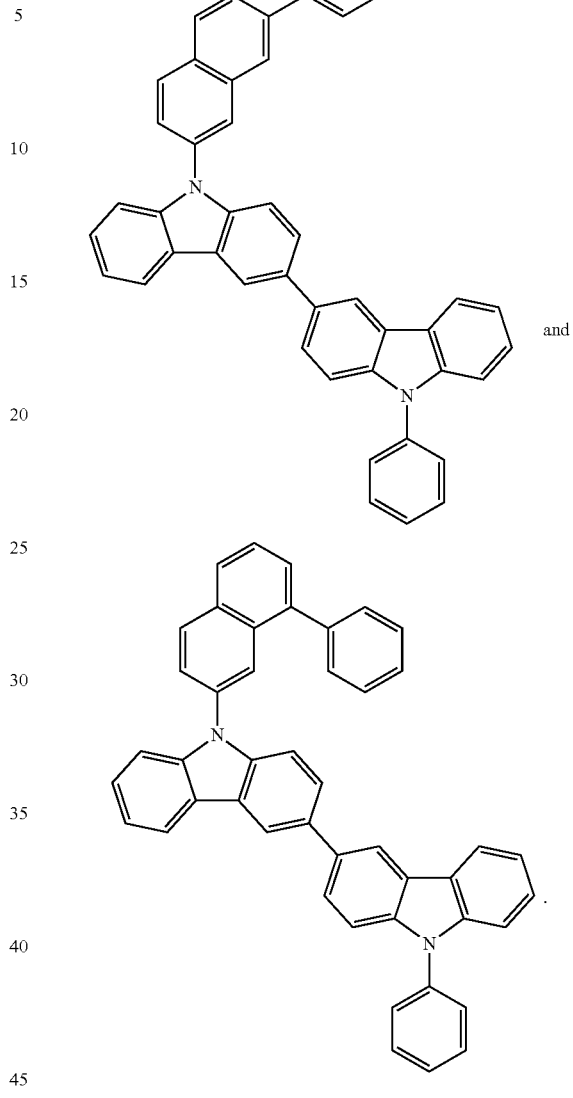
and
* * * * *

UNITED STATES PATENT AND TRADEMARK OFFICE
CERTIFICATE OF CORRECTION

| | | |
|---|---|---|
| PATENT NO. | : 12,041,851 B2 | Page 1 of 1 |
| APPLICATION NO. | : 17/291539 | |
| DATED | : July 16, 2024 | |
| INVENTOR(S) | : Suh et al. | |

It is certified that error appears in the above-identified patent and that said Letters Patent is hereby corrected as shown below:

In the Claims

In Claim 10, at Column 167, Line 37, "claim 5" should be replaced with —claim 9—.

Signed and Sealed this
Third Day of September, 2024

*Katherine Kelly Vidal*

Katherine Kelly Vidal
*Director of the United States Patent and Trademark Office*